United States Patent
Weinstein et al.

(10) Patent No.: US 10,781,239 B2
(45) Date of Patent: *Sep. 22, 2020

(54) IN VIVO ENGINEERED CEREBLON PROTEIN

(71) Applicants: Vividion Therapeutics, Inc., San Diego, CA (US); The Scripps Research Institute, La Jolla, CA (US)

(72) Inventors: David Weinstein, San Diego, CA (US); Benjamin F. Cravatt, La Jolla, CA (US); Matthew Patricelli, San Diego, CA (US); Dean Stamos, San Diego, CA (US); Gabe Simon, San Diego, CA (US); Benjamin Horning, San Diego, CA (US); Ekaterina Vinogradova, San Diego, CA (US); Brian Nordin, San Diego, CA (US); Kristen Baltgalvis, San Diego, CA (US); Todd Kinsella, San Diego, CA (US)

(73) Assignees: VIVIDION THERAPEUTICS, INC., San Diego, CA (US); THE SCRIPPS RESEARCH INSTITUTE, La Jolla, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/536,227

(22) Filed: Aug. 8, 2019

(65) Prior Publication Data

US 2020/0216507 A1 Jul. 9, 2020

Related U.S. Application Data

(63) Continuation-in-part of application No. 16/503,415, filed on Jul. 3, 2019.

(60) Provisional application No. 62/786,132, filed on Dec. 28, 2018.

(51) Int. Cl.
C07K 14/47 (2006.01)
C07D 211/94 (2006.01)

(52) U.S. Cl.
CPC ........ *C07K 14/4703* (2013.01); *C07D 211/94* (2013.01)

(58) Field of Classification Search
None
See application file for complete search history.

(56) References Cited

U.S. PATENT DOCUMENTS

2017/0362660 A1 12/2017 Thakurta et al.
2018/0343839 A1 12/2018 Ebert et al.

FOREIGN PATENT DOCUMENTS

WO WO-2017210600 A1 12/2017

OTHER PUBLICATIONS

Genest et al.,"The aza-Michael reaction as an alternative strategy to generate advanced silicon-based (macro)molecules and materials", Progress in Polymer Science 72: 61-110 (2017) (Year: 2017).*
Gunay et al.,"Ultrafast and efficient aza- and thiol-Michael reactions on a polyester scaffold with internal electron deficient triple bonds", Polym. Chem., 2018, 9, 3037. (Year: 2018).*
Backus et al. Proteome-wide covalent ligand discovery in native biological systems. Nature 534(7608):570-574 (2016).
Cravatt et al. Expedited Mapping of the Ligandable Proteome Using Fully Functionalized Enantiomeric Probe Pairs. ChemRxiv. Available at s://doi.org/10.26434/chemrxiv.7764638.v1 (75 pgs) (2019).
Matyskiela et al. A cereblon modulator (CC-220) with improved degradation of Ikaros and Aiolos. J Med Chem 61(2):535-542 (2018).
Weerapana et al. Quantitative reactivity profiling predicts functional cysteines in proteomes. Nature 468:790-795 (2010).
Serafimova et al. Reversible targeting of noncatalytic cysteines with chemically tuned electrophiles. Nat Chem Biol 8(5):471-476 (2012).
PCT/US2019/068749 Invitation to Pay Additional Fees dated Apr. 9, 2020.
U.S. Appl. No. 16/503,415 Office Action dated Mar. 17, 2020.
Gemechu et al. Humanized Cereblon Mice Revealed Two Distinct Therapeutic Pathways of Immunomodulatory Drugs. PNAS USA 115(46):11802-11807 (2018).
PCT/US2019/068749 International Search Report and Written Opinion dated Jun. 8, 2020.

* cited by examiner

*Primary Examiner* — Anand U Desai
(74) *Attorney, Agent, or Firm* — Wilson Sonsini Goodrich & Rosati; Kristin Eaton

(57) ABSTRACT

Disclosed herein are in vivo engineered cereblon protein and methods of making the same. The in vivo engineered cereblon protein can include a site-specific non-naturally occurring modification at cysteine 287 as set forth in SEQ ID NO:1, or cysteine 286 as set forth in SEQ ID NO:2 or 3, the modification comprising a moiety resulting from an in vivo Michael addition reaction between an exogenous Michael acceptor and the cysteine 287 as set forth in SEQ ID NO:1, or cysteine 286 as set forth in SEQ ID NO:2 or 3.

24 Claims, 7 Drawing Sheets
(7 of 7 Drawing Sheet(s) Filed in Color)

Specification includes a Sequence Listing.

A.

| Cpd | 4088 |
|---|---|
| CRBN_287 | 98 |
| CRBN_318 | 96 |
| PRTN_A | 10 |
| PRTN_B | 3 |
| PRTN_C | 14 |
| PRTN_D | 17 |
| PRTN_E | 12 |
| PRTN_F | 2 |
| PRTN_G | 13 |
| PRTN_H | 4 |
| PRTN_I | 14 |
| PRTN_J | 11 |
| PRTN_K | 22 |

B.

C.

Conformational change prevents binding

SEQUENCE LISTING

<160> NUMBER OF SEQ ID NOS: 10

<210> SEQ ID NO 1
<211> LENGTH: 442
<212> TYPE: PRT
<213> ORGANISM: Homo sapiens

<400> SEQUENCE: 1

Met Ala Gly Glu Gly Asp Gln Gln Asp Ala Ala His Asn Met Gly Asn
1               5                   10                  15

His Leu Pro Leu Leu Pro Ala Glu Ser Glu Glu Glu Asp Glu Met Glu
                20                  25                  30

Val Glu Asp Gln Asp Ser Lys Glu Ala Lys Lys Pro Asn Ile Ile Asn
            35                  40                  45

Phe Asp Thr Ser Leu Pro Thr Ser His Thr Tyr Leu Gly Ala Asp Met
        50                  55                  60

Glu Glu Phe His Gly Arg Thr Leu His Asp Asp Asp Ser Cys Gln Val
65                  70                  75                  80

Ile Pro Val Leu Pro Gln Val Met Met Ile Leu Ile Pro Gly Gln Thr
                85                  90                  95

```
Leu Pro Leu Gln Leu Phe His Pro Gln Glu Val Ser Met Val Arg Asn
            100                 105                 110

Leu Ile Gln Lys Asp Arg Thr Phe Ala Val Leu Ala Tyr Ser Asn Val
        115                 120                 125

Gln Glu Arg Glu Ala Gln Phe Gly Thr Thr Ala Glu Ile Tyr Ala Tyr
130                 135                 140

Arg Glu Glu Gln Asp Phe Gly Ile Glu Ile Val Lys Val Lys Ala Ile
145                 150                 155                 160

Gly Arg Gln Arg Phe Lys Val Leu Glu Leu Arg Thr Gln Ser Asp Gly
                165                 170                 175

Ile Gln Gln Ala Lys Val Gln Ile Leu Pro Glu Cys Val Leu Pro Ser
            180                 185                 190

Thr Met Ser Ala Val Gln Leu Glu Ser Leu Asn Lys Cys Gln Ile Phe
        195                 200                 205

Pro Ser Lys Pro Val Ser Arg Glu Asp Gln Cys Ser Tyr Lys Trp Trp
    210                 215                 220

Gln Lys Tyr Gln Lys Arg Lys Phe His Cys Ala Asn Leu Thr Ser Trp
225                 230                 235                 240

Pro Arg Trp Leu Tyr Ser Leu Tyr Asp Ala Glu Thr Leu Met Asp Arg
                245                 250                 255

Ile Lys Lys Gln Leu Arg Glu Trp Asp Glu Asn Leu Lys Asp Asp Ser
            260                 265                 270

Leu Pro Ser Asn Pro Ile Asp Phe Ser Tyr Arg Val Ala Ala Cys Leu
        275                 280                 285

Pro Ile Asp Asp Val Leu Arg Ile Gln Leu Leu Lys Ile Gly Ser Ala
    290                 295                 300

Ile Gln Arg Leu Arg Cys Glu Leu Asp Ile Met Asn Lys Cys Thr Ser
305                 310                 315                 320

Leu Cys Cys Lys Gln Cys Gln Glu Thr Glu Ile Thr Thr Lys Asn Glu
                325                 330                 335

Ile Phe Ser Leu Ser Leu Cys Gly Pro Met Ala Ala Tyr Val Asn Pro
            340                 345                 350

His Gly Tyr Val His Glu Thr Leu Thr Val Tyr Lys Ala Cys Asn Leu
        355                 360                 365

Asn Leu Ile Gly Arg Pro Ser Thr Glu His Ser Trp Phe Pro Gly Tyr
    370                 375                 380

Ala Trp Thr Val Ala Gln Cys Lys Ile Cys Ala Ser His Ile Gly Trp
385                 390                 395                 400

Lys Phe Thr Ala Thr Lys Lys Asp Met Ser Pro Gln Lys Phe Trp Gly
                405                 410                 415

Leu Thr Arg Ser Ala Leu Leu Pro Thr Ile Pro Asp Thr Glu Asp Glu
            420                 425                 430

Ile Ser Pro Asp Lys Val Ile Leu Cys Leu
        435                 440

<210> SEQ ID NO 2
<211> LENGTH: 441
<212> TYPE: PRT
<213> ORGANISM: Homo sapiens

<400> SEQUENCE: 2

Met Ala Gly Glu Gly Asp Gln Gln Asp Ala Ala His Asn Met Gly Asn
1               5                   10                  15

His Leu Pro Leu Leu Pro Glu Ser Glu Glu Glu Asp Glu Met Glu Val
```

```
              20                  25                  30
Glu Asp Gln Asp Ser Lys Glu Ala Lys Lys Pro Asn Ile Ile Asn Phe
             35                  40                  45
Asp Thr Ser Leu Pro Thr Ser His Thr Tyr Leu Gly Ala Asp Met Glu
 50                  55                  60
Glu Phe His Gly Arg Thr Leu His Asp Asp Ser Cys Gln Val Ile
 65                  70                  75                  80
Pro Val Leu Pro Gln Val Met Met Ile Leu Ile Pro Gly Gln Thr Leu
                 85                  90                  95
Pro Leu Gln Leu Phe His Pro Gln Glu Val Ser Met Val Arg Asn Leu
                100                 105                 110
Ile Gln Lys Asp Arg Thr Phe Ala Val Leu Ala Tyr Ser Asn Val Gln
             115                 120                 125
Glu Arg Glu Ala Gln Phe Gly Thr Thr Ala Glu Ile Tyr Ala Tyr Arg
         130                 135                 140
Glu Glu Gln Asp Phe Gly Ile Glu Ile Val Lys Val Lys Ala Ile Gly
145                 150                 155                 160
Arg Gln Arg Phe Lys Val Leu Glu Leu Arg Thr Gln Ser Asp Gly Ile
                 165                 170                 175
Gln Gln Ala Lys Val Gln Ile Leu Pro Glu Cys Val Leu Pro Ser Thr
             180                 185                 190
Met Ser Ala Val Gln Leu Glu Ser Leu Asn Lys Cys Gln Ile Phe Pro
         195                 200                 205
Ser Lys Pro Val Ser Arg Glu Asp Gln Cys Ser Tyr Lys Trp Trp Gln
    210                 215                 220
Lys Tyr Gln Lys Arg Lys Phe His Cys Ala Asn Leu Thr Ser Trp Pro
225                 230                 235                 240
Arg Trp Leu Tyr Ser Leu Tyr Asp Ala Glu Thr Leu Met Asp Arg Ile
                 245                 250                 255
Lys Lys Gln Leu Arg Glu Trp Asp Glu Asn Leu Lys Asp Asp Ser Leu
             260                 265                 270
Pro Ser Asn Pro Ile Asp Phe Ser Tyr Arg Val Ala Ala Cys Leu Pro
         275                 280                 285
Ile Asp Asp Val Leu Arg Ile Gln Leu Leu Lys Ile Gly Ser Ala Ile
    290                 295                 300
Gln Arg Leu Arg Cys Glu Leu Asp Ile Met Asn Lys Cys Thr Ser Leu
305                 310                 315                 320
Cys Cys Lys Gln Cys Gln Glu Thr Glu Ile Thr Thr Lys Asn Glu Ile
                 325                 330                 335
Phe Ser Leu Ser Leu Cys Gly Pro Met Ala Ala Tyr Val Asn Pro His
             340                 345                 350
Gly Tyr Val His Glu Thr Leu Thr Val Tyr Lys Ala Cys Asn Leu Asn
         355                 360                 365
Leu Ile Gly Arg Pro Ser Thr Glu His Ser Trp Phe Pro Gly Tyr Ala
    370                 375                 380
Trp Thr Val Ala Gln Cys Lys Ile Cys Ala Ser His Ile Gly Trp Lys
385                 390                 395                 400
Phe Thr Ala Thr Lys Lys Asp Met Ser Pro Gln Lys Phe Trp Gly Leu
                 405                 410                 415
Thr Arg Ser Ala Leu Leu Pro Thr Ile Pro Asp Thr Glu Asp Glu Ile
             420                 425                 430
Ser Pro Asp Lys Val Ile Leu Cys Leu
         435                 440
```

```
<210> SEQ ID NO 3
<211> LENGTH: 441
<212> TYPE: PRT
<213> ORGANISM: Homo sapiens

<400> SEQUENCE: 3
```

| | | | | | | | | | | | | | | |
|---|---|---|---|---|---|---|---|---|---|---|---|---|---|---|
|Met|Ala|Gly|Glu|Gly|Asp|Gln|Gln|Asp|Ala|Ala|His|Asn|Met|Gly|Asn|
|1| | | |5| | | | |10| | | | |15| |

| | | | | | | | | | | | | | | |
|---|---|---|---|---|---|---|---|---|---|---|---|---|---|---|
|His|Leu|Pro|Leu|Pro|Glu|Ser|Glu|Glu|Asp|Glu|Met|Glu|Val|
| | | |20| | | |25| | | |30| | | |

| | | | | | | | | | | | | | |
|---|---|---|---|---|---|---|---|---|---|---|---|---|---|
|Glu|Asp|Gln|Asp|Ser|Lys|Glu|Ala|Lys|Lys|Pro|Asn|Ile|Ile|Asn|Phe|
| | |35| | | |40| | | |45| | | | |

| | | | | | | | | | | | | | |
|---|---|---|---|---|---|---|---|---|---|---|---|---|---|
|Asp|Thr|Ser|Leu|Pro|Thr|Ser|His|Thr|Tyr|Leu|Gly|Ala|Asp|Met|Glu|
| |50| | | |55| | | |60| | | | |

| | | | | | | | | | | | | | |
|---|---|---|---|---|---|---|---|---|---|---|---|---|---|
|Glu|Phe|His|Gly|Arg|Thr|Leu|His|Asp|Asp|Ser|Cys|Gln|Val|Ile|
|65| | | |70| | | |75| | | |80|

| | | | | | | | | | | | | | |
|---|---|---|---|---|---|---|---|---|---|---|---|---|---|
|Pro|Val|Leu|Pro|Gln|Val|Met|Met|Ile|Leu|Ile|Pro|Gly|Gln|Thr|Leu|
| | | |85| | | |90| | | |95| | |

| | | | | | | | | | | | | | |
|---|---|---|---|---|---|---|---|---|---|---|---|---|---|
|Pro|Leu|Gln|Leu|Phe|His|Pro|Gln|Glu|Val|Ser|Met|Val|Arg|Asn|Leu|
| | | |100| | | |105| | | |110| | |

| | | | | | | | | | | | | | |
|---|---|---|---|---|---|---|---|---|---|---|---|---|---|
|Ile|Gln|Lys|Asp|Arg|Thr|Phe|Ala|Val|Leu|Ala|Tyr|Ser|Asn|Val|Gln|
| | |115| | | |120| | | |125| | | |

| | | | | | | | | | | | | | |
|---|---|---|---|---|---|---|---|---|---|---|---|---|---|
|Glu|Arg|Glu|Ala|Gln|Phe|Gly|Thr|Thr|Ala|Glu|Ile|Tyr|Ala|Tyr|Arg|
| |130| | | |135| | | |140| | | | |

| | | | | | | | | | | | | | |
|---|---|---|---|---|---|---|---|---|---|---|---|---|---|
|Glu|Glu|Gln|Asp|Phe|Gly|Ile|Glu|Ile|Val|Lys|Val|Lys|Ala|Ile|Gly|
|145| | | |150| | | |155| | | |160|

| | | | | | | | | | | | | | |
|---|---|---|---|---|---|---|---|---|---|---|---|---|---|
|Arg|Gln|Arg|Phe|Lys|Val|Leu|Glu|Leu|Arg|Thr|Gln|Ser|Asp|Gly|Ile|
| | | |165| | | |170| | | |175| | |

| | | | | | | | | | | | | | |
|---|---|---|---|---|---|---|---|---|---|---|---|---|---|
|Gln|Gln|Ala|Lys|Val|Gln|Ile|Leu|Pro|Glu|Cys|Val|Leu|Pro|Ser|Thr|
| | |180| | | |185| | | |190| | | |

| | | | | | | | | | | | | | |
|---|---|---|---|---|---|---|---|---|---|---|---|---|---|
|Met|Ser|Ala|Val|Gln|Leu|Glu|Ser|Leu|Asn|Lys|Cys|Gln|Ile|Phe|Pro|
| |195| | | |200| | | |205| | | | |

| | | | | | | | | | | | | | |
|---|---|---|---|---|---|---|---|---|---|---|---|---|---|
|Ser|Lys|Pro|Val|Ser|Arg|Glu|Asp|Gln|Cys|Ser|Tyr|Lys|Trp|Trp|Gln|
|210| | | |215| | | |220| | | | |

| | | | | | | | | | | | | | |
|---|---|---|---|---|---|---|---|---|---|---|---|---|---|
|Lys|Tyr|Gln|Arg|Arg|Lys|Phe|His|Cys|Ala|Asn|Leu|Thr|Ser|Trp|Pro|
|225| | | |230| | | |235| | | |240|

| | | | | | | | | | | | | | |
|---|---|---|---|---|---|---|---|---|---|---|---|---|---|
|Arg|Trp|Leu|Tyr|Ser|Leu|Tyr|Asp|Ala|Glu|Thr|Leu|Met|Asp|Arg|Ile|
| | | |245| | | |250| | | |255| |

| | | | | | | | | | | | | | |
|---|---|---|---|---|---|---|---|---|---|---|---|---|---|
|Lys|Lys|Gln|Leu|Arg|Glu|Trp|Asp|Glu|Asn|Leu|Lys|Asp|Asp|Ser|Leu|
| | |260| | | |265| | | |270| | | |

| | | | | | | | | | | | | | |
|---|---|---|---|---|---|---|---|---|---|---|---|---|---|
|Pro|Ser|Asn|Pro|Ile|Asp|Phe|Ser|Tyr|Arg|Val|Ala|Ala|Cys|Leu|Pro|
| |275| | | |280| | | |285| | | | |

| | | | | | | | | | | | | | |
|---|---|---|---|---|---|---|---|---|---|---|---|---|---|
|Ile|Asp|Asp|Val|Leu|Arg|Ile|Gln|Leu|Leu|Lys|Ile|Gly|Ser|Ala|Ile|
| |290| | | |295| | | |300| | | | |

| | | | | | | | | | | | | | |
|---|---|---|---|---|---|---|---|---|---|---|---|---|---|
|Gln|Arg|Leu|Arg|Cys|Glu|Leu|Asp|Ile|Met|Asn|Lys|Cys|Thr|Ser|Leu|
|305| | | |310| | | |315| | | |320|

| | | | | | | | | | | | | | |
|---|---|---|---|---|---|---|---|---|---|---|---|---|---|
|Cys|Cys|Lys|Gln|Cys|Gln|Glu|Thr|Glu|Ile|Thr|Thr|Lys|Asn|Glu|Ile|
| | | |325| | | |330| | | |335| |

| | | | | | | | | | | | | | |
|---|---|---|---|---|---|---|---|---|---|---|---|---|---|
|Phe|Ser|Leu|Ser|Leu|Cys|Gly|Pro|Met|Ala|Ala|Tyr|Val|Asn|Pro|His|
| | |340| | | |345| | | |350| | | |

| | | | | | | | | | | | | | |
|---|---|---|---|---|---|---|---|---|---|---|---|---|---|
|Gly|Tyr|Val|His|Glu|Thr|Leu|Thr|Val|Tyr|Lys|Ala|Cys|Asn|Leu|Asn|
| |355| | | |360| | | |365| | | | |

| | | | | | | | | | | | | | |
|---|---|---|---|---|---|---|---|---|---|---|---|---|---|
|Leu|Ile|Gly|Arg|Pro|Ser|Thr|Glu|His|Ser|Trp|Phe|Pro|Gly|Tyr|Ala|

```
                    370             375                 380
Trp Thr Val Ala Gln Cys Lys Ile Cys Ala Ser His Ile Gly Trp Lys
385                 390                 395                 400

Phe Thr Ala Thr Lys Lys Asp Met Ser Pro Gln Lys Phe Trp Gly Leu
            405                 410                 415

Thr Arg Ser Ala Leu Leu Pro Thr Ile Pro Asp Thr Glu Asp Glu Ile
                420                 425                 430

Ser Pro Asp Lys Val Ile Leu Cys Leu
            435                 440

<210> SEQ ID NO 4
<211> LENGTH: 237
<212> TYPE: PRT
<213> ORGANISM: Homo sapiens

<400> SEQUENCE: 4

Ile Pro Val Leu Pro Gln Val Met Met Ile Leu Ile Pro Gly Gln Thr
1               5                   10                  15

Leu Pro Leu Gln Leu Phe His Pro Gln Glu Val Ser Met Val Arg Asn
            20                  25                  30

Leu Ile Gln Lys Asp Arg Thr Phe Ala Val Leu Ala Tyr Ser Asn Val
        35                  40                  45

Gln Glu Arg Glu Ala Gln Phe Gly Thr Thr Ala Glu Ile Tyr Ala Tyr
    50                  55                  60

Arg Glu Glu Gln Asp Phe Gly Ile Glu Ile Val Lys Val Lys Ala Ile
65                  70                  75                  80

Gly Arg Gln Arg Phe Lys Val Leu Glu Leu Arg Thr Gln Ser Asp Gly
                85                  90                  95

Ile Gln Gln Ala Lys Val Gln Ile Leu Pro Glu Cys Val Leu Pro Ser
            100                 105                 110

Thr Met Ser Ala Val Gln Leu Glu Ser Leu Asn Lys Cys Gln Ile Phe
        115                 120                 125

Pro Ser Lys Pro Val Ser Arg Glu Asp Gln Cys Ser Tyr Lys Trp Trp
    130                 135                 140

Gln Lys Tyr Gln Lys Arg Lys Phe His Cys Ala Asn Leu Thr Ser Trp
145                 150                 155                 160

Pro Arg Trp Leu Tyr Ser Leu Tyr Asp Ala Glu Thr Leu Met Asp Arg
                165                 170                 175

Ile Lys Lys Gln Leu Arg Glu Trp Asp Glu Asn Leu Lys Asp Asp Ser
            180                 185                 190

Leu Pro Ser Asn Pro Ile Asp Phe Ser Tyr Arg Val Ala Ala Cys Leu
        195                 200                 205

Pro Ile Asp Asp Val Leu Arg Ile Gln Leu Leu Lys Ile Gly Ser Ala
    210                 215                 220

Ile Gln Arg Leu Arg Cys Glu Leu Asp Ile Met Asn Lys
225                 230                 235

<210> SEQ ID NO 5
<211> LENGTH: 237
<212> TYPE: PRT
<213> ORGANISM: Homo sapiens

<400> SEQUENCE: 5

Ile Pro Val Leu Pro Gln Val Met Met Ile Leu Ile Pro Gly Gln Thr
1               5                   10                  15

Leu Pro Leu Gln Leu Phe His Pro Gln Glu Val Ser Met Val Arg Asn
```

```
                  20                  25                  30

Leu Ile Gln Lys Asp Arg Thr Phe Ala Val Leu Ala Tyr Ser Asn Val
             35                  40                  45

Gln Glu Arg Glu Ala Gln Phe Gly Thr Thr Ala Glu Ile Tyr Ala Tyr
         50                  55                  60

Arg Glu Glu Gln Asp Phe Gly Ile Glu Ile Val Lys Val Lys Ala Ile
 65                  70                  75                  80

Gly Arg Gln Arg Phe Lys Val Leu Glu Leu Arg Thr Gln Ser Asp Gly
                 85                  90                  95

Ile Gln Gln Ala Lys Val Gln Ile Leu Pro Glu Cys Val Leu Pro Ser
            100                 105                 110

Thr Met Ser Ala Val Gln Leu Glu Ser Leu Asn Lys Cys Gln Ile Phe
        115                 120                 125

Pro Ser Lys Pro Val Ser Arg Glu Asp Gln Cys Ser Tyr Lys Trp Trp
    130                 135                 140

Gln Lys Tyr Gln Arg Arg Lys Phe His Cys Ala Asn Leu Thr Ser Trp
145                 150                 155                 160

Pro Arg Trp Leu Tyr Ser Leu Tyr Asp Ala Glu Thr Leu Met Asp Arg
                165                 170                 175

Ile Lys Lys Gln Leu Arg Glu Trp Asp Glu Asn Leu Lys Asp Asp Ser
            180                 185                 190

Leu Pro Ser Asn Pro Ile Asp Phe Ser Tyr Arg Val Ala Ala Cys Leu
        195                 200                 205

Pro Ile Asp Asp Val Leu Arg Ile Gln Leu Leu Lys Ile Gly Ser Ala
    210                 215                 220

Ile Gln Arg Leu Arg Cys Glu Leu Asp Ile Met Asn Lys
225                 230                 235

<210> SEQ ID NO 6
<211> LENGTH: 6
<212> TYPE: PRT
<213> ORGANISM: Homo sapiens
<220> FEATURE:
<221> NAME/KEY: MOD_RES
<222> LOCATION: (2)..(3)
<223> OTHER INFORMATION: Any amino acid

<400> SEQUENCE: 6

Cys Xaa Xaa Met Ala Ala
1               5

<210> SEQ ID NO 7
<211> LENGTH: 9
<212> TYPE: PRT
<213> ORGANISM: Homo sapiens
<220> FEATURE:
<221> NAME/KEY: MOD_RES
<222> LOCATION: (2)..(3)
<223> OTHER INFORMATION: Any amino acid
<220> FEATURE:
<221> NAME/KEY: MOD_RES
<222> LOCATION: (6)..(7)
<223> OTHER INFORMATION: Any amino acid

<400> SEQUENCE: 7

Asp Xaa Xaa Tyr Arg Xaa Xaa Ala Cys
1               5

<210> SEQ ID NO 8
<211> LENGTH: 4
<212> TYPE: PRT
```

```
<213> ORGANISM: Homo sapiens

<400> SEQUENCE: 8

Pro Gly Gln Thr
1

<210> SEQ ID NO 9
<211> LENGTH: 6
<212> TYPE: PRT
<213> ORGANISM: Homo sapiens
<220> FEATURE:
<221> NAME/KEY: MOD_RES
<222> LOCATION: (2)..(3)
<223> OTHER INFORMATION: Any amino acid

<400> SEQUENCE: 9

Val Xaa Xaa Cys Leu Pro
1               5

<210> SEQ ID NO 10
<211> LENGTH: 6
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Any amino acid

<400> SEQUENCE: 10

Arg Ser Xaa Leu Leu Pro
1               5
```

IN VIVO ENGINEERED CEREBLON PROTEIN

CROSS REFERENCE

This application is a continuation in part of U.S. application Ser. No. 16/503,415, filed on Jul. 3, 2019, which claims the benefit of U.S. Provisional Application No. 62/786,132, filed on Dec. 28, 2018, each of which are incorporated herein by reference in their entireties.

SEQUENCE LISTING

The instant application contains a Sequence Listing which has been filed electronically in ASCII format and is hereby incorporated by reference in its entirety. Said ASCII copy, created on Aug. 22, 2019, is named 48054-709_202_SL.txt and is 16,793 bytes in size.

BACKGROUND OF THE DISCLOSURE

Cereblon is a eukaryotic protein ranging from 400-600 residues in length. The human cereblon (SEQ ID NO: 1) is about 442 residues in length, and is encoded by the CRBN gene. The cereblon protein comprises a central LON domain (residues 80-317) followed by a C-terminal CULT domain. The LON domain is further subdivided into an N-terminal LON-N subdomain, a four helix bundle, and a C-terminal LON-C subdomain.

Ubiquitin-proteasome system is characterized by the E1, E2, and E3 enzyme. First, a ubiquitin molecule is chemically activated in an ATP-dependent manner by an E1-activating enzyme forming a thioester bond between the C-terminal glycine residue of ubiquitin and a conserved cysteine residue of the E1. Then, ubiquitin is transferred on to an E2-conjugated enzyme via a trans-thiolation reaction. Next, an isopeptide bond between the ε-amino group of a substrate lysine residue and the C-terminal glycine residue of ubiquitin is formed via E3 ligase-mediated catalysis and then between ubiquitin molecules to form poly-ubiquitin chains. Upon completion of the ubiquination process, the tagged substrate is subsequently recognized and degraded by the 26S proteasome in an ATP-dependent manner.

Protein biosynthesis and degradation is a dynamic process which sustains normal cell metabolism. Proteins can be degraded through one of two proteolytic mechanisms, the lysosome degradation system or the ubiquitin proteasome pathway. There remains a need for modulating protein degradation pathway.

SUMMARY OF THE DISCLOSURE

Some embodiments relate to an in vivo engineered cereblon protein consisting of a site-specific non-naturally occurring modification at cysteine 287 as set forth in SEQ ID NO:1, or cysteine 286 as set forth in SEQ ID NO: 2 or 3, the modification comprising a moiety resulting from an in vivo Michael addition reaction between an exogenous Michael acceptor and the cysteine 287 as set forth in SEQ ID NO:1, or cysteine 286 as set forth in SEQ ID NO: 2 or 3.

In some embodiments, the IMiD pocket-dependent binding on the engineered cereblon protein is prevented by the modification. In some embodiments, the engineered cereblon protein has an inhibited or reduced binding for immunomodulatory drugs as compared to unmodified cereblon.

In some embodiments, the engineered cereblon has reduced engagement potency at cysteine 318 as set forth in SEQ ID NO:1 or at cysteine 317 as set forth in SEQ ID NO: 2 or 3. In some embodiments, the amino acid residue at cysteine 318 as set forth in SEQ ID NO:1 or cysteine 317 as set forth in SEQ ID NO: 2 or 3 is not modified. In some embodiments, the amino acid residues at cysteine 234, cysteine 205, cysteine 219, cysteine 366, cysteine 188, and cysteine 343 as set forth in SEQ ID NO:1 are not modified. In some embodiments, the engineered cereblon protein is only modified at cysteine 287 as set forth in SEQ ID NO:1 or cysteine 286 as set forth in SEQ ID NO: 2 or 3.

In some embodiments, the exogenous Michael acceptor has a global promiscuity that is no greater than the global promiscuity of KB02. In some embodiments, the exogenous Michael acceptor has a global promiscuity that is no greater than ⅓ of the global promiscuity of KB02.

In some embodiments, the exogenous Michael acceptor has a global promiscuity of no greater than 20% at 500 μM. In some embodiments, the exogenous Michael acceptor has a global promiscuity of no greater than 10% at 500 μM.

In some embodiments, the exogenous Michael acceptor has a $TE_{50}$ of no greater than 80 μM. In some embodiments, the exogenous Michael acceptor has a $TE_{50}$ of no greater than 60 μM. In some embodiments, the exogenous Michael acceptor has a global promiscuity no greater than 5% at the $TE_{50}$. In some embodiments, the exogenous Michael acceptor has a global promiscuity no greater than 2.5% at the $TE_{50}$.

In some embodiments, the exogenous Michael acceptor has a lower $TE_{50}$ than

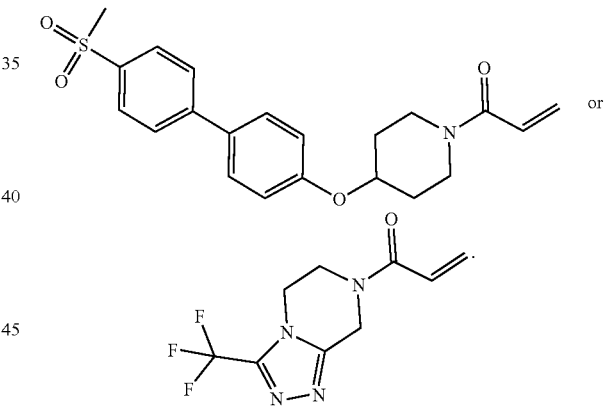

In some embodiments, the exogenous Michael acceptor is an acrylamide.

In some embodiments, the cereblon has a sequence as set forth in SEQ ID NO: 1 and the modification is at the cysteine residue C287. In some embodiments, the cereblon has a sequence as set forth in SEQ ID NO: 2 or 3 and the modification is at the cysteine residue C286.

In some embodiments, the ligand forms a hydrophobic interaction with the one or more residues selected from Pro 93, Ile 160, Met 246, Pro 274, Tyr 282, Ala 286, Cys 287, Cys 343, Ala 347, Ala 348, or a combination thereof. In some embodiments, the ligand forms a hydrophobic interaction with the one or more residues selected from Met 345, Leu 321, Leu 422, Leu 423, Pro 424, Leu 360, or a combination thereof. In some embodiments, the ligand forms a charged interaction with the one or more residues selected from Asp279, Asp 265, Arg 162, Arg 283, Lys 324, Arg 419, or a combination thereof. In some embodiments, the ligand forms a polar interaction with the one or more residues selected from Gln 95, Thr 96, or Ser 420.

In some embodiments, the exogenous Michael acceptor comprises at least one double bond. In some embodiments, the sulfur atom at the cysteine residue undergoes the Michael reaction with the double bond of the exogenous Michael acceptor. In some embodiments, the exogenous Michael acceptor does not have a triple bond.

In some embodiments, the cereblon is a human cereblon protein.

In certain embodiments, disclosed herein is a modified cereblon wherein the cysteine C287 of SEQ ID NO: 1 or corresponding cysteine of a cereblon homolog, active fragment, or variant thereof is conjugated to a compound of Formula (I)

BRIEF DESCRIPTION OF THE DRAWINGS

Various aspects of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings below. The patent application file contains at least one drawing executed in color. Copies of this patent application publication with color drawing(s) will be provided by the Office upon request and payment of the necessary fee.

FIG. 3A shows part of table 1 from Example 45 where compounds are shown to be highly selective in causing inhibition of probe labeling at C287 and C318; FIG. 3B is an illustration of a direct mechanism of co-inhibition of C287 and C318, where compounds bind to both cysteines, for instance in independent liganding events. FIG. 3B is an illustration of an indirect mechanism of co-inhibition of cysteines 287 and 318 on cereblon where one of the cysteines is bound and the other cysteine is no longer probe-accessible due to a conformational change.

FIG. 6A is a schematic of cereblon with FKBP12 as a substrate for degrading. FIG. 6B represents the data with no compound washout step and the percent NanoLuc activity from an assay which correlates the amount of FKBP-12 degraded to measurable brightness. FIG. 6C represents data with compound washout showing percent NanoLuc activity from the assay which correlates the amount of FKBP-12 degraded to measurable brightness.

FIG. 6 discloses SEQ ID NOS 6-8, respectively, in order of appearance.

FIG. 7 discloses SEQ ID NOS 9-10, respectively, in order of appearance.

DETAILED DESCRIPTION OF THE DISCLOSURE

Reaction at a single amino acid or site, among various reactive carboxylic acids, amides, amines, alcohols and thiols, is a challenge in both chemo- and regioselectivity. Selective reactions at specific cysteine over other cysteine residues and other nucleophilic residues such as lysine and histidine have been achieved using the methods describe herein. Use of Michael addition reaction can selectively modify cereblon at C287 position (or C286 for isoform) and lead to an in vivo engineered cereblon protein with site specified modification. The use of an exogenous Michael acceptor not only preferentially modifies cysteine over other amino acid residues such as lysine and histidine, and more surprisingly it selectively modifies C287 positions over that other cysteine positions such as C318, C234, C205, C219, C366, C188, and C343.

Figure 1:
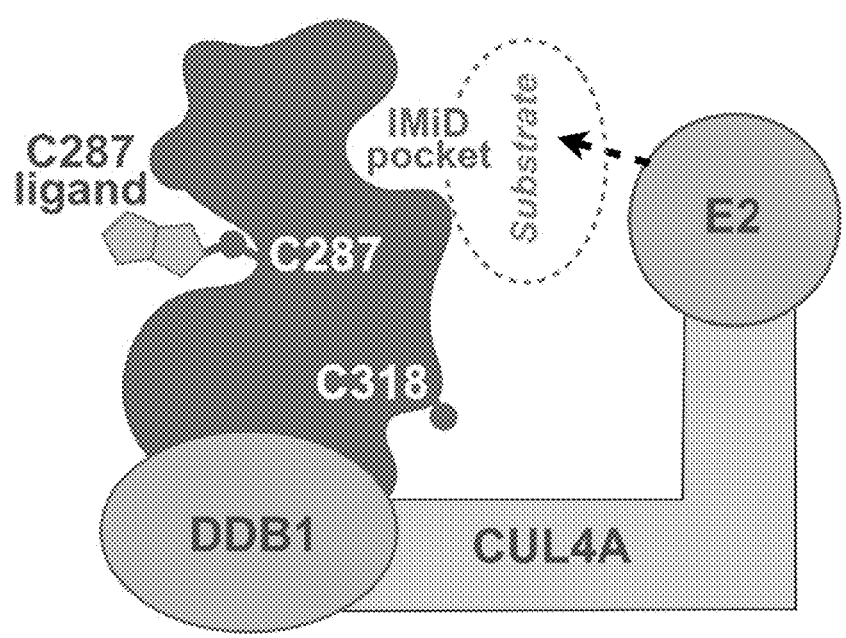
FIG. 1 is an illustration of cereblon and the positions on cereblon in its native configuration of C287, C318, and the immunomodulatory (IMiD) binding pocket.
Figure 2:
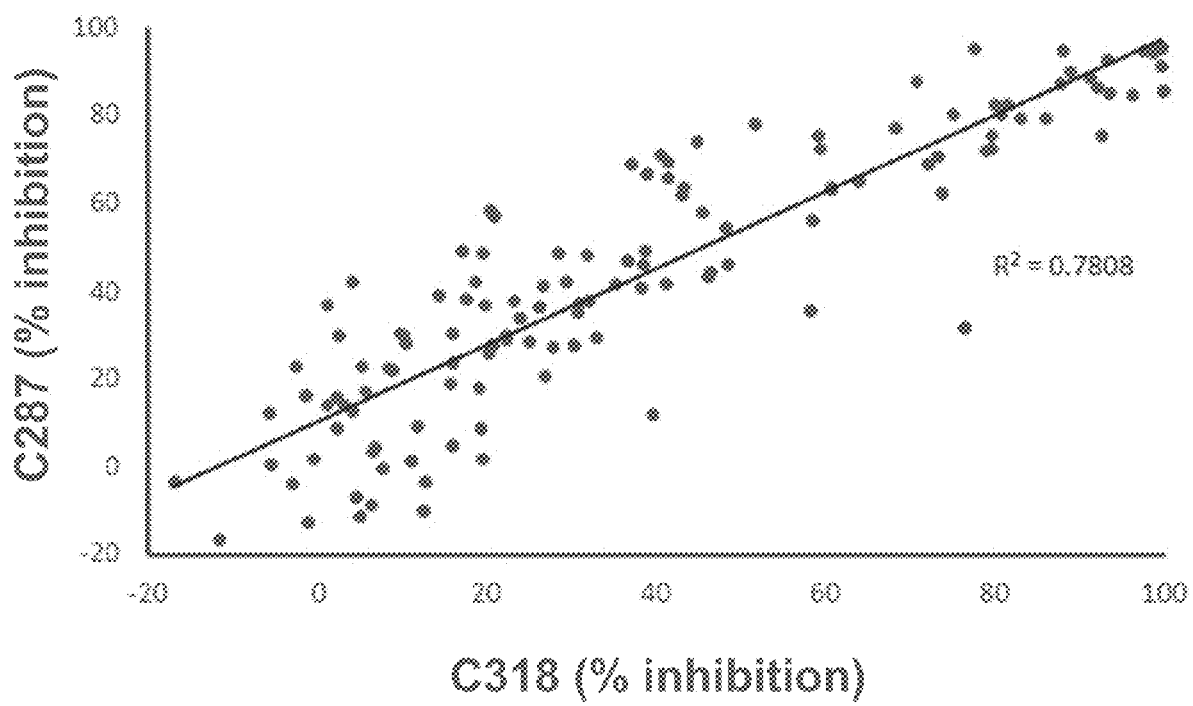
FIG. 2 illustrates the correlation between probe inhibition of two cysteines on cereblon, C287 and C318.
Figure 3:
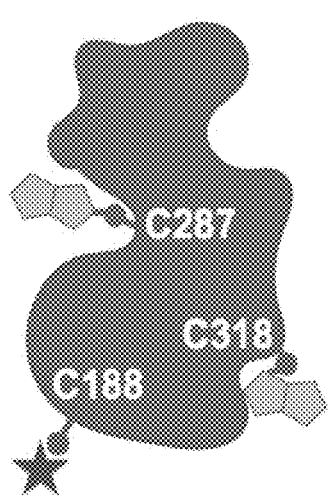
FIG. 3 illustrates the co-inhibition of C287 and C318 and shows illustrations of proposed direct and indirect mechanisms by which the inhibition occurs.
Figure 3:
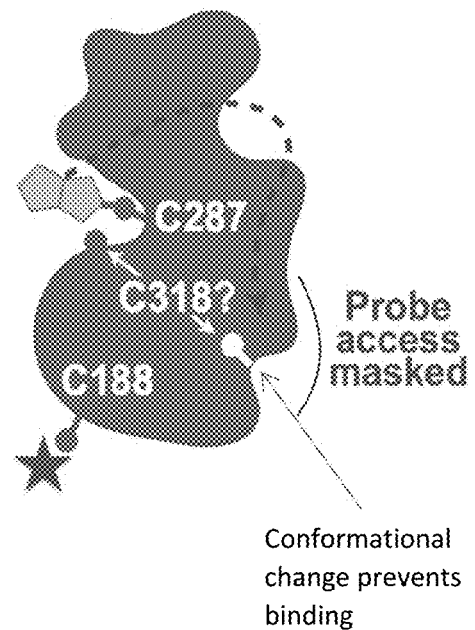

The in vivo engineered cereblon protein disclosed herein displays a conformational change which in turn prevents modification at other cysteine residue such as C318 and provides better stability than unmodified cereblon protein. As shown in FIG. 1, C287 and C318 are positioned on the opposite faces of the cereblon protein. It was unexpected that after the CRBN was modified with a Michael acceptor, C287 and C318 on CRBN displayed highly correlated structure activity relationship (SAR). Michael acceptor (e.g., acrylamide) compounds have been used to modify the cereblon protein. After the pretreatment, the protein was tested using a labeling probe at a screening concentration of 500 µM, and the percentage of inhibition of probe labeling at screening concentration for both C287 and C318 showed unexpected correlation. As shown in FIG. 3B, changes in the probe-accessibility of C318 upon C287 modification/liganding involves an indirect allosteric mechanism. For instance, when CRBN was modified with various Michael acceptor compounds and the probe was later added with the protein at its native state, the C287 modification prevented further probe labeling at both C287 and C318; In contrast, when the Michael acceptor compounds were used to modify CRBN and the probe was later added after the protein was denatured, C318 labeling was no longer inhibited. Therefore, C287 liganding/modification induces conformational changes at C318 and prevents further liganding or binding at C318.

In addition, modification at C287 of cereblon also induces conformational changes that prevent the IMiD binding pocket and inhibit binding of IMiD to cereblon. As shown in Figure xx, modification at C287 also prevents IMiDs binding. After HEK293 cells were pretreated with Michael acceptor compounds and the cereblon protein was modified by the Michael acceptor compounds, the PROTAC dFKBP13 was added and the activity of a cereblon dependent degradation assay was measured to determine the interaction between C287 and IMiD binding pocket. The results showed that C287 modification inhibited PROTAC dEKBP13 function and induced inhibition or prevention of the IMiD binding. Therefore, it was unexpected that the modification method described herein can yield in vivo engineered cereblon protein described herein has site specific modification and also has reduced engagement activity at both C318 residue and IMiD binding pocket.

In Vivo Engineered Cereblon Protein:

An in vivo engineered cereblon protein consisting of a site-specific non-naturally occurring modification at cysteine 287 as set forth in SEQ ID NO:1, or cysteine 286 as set forth in SEQ ID NO: 2 or 3, the modification comprising a moiety resulting from an in vivo Michael addition reaction between an exogenous Michael acceptor and the cysteine 287 as set forth in SEQ ID NO:1, or cysteine 286 as set forth in SEQ ID NO: 2 or 3.

The in vivo engineered cereblon has reduced engagement potency at other cysteine positions. In some embodiments, the engineered cereblon has reduced engagement potency at C318 as set forth in SEQ ID NO:1 or cysteine 317 as set forth in SEQ ID NO: 2 or 3. In some embodiments, the cysteine binding or labeling at C318 is inhibited by the modification at C287 as set forth in SEQ ID NO:1. In some embodiments, the cysteine binding or labeling at C317 is inhibited by the modification at C286 as set forth in SEQ ID NO: 2 or 3.

The in vivo engineered cereblon protein having the SEQ ID NO: 1 is only modified at C287 and does not comprise modification at other amino acid residues. In some embodiments, the in vivo engineered cereblon protein does not comprise modification at C318. In some embodiments, the in vivo engineered cereblon protein does not comprise modification at C234. In some embodiments, the in vivo engineered cereblon protein does not comprise modification at C205. In some embodiments, the in vivo engineered cereblon protein does not comprise modification at C219. In some embodiments, the in vivo engineered cereblon protein does not comprise modification at C366. In some embodiments, the in vivo engineered cereblon protein does not comprise modification at C188. In some embodiments, the in vivo engineered cereblon protein does not comprise modification at C343. In some embodiments, the in vivo engineered cereblon protein is not modified at C318. In some embodiments, the in vivo engineered cereblon protein is not modified at C234. In some embodiments, the in vivo engineered cereblon protein is not modified at C205. In some embodiments, the in vivo engineered cereblon protein is not modified at C219. In some embodiments, the in vivo engineered cereblon protein is not modified at C366. In some embodiments, the in vivo engineered cereblon protein is not modified at C188. In some embodiments, the in vivo engineered cereblon protein is not modified at C343.

The in vivo engineered cereblon protein having the SEQ ID NO: 2 or 3 is only modified at C286 and does not comprise modification at other amino acid residues. In some embodiments, the in vivo engineered cereblon protein does not comprise modification at C317. In some embodiments, the in vivo engineered cereblon protein does not comprise modification at C233. In some embodiments, the in vivo engineered cereblon protein does not comprise modification at C204. In some embodiments, the in vivo engineered cereblon protein does not comprise modification at C218. In some embodiments, the in vivo engineered cereblon protein does not comprise modification at C365. In some embodiments, the in vivo engineered cereblon protein does not comprise modification at C187. In some embodiments, the in vivo engineered cereblon protein does not comprise modification at C342. In some embodiments, the in vivo engineered cereblon protein is not modified at C317. In some embodiments, the in vivo engineered cereblon protein is not modified at C233. In some embodiments, the in vivo engineered cereblon protein is not modified at C204. In some embodiments, the in vivo engineered cereblon protein is not modified at C218. In some embodiments, the in vivo engineered cereblon protein is not modified at C365. In some embodiments, the in vivo engineered cereblon protein is not modified at C187. In some embodiments, the in vivo engineered cereblon protein is not modified at C342.

The engagement efficiency of cysteine 318 as set forth in SEQ ID NO:1 or cysteine 317 as set forth in SEQ ID NO: 2 or 3 can be substantially reduced due to the in vivo modification described herein. In some embodiments, the engagement efficiency of cysteine 318 as set forth in SEQ ID NO:1 or cysteine 317 as set forth in SEQ ID NO: 2 or 3 in the in vivo engineered cereblon protein is reduced by at least about 95%, 90%, 80%, 70%, 60%, 50%, 40%, or 30% when compared with unmodified cereblon protein. In some embodiments, the engagement efficiency of cysteine 318 as set forth in SEQ ID NO:1 or cysteine 317 as set forth in SEQ ID NO: 2 or 3 in the in vivo engineered cereblon protein is completely reduced to 0%.

The in vivo engineered cereblon protein described herein not only has a specific site modification but also has reduced engagement activity at highly selected sites. In some embodiments, the IMiD pocket-dependent binding on the in vivo engineered cereblon protein is prevented by the modification. In some embodiments, the in vivo engineered cereblon has a reduced binding for immunomodulatory drugs as compared to unmodified cereblon. In some embodiments, the in vivo engineered cereblon has a reduced binding for immunomodulatory drugs at tri-Trp pocket compared to unmodified cereblon. In some embodiments, the thalidomide-dependent binding on the in vivo engineered cereblon protein is prevented by the modification. In some embodiments, the in vivo engineered cereblon protein's binding to immunomodulatory drugs is reduced by at least about 95%, 90%, 80%, 70%, 60%, 50%, 40%, or 30% when compared with unmodified cereblon protein. In some embodiments, the in vivo engineered cereblon protein's binding to immunomodulatory drugs is completely prevented (reduced to 0%).

In some cases, the E3 ubiquitin ligase family is divided into three families, the HECT (homologous with E6-associated protein C-terminus) family, the RING finger family, and the RBR (RING-between RING RING) family. HECT E3 enzyme forms a covalent thioester intermediate by accepting a ubiquitin molecule from the E2-ubiquitin via a conserved cysteine residue prior to transferring the ubiquitin molecule to a substrate. RING E3 enzyme directly transfers a ubiquitin molecule to a substrate by bringing both the E2-ubiquitin and the substrate in close proximity to each other. The RBR family recruit E3-ubiquitin conjugated by an N-terminal RING domain and then transfer ubiquitin on to a HECT-type C-terminal catalytic cysteine residue of the E3 before transferring on to the substrate.

In some instances, the RING finger family is further categorized into two subgroups, CRL and APC/C (anaphase-promoting complex/cyclosome). In some cases, the CRL and APC/C subfamilies comprise multi-subunit complexes comprising an adaptor, a substrate receptor subunit, a Cullin scaffold, and a RING-box subunit.

In some embodiments, the CUL4-RBX1-DDB1-CRBN complex (CRL4$^{CRBN}$) is an E3 ligase that falls under the CRL subgroup of the RING finger family. The CRL4$^{CRBN}$ complex comprises the adaptor protein DDB1, which connects the substrate receptor cereblon (CRBN) to the Cullin 4 (CUL4) scaffold. The Cullin 4 scaffold further binds to RBX1. Upon substrate binding, the CUL4-RBX1-DDB1-CRBN complex bridges the substrate to the E2-ubiquitin to initiate a direct transfer of ubiquitin molecule onto the substrate.

In some instances, thalidomide and related immunomodulatory (IMiD) compounds such as lenalidomide and pomalidomide promote and modulate cereblon recruitment of neosubstrates. For example, a cereblon modulator CC-220 has been shown to improve degradation of Ikaros and Aiolos, two zinc finger transcription factors that have been implicated in lymphoid development and differentiation (Matyskiela, et al., "A cereblon modulator (CC-220) with improved degradation of Ikaros and Aiolos,"*J Med Chem*. Apr. 20, 2017). Further, dBET1, a bifunctional phthalimide-conjugated ligand which is a substrate for cereblon, selectively targets BRD4, a transcriptional coactivator, for degradation.

In some embodiments, provided herein are cereblon-probe adducts and synthetic ligands that inhibit cereblon-probe adduct formation. In some instances, also provided herein are cereblon binding domains that interact with a probe and/or a ligand described herein.

In some embodiments, additionally described herein is a method of modulating cereblon for recruitment of neosubstrates. In some instances, the method comprises covalent binding of a reactive residue on cereblon for modulation of substrate interaction. In some cases, the method comprises covalent binding of a reactive cysteine residue on cereblon for substrate modulation.

In some embodiments, the cereblon is a human cereblon. The human cereblon (SEQ ID NO: 1) is about 442 residues in length, and is encoded by the CRBN gene. The cereblon protein comprises a central LON domain (residues 80-317) followed by a C-terminal CULT domain. The LON domain is further subdivided into an N-terminal LON-N subdomain, a four helix bundle, and a C-terminal LON-C subdomain.

In some instances, cereblon further comprises two variants, in which the sequences are respectively denoted as SEQ ID NO: 2 and SEQ ID NO: 3.

In some cases, the Lon N-terminal domain of cereblon is represented by SEQ ID NO: 4.

In additional cases, the Lon N-terminal domain of cereblon is represented by SEQ ID NO: 5.

In some embodiments, described herein are modified cereblon proteins comprising a modification at cysteine C287 of SEQ ID NO: 1 or corresponding cysteine of a cereblon homolog, active fragment, or variant thereof, wherein the cysteine forms an adduct with a reactive compound. In some instances, the modified cereblon protein comprises a modification at cysteine 287 of SEQ ID NO: 1. In some instances, the modified cereblon protein comprises a modification at cysteine 286 of SEQ ID NO: 2 or 3.

In some embodiments, one or more additional residues in cereblon forms a non-covalent interaction with a compound described herein. In some instances, the non-covalent interaction is a hydrophobic interaction, charged interaction (e.g., either positively charged or negatively charged interaction), polar interaction, H-bonding, salt bridge, pi-pi stacking, or pi-cation interaction.

In some instances, the interaction is a hydrophobic interaction. In some cases, residues Pro 93, Ile 160, Met 246, Pro 274, Tyr 282, Ala 286, Cys 287, Cys 343, Ala 347, Ala 348, or a combination thereof forms a hydrophobic interaction with a compound described herein. In some instances, residues Pro 274 forms a hydrophobic interaction with a compound described herein. In some instances, residue Ile 160 forms a hydrophobic interaction with a compound described herein. In some instances, residue Pro 93 forms a hydrophobic interaction with a compound described herein. In some instances, residue Tyr 282 forms a hydrophobic interaction with a compound described herein. In some instances, residue Ala 286, Cys 287, or a combination thereof forms a hydrophobic interaction with a compound described herein. In some instances, residue Cys 343, Met 346, Ala 347, Ala 348, or a combination thereof forms a hydrophobic interaction with a compound described herein. In some instances, Met 345, Leu 321, Leu 422, Leu 423, Pro 424, Leu 360, or a combination thereof forms a hydrophobic interaction with a compound described herein. In some instances, Val 284, Cys 287, Leu 288, Pro 289, Trp 264, or a combination thereof forms a hydrophobic interaction with a compound described herein. In some instances, the residue position is in reference to SEQ ID NO: 1.

In some instances, the interaction is a charged interaction. In some instances, the interaction is a negatively charged interaction. In some instances, Asp 279 forms a negatively charged interaction with a compound described herein. In some instances, Asp 265 forms a negatively charged interaction with a compound described herein. In some cases, the residue position is in reference to SEQ ID NO: 1.

In some instances, the interaction is a positively charged interaction. In some instances, Arg 162, Arg 283, or a combination thereof forms a positively charged interaction with a compound described herein. In some instances, Lys 324, Arg 419, or a combination thereof forms a positively charged interaction with a compound described herein. In some cases, the residue position is in reference to SEQ ID NO: 1.

In some instances, the interaction is a polar interaction. In some instances, Gln 95, Thr 96, or a combination thereof forms a polar interaction with a compound described herein. In some instances, Ser 420 forms a polar interaction with a compound described herein. In some cases, the residue position is in reference to SEQ ID NO: 1.

Michael Acceptor

The modification of cereblon described herein involves any suitable reagents that can undergo a Michael addition reaction with cereblon in vivo. The reaction occurs highly selectively at cysteine 318 as set forth in SEQ ID NO:1 or cysteine 317 as set forth in SEQ ID NO: 2 or 3. In some embodiments, the Michael acceptor does not exist naturally in vivo. In some embodiments, the Michael acceptor is an exogenous agent.

The in situ engagement is read out as a $TE_{50}$ value which is derived from treating whole cells with test compound followed by iodoacetamide probe. It is generally deemed to be a more physiologically relevant measure of target engagement, since whole cells better represent an organism than do cell lysates. The in situ $TE_{50}$ can represent what will likely be a steady state drug exposure in vivo at a minimally efficacious dose. In some embodiments, the in situ engagement of the exogenous Michael acceptor is no greater than about 80 µM. In some embodiments, the in situ engagement of the exogenous Michael acceptor is no greater than about 5 µM, 10 µM, 12.5 µM, 15 µM, 17.5 µM, 20 µM, 22.5 µM, 25 µM, 27.5 µM, 30 µM, 35 µM, 40 µM, 45 µM, 50 µM, 55 µM, 60 µM, 65 µM, 70 µM, 75 µM, 80 µM, 85 µM, 90 µM, or 95 µM. In some embodiments, the in situ engagement of the exogenous Michael acceptor is higher than 0.1 µM, 0.25 µM, 0.5 µM, 1 µM, 1.5 µM, 2 µM, 2.5 µM, 3 µM, 4 µM, 5 µM, 6 µM, 7 µM, 8 µM, 9 µM, 10 µM, 12.5 µM, 15 µM, 17.5 µM, 20 µM, or 25 µM. In some embodiments, the in situ engagement of the exogenous Michael acceptor is in the range of about 1 µM-90 µM, about 5 µM-80 µM, about 5 µM-60 µM, or about 10 µM-50 µM.

In some embodiments, the exogenous Michael acceptor has a standard promiscuity of that is smaller than KB02

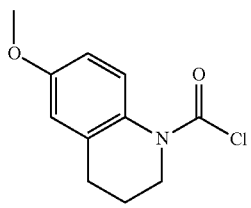

In some embodiments, the exogenous Michael acceptor has a global promiscuity of that is no greater than ⅓ of KB02. The in vivo engineered cereblon of claim 1, wherein the exogenous Michael acceptor has a lower global promiscuity than

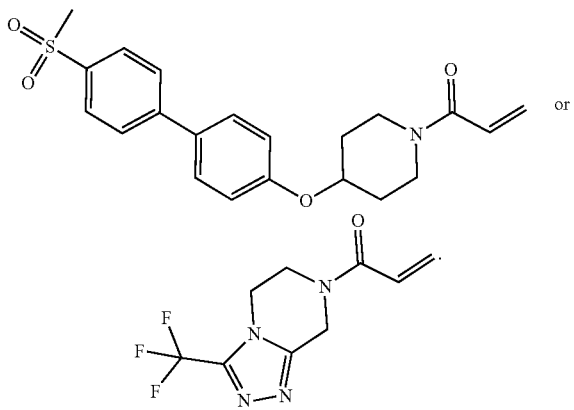

In some embodiments, the exogenous Michael acceptor has a global promiscuity of no greater than 20.6% at 500 μM. In some embodiments, the exogenous Michael acceptor has a global promiscuity in the range of no greater than about 0.1%, 0.25%, 0.5%, 1%, 1.5%, 2%, 2.5%, 3%, 4%, 5%, 10%, 12.5%, 15%, 17.5%, 20%, 22.5%, 25%, 27.5%, 30%, 35%, 40%, 45%, 50%, 55%, 60%, 65%, 70%, 75%, 80%, 85%, 90%, or 95%. In some embodiments, the exogenous Michael acceptor has a global promiscuity of higher than about 0.1%, 0.25%, 0.5%, 1%, 1.5%, 2%, 2.5%, 3%, 4%, 5%, 6%, 7%, 8%, 9%, 10%, 12.5%, 15%, 17.5%, 20%, or 25% at 500 μM. In some embodiments, the exogenous Michael acceptor has a global promiscuity of in the range of about 0.1%-90%, about 0.5%-80%, about 1%-60%, or about 3%-50% at 500 μM.

In some embodiments, the exogenous Michael acceptor has a $TE_{50}$ of no greater than about 80 μM. In some embodiments, the exogenous Michael acceptor has a $TE_{50}$ of no greater than about 5 μM, 10 μM, 12.5 μM, 15 μM, 17.5 μM, 20 μM, 22.5 μM, 25 μM, 27.5 μM, 30 μM, 35 μM, 40 μM, 45 μM, 50 μM, 55 μM, 60 μM, 65 μM, 70 μM, 75 μM, 80 μM, 85 μM, 90 μM, or 95 μM. In some embodiments, the exogenous Michael acceptor has a $TE_{50}$ of higher than 0.1 μM, 0.25 μM, 0.5 μM, 1 μM, 1.5 μM, 2 μM, 2.5 μM, 3 μM, 4 μM, 5 μM, 6 μM, 7 μM, 8 μM, 9 μM, 10 μM, 12.5 μM, 15 μM, 17.5 μM, 20 μM, or 25 μM. In some embodiments, the exogenous Michael acceptor has a $TE_{50}$ in the range of about 1 μM-90 μM, about 5 μM-80 μM, about 5 μM-60 μM, or about 10 μM-50 μM.

In some embodiments, the exogenous Michael acceptor is an acrylamide.

In some embodiments, the exogenous Michael acceptor has a structure of Formula (I):

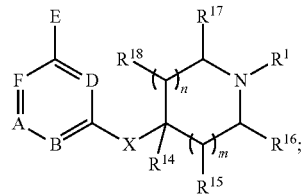

Formula (I)

wherein
A is N or $C(R^2)$;
B is N or $C(R^3)$;
D is N or $C(R^4)$;
E is H or

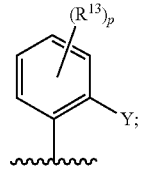

F is N or $C(R^5)$;
X is absent, —O—, —NH—, or —S—;
Y is H, halogen, —$OR^6$, substituted or unsubstituted $C_1$-$C_6$alkyl, or substituted or unsubstituted $C_1$-$C_6$haloalkyl;
$R^1$ is —C(=O)$CR^7$=$CR^8R^9$, —S(=O)$_2CR^7$=$CR^8R^9$, or —C(=O)C≡$CR^9$;
$R^2$ is H, halogen, —CN, —N($R^{12}$)$_2$, —$OR^6$, —CH($OR^6$)$R^{12}$, —C(=O)$R^{12}$, —C(=O)N($R^{12}$)$_2$, —S(=O)$_2R^{12}$, —S(=O)$_2$N($R^{12}$)$_2$, —N($R^{12}$)C(=O)$R^{12}$, —N($R^{12}$)S(=O)$_2R^{12}$, substituted or unsubstituted $C_1$-$C_6$ alkyl, substituted or unsubstituted $C_1$-$C_6$haloalkyl, substituted or unsubstituted $C_3$-$C_6$cycloalkyl, substituted or unsubstituted $C_2$-$C_5$heterocycloalkyl, substituted or unsubstituted aryl, or substituted or unsubstituted heteroaryl;
$R^3$ is H, halogen, —CN, —N($R^{12}$)$_2$, —$OR^6$, —CH($OR^6$)$R^{12}$, —C(=O)$R^{12}$, —C(=O)N($R^{12}$)$_2$, —S(=O)$_2R^{12}$, —S(=O)$_2$N($R^{12}$)$_2$, —N($R^{12}$)C(=O)$R^{12}$, —N($R^{12}$)S(=O)$_2R^{12}$, substituted or unsubstituted $C_1$-$C_6$ alkyl, substituted or unsubstituted $C_1$-$C_6$haloalkyl, substituted or unsubstituted $C_3$-$C_6$cycloalkyl, substituted or unsubstituted $C_2$-$C_5$heterocycloalkyl, substituted or unsubstituted aryl, or substituted or unsubstituted heteroaryl;
$R^4$ is H, halogen, —CN, —N($R^{12}$)$_2$, —C(=O)$R^{12}$, —C(=O)N($R^{12}$)$_2$, —S(=O)$_2R^{12}$, substituted or unsubstituted $C_1$-$C_6$alkyl, substituted or unsubstituted $C_1$-$C_6$haloalkyl, substituted or unsubstituted aryl, or substituted or unsubstituted heteroaryl;
$R^5$ is H, halogen, —CN, —N($R^{12}$)$_2$, —$OR^6$, —C(=O)$R^{12}$, —C(=O)N($R^{12}$)$_2$, —N($R^{12}$)C(=O)$R^{12}$, —S(=O)$_2R^{12}$, —N($R^{12}$)S(=O)$_2R^{12}$, —S(=O)$_2$N($R^{12}$)$_2$, substituted or unsubstituted $C_1$-$C_6$alkyl, substituted or unsubstituted $C_1$-$C_6$haloalkyl, substituted or unsubstituted aryl, or substituted or unsubstituted heteroaryl;
each $R^6$ is independently H, substituted or unsubstituted $C_1$-$C_6$alkyl, substituted or unsubstituted $C_1$-$C_6$haloalkyl, or substituted or unsubstituted $C_1$-$C_{10}$ heteroalkyl.
$R^7$ is H, CN, substituted or unsubstituted $C_1$-$C_6$alkyl, substituted or unsubstituted $C_3$-$C_6$cycloalkyl, or substituted or unsubstituted aryl;

$R^8$ is H, —$NR^{10}R^{11}$, substituted or unsubstituted $C_1$-$C_6$alkyl, substituted or unsubstituted $C_1$-$C_6$aminoalkyl, substituted or unsubstituted $C_3$-$C_6$cycloalkyl, or substituted or unsubstituted $C_2$-$C_6$heterocycloalkyl;

$R^9$ is H or substituted or unsubstituted $C_1$-$C_6$alkyl;

$R^{10}$ and $R^{11}$ are each independently H, substituted or unsubstituted $C_1$-$C_6$alkyl, or substituted or unsubstituted $C_1$-$C_8$heteroalkyl; or $R^{10}$ and $R^{11}$ are taken together with the nitrogen to which they are attached to form a substituted or unsubstituted $C_2$-$C_9$heterocycloalkyl;

each $R^{12}$ is independently H, substituted or unsubstituted $C_1$-$C_6$alkyl, or substituted or unsubstituted aryl;

each $R^{13}$ is independently halogen, —CN, —$OR^6$, —C(=O)N($R^{12}$)$_2$, —N($R^{12}$)C(=O)$R^{12}$, —N($R^{12}$)S(=O)$_2R^{12}$, —N(S(=O)$_2R^{12}$)$_2$, —S(=O)$_2R^{12}$, —S(=O)$_2$N($R^{12}$)$_2$, substituted or unsubstituted $C_1$-$C_6$ alkyl, substituted or unsubstituted $C_1$-$C_6$haloalkyl, or substituted or unsubstituted $C_1$-$C_{10}$heteroalkyl;

$R^{14}$ is H or substituted or unsubstituted $C_1$-$C_6$alkyl; or when B is C($R^3$), then $R^3$ and $R^{14}$ are taken together with the carbon atoms to which they are attached to form a substituted or unsubstituted heterocycloalkyl;

each $R^{15}$, $R^{16}$, $R^{17}$, and $R^{18}$ is independently selected from the group consisting of H, F, —$OR^6$, and substituted or unsubstituted $C_1$-$C_6$ alkyl; or $R^{15}$ and $R^{17}$ are taken together with the carbon atoms to which they are attached to form a substituted or unsubstituted $C_4$-$C_7$cycloalkyl; or $R^{15}$ and $R^{18}$ are taken together with the carbon atoms to which they are attached to form a substituted or unsubstituted $C_4$-$C_7$cycloalkyl; or $R^{16}$ and $R^{17}$ are taken together with the carbon atoms to which they are attached to form a substituted or unsubstituted $C_4$-$C_7$cycloalkyl; or $R^{16}$ and $R^{18}$ are taken together with the carbon atoms to which they are attached to form a substituted or unsubstituted $C_4$-$C_7$cycloalkyl;

m is 0, 1, or 2;

n is 0 or 1; and p is 0, 1, 2, or 3; or a pharmaceutically acceptable salt or solvate thereof.

In some embodiments, the reactive compound of Formula (I) has a structure of Formula (II), or a pharmaceutically acceptable salt or solvate thereof:

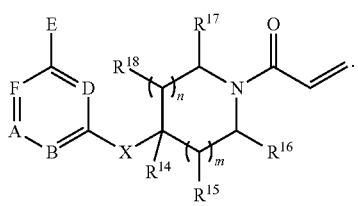

Formula (II)

In some embodiments, the reactive compound of Formula (II) has a structure of Formula (IIa), or a pharmaceutically acceptable salt or solvate thereof:

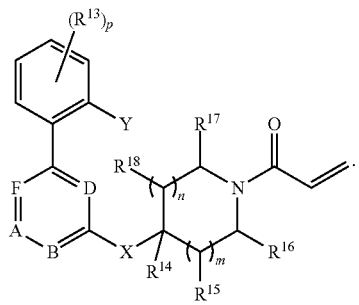

Formula (IIa)

In some embodiments, the reactive compound of Formula (I) has a structure of Formula (III), or a pharmaceutically acceptable salt or solvate thereof:

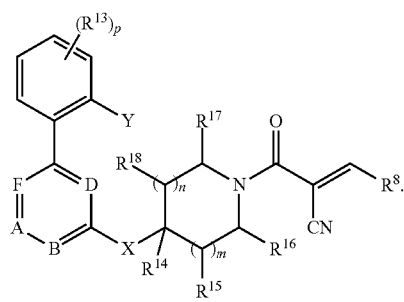

Formula (III)

In some embodiments, $R^8$ is $C_1$-$C_6$alkyl substituted with amino. In some embodiments, $R^8$ is substituted or unsubstituted $C_1$-$C_6$alkyl. In some embodiments, $R^8$ is —$CH_3$, —$CH_2CH_3$, —$CH_2CH_2CH_3$, —$CH(CH_3)_2$, —$CH_2CH_2CH_2CH_3$, —$CH_2CH(CH_3)CH_3$, —$CH(CH_3)$$CH_2CH_3$, or —$C(CH_3)_3$. In some embodiments, $R^8$ is —$CH_3$, —$CH(CH_3)_2$, or —$C(CH_3)_3$. In some embodiments, $R^8$ is —$CH(CH_3)_2$.

In some embodiments, the reactive compound of Formula (I) has a structure of Formula (IV), or a pharmaceutically acceptable salt or solvate thereof:

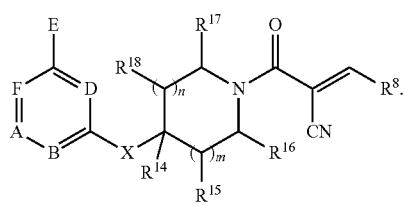

Formula (IV)

In some embodiments, $R^8$ is $C_1$-$C_6$alkyl substituted with amino. In some embodiments, $R^8$ is —$CH_2N(CH_3)_2$. In some embodiments, $R^8$ is $C_1$-$C_6$alkyl substituted with substituted or unsubstituted aryl. In some embodiments, the aryl is phenyl. In some embodiments, $R^8$ is —$CH_2$-phenyl, —$CH_2CH_2$-phenyl, —CH(phenyl)$CH_3$, —$CH_2CH_2CH_2$-phenyl, —$CH_2$CH(phenyl)$CH_3$, —CH(phenyl)$CH_2CH_3$, —$CH(CH_3)(CH_2$-phenyl), or —C(phenyl)$(CH_3)_2$. In some embodiments, $R^8$ is —CH(phenyl)$CH_3$ or —C(phenyl)$(CH_3)_2$. In some embodiments, $R^8$ is $C_3$-$C_6$cycloalkyl substituted with substituted or unsubstituted aryl. In some embodiments, the aryl is phenyl. In some embodiments, $R^8$ is

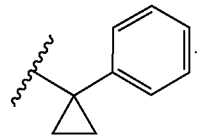 [SMILES: *C1(c2ccccc2)CC1]

In some embodiments, A is N. In some embodiments, A is $C(R^2)$.

In some embodiments, $R^2$ is —CN. In some embodiments, $R^2$ is H. In some embodiments, $R^2$ is halogen, —CN, —$N(R^{12})_2$, —$OR^6$, —$CH(OR^6)R^{12}$, —$C(O)R^{12}$, —$C(=O)N(R^{12})_2$, —$S(=O)_2R_{12}$, —$S(=O)_2N(R^{12})_2$, or —$N(R^{12})C(=O)R^{12}$. In some embodiments, $R^2$ is halogen, —CN, —$N(R^{12})_2$, —$OR^6$, —$C(=O)N(R^{12})_2$, —$S(=O)_2R^{12}$, or —$N(R^{12})C(=O)R^{12}$. In some embodiments, $R^2$ is H, halogen, —CN, —$N(R^{12})_2$, —$OR^6$, —$C(=O)N(R^{12})_2$, —$S(=O)_2R^{12}$, or —$S(=O)_2N(R^{12})_2$. In some embodiments, $R^2$ is F, Cl, —CN, —$NH_2$, —$NHCH_3$, —$N(CH_3)_2$, —OH, —$OCH_3$, —$OCH_2CH_3$, —$OCH_2CH_2CH_3$, —$OCH(CH_3)_2$, —$OCF_3$, —$C(=O)NH_2$, —$C(=O)NHCH_3$, —$C(=O)N(CH_3)_2$, —$S(=O)_2CH_3$, —$NHC(=O)CH_3$, or —$NHS(=O)_2CH_3$.

In some embodiments, $R^2$ is substituted or unsubstituted aryl. In some embodiments, the aryl is phenyl. In some embodiments, $R^2$ is phenyl substituted with 1, 2, or 3 substituents each independently selected from F, Cl, —CN, —$CH_3$, —$CH_2CH_3$, —$CH_2CH_2CH_3$, —$CH(CH_3)_2$, —OH, —$OCH_3$, —$OCH_2CH_3$, —$OCF_3$, —$CH_2F$, —$CHF_2$, —$CF_3$, —$CH(OH)CH_3$, —$C(=O)CH_3$, —$C(=O)NH_2$, —$C(=O)N(CH_3)_2$, —$S(=O)_2CH_3$, —$S(=O)_2NH_2$, —$S(=O)_2N(CH_3)_2$, —$NHC(=O)CH_3$, and —$NHS(=O)_2CH_3$. In some embodiments, $R^2$ is phenyl substituted with

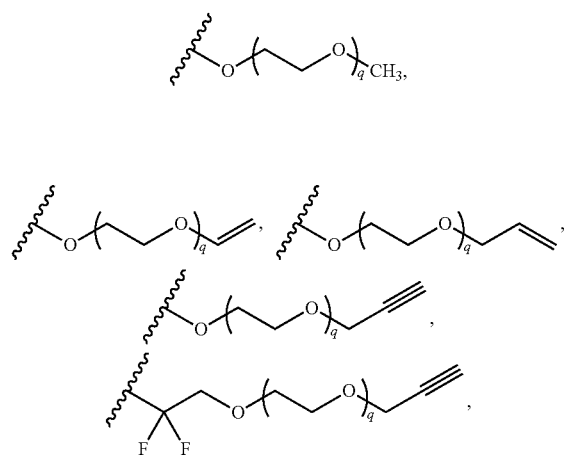

or

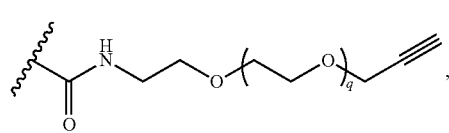

wherein q is 1, 2, 3, 4, 5, or 6. In some embodiments, $R^2$ is phenyl substituted with

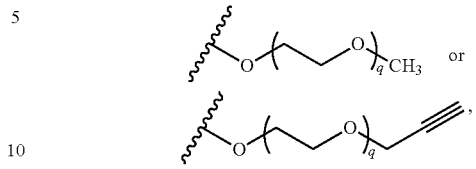

wherein q is 1, 2, 3, 4, 5, or 6.

In some embodiments, $R^2$ is substituted or unsubstituted heteroaryl.

In some embodiments, the heteroaryl is a 5-membered monocyclic heteroaryl or a 6-membered monocyclic heteroaryl.

In some embodiments, $R^2$ is a 5-membered monocyclic heteroaryl. In some embodiments, $R^2$ is a 5-membered monocyclic heteroaryl selected from substituted or unsubstituted pyrrolyl, substituted or unsubstituted imidazolyl, substituted or unsubstituted pyrazolyl, substituted or unsubstituted oxazolyl, substituted or unsubstituted isoxazolyl, substituted or unsubstituted thiazolyl, substituted or unsubstituted isothiazolyl, substituted or unsubstituted triazolyl, substituted or unsubstituted tetrazolyl, substituted or unsubstituted oxadiazolyl, substituted or unsubstituted thiadiazolyl, or substituted or unsubstituted dithiazolyl.

In some embodiments, $R^2$ is a 5-membered monocyclic heteroaryl selected from

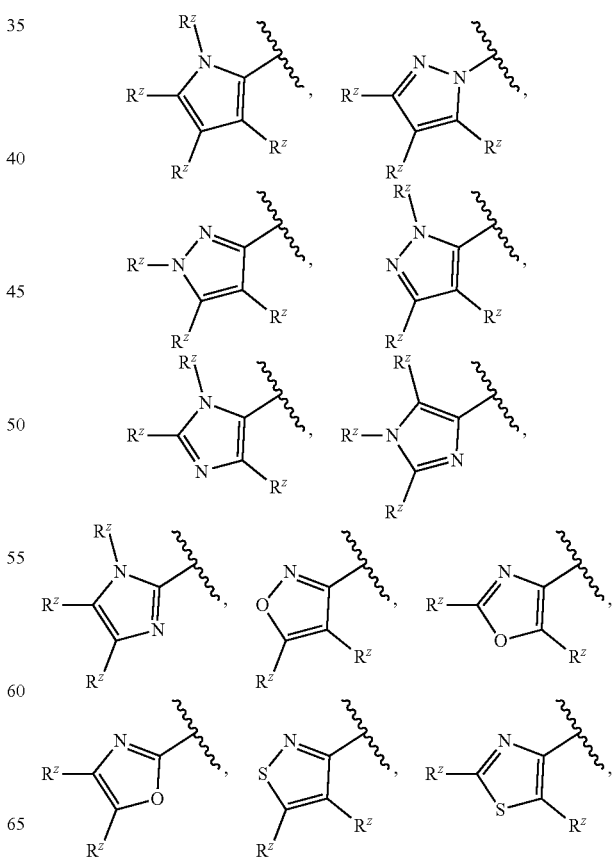

-continued

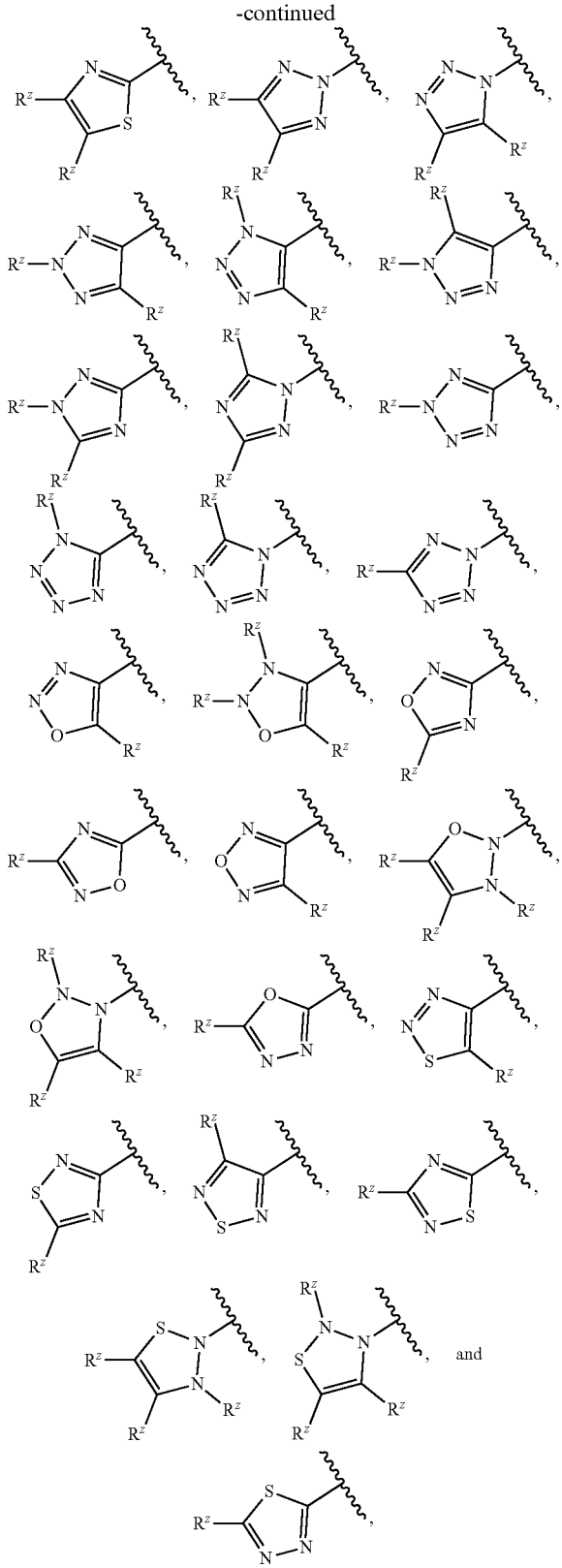

wherein each $R^z$ is independently selected from F, Cl, —CN, —CH$_3$, —CH$_2$CH$_3$, —CH$_2$CH$_2$CH$_3$, —CH(CH$_3$)$_2$, —OH, —OCH$_3$, —OCH$_2$CH$_3$, —OCF$_3$, —CH$_2$F, —CHF$_2$, —CF$_3$, —CH(OH)CH$_3$, —C(=O)CH$_3$, —C(=O)NH$_2$, —C(=O)N(CH$_3$)$_2$, —S(=O)$_2$CH$_3$, —S(=O)$_2$NH$_2$, —S(=O)$_2$N(CH$_3$)$_2$, —NHC(=O)CH$_3$, and —NHS(=O)$_2$CH$_3$.

In some embodiments, $R^2$ is a 6-membered monocyclic heteroaryl. In some embodiments, $R^2$ is a 6-membered monocyclic heteroaryl selected from substituted or unsubstituted pyridinyl, substituted or unsubstituted pyrazinyl, substituted or unsubstituted pyrimidinyl, or substituted or unsubstituted pyridazinyl.

In some embodiments, $R^2$ is a 6-membered monocyclic heteroaryl selected from

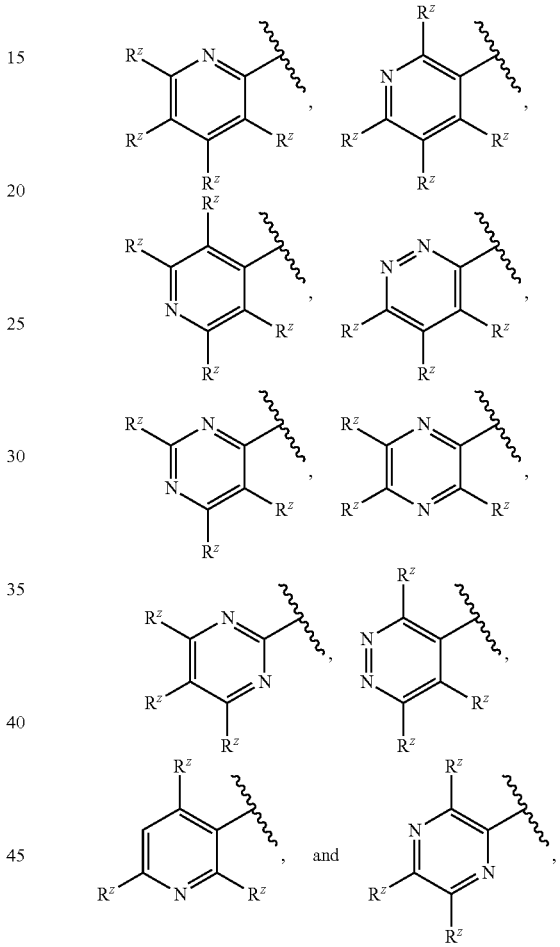

wherein each $R^z$ is independently selected from F, Cl, —CN, —CH$_3$, —CH$_2$CH$_3$, —CH$_2$CH$_2$CH$_3$, —CH(CH$_3$)$_2$, —OH, —OCH$_3$, —OCH$_2$CH$_3$, —OCF$_3$, —CH$_2$F, —CHF$_2$, —CF$_3$, —CH(OH)CH$_3$, —C(=O)CH$_3$, —C(=O)NH$_2$, —C(=O)N(CH$_3$)$_2$, —S(=O)$_2$CH$_3$, —S(=O)$_2$NH$_2$, —S(=O)$_2$N(CH$_3$)$_2$, —NHC(=O)CH$_3$, and —NHS(=O)$_2$CH$_3$.

In some embodiments, B is N. In some embodiments, B is C($R^3$).

In some embodiments, $R^3$ is —CN. In some embodiments, $R^3$ is H. In some embodiments, $R^3$ is halogen, —CN, —N($R^{12}$)$_2$, —OR$^6$, —CH(OR$^6$)R$^{12}$, —C(=O)R$_{12}$—C(=O)N($R^{12}$)$_2$, —S(=O)$_2$R$^{12}$, —S(=O)$_2$N($R^{12}$)$_2$, or —N($R^{12}$)—(=O)R$^{12}$. In some embodiments, $R^3$ is halogen, —CN, —N($R^{12}$)$_2$, —OR$^6$, —C(=O)N($R^{12}$)$_2$, —S(=O)$_2$R$^{12}$, or —N($R^{12}$)C(=O)R$^{12}$. In some embodiments, $R^3$ is F, Cl, —CN, —NH$_2$, —NHCH$_3$, —N(CH$_3$)$_2$, —OH, —OCH$_3$, —OCH$_2$CH$_3$, —OCH$_2$CH$_2$CH$_3$, —OCH (CH$_3$)$_2$, —OCF$_3$, —C(=O)NH$_2$, —C(=O)NHCH$_3$, —C(=O)N(CH$_3$)$_2$, —S(=O)$_2$CH$_3$, —NHC(=O)CH$_3$, or —NHS(=O)$_2$CH$_3$.

In some embodiments, R$^3$ is substituted or unsubstituted aryl. In some embodiments, the aryl is phenyl. In some embodiments, R$^3$ is phenyl substituted with 1, 2, or 3 substituents each independently selected from F, Cl, —CN, —CH$_3$, —CH$_2$CH$_3$, —CH$_2$CH$_2$CH$_3$, —CH(CH$_3$)$_2$, —OH, —OCH$_3$, —OCH$_2$CH$_3$, —OCF$_3$, —CH$_2$F, —CHF$_2$, —CF$_3$, —CH(OH)CH$_3$, —C(=O)CH$_3$, —C(=O)NH$_2$, —C(=O)N(CH$_3$)$_2$, —S(=O)$_2$CH$_3$, —S(=O)$_2$NH$_2$, —S(=O)$_2$N(CH$_3$)$_2$, —NHC(=O)CH$_3$, and —NHS(=O)$_2$CH$_3$. In some embodiments, R$^3$ is phenyl substituted with

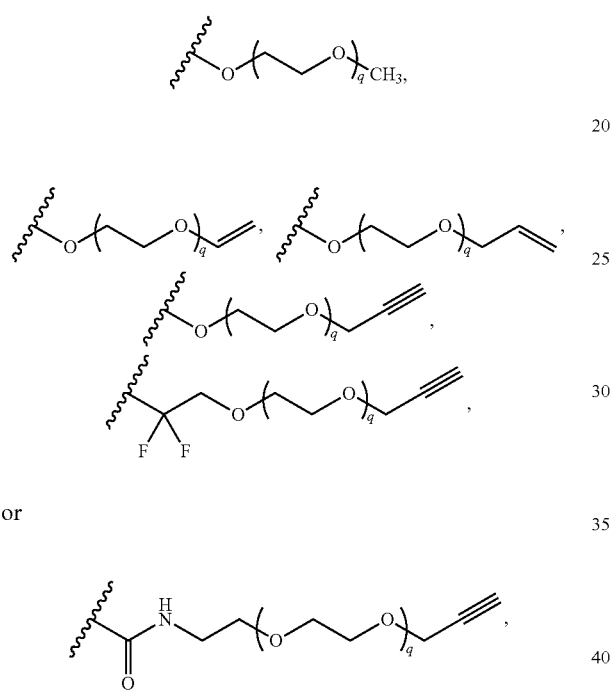

wherein q is 1, 2, 3, 4, 5, or 6. In some embodiments, R$^3$ is phenyl substituted with

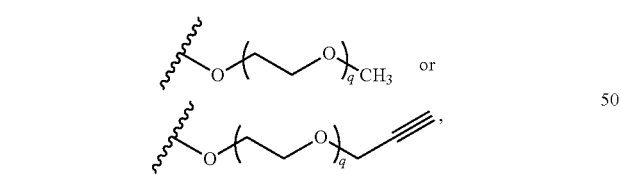

wherein q is 1, 2, 3, 4, 5, or 6.

In some embodiments, R$^3$ is substituted or unsubstituted heteroaryl.

In some embodiments, the heteroaryl is a 5-membered monocyclic heteroaryl or a 6-membered monocyclic heteroaryl.

In some embodiments, R$^3$ is a 5-membered monocyclic heteroaryl.

In some embodiments, R$^3$ is a 5-membered monocyclic heteroaryl selected from substituted or unsubstituted pyrrolyl, substituted or unsubstituted imidazolyl, substituted or unsubstituted pyrazolyl, substituted or unsubstituted oxazolyl, substituted or unsubstituted isoxazolyl, substituted or unsubstituted thiazolyl, substituted or unsubstituted isothiazolyl, substituted or unsubstituted triazolyl, substituted or unsubstituted tetrazolyl, substituted or unsubstituted oxadiazolyl, substituted or unsubstituted thiadiazolyl, or substituted or unsubstituted dithiazolyl.

In some embodiments, R$^3$ is a 5-membered monocyclic heteroaryl selected from

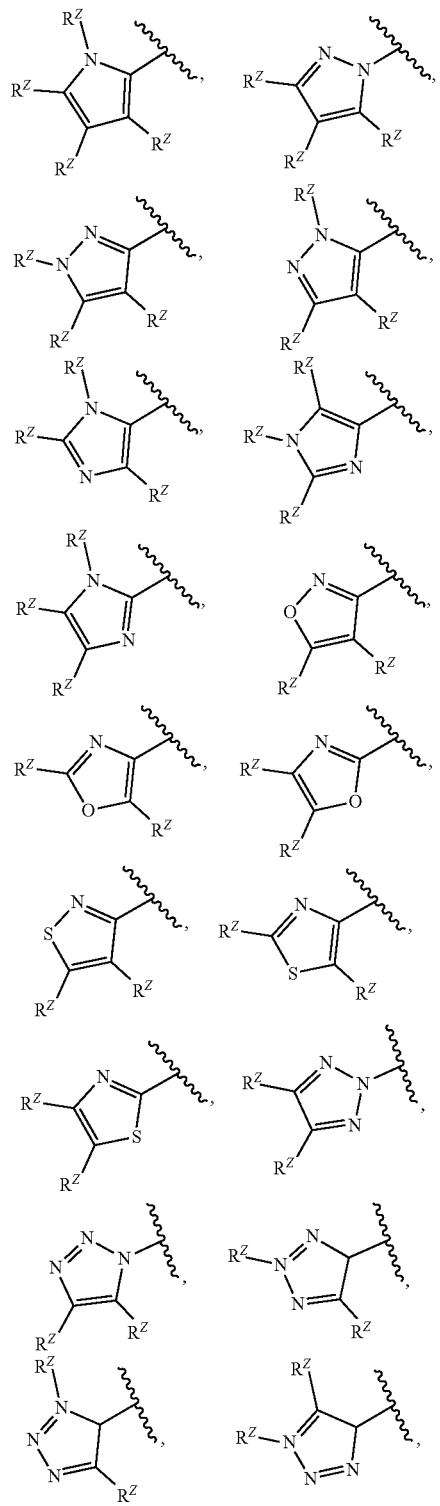

-continued

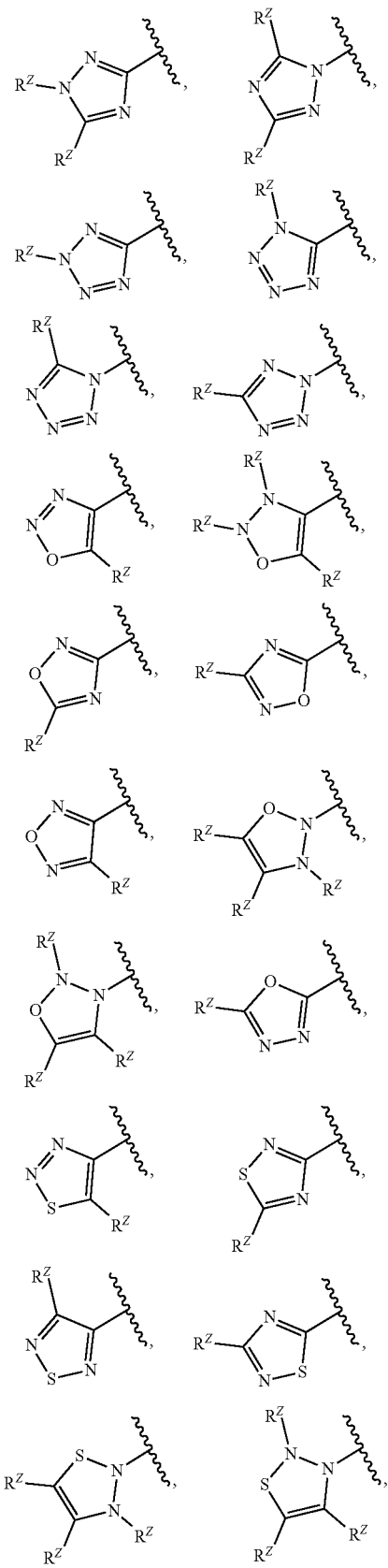

and

-continued

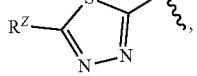

wherein each $R^z$ is independently selected from F, Cl, —CN, —CH$_3$, —CH$_2$CH$_3$, —CH$_2$CH$_2$CH$_3$, —CH(CH$_3$)$_2$, —OH, —OCH$_3$, —OCH$_2$CH$_3$, —OCF$_3$, —CH$_2$F, —CHF$_2$, —CF$_3$, —CH(OH)CH$_3$, —C(=O)CH$_3$, —C(=O)NH$_2$, —C(=O)N(CH$_3$)$_2$, —S(=O)$_2$CH$_3$, —S(=O)$_2$NH$_2$, —S(=O)$_2$N(CH$_3$)$_2$, —NHC(=O)CH$_3$, and —NHS(=O)$_2$CH$_3$.

In some embodiments, $R^3$ is a 6-membered monocyclic heteroaryl. In some embodiments, $R^3$ is a 6-membered monocyclic heteroaryl selected from substituted or unsubstituted pyridinyl, substituted or unsubstituted pyrazinyl, substituted or unsubstituted pyrimidinyl, or substituted or unsubstituted pyridazinyl.

In some embodiments, $R^3$ is a 6-membered monocyclic heteroaryl selected from

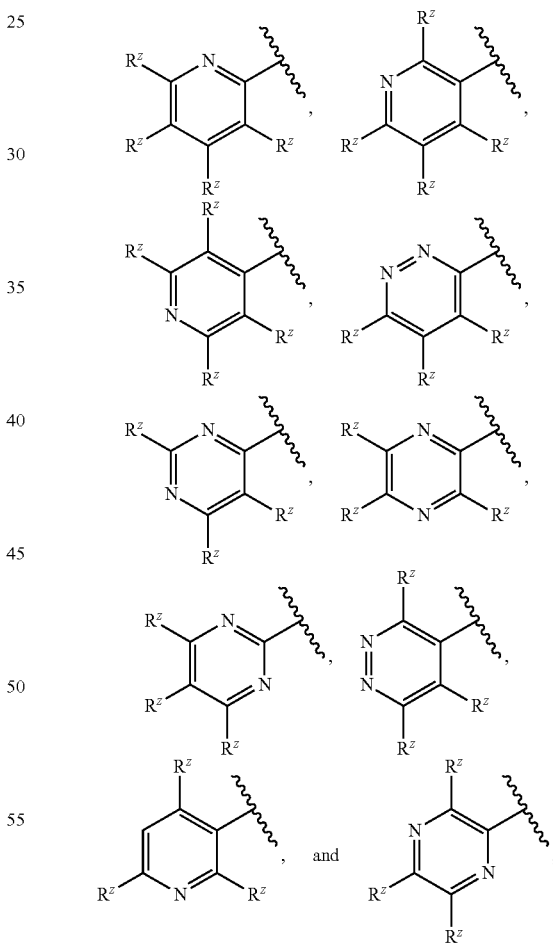

wherein each $R^z$ is independently selected from F, Cl, —CN, —CH$_3$, —CH$_2$CH$_3$, —CH$_2$CH$_2$CH$_3$, —CH(CH$_3$)$_2$, —OH, —OCH$_3$, —OCH$_2$CH$_3$, —OCF$_3$, —CH$_2$F, —CHF$_2$, —CF$_3$, —CH(OH)CH$_3$, —C(=O)CH$_3$, —C(=O)NH$_2$, —C(=O)N(CH$_3$)$_2$, —S(=O)$_2$CH$_3$, —S(=O)$_2$NH$_2$, —S(=O)$_2$N(CH$_3$)$_2$, —NHC(=O)CH$_3$, and —NHS(=O)$_2$CH$_3$.

In some embodiments, D is N. In some embodiments, D is C(R$^4$).

In some embodiments, R$^4$ is —CN. In some embodiments, R$^4$ is H.

In some embodiments, R$^4$ is halogen, —CN, —N(R$^{12}$)$_2$, —C(=O)N(R$^{12}$)$_2$, —S(=O)$_2$R$^{12}$, or substituted or unsubstituted C$_1$-C$_6$alkyl. In some embodiments, R$^4$ is halogen, —CN, —N(R$^{12}$)C(=O)R$^{12}$, —C(=O)N(R$^{12}$)$_2$, or —S(=O)$_2$R$^{12}$. In some embodiments, R$^4$ is F, Cl, —CN, —NH$_2$, —NHCH$_3$, —N(CH$_3$)$_2$, —C(=O)NH$_2$, —C(=O)CH$_3$, —C(=O)NHCH$_3$, —C(=O)N(CH$_3$)$_2$, or —S(=O)$_2$CH$_3$.

In some embodiments, R$^4$ is substituted or unsubstituted aryl. In some embodiments, the aryl is phenyl. In some embodiments, R$^4$ is phenyl substituted with 1, 2, or 3 substituents each independently selected from F, Cl, —CN, —CH$_3$, —CH$_2$CH$_3$, —CH$_2$CH$_2$CH$_3$, —CH(CH$_3$)$_2$, —OH, —OCH$_3$, —OCH$_2$CH$_3$, —OCF$_3$, —CH$_2$F, —CHF$_2$, —CF$_3$, —CH(OH)CH$_3$, —C(=O)CH$_3$, —C(=O)NH$_2$, —C(=O)N(CH$_3$)$_2$, —S(=O)$_2$CH$_3$, —S(=O)$_2$NH$_2$, —S(=O)$_2$N(CH$_3$)$_2$, —NHC(=O)CH$_3$, and —NHS(=O)$_2$CH$_3$. In some embodiments, R$^4$ is phenyl substituted with

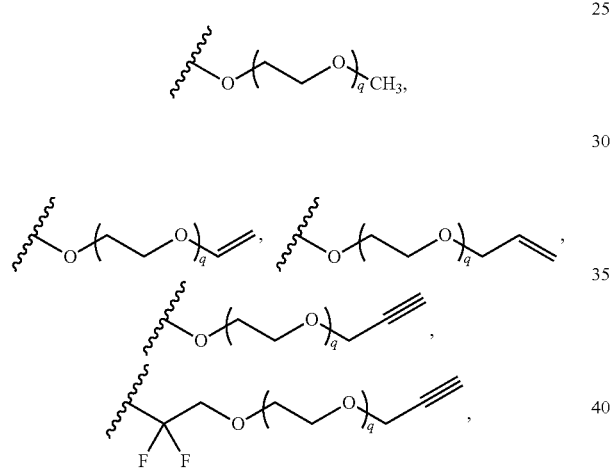

or

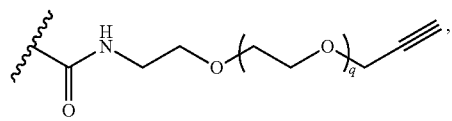

wherein q is 1, 2, 3, 4, 5, or 6. In some embodiments, R$^4$ is phenyl substituted with

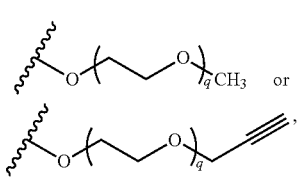

wherein q is 1, 2, 3, 4, 5, or 6.

In some embodiments, R$^4$ is substituted or unsubstituted heteroaryl.

In some embodiments, the heteroaryl is a 5-membered monocyclic heteroaryl or a 6-membered monocyclic heteroaryl.

In some embodiments, R$^4$ is a 5-membered monocyclic heteroaryl. In some embodiments, R$^4$ is a 5-membered monocyclic heteroaryl selected from substituted or unsubstituted pyrrolyl, substituted or unsubstituted imidazolyl, substituted or unsubstituted pyrazolyl, substituted or unsubstituted oxazolyl, substituted or unsubstituted isoxazolyl, substituted or unsubstituted thiazolyl, substituted or unsubstituted isothiazolyl, substituted or unsubstituted triazolyl, substituted or unsubstituted tetrazolyl, substituted or unsubstituted oxadiazolyl, substituted or unsubstituted thiadiazolyl, or substituted or unsubstituted dithiazolyl.

In some embodiments, R$^4$ is a 5-membered monocyclic heteroaryl selected from

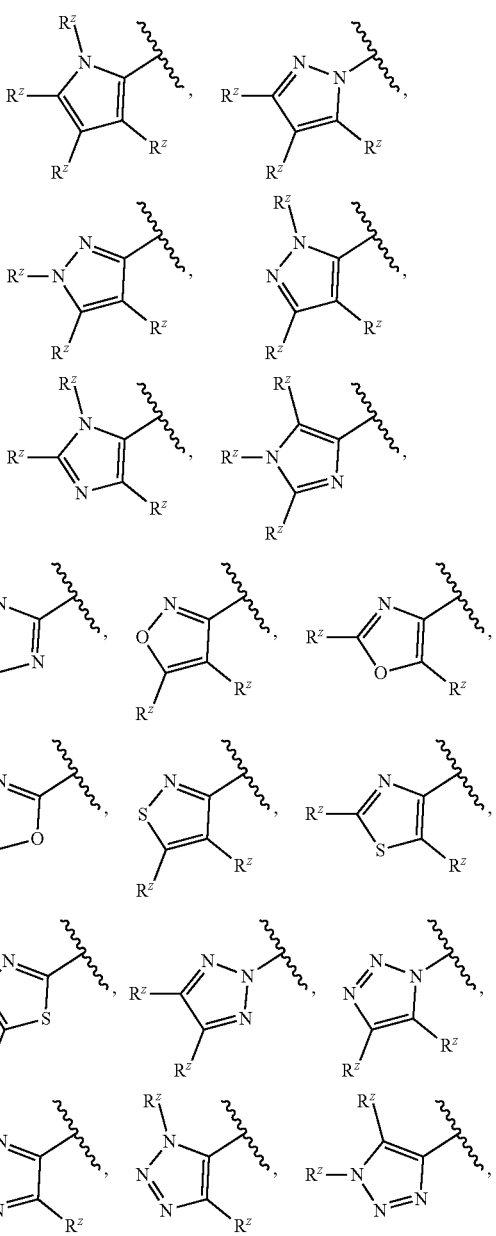

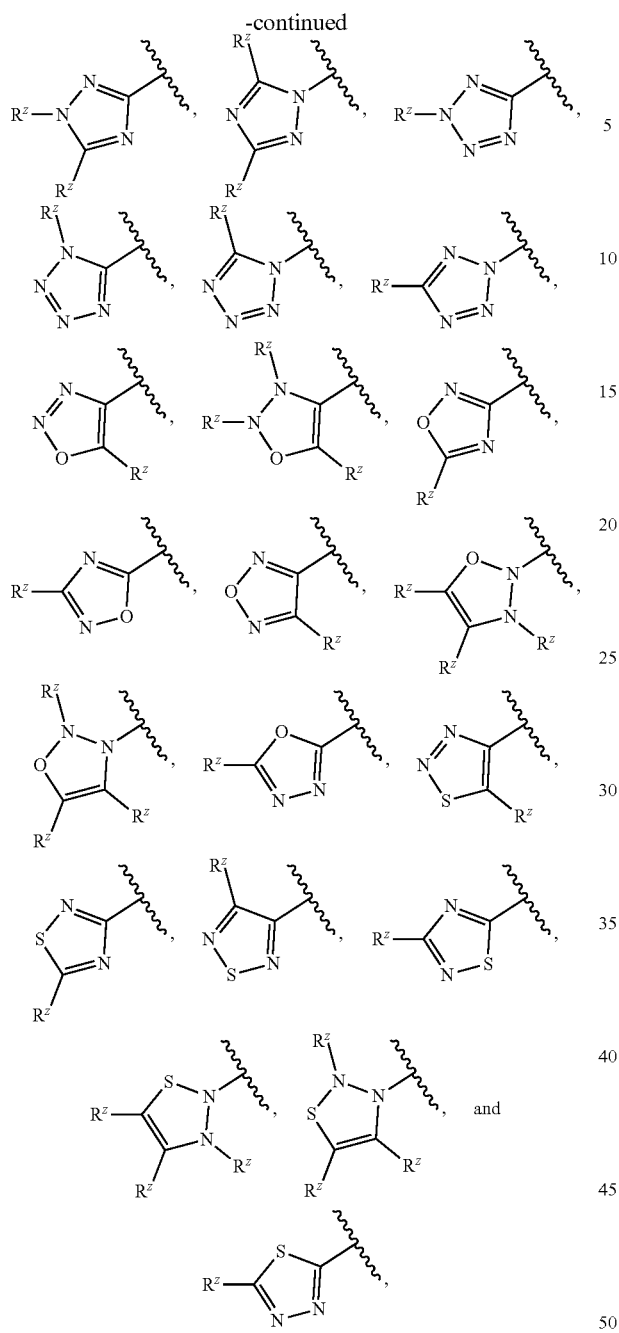

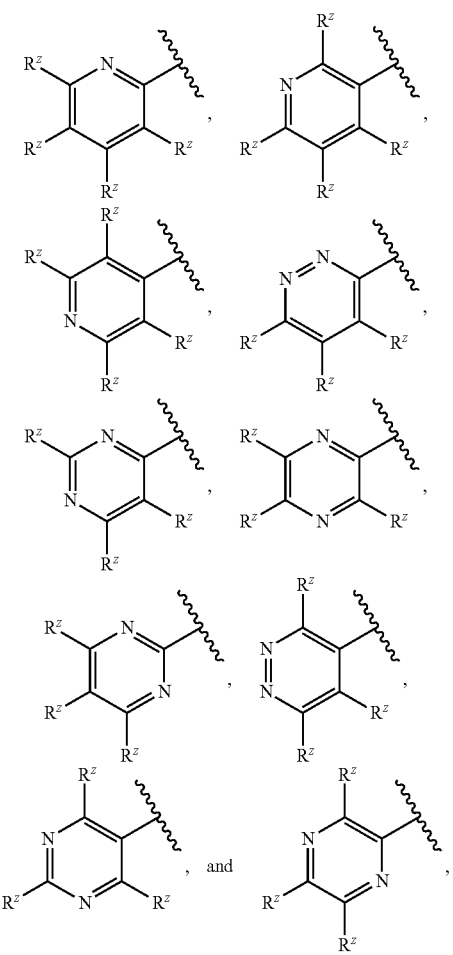

wherein each R$^z$ is independently selected from F, Cl, —CN, —CH$_3$, —CH$_2$CH$_3$, —CH$_2$CH$_2$CH$_3$, —CH(CH$_3$)$_2$, —OH, —OCH$_3$, —OCH$_2$CH$_3$, —OCF$_3$, —CH$_2$F, —CHF$_2$, —CF$_3$, —CH(OH)CH$_3$, —C(=O)CH$_3$, —C(=O)NH$_2$, —C(=O)N(CH$_3$)$_2$, —S(=O)$_2$CH$_3$, —S(=O)$_2$NH$_2$, —S(=O)$_2$N(CH$_3$)$_2$, —NHC(=O)CH$_3$, and —NHS(=O)$_2$CH$_3$.

In some embodiments, R$^4$ is a 6-membered monocyclic heteroaryl. In some embodiments, R$^4$ is a 6-membered monocyclic heteroaryl selected from substituted or unsubstituted pyridinyl, substituted or unsubstituted pyrazinyl, substituted or unsubstituted pyrimidinyl, or substituted or unsubstituted pyridazinyl.

In some embodiments, R$^4$ is a 6-membered monocyclic heteroaryl selected from wherein each R$^z$ is independently selected from F, Cl, —CN, —CH$_3$, —CH$_2$CH$_3$, —CH$_2$CH$_2$CH$_3$, —CH(CH$_3$)$_2$, —OH, —OCH$_3$, —OCH$_2$CH$_3$, —OCF$_3$, —CH$_2$F, —CHF$_2$, —CF$_3$, —CH(OH)CH$_3$, —C(=O)CH$_3$, —C(=O)NH$_2$, —C(=O)N(CH$_3$)$_2$, —S(=O)$_2$CH$_3$, —S(=O)$_2$NH$_2$, —S(=O)$_2$N(CH$_3$)$_2$, —NHC(=O)CH$_3$, and —NHS(=O)$_2$CH$_3$.

In some embodiments, E is H. In some embodiments, E is

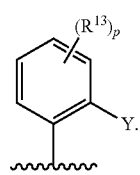

In some embodiments, E is

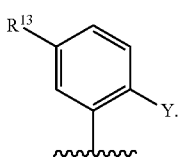

In some embodiments, Y is H. In some embodiments, Y is —OR$^6$. In some embodiments, Y is —OH, —OCH$_3$, —OCH$_2$CH$_3$, or —OCF$_3$. In some embodiments, Y is —OCH$_3$. In some embodiments, Y is halogen, substituted or unsubstituted C$_1$-C$_6$alkyl, or substituted or unsubstituted C$_1$-C$_6$haloalkyl. In some embodiments, Y is F, Cl, Br, —CH$_3$, —CH$_2$CH$_3$, —CH$_2$CH$_2$CH$_3$, —CH(CH$_3$)$_2$, —CF$_3$, —CF$_2$CH$_3$, or —CH$_2$CF$_3$. In some embodiments, Y is H, —OR$^6$, halogen, substituted or unsubstituted C$_1$-C$_6$alkyl, or substituted or unsubstituted C$_1$-C$_6$haloalkyl. In some embodiments, Y is H, —OH, —OCH$_3$, —OCH$_2$CH$_3$, —OCF$_3$, F, Cl, Br, —CH$_3$, —CH$_2$CH$_3$, —CH$_2$CH$_2$CH$_3$, —CH(CH$_3$)$_2$, —CF$_3$, —CF$_2$CH$_3$, or —CH$_2$CF$_3$.

In some embodiments, each R$^{13}$ is independently selected from F, Cl, —CN, —CH$_3$, —CH$_2$CH$_3$, —CH$_2$CH$_2$CH$_3$, —CH(CH$_3$)$_2$, —OH, —OCH$_3$, —OCH$_2$CH$_3$, —OCH$_2$CH$_2$CH$_3$, —OCH(CH$_3$)$_2$, —OCF$_3$, —CF$_3$, —CH(OH)CH$_3$, —C(=O)CH$_3$, —C(=O)NH$_2$, —C(=O)N(CH$_3$)$_2$, —S(=O)$_2$CH$_3$, —S(=O)$_2$NH$_2$, —S(=O)$_2$N(CH$_3$)$_2$, —NHC(=O)CH$_3$, —NHS(=O)$_2$CH$_3$, and —N(S(=O)$_2$CH$_3$)$_2$. In some embodiments, R$^{13}$ is

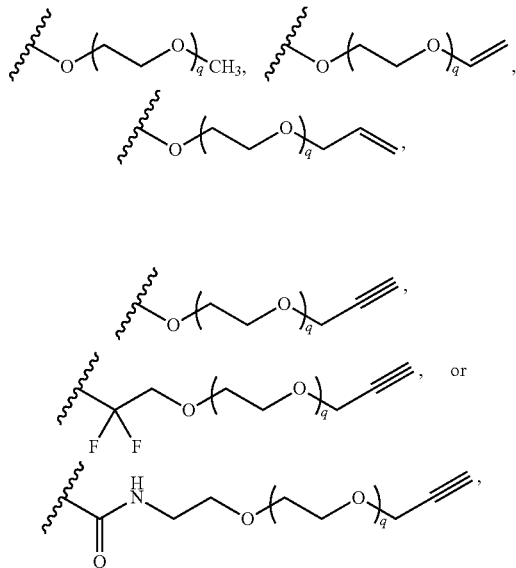

wherein q is 1, 2, 3, 4, 5, or 6. In some embodiments, R$^{13}$ is

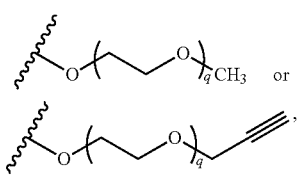

wherein q is 1, 2, 3, 4, 5, or 6.

In some embodiments, R$^{13}$ is —(CH$_2$)$_p$—(OCH$_2$CH$_2$)$_q$—O-substituted or unsubstituted C$_{1-4}$ alkyl. In some embodiments, R$^{13}$ is —(OCH$_2$CH$_2$)$_4$—OCH$_2$CN.

In some embodiments, F is N. In some embodiments, F is C(R$^5$).

In some embodiments, R$^5$ is —CN. In some embodiments, R$^5$ is H. In some embodiments, R$^5$ is halogen, —CN, —N(R$^{12}$)$_2$, —C(=O)R$^{12}$, —C(=O)N(R$^{12}$)$_2$, —S(=O)$_2$R$^{12}$, or substituted or unsubstituted C$_1$-C$_6$alkyl. In some embodiments, R$^5$ is halogen, —CN, —N(R$^{12}$)$_2$, —C(=O)R$^{12}$, —C(=O)N(R$^{12}$)$_2$, or —S(=O)$_2$R$^{12}$. In some embodiments, R$^5$ is F, Cl, —CN, —NH$_2$, —NHCH$_3$, —N(CH$_3$)$_2$, —C(=O)NH$_2$, —C(=O)CH$_3$, —C(=O)NHCH$_3$, —C(=O)N(CH$_3$)$_2$, or —S(=O)$_2$CH$_3$.

In some embodiments, R$^5$ is substituted or unsubstituted aryl. In some embodiments, the aryl is phenyl. In some embodiments, R$^5$ is phenyl substituted with 1, 2, or 3 substituents each independently selected from F, Cl, —CN, —CH$_3$, —CH$_2$CH$_3$, —CH$_2$CH$_2$CH$_3$, —CH(CH$_3$)$_2$, —OH, —OCH$_3$, —OCH$_2$CH$_3$, —OCF$_3$, —CH$_2$F, —CHF$_2$, —CF$_3$, —CH(OH)CH$_3$, —C(=O)CH$_3$, —C(=O)NH$_2$, —C(=O)N(CH$_3$)$_2$, —S(=O)$_2$CH$_3$, —S(=O)$_2$NH$_2$, —S(=O)$_2$N(CH$_3$)$_2$, —NHC(=O)CH$_3$, and —NHS(=O)$_2$CH$_3$. In some embodiments, R$^5$ is phenyl substituted with

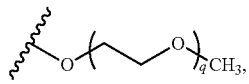

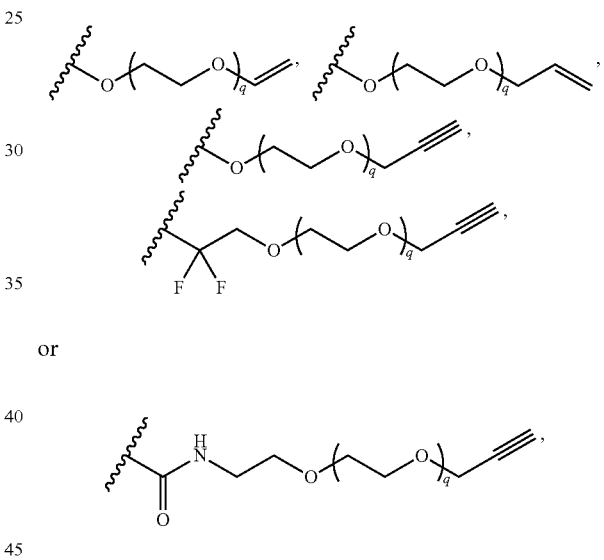

wherein q is 1, 2, 3, 4, 5, or 6. In some embodiments, R$^5$ is phenyl substituted with

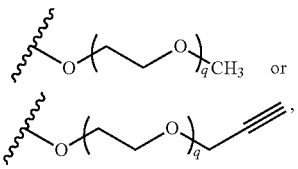

wherein q is 1, 2, 3, 4, 5, or 6.

In some embodiments, R$^5$ is substituted or unsubstituted heteroaryl.

In some embodiments, the heteroaryl is a 5-membered monocyclic heteroaryl or a 6-membered monocyclic heteroaryl.

In some embodiments, R$^5$ is a 5-membered monocyclic heteroaryl. In some embodiments, R$^5$ is a 5-membered monocyclic heteroaryl selected from substituted or unsubstituted pyrrolyl, substituted or unsubstituted imidazolyl, substituted or unsubstituted pyrazolyl, substituted or unsubstituted oxazolyl, substituted or unsubstituted isoxazolyl, substituted or unsubstituted thiazolyl, substituted or unsubstituted isothiazolyl, substituted or unsubstituted triazolyl, substituted or unsubstituted tetrazolyl, substituted or unsubstituted oxadiazolyl, substituted or unsubstituted thiadiazolyl, or substituted or unsubstituted dithiazolyl.

In some embodiments, $R^5$ is a 5-membered monocyclic heteroaryl selected from

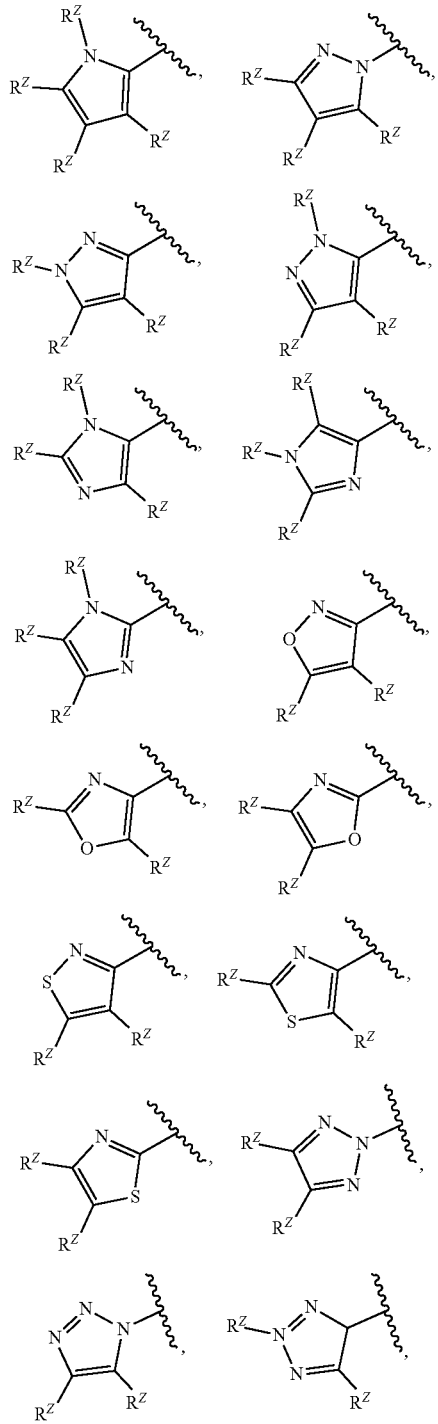

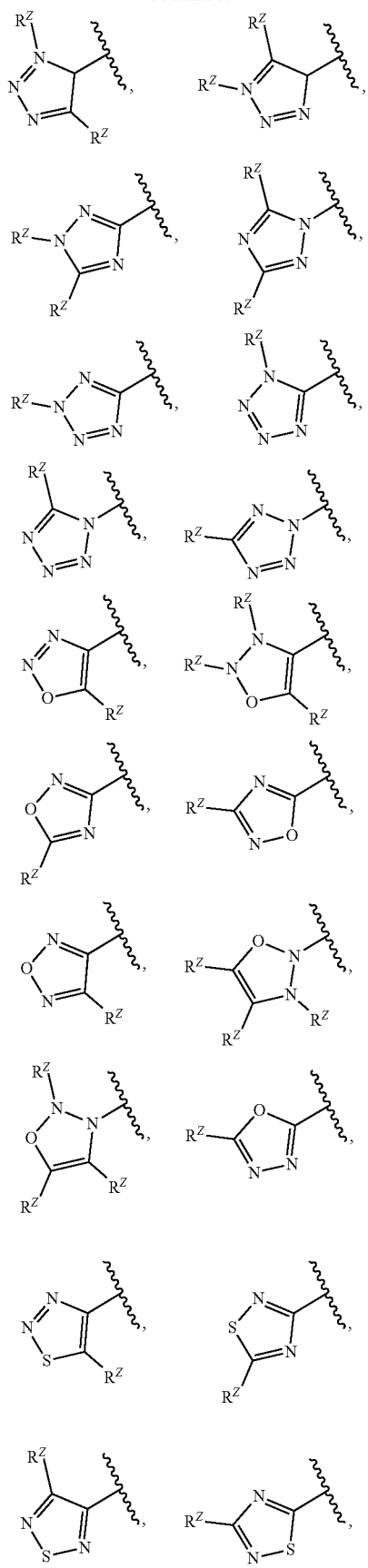

-continued

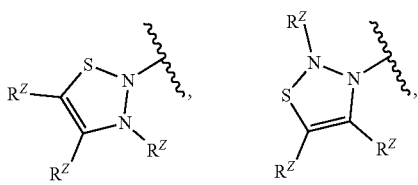

and

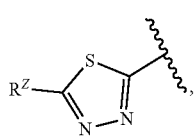

wherein each $R^z$ is independently selected from F, Cl, —CN, —CH$_3$, —CH$_2$CH$_3$, —CH$_2$CH$_2$CH$_3$, —CH(CH$_3$)$_2$, —OH, —OCH$_3$, —OCH$_2$CH$_3$, —OCF$_3$, —CH$_2$F, —CHF$_2$, —CF$_3$, —CH(OH)CH$_3$, —C(=O)CH$_3$, —C(=O)NH$_2$, —C(=O)N(CH$_3$)$_2$, —S(=O)$_2$CH$_3$, —S(=O)$_2$NH$_2$, —S(=O)$_2$N(CH$_3$)$_2$, —NHC(=O)CH$_3$, and —NHS(=O)$_2$CH$_3$.

In some embodiments, $R^5$ is a 6-membered monocyclic heteroaryl. In some embodiments, $R^5$ is a 6-membered monocyclic heteroaryl selected from substituted or unsubstituted pyridinyl, substituted or unsubstituted pyrazinyl, substituted or unsubstituted pyrimidinyl, or substituted or unsubstituted pyridazinyl.

In some embodiments, $R^5$ is a 6-membered monocyclic heteroaryl selected from

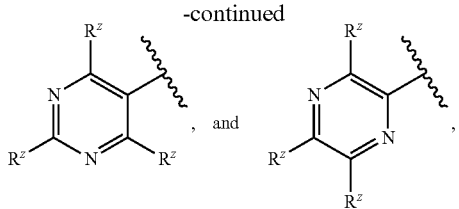

wherein each $R^z$ is independently selected from F, Cl, —CN, —CH$_3$, —CH$_2$CH$_3$, —CH$_2$CH$_2$CH$_3$, —CH(CH$_3$)$_2$, —OH, —OCH$_3$, —OCH$_2$CH$_3$, —OCF$_3$, —CH$_2$F, —CHF$_2$, —CF$_3$, —CH(OH)CH$_3$, —C(=O)CH$_3$, —C(=O)NH$_2$, —C(=O)N(CH$_3$)$_2$, —S(=O)$_2$CH$_3$, —S(=O)$_2$NH$_2$, —S(=O)$_2$N(CH$_3$)$_2$, —NHC(=O)CH$_3$, and —NHS(=O)$_2$CH$_3$.

In some embodiments, A is $CR^2$, and B, D, and F are each CH. In some embodiments, $R^2$ is CN.

In some embodiments, X is absent or —O—. In some embodiments, X is absent. In some embodiments, X is —O—. In some embodiments, X is —S—. In some embodiments, X is —NH—.

In some embodiments, $R^{14}$ is H. In some embodiments, $R^{14}$ is substituted or unsubstituted C$_1$-C$_6$alkyl. In some embodiments, $R^{14}$ is —CH$_3$, —CH$_2$CH$_3$, —CH$_2$CH$_2$CH$_3$, or —CH(CH$_3$)$_2$. In some embodiments, $R^{14}$ is —CH$_3$.

In some embodiments, each $R^{15}$, $R^{16}$, $R^{17}$, and $R^{18}$ is H.

In some embodiments, one or more of $R^{15}$, $R^{16}$, $R^{17}$, and $R^{18}$ is independently selected from the group consisting of F, —OR$^6$, and substituted or unsubstituted C$_1$-C$_6$alkyl. In some embodiments, one or more of $R^{15}$, $R^{16}$, $R^{17}$, and $R^{18}$ is independently selected from the group consisting of H, F, —OR$^6$, and substituted or unsubstituted C$_1$-C$_4$alkyl.

In some embodiments, one or more of $R^{15}$, $R^{16}$, $R^{17}$, and $R^{18}$ is independently selected from the group consisting of F, —OCH$_3$, and —CH$_3$. In some embodiments, $R^{15}$ is —CH$_3$. In some embodiments, $R^{18}$ is —CH$_3$. In some embodiments, $R^{15}$ is F. In some embodiments, $R^{18}$ is F. In some embodiments, $R^{16}$ is —CH$_3$. In some embodiments, $R^{17}$ is —CH$_3$.

In some embodiments, m is 0 or 1. In some embodiments, m is 0. In some embodiments, m is 1. In some embodiments, n is 0. In some embodiments, n is 1. In some embodiments, p is 0, 1, or 2. In some embodiments, p is 1 or 2. In some embodiments, p is 0 or 1. In some embodiments, p is 0. In some embodiments, p is 1. In some embodiments, m is 0 or 1 and p is 0, 1, or 2.

In some embodiments, the reactive compound before reaction with cereblon is selected from:

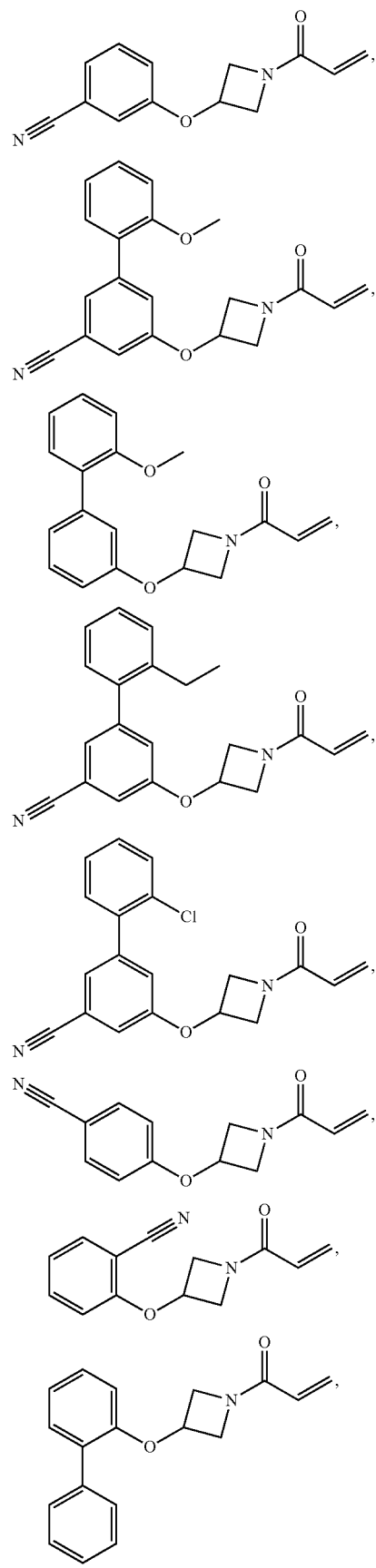
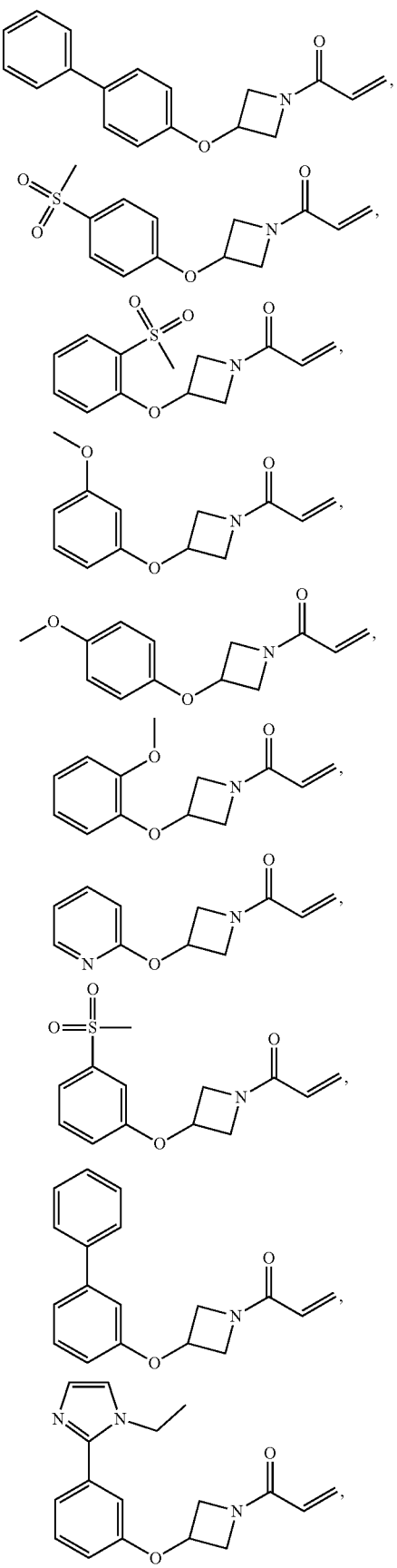

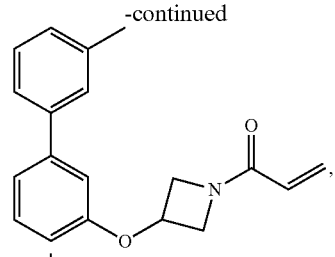
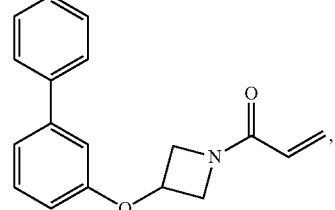
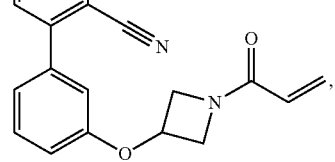
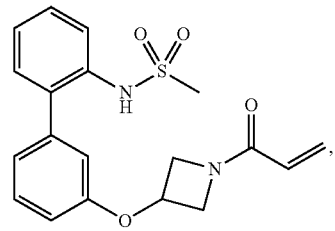
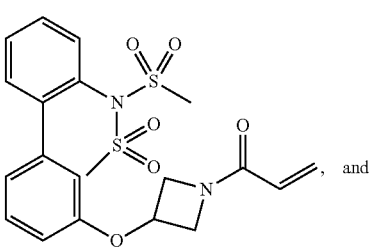
, and
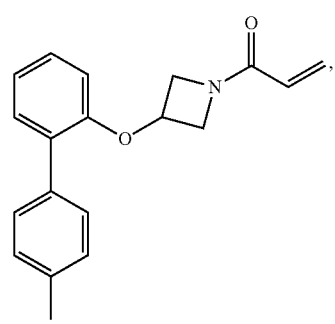 [SMILES: C=CC(=O)N1CC(Oc2ccccc2-c2ccc(C)cc2)C1]
or a pharmaceutically acceptable salt or solvate thereof.
In some embodiments, the reactive compound before reaction with cereblon is selected from:
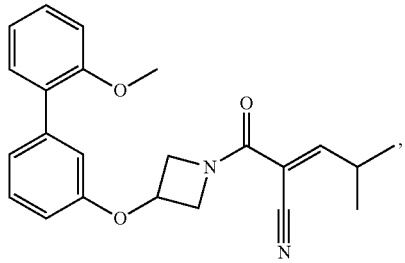
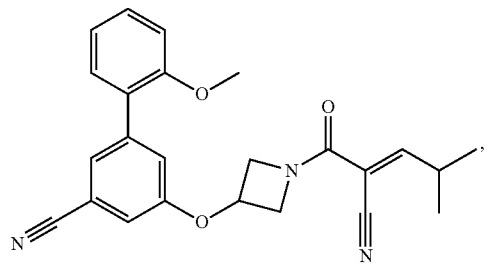
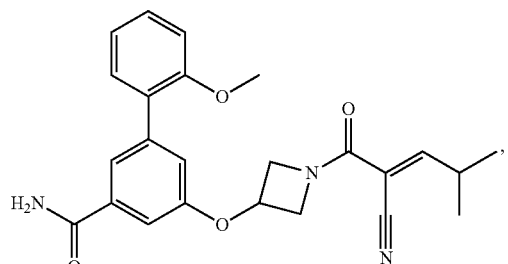
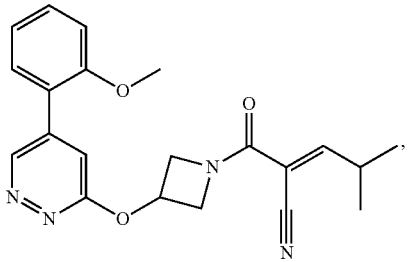
and
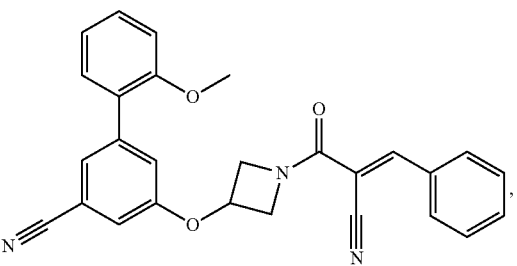 [SMILES: COc1ccccc1-c1cc(C#N)cc(OC2CN(C(=O)/C(C#N)=C/c3ccccc3)C2)c1]
or a pharmaceutically acceptable salt or solvate thereof.
In some embodiments, the reactive compound before reaction with cereblon is selected from:

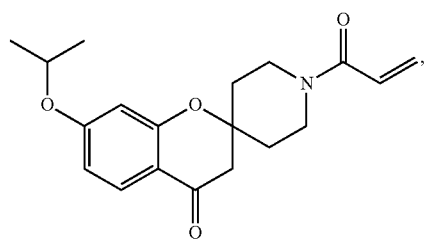
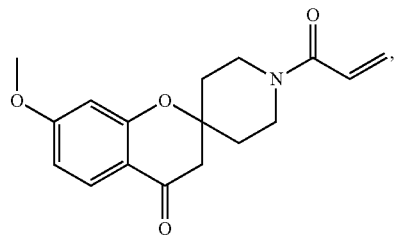
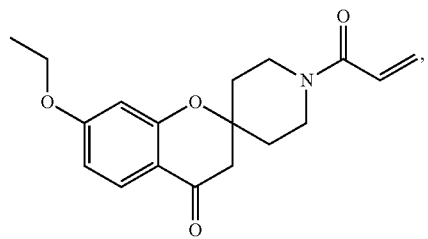
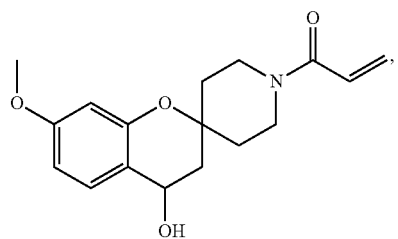
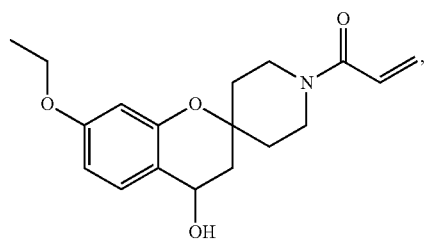
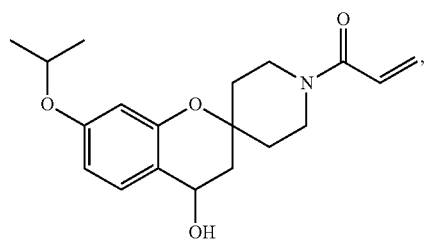
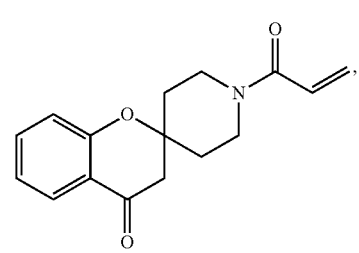
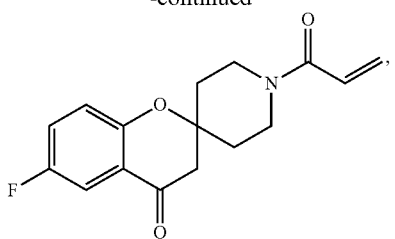
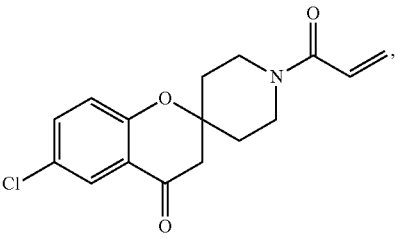
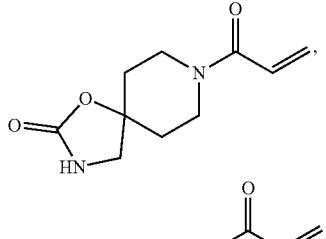
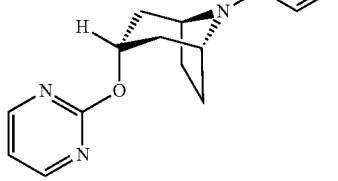
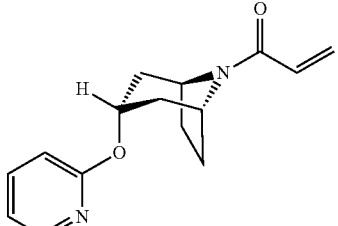
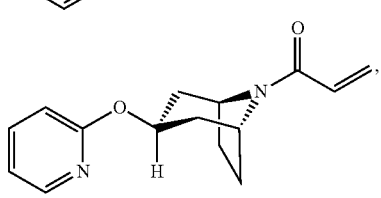
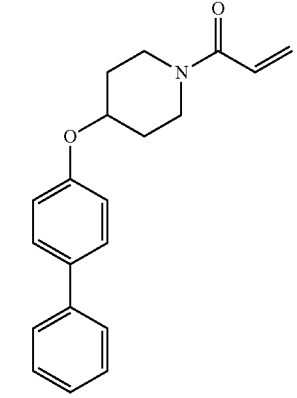

-continued
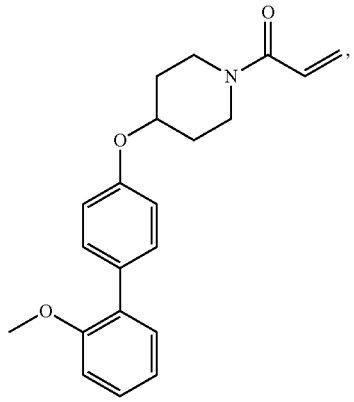
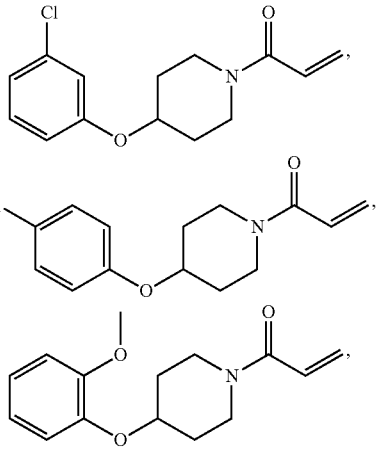
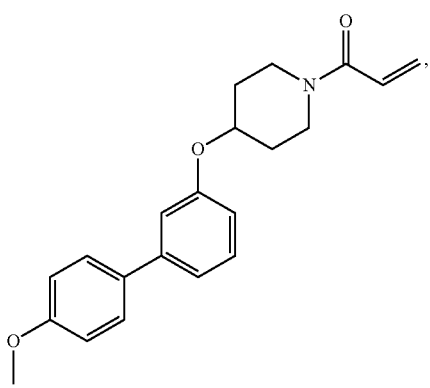
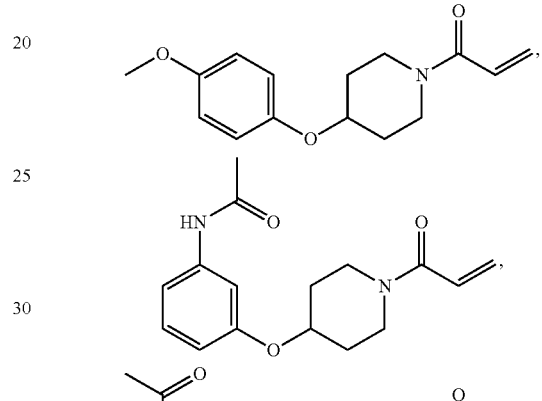
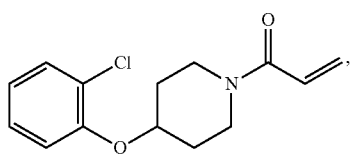
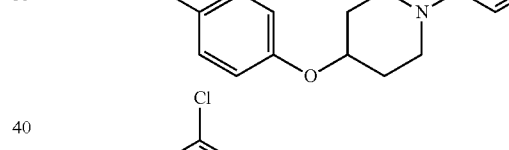
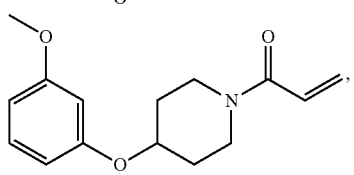
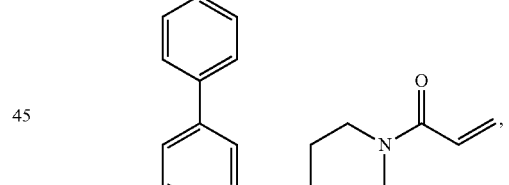
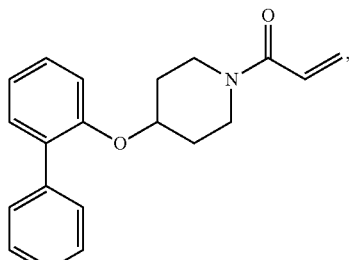
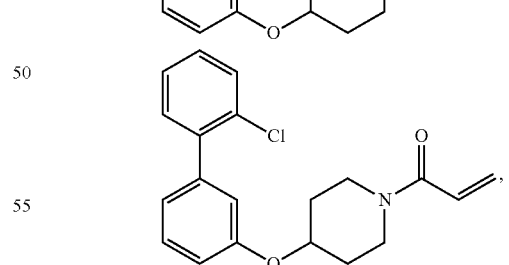
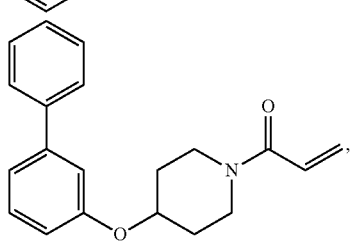
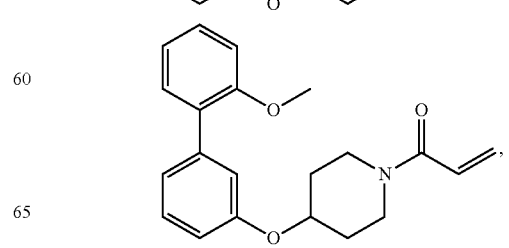

-continued
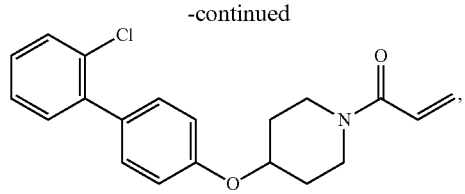
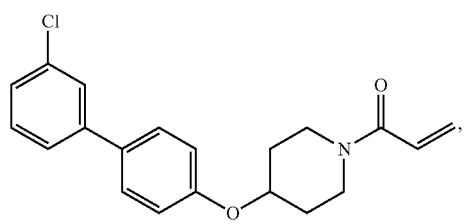
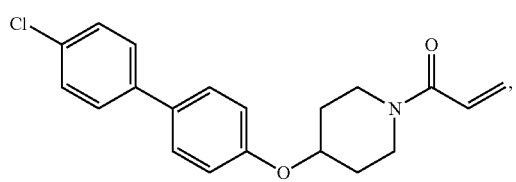
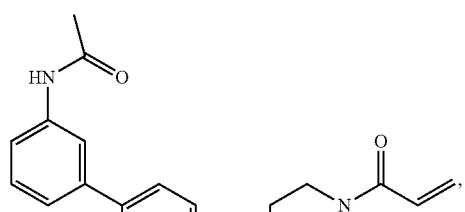
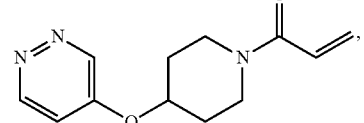
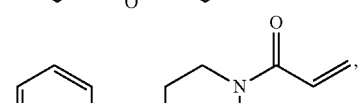
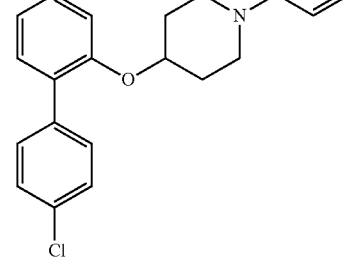
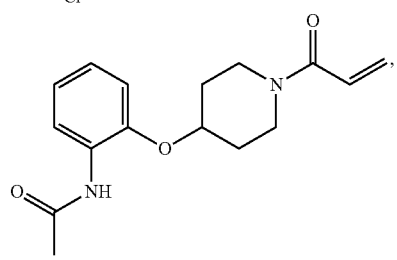
-continued
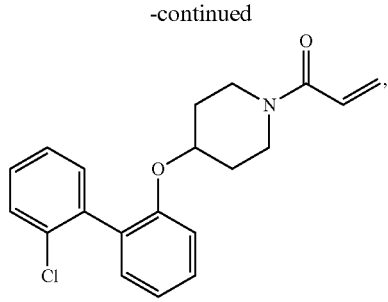
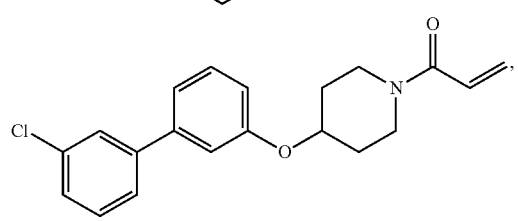
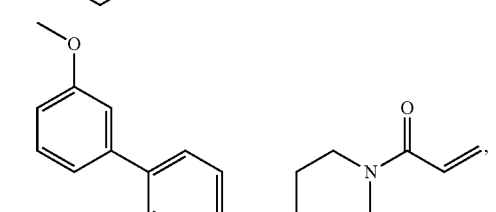
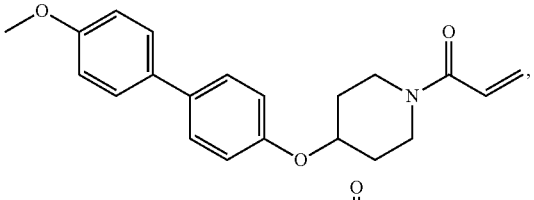
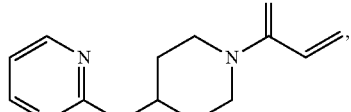
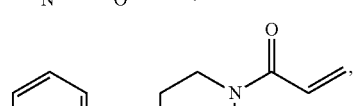
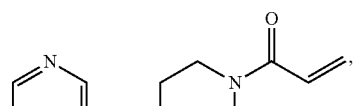
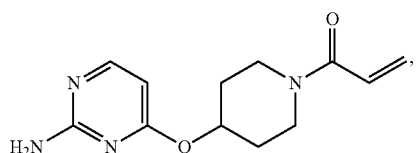
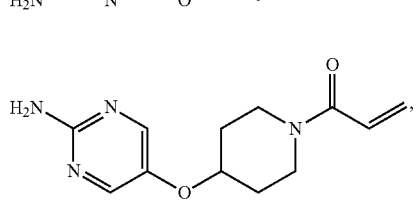

-continued
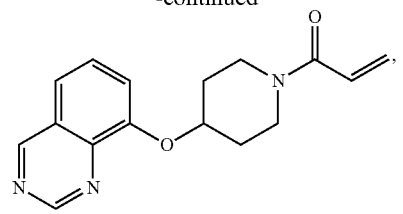
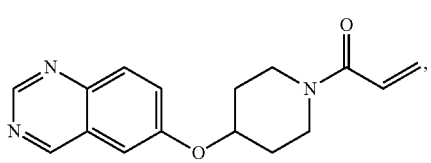
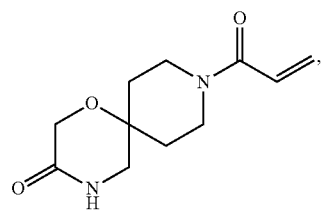
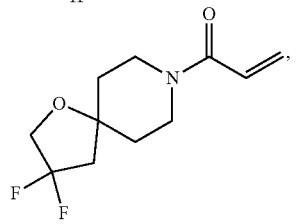
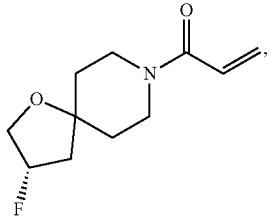
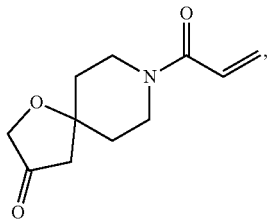
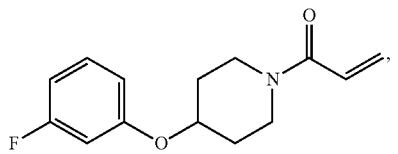
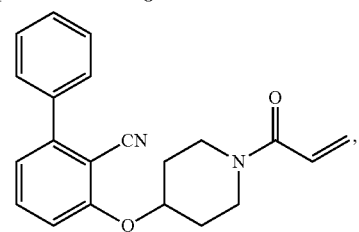
-continued
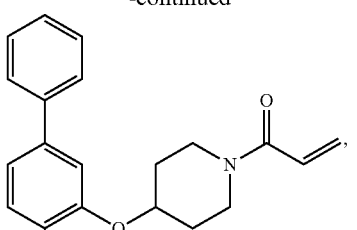
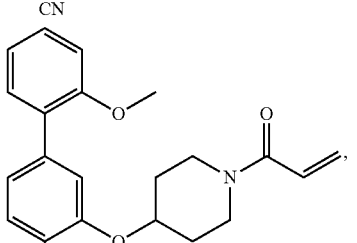
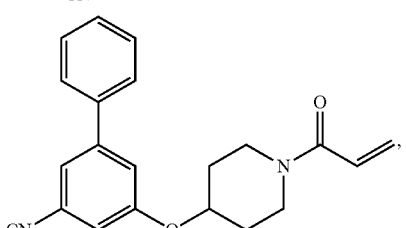
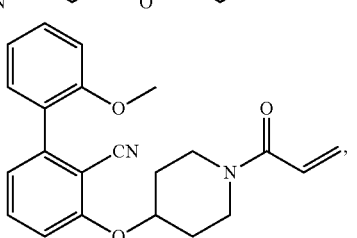
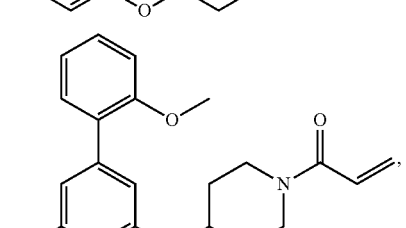
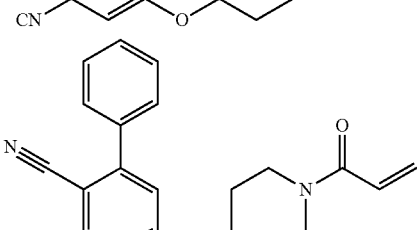
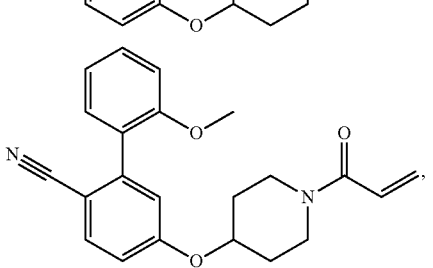

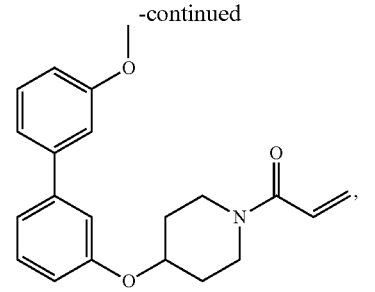
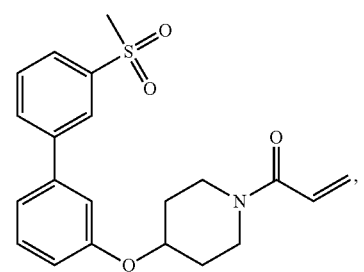
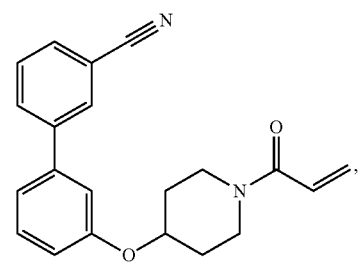
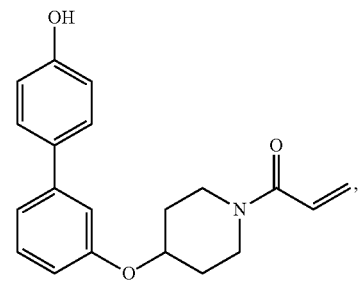
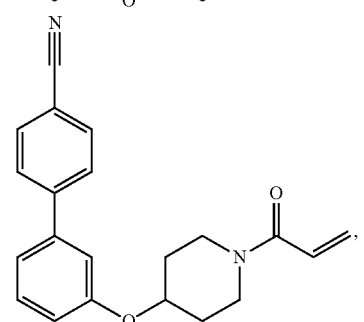
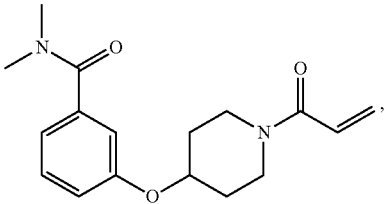
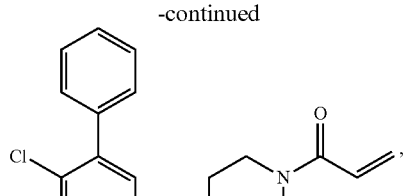
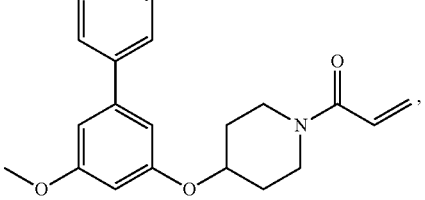
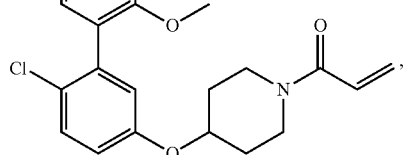
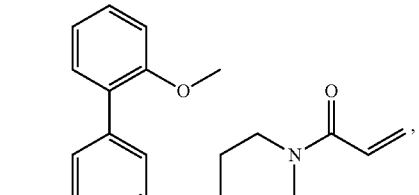
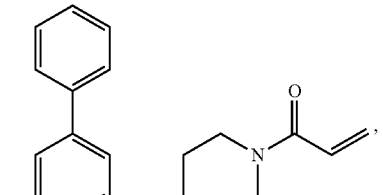
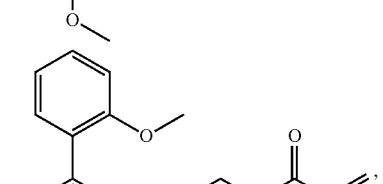
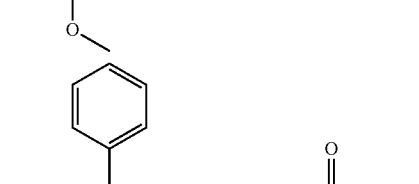

45
-continued
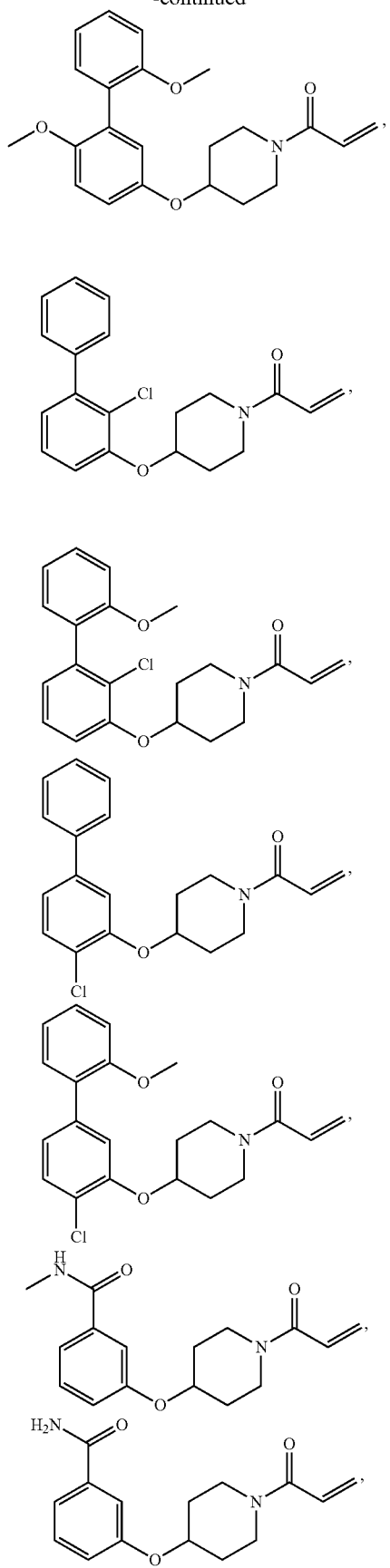
46
-continued
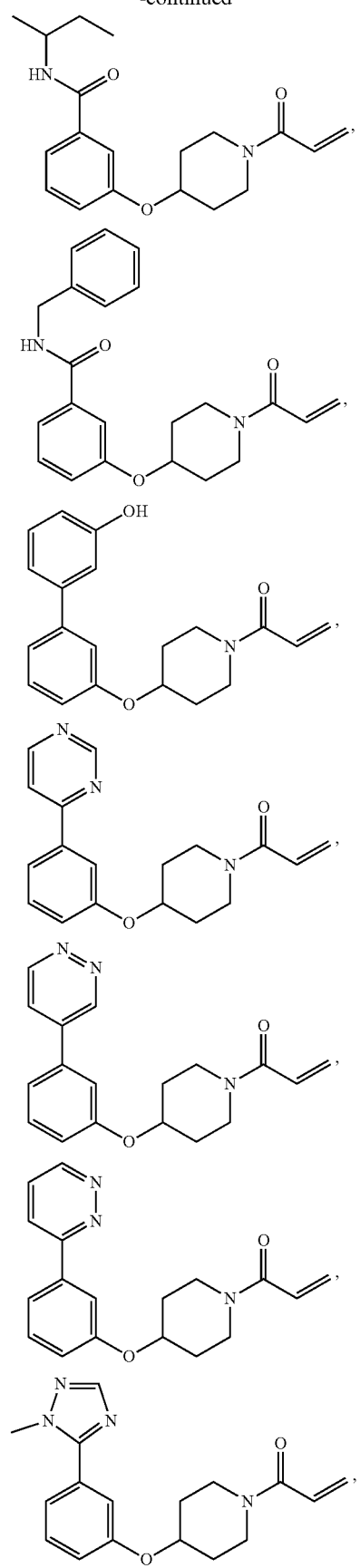

-continued
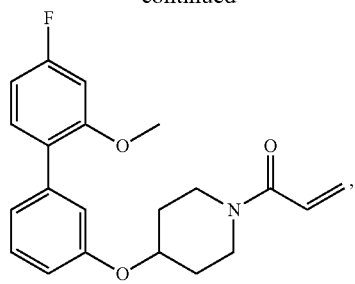
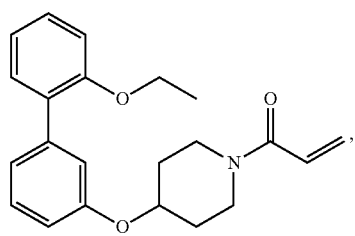
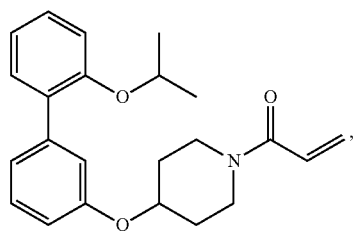
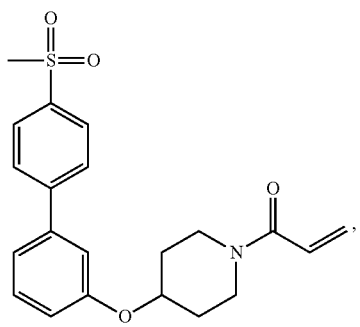
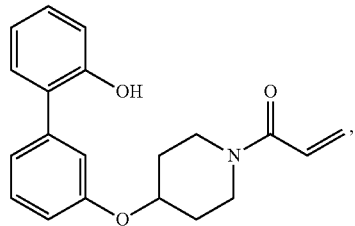
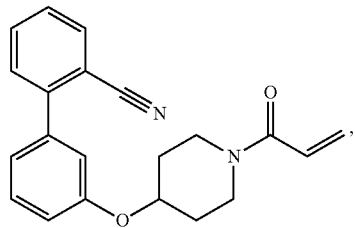
-continued
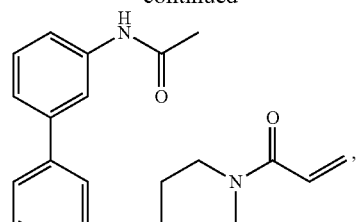
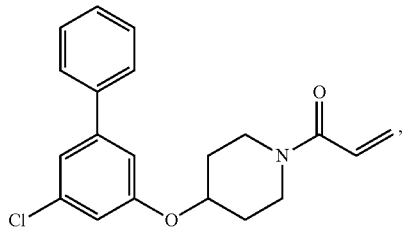
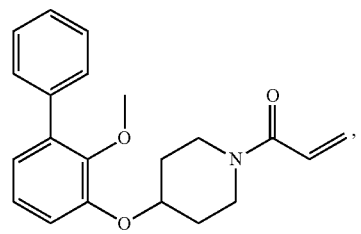
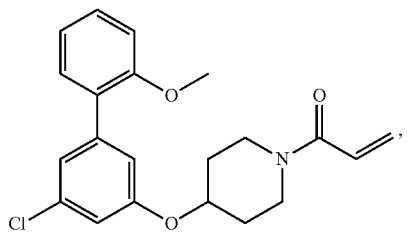
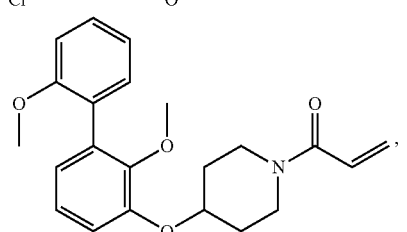
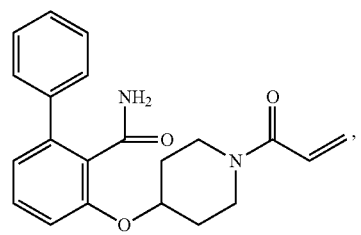
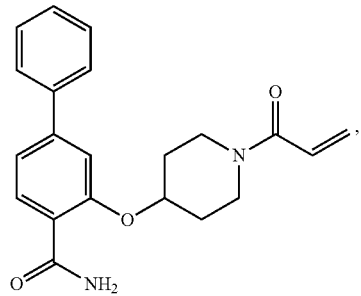

49
-continued
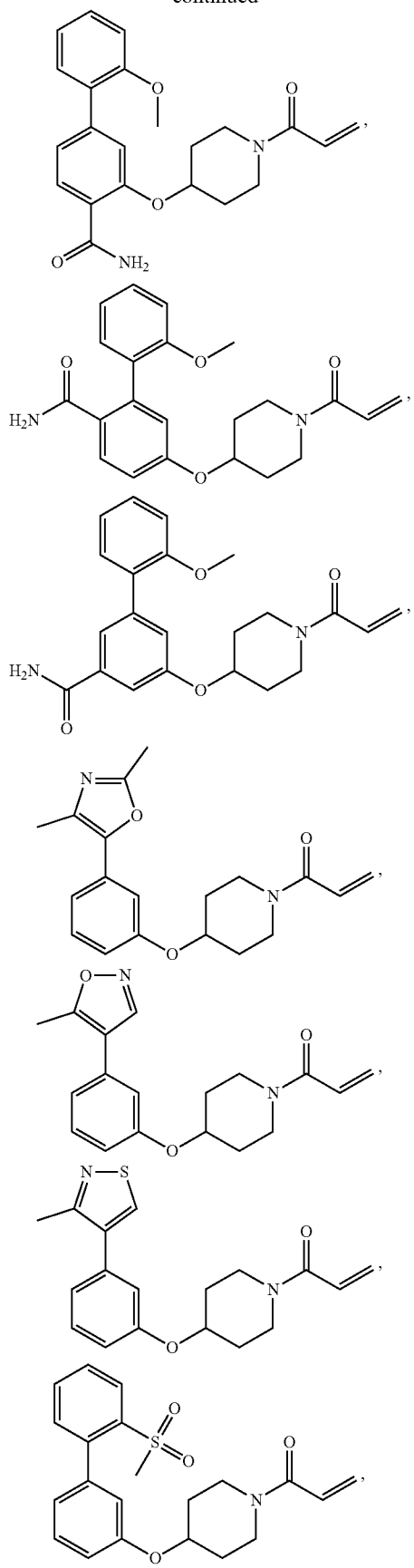
50
-continued
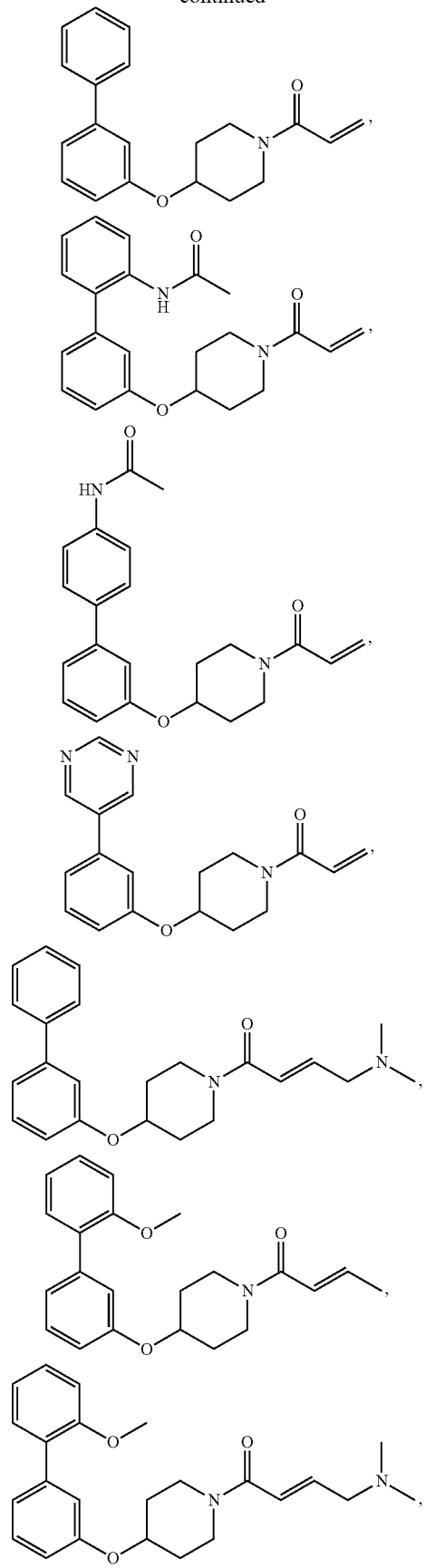

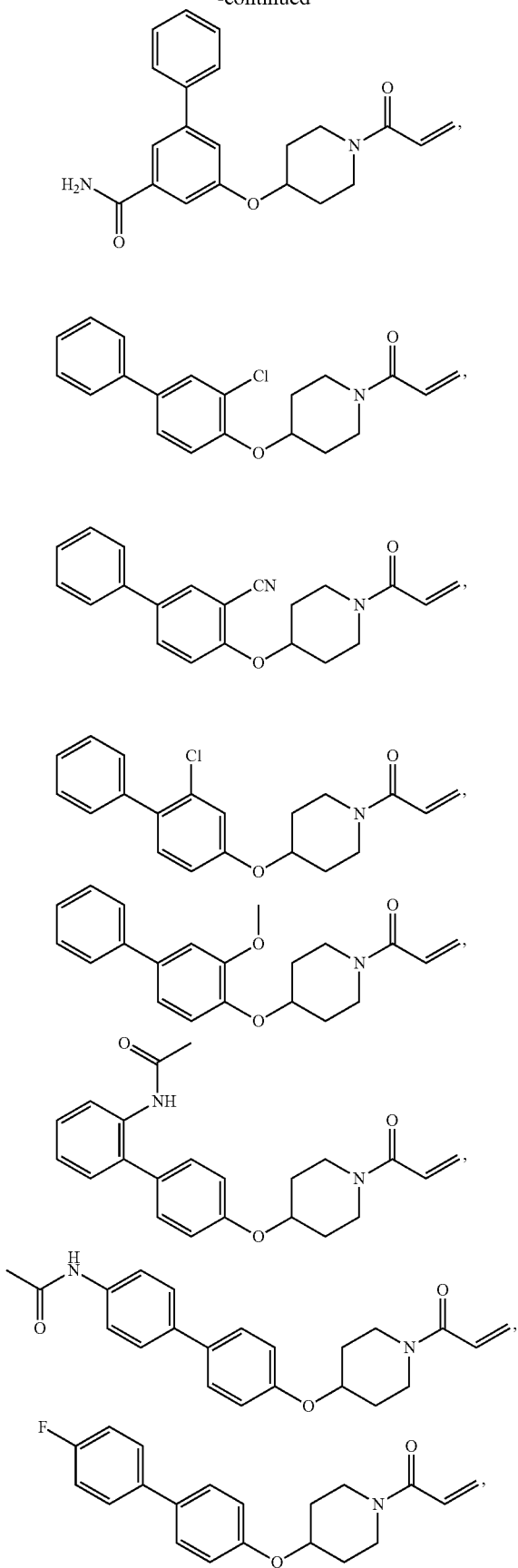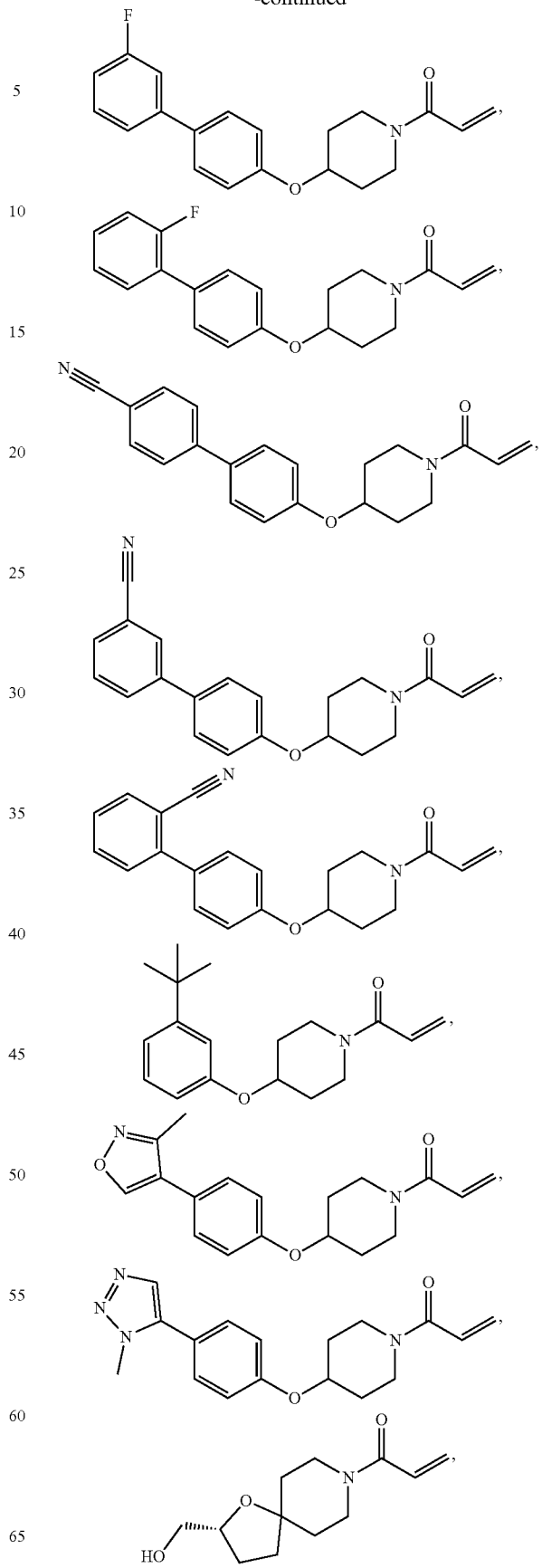

53
-continued
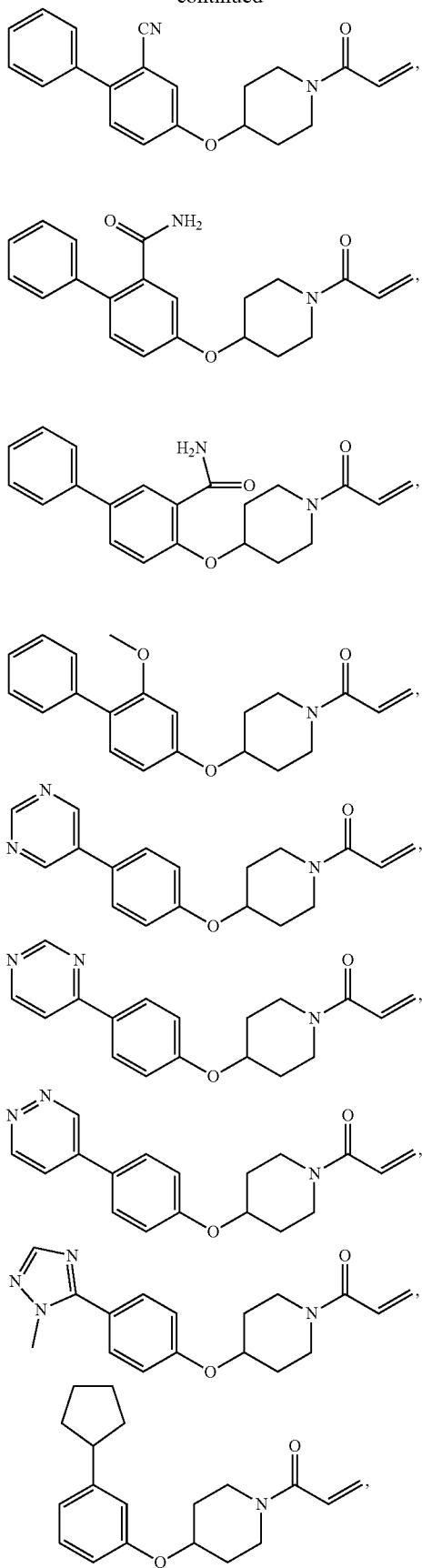
54
-continued
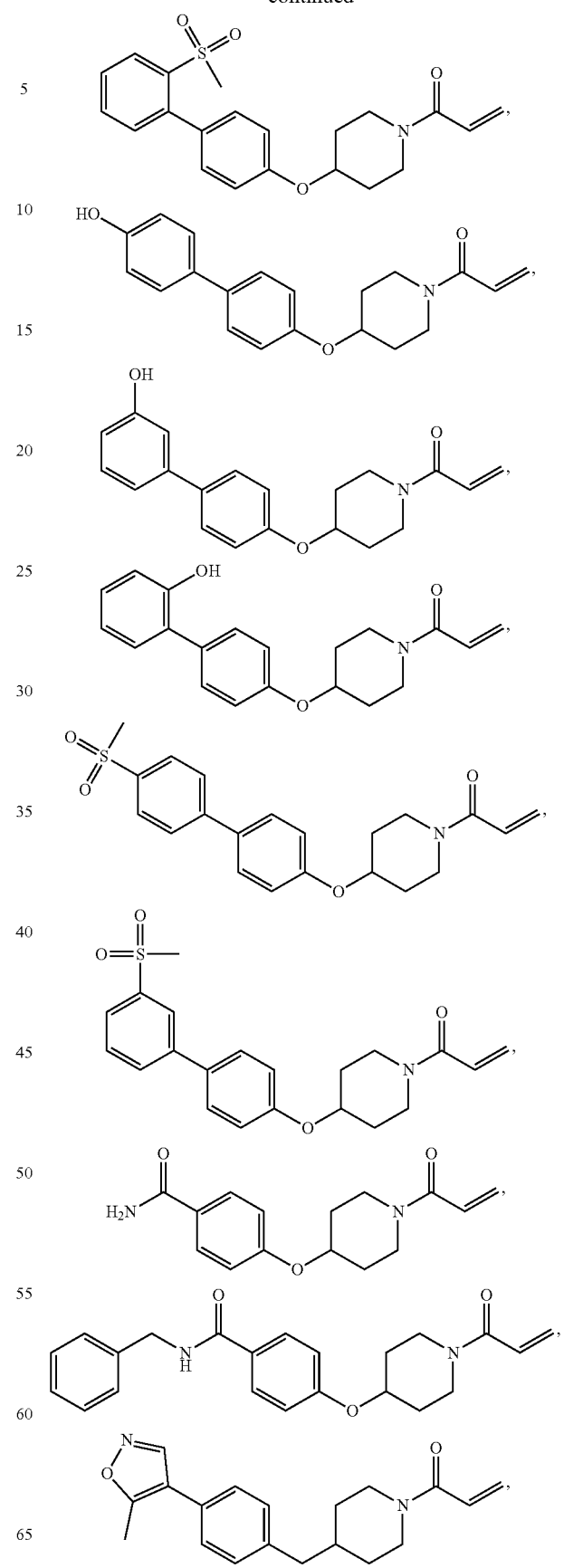

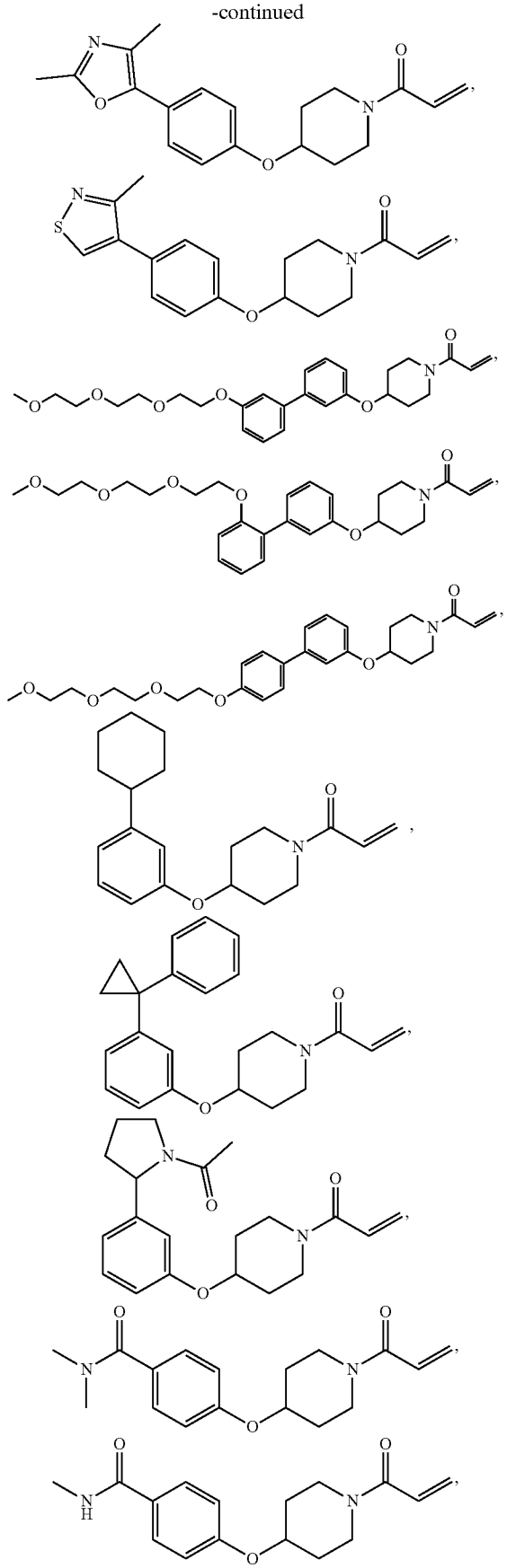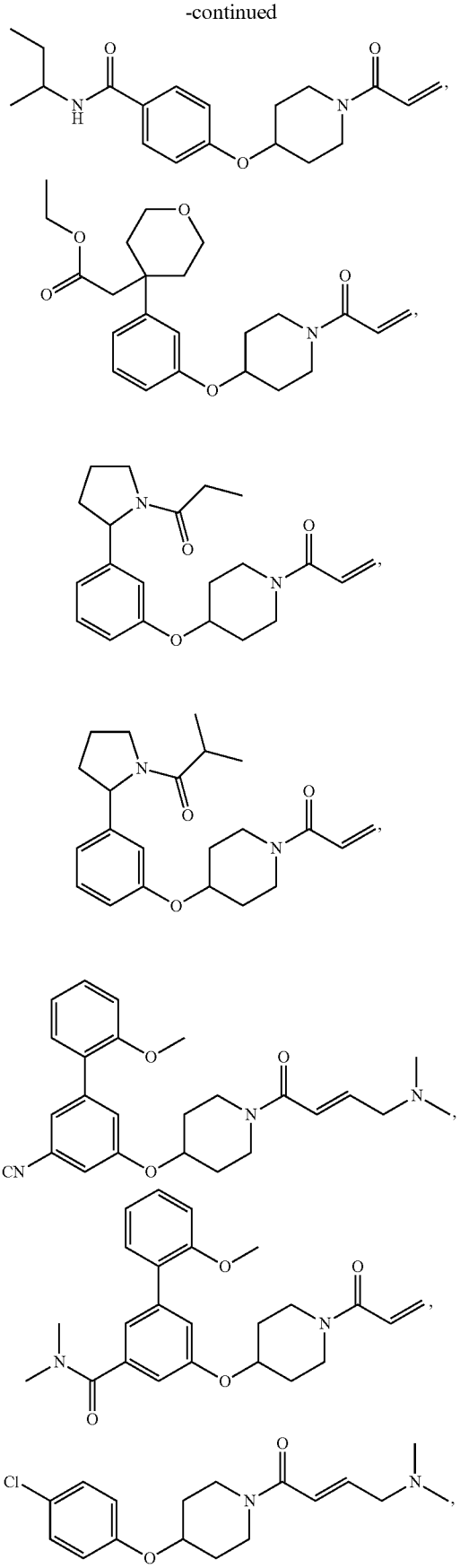

57
-continued
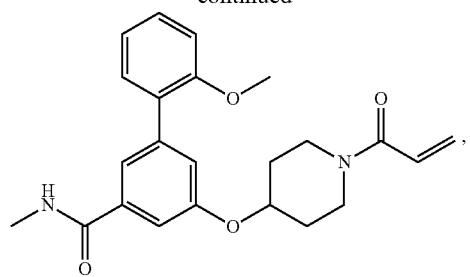
,
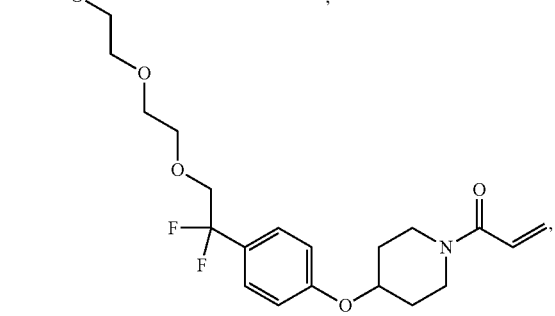
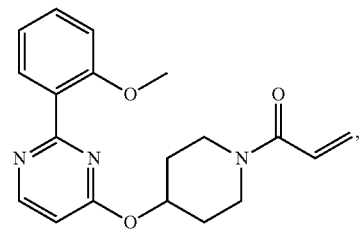
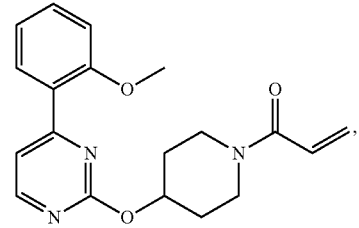
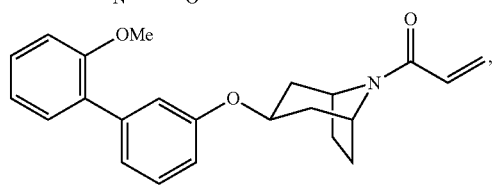
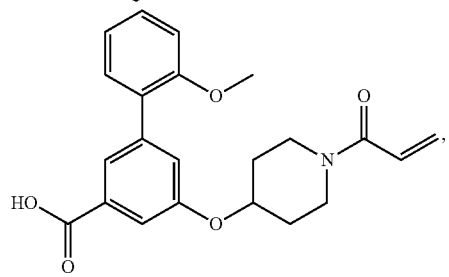
58
-continued
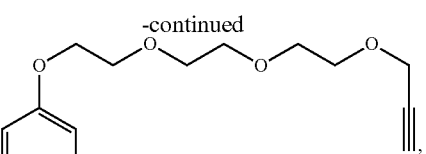,
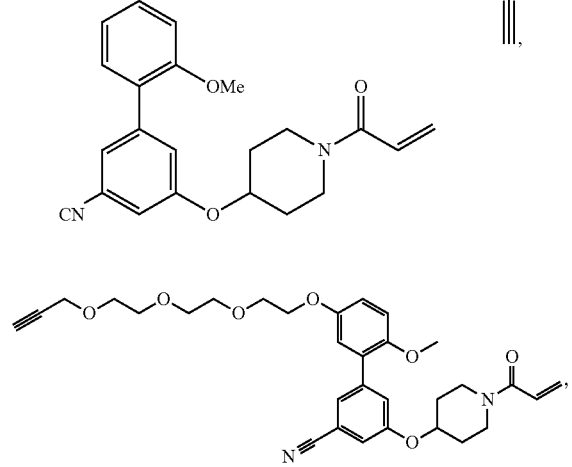,
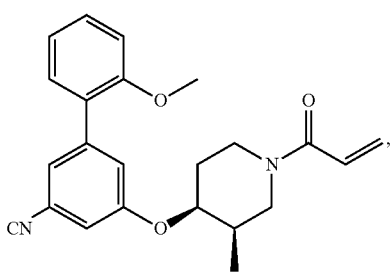
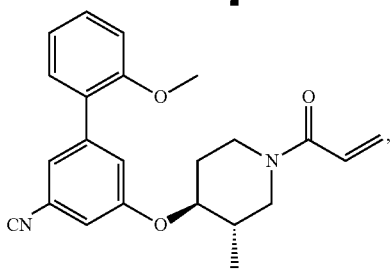
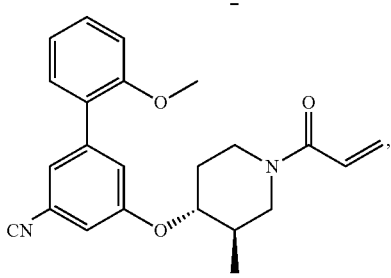
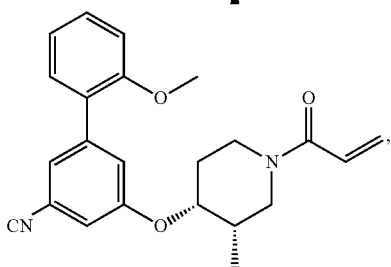
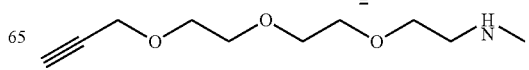

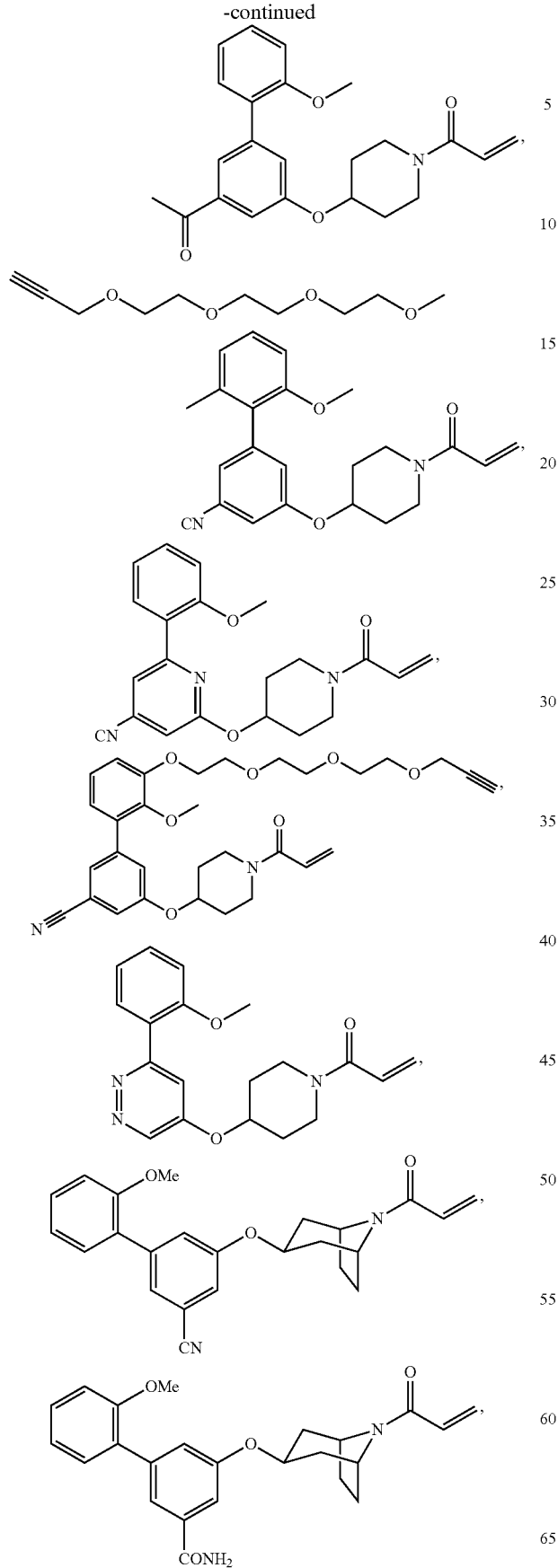
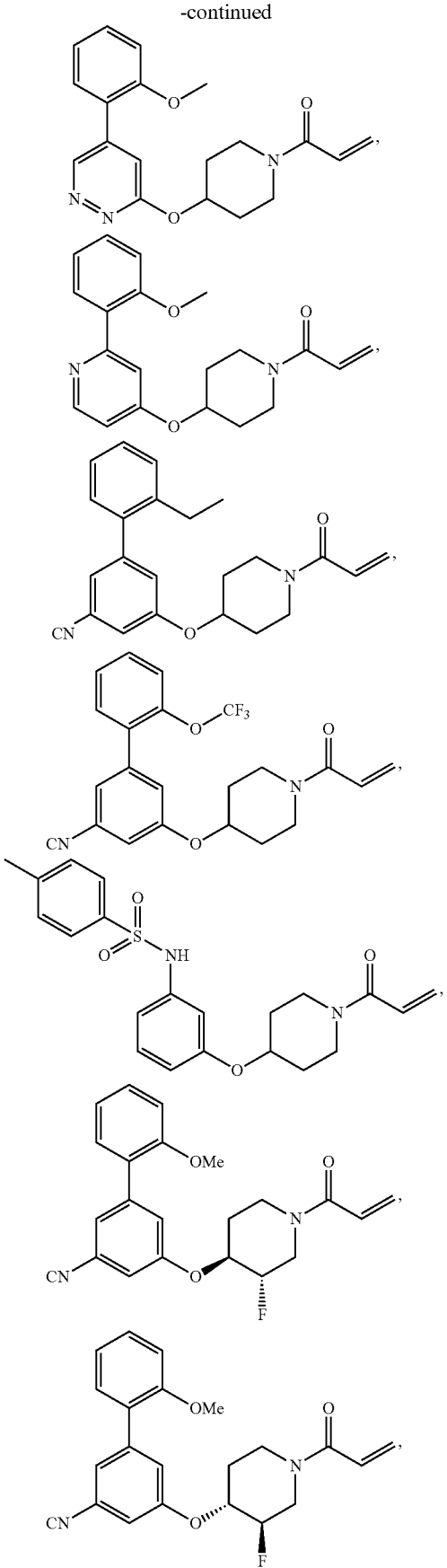

61
-continued
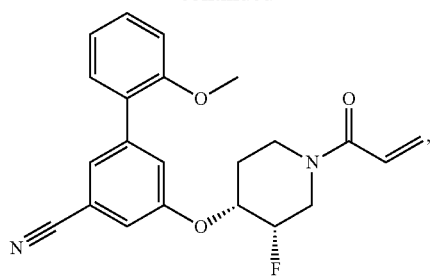
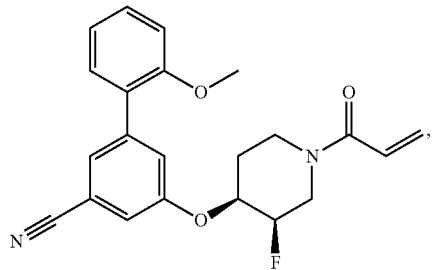
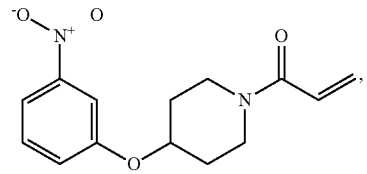
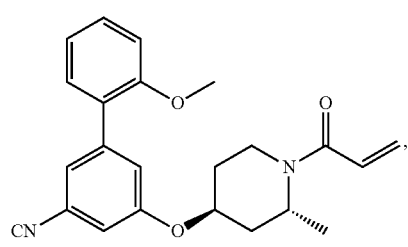
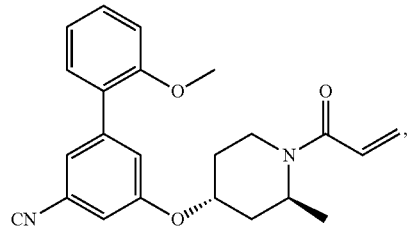
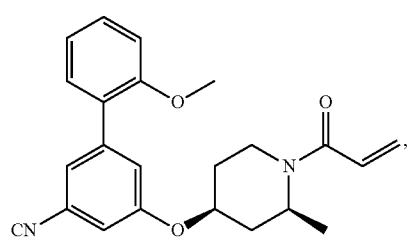
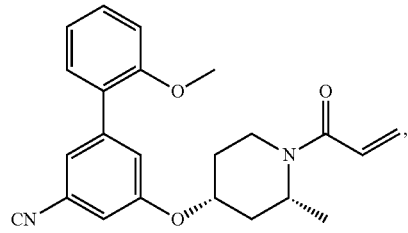
62
-continued
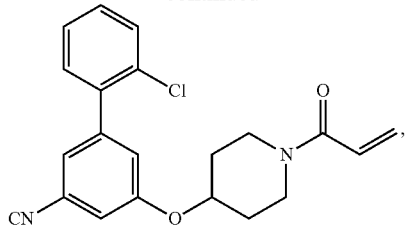
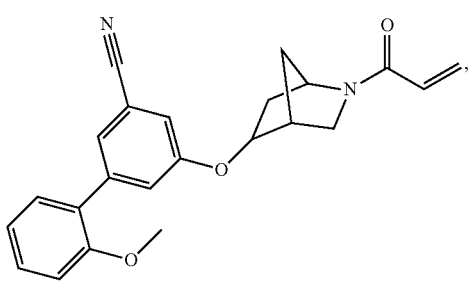
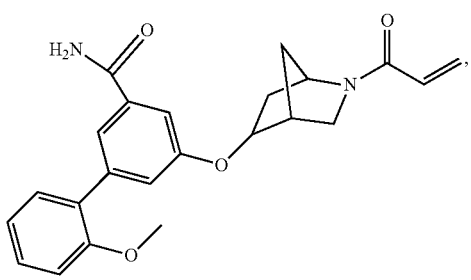
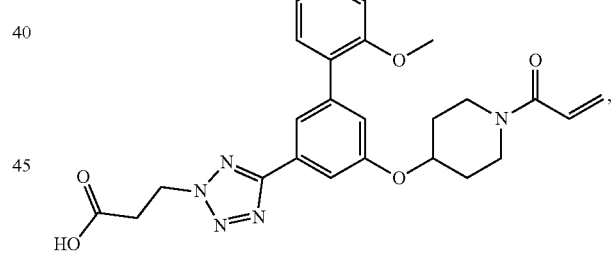
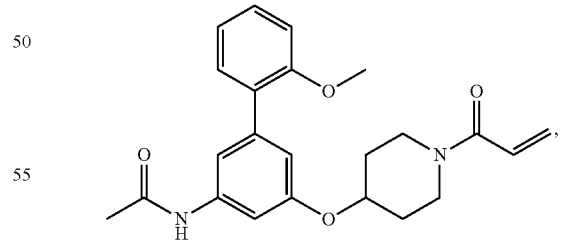
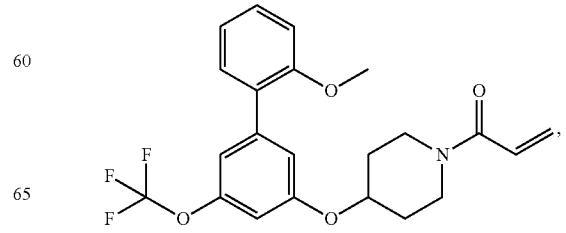

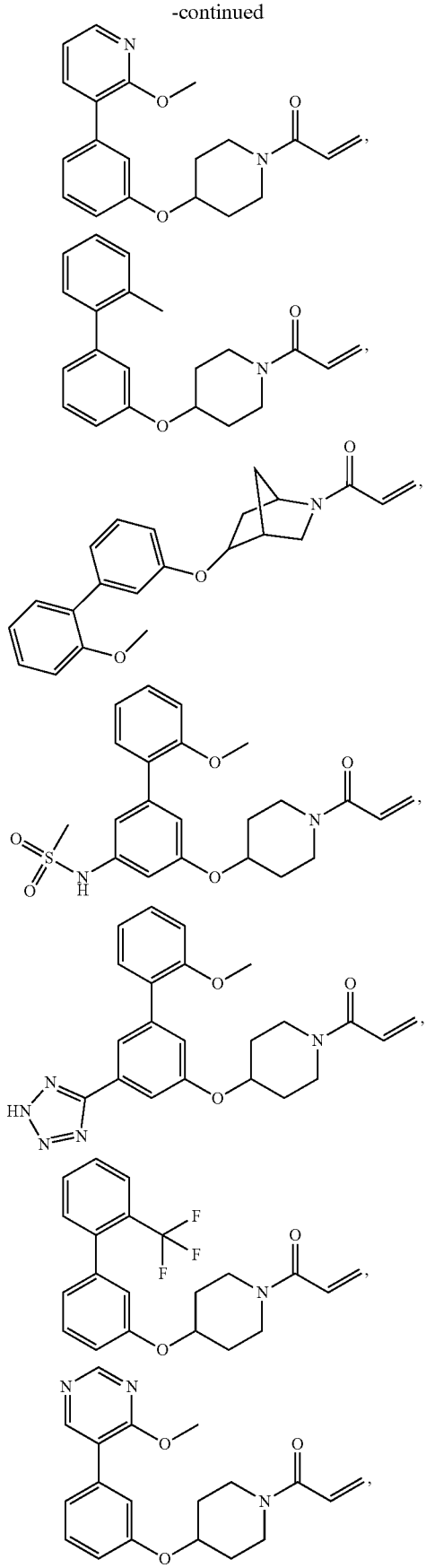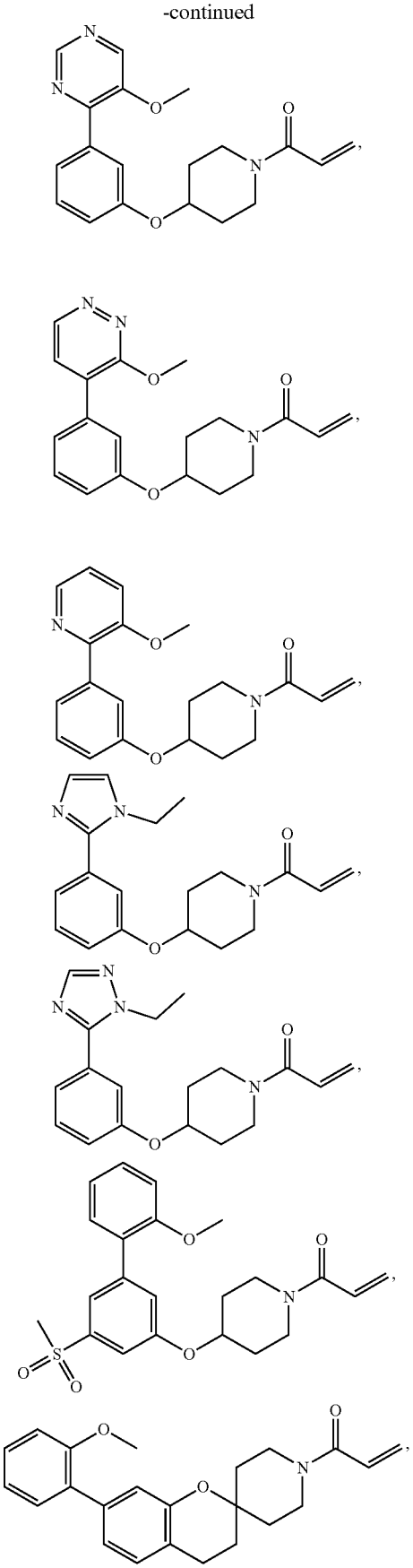

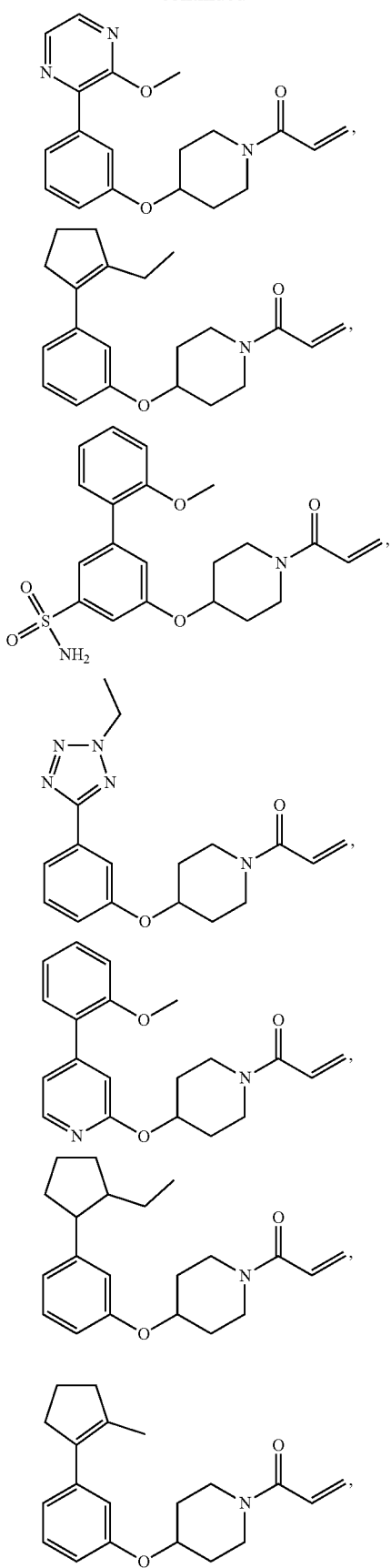
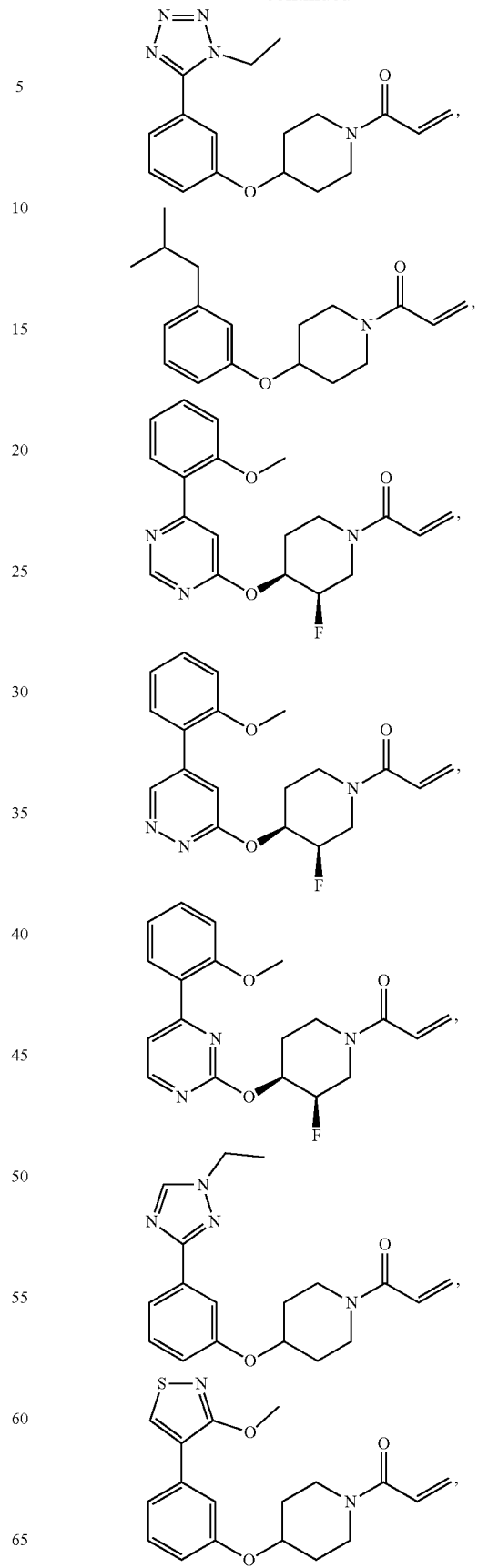

-continued
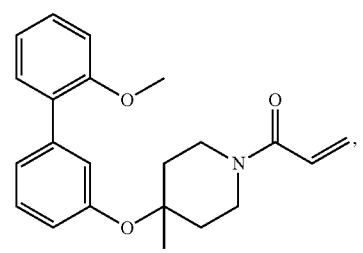
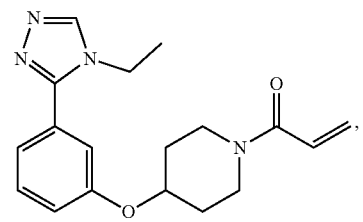
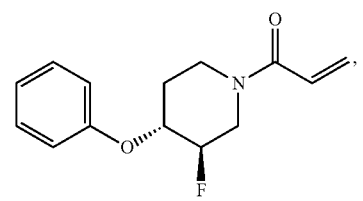
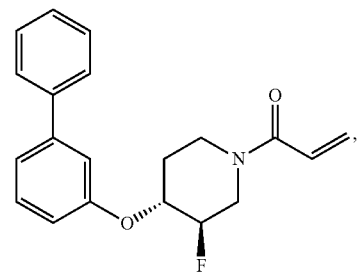
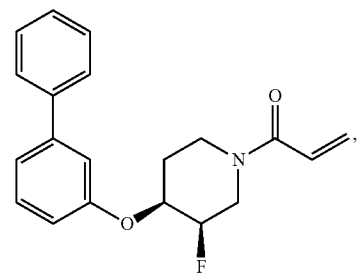
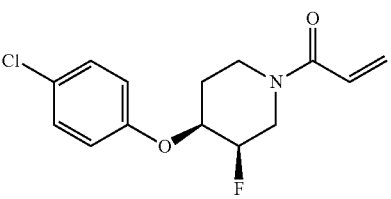
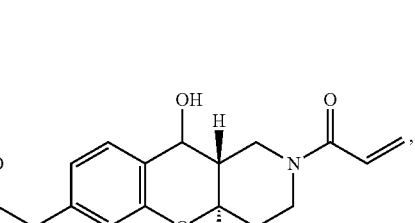
-continued
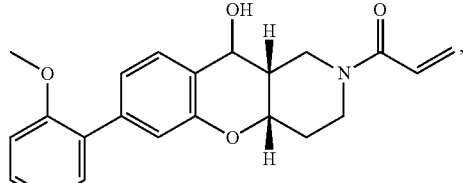
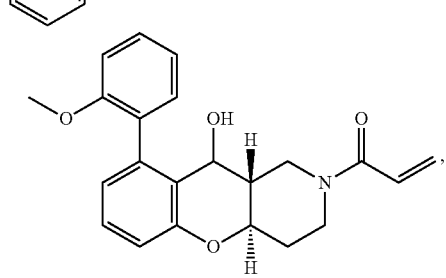
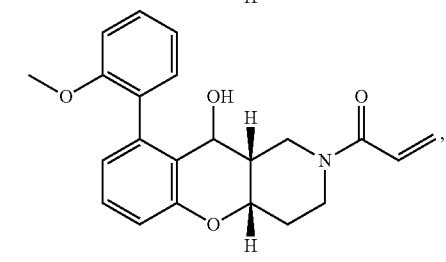
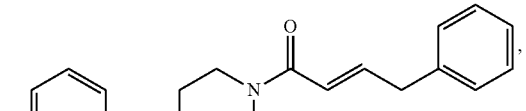
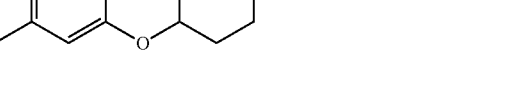
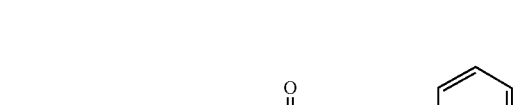
or a pharmaceutically acceptable salt or solvate thereof.
In some embodiments, the reactive compound before reaction with cereblon is selected from:
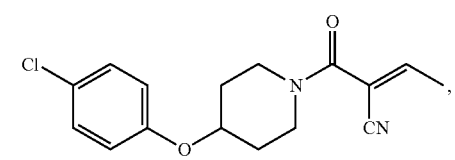

-continued
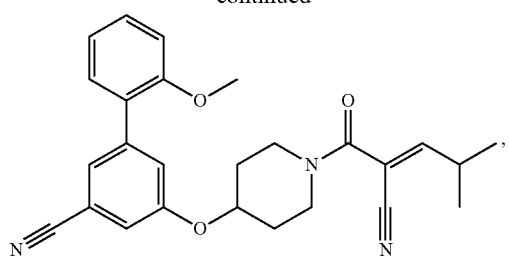
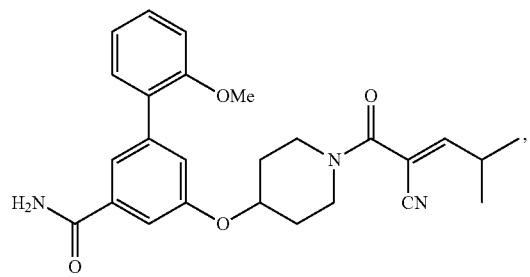
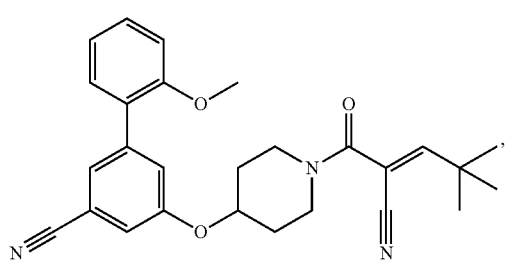
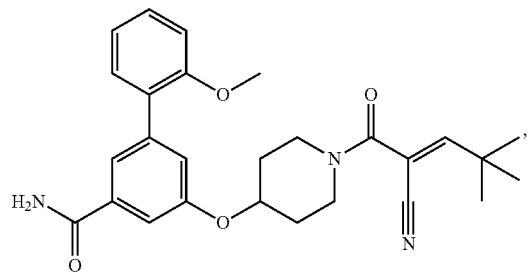
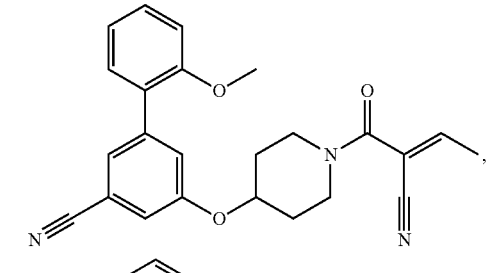
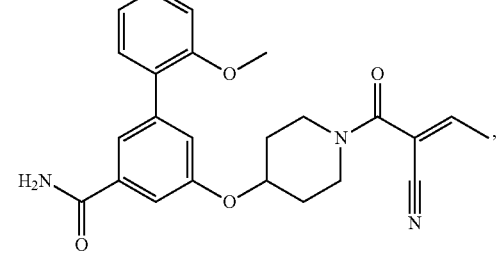
-continued
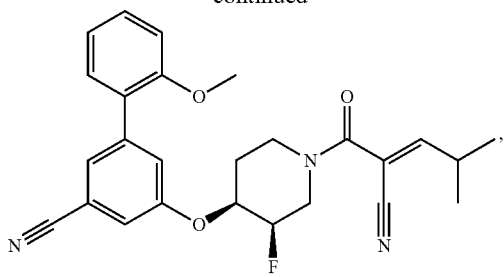
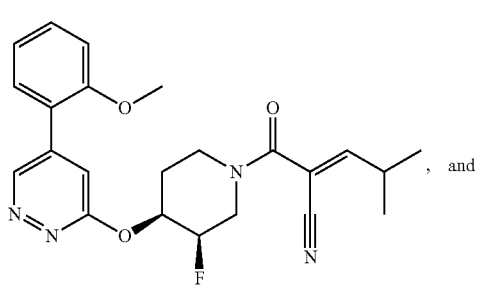
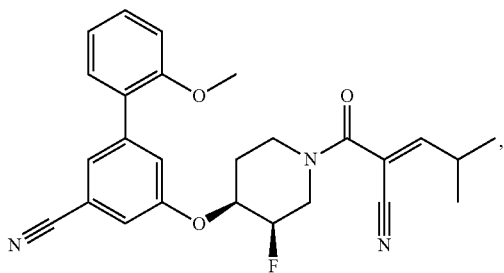
or a pharmaceutically acceptable salt or solvate thereof.
In some embodiments, the reactive compound before reaction with cereblon is selected from:
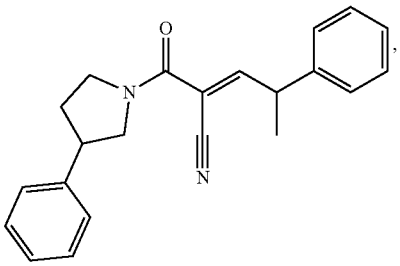
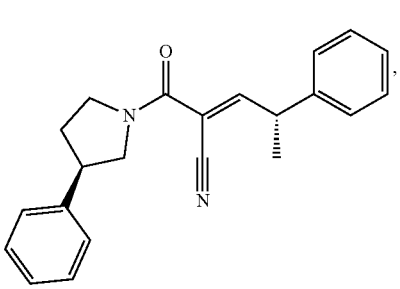

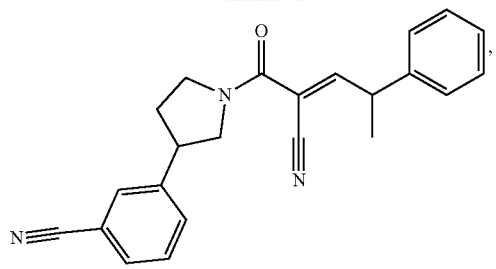
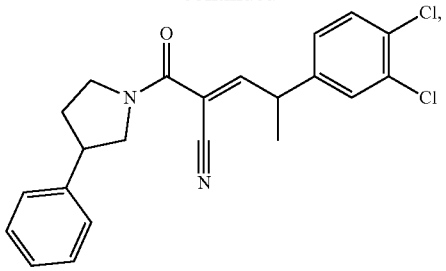 [SMILES: CC(/C=C(\C#N)C(=O)N1CCC(c2ccccc2)C1)c1ccc(Cl)cc1]
or a pharmaceutically acceptable salt or solvate thereof.
In some embodiments, the reactive compound before reaction with cereblon is selected from:

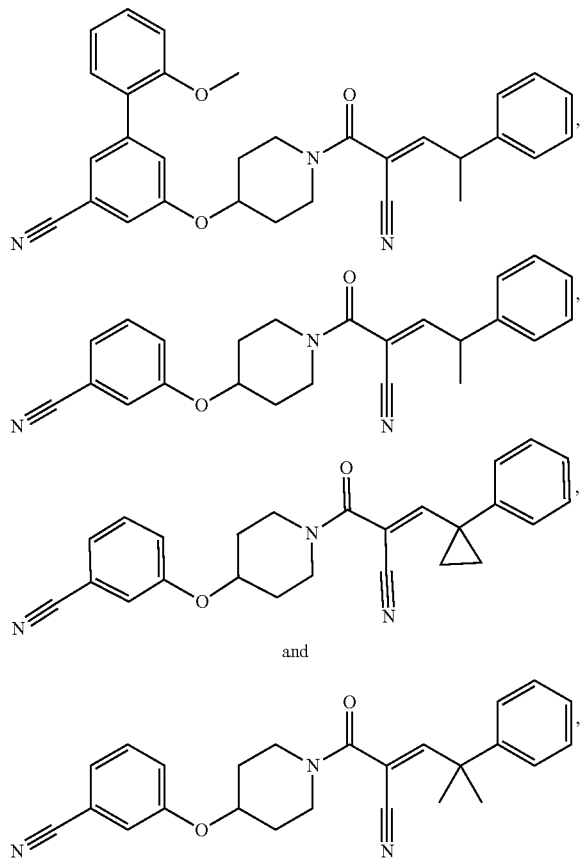

or a pharmaceutically acceptable salt or solvate thereof.

In certain embodiments, disclosed herein is a cereblon binding domain wherein said binding domain comprises a cysteine, wherein said cysteine forms an adduct with a compound of Formula (I):

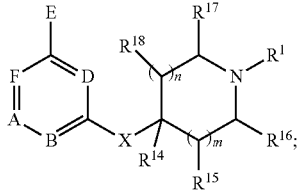
Formula (I)

wherein
A is N or $C(R^2)$;
B is N or $C(R^3)$;
D is N or $C(R^4)$;
E is H or

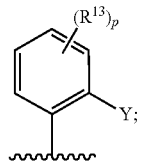

F is N or $C(R^5)$;
X is absent, —O—, —NH—, or —S—;
Y is H, halogen, —$OR^6$, substituted or unsubstituted $C_1$-$C_6$alkyl, or substituted or unsubstituted $C_1$-$C_6$haloalkyl;
$R^1$ is —C(=O)$CR^7$=$CR^8R^9$, —S(=O)$_2CR^7$=$CR^8R^9$, or —C(=O)C≡$CR^9$;
$R^2$ is H, halogen, —CN, —N($R^{12}$)$_2$, —$OR^6$, —CH(O$R^6$) $R^{12}$, —C(=O)$R^{12}$, —C(=O)N($R^{12}$)$_2$, —S(=O)$_2R^{12}$, —S(=O)$_2$N($R^{12}$)$_2$, —N($R^{12}$)C(=O)$R^{12}$, —N($R^{12}$)S(=O)$_2R^{12}$, substituted or unsubstituted $C_1$-$C_6$ alkyl, substituted or unsubstituted $C_1$-$C_6$haloalkyl, substituted or unsubstituted $C_3$-$C_6$cycloalkyl, substituted or unsubstituted $C_2$-$C_5$heterocycloalkyl, substituted or unsubstituted aryl, or substituted or unsubstituted heteroaryl;
$R^3$ is H, halogen, —CN, —N($R^{12}$)$_2$, —$OR^6$, —CH(O$R^6$) $R^{12}$, —C(=O)$R^{12}$, —C(=O)N($R^{12}$)$_2$, —S(=O)$_2R^{12}$, —S(=O)$_2$N($R^{12}$)$_2$, —N($R^{12}$)C(=O)$R^{12}$, —N($R^{12}$)S(=O)$_2R^{12}$, substituted or unsubstituted $C_1$-$C_6$ alkyl, substituted or unsubstituted $C_1$-$C_6$haloalkyl, substituted or unsubstituted $C_3$-$C_6$cycloalkyl, substituted or unsubstituted $C_2$-$C_5$heterocycloalkyl, substituted or unsubstituted aryl, or substituted or unsubstituted heteroaryl;
$R^4$ is H, halogen, —CN, —N($R^{12}$)$_2$, —C(=O)$R^{12}$, —C(=O)N($R^{12}$)$_2$, —S(=O)$_2R^{12}$, substituted or unsubstituted $C_1$-$C_6$alkyl, substituted or unsubstituted $C_1$-$C_6$haloalkyl, substituted or unsubstituted aryl, or substituted or unsubstituted heteroaryl;
$R^5$ is H, halogen, —CN, —N($R^{12}$)$_2$, —$OR^6$, —C(=O)$R^{12}$, —C(=O)N($R^{12}$)$_2$, —N($R^{12}$)C(=O)$R^{12}$, —S(=O)$_2R^{12}$, —N($R^{12}$)S(=O)$_2R^{12}$, —S(=O)$_2$N($R^{12}$)$_2$, substituted or unsubstituted $C_1$-$C_6$alkyl, substituted or unsubstituted $C_1$-$C_6$haloalkyl, substituted or unsubstituted aryl, or substituted or unsubstituted heteroaryl;
each $R^6$ is independently H, substituted or unsubstituted $C_1$-$C_6$alkyl, substituted or unsubstituted $C_1$-$C_6$haloalkyl, or substituted or unsubstituted $C_1$-$C_{10}$heteroalkyl.
$R^7$ is H, CN, substituted or unsubstituted $C_1$-$C_6$alkyl, substituted or unsubstituted $C_3$-$C_6$cycloalkyl, or substituted or unsubstituted aryl;
$R^8$ is H, —$NR^{10}R^{11}$, substituted or unsubstituted $C_1$-$C_6$alkyl, substituted or unsubstituted $C_1$-$C_6$aminoalkyl, substituted or unsubstituted $C_3$-$C_6$cycloalkyl, or substituted or unsubstituted $C_2$-$C_6$heterocycloalkyl;
$R^9$ is H or substituted or unsubstituted $C_1$-$C_6$alkyl;
$R^{10}$ and $R^{11}$ are each independently H, substituted or unsubstituted $C_1$-$C_6$alkyl, or substituted or unsubstituted $C_1$-$C_8$heteroalkyl; or
$R^{10}$ and $R^{11}$ are taken together with the nitrogen to which they are attached to form a substituted or unsubstituted $C_2$-$C_9$heterocycloalkyl;
each $R^{12}$ is independently H, substituted or unsubstituted $C_1$-$C_6$alkyl, or substituted or unsubstituted aryl;
each $R^{13}$ is independently halogen, —CN, —$OR^6$, —C(=O)N($R^{12}$)$_2$, —N($R^{12}$)C(=O)$R^{12}$, —N($R^{12}$)S(=O)$_2R^{12}$, —N(S(=O)$_2R^{12}$)$_2$, —S(=O)$_2R^{12}$, —S(=O)$_2$N($R^{12}$)$_2$, substituted or unsubstituted $C_1$-$C_6$alkyl, substituted or unsubstituted $C_1$-$C_6$haloalkyl, or substituted or unsubstituted $C_1$-$C_{10}$heteroalkyl;
$R^{14}$ is H or substituted or unsubstituted $C_1$-$C_6$alkyl; or when B is C(R$^3$), then R$^3$ and R$^{14}$ are taken together with the carbon atoms to which they are attached to form a substituted or unsubstituted heterocycloalkyl;

each R$^{15}$, R$^{16}$, R$^{17}$, and R$^{18}$ is independently selected from the group consisting of H, F, —OR$^6$, and substituted or unsubstituted C$_1$-C$_6$alkyl; or R$^{15}$ and R$^{17}$ are taken together with the carbon atoms to which they are attached to form a substituted or unsubstituted C$_4$-C$_7$cycloalkyl; or R$^{15}$ and R$^{18}$ are taken together with the carbon atoms to which they are attached to form a substituted or unsubstituted C$_4$-C$_7$cycloalkyl; or R$^{16}$ and R$^{17}$ are taken together with the carbon atoms to which they are attached to form a substituted or unsubstituted C$_4$-C$_7$cycloalkyl; or R$^{16}$ and R$^{18}$ are taken together with the carbon atoms to which they are attached to form a substituted or unsubstituted C$_4$-C$_7$cycloalkyl;

m is 0, 1, or 2;

n is 0 or 1; and p is 0, 1, 2, or 3; or a pharmaceutically acceptable salt or solvate thereof.

In some embodiments, the compound binds to cysteine residue C287 of SEQ ID NO: 1 or corresponding cysteine of a cereblon homolog, active fragment, or variant thereof.

In certain embodiments, disclosed herein is a cereblon adduct comprising an acrylamide bond to cysteine 287 of SEQ ID NO: 1 or corresponding cysteine of a cereblon homolog, active fragment, or variant thereof.

In certain embodiments, disclosed herein is a modified cereblon wherein the cysteine C287 of SEQ ID NO: 1 or corresponding cysteine of a cereblon homolog, active fragment, or variant thereof is conjugated to a compound of Formula (I):

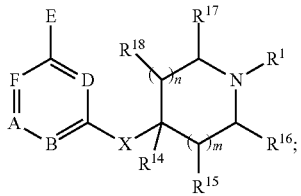

Formula (I)

wherein

A is N or C(R$^2$);
B is N or C(R$^3$);
D is N or C(R$^4$);
E is H or

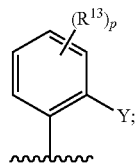

F is N or C(R$^5$);
X is absent, —O—, —NH—, or —S—;
Y is H, halogen, —OR$^6$, substituted or unsubstituted C$_1$-C$_6$alkyl, or substituted or unsubstituted C$_1$-C$_6$haloalkyl;
R$^1$ is —C(=O)CR$^7$=CR$^8$R$^9$, —S(=O)$_2$CR$^7$=CR$^8$R$^9$, or —C(=O)C≡CR$^9$;

R$^2$ is H, halogen, —CN, —N(R$^{12}$)$_2$, —OR$^6$, —CH(OR$^6$)R$^{12}$, —C(=O)R$^{12}$, —C(=O)N(R$^{12}$)$_2$, —S(=O)$_2$R$^{12}$, —S(=O)$_2$N(R$^{12}$)$_2$, —N(R$^{12}$)C(=O)R$^{12}$, —N(R$^{12}$)S(=O)$_2$R$^{12}$, substituted or unsubstituted C$_1$-C$_6$ alkyl, substituted or unsubstituted C$_1$-C$_6$haloalkyl, substituted or unsubstituted C$_3$-C$_6$cycloalkyl, substituted or unsubstituted C$_2$-C$_5$heterocycloalkyl, substituted or unsubstituted aryl, or substituted or unsubstituted heteroaryl;

R$^3$ is H, halogen, —CN, —N(R$^{12}$)$_2$, —OR$^6$, —CH(OR$^6$)R$^{12}$, —C(=O)R$^{12}$, —C(=O)N(R$^{12}$)$_2$, —S(=O)$_2$R$^{12}$, —S(=O)$_2$N(R$^{12}$)$_2$, —N(R$^{12}$)C(=O)R$^{12}$, —N(R$^{12}$)S(=O)$_2$R$^{12}$, substituted or unsubstituted C$_1$-C$_6$ alkyl, substituted or unsubstituted C$_1$-C$_6$haloalkyl, substituted or unsubstituted C$_3$-C$_6$cycloalkyl, substituted or unsubstituted C$_2$-C$_5$heterocycloalkyl, substituted or unsubstituted aryl, or substituted or unsubstituted heteroaryl;

R$^4$ is H, halogen, —CN, —N(R$^{12}$)$_2$, —C(=O)R$^{12}$, —C(=O)N(R$^{12}$)$_2$, —S(=O)$_2$R$^{12}$, substituted or unsubstituted C$_1$-C$_6$alkyl, substituted or unsubstituted C$_1$-C$_6$haloalkyl, substituted or unsubstituted aryl, or substituted or unsubstituted heteroaryl;

R$^5$ is H, halogen, —CN, —N(R$^{12}$)$_2$, —OR$^6$, —C(=O)R$^{12}$, —C(=O)N(R$^{12}$)$_2$, —N(R$^{12}$)C(=O)R$^{12}$, —S(=O)$_2$R$^{12}$, —N(R$^{12}$)S(=O)$_2$R$^{12}$, —S(=O)$_2$N(R$^{12}$)$_2$, substituted or unsubstituted C$_1$-C$_6$alkyl, substituted or unsubstituted C$_1$-C$_6$haloalkyl, substituted or unsubstituted aryl, or substituted or unsubstituted heteroaryl;

each R$^6$ is independently H, substituted or unsubstituted C$_1$-C$_6$alkyl, substituted or unsubstituted C$_1$-C$_6$haloalkyl, or substituted or unsubstituted C$_1$-C$_{10}$heteroalkyl.

R$^7$ is H, CN, substituted or unsubstituted C$_1$-C$_6$alkyl, substituted or unsubstituted C$_3$-C$_6$ cycloalkyl, or substituted or unsubstituted aryl;

R$^8$ is H, —NR$^{10}$R$^{11}$, substituted or unsubstituted C$_1$-C$_6$alkyl, substituted or unsubstituted C$_1$-C$_6$aminoalkyl, substituted or unsubstituted C$_3$-C$_6$cycloalkyl, or substituted or unsubstituted C$_2$-C$_6$heterocycloalkyl;

R$^9$ is H or substituted or unsubstituted C$_1$-C$_6$alkyl;

R$^{10}$ and hR$^{11}$ are each independently H, substituted or unsubstituted C$_1$-C$_6$alkyl, or substituted or unsubstituted C$_1$-C$_8$heteroalkyl; or R$^{10}$ and R$^{11}$ are taken together with the nitrogen to which they are attached to form a substituted or unsubstituted C$_2$-C$_9$heterocycloalkyl;

each R$^{12}$ is independently H, substituted or unsubstituted C$_1$-C$_6$alkyl, or substituted or unsubstituted aryl;

each R$^{13}$ is independently halogen, —CN, —OR$^6$, —C(=O)N(R$^{12}$)$_2$, —N(R$^{12}$)C(=O)R$^{12}$, —N(R$^{12}$)S(=O)$_2$R$^{12}$, —N(S(=O)$_2$R$^{12}$)$_2$, —S(=O)$_2$R$^{12}$, —S(=O)$_2$N(R$^{12}$)$_2$, substituted or unsubstituted C$_1$-C$_6$alkyl, substituted or unsubstituted C$_1$-C$_6$haloalkyl, or substituted or unsubstituted C$_1$-C$_{10}$heteroalkyl;

R$^{14}$ is H or substituted or unsubstituted C$_1$-C$_6$alkyl; or when B is C(R$^3$), then R$^3$ and R$^{14}$ are taken together with the carbon atoms to which they are attached to form a substituted or unsubstituted heterocycloalkyl;

each R$^{15}$, R$^{16}$, R$^{17}$, and R$^{18}$ is independently selected from the group consisting of H, F, —OR$^6$, and substituted or unsubstituted C$_1$-C$_6$alkyl; or $R^{15}$ and $R^{17}$ are taken together with the carbon atoms to which they are attached to form a substituted or unsubstituted $C_4$-$C_7$cycloalkyl; or $R^{15}$ and $R^{18}$ are taken together with the carbon atoms to which they are attached to form a substituted or unsubstituted $C_4$-$C_7$cycloalkyl; or $R^{16}$ and $R^{17}$ are taken together with the carbon atoms to which they are attached to form a substituted or unsubstituted $C_4$-$C_7$cycloalkyl; or $R^{16}$ and $R^{18}$ are taken together with the carbon atoms to which they are attached to form a substituted or unsubstituted $C_4$-$C_7$cycloalkyl;

m is 0, 1, or 2;

n is 0 or 1; and p is 0, 1, 2, or 3; or a pharmaceutically acceptable salt or solvate thereof.

In certain embodiments, disclosed herein is small molecule modulator of Formula (I*), or a pharmaceutically acceptable salt or solvate thereof:

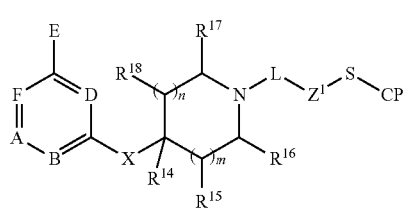

Formula (I*)

wherein,

A is N or $C(R^2)$;

B is N or $C(R^3)$;

D is N or $C(R^4)$;

E is H or

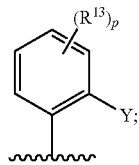

F is N or $C(R^5)$;

X is absent, —O—, —$NR^6$—, or —S—;

Y is H, halogen, —$OR^6$, substituted or unsubstituted $C_1$-$C_6$alkyl, or substituted or unsubstituted $C_1$-$C_6$haloalkyl;

L is —C(=O)—, —S(=O)—, or —S(=O)$_2$—;

$Z^1$ is —$C(R^7)_2$—$CR^8R^9$— or —$CR^7$=$CR^8$—;

$R^2$ is H, halogen, —CN, —$N(R^{12})_2$, —$OR^6$, —$CH(OR^6)R^{12}$, —$C(=O)R^{12}$, —$C(=O)N(R^{12})_2$, —$S(=O)_2R^{12}$, —$S(=O)_2N(R^{12})_2$, —$N(R^{12})C(=O)R^{12}$, —$N(R^{12})S(=O)_2R^{12}$, substituted or unsubstituted $C_1$-$C_6$ alkyl, substituted or unsubstituted $C_1$-$C_6$haloalkyl, substituted or unsubstituted $C_3$-$C_6$cycloalkyl, substituted or unsubstituted $C_2$-$C_5$heterocycloalkyl, substituted or unsubstituted aryl, or substituted or unsubstituted heteroaryl;

$R^3$ is H, halogen, —CN, —$N(R^{12})_2$, —$OR^6$, —$CH(OR^6)R^{12}$, —$C(=O)R^{12}$, —$C(=O)N(R^{12})_2$, —$S(=O)_2R^{12}$, —$S(=O)_2N(R^{12})_2$, —$N(R^{12})C(=O)R^{12}$, —$N(R^{12})S(=O)_2R^{12}$, substituted or unsubstituted $C_1$-$C_6$ alkyl, substituted or unsubstituted $C_1$-$C_6$haloalkyl, substituted or unsubstituted $C_3$-$C_6$cycloalkyl, substituted or unsubstituted $C_2$-$C_5$heterocycloalkyl, substituted or unsubstituted aryl, or substituted or unsubstituted heteroaryl;

$R^4$ is H, halogen, —CN, —$N(R^{12})_2$, —$C(=O)R^{12}$, —$C(=O)N(R^{12})_2$, —$S(=O)_2R^{12}$, substituted or unsubstituted $C_1$-$C_6$alkyl, substituted or unsubstituted $C_1$-$C_6$haloalkyl, substituted or unsubstituted aryl, or substituted or unsubstituted heteroaryl;

$R^5$ is H, halogen, —CN, —$N(R^{12})_2$, —$OR^6$, —$C(=O)R^{12}$, —$C(=O)N(R^{12})_2$, —$N(R^{12})C(=O)R^{12}$, —$S(=O)_2R^{12}$, —$N(R^{12})S(=O)_2R^{12}$, —$S(=O)_2N(R^{12})_2$, substituted or unsubstituted $C_1$-$C_6$alkyl, substituted or unsubstituted $C_1$-$C_6$haloalkyl, substituted or unsubstituted aryl, or substituted or unsubstituted heteroaryl;

each $R^6$ is independently H, substituted or unsubstituted $C_1$-$C_6$alkyl, substituted or unsubstituted $C_1$-$C_6$haloalkyl, or substituted or unsubstituted $C_1$-$C_{10}$heteroalkyl;

$R^7$ is H, —CN, substituted or unsubstituted $C_1$-$C_6$alkyl, substituted or unsubstituted $C_3$-$C_6$cycloalkyl, or substituted or unsubstituted aryl;

$R^8$ is H, —$NR^{10}R^{11}$, substituted or unsubstituted $C_1$-$C_6$alkyl, substituted or unsubstituted $C_1$-$C_6$aminoalkyl, substituted or unsubstituted $C_3$-$C_6$cycloalkyl, substituted or unsubstituted $C_{1-6}$alkylene-$C_{6-10}$ aryl, or substituted or unsubstituted $C_2$-$C_6$heterocycloalkyl;

$R^9$ is H or substituted or unsubstituted $C_1$-$C_6$alkyl;

$R^{10}$ and $R^{11}$ are each independently H, substituted or unsubstituted $C_1$-$C_6$alkyl, or substituted or unsubstituted $C_1$-$C_8$heteroalkyl; or $R^{10}$ and $R^{11}$ are taken together with the nitrogen to which they are attached to form a substituted or unsubstituted $C_2$-$C_9$heterocycloalkyl;

each $R^{12}$ is independently H, substituted or unsubstituted $C_1$-$C_6$alkyl, substituted or unsubstituted $C_1$-$C_6$heteroalkyl, or substituted or unsubstituted aryl; or two $R^{12}$ on the same nitrogen are taken together with the nitrogen to which they are attached to form a substituted or unsubstituted $C_2$-$C_9$heterocycloalkyl;

each $R^{13}$ is independently halogen, —CN, —$OR^6$, —$C(=O)N(R^{12})_2$, —$N(R^{12})C(=O)R^{12}$, —$N(R^{12})S(=O)_2R^{12}$, —$N(S(=O)_2R^{12})_2$, —$S(=O)_2R^{12}$, —$S(=O)_2N(R^{12})_2$, —$(CH_2)_p$—$(OCH_2CH_2)_q$— substituted $C_{1-4}$ alkyl, substituted or unsubstituted $C_1$-$C_6$alkyl, substituted or unsubstituted $C_1$-$C_6$haloalkyl, or substituted or unsubstituted $C_1$-$C_{20}$heteroalkyl;

$R^{14}$ is H or substituted or unsubstituted $C_1$-$C_6$alkyl;

each $R^{15}$, $R^{16}$, $R^{17}$, and $R^{18}$ is independently selected from the group consisting of H, F, —$OR^6$, and substituted or unsubstituted $C_1$-$C_6$alkyl;

m is 0, 1, or 2;

n is 0 or 1;

each p is independently 0, 1, 2, or 3;

p is 1-6;

S represents the sulfur atom of a cysteine residue C287 as set forth in SEQ ID NO: 1, or cysteine residue C286 as set forth in SEQ ID NO: 2 or 3; and CP represents the cereblon polypeptide set forth in SEQ ID NO: 1, 2, or 3.

In some embodiments, S is the cysteine residue C287 as set forth in SEQ ID NO: 1.

In some embodiments, S is the cysteine residue C286 as set forth in SEQ ID NO: 2.

In some embodiments, S is the cysteine residue C286 as set forth in SEQ ID NO: 3.

In some embodiments, the compound of Formula (I*) has a structure of Formula (Ia), or a pharmaceutically acceptable salt or solvate thereof:

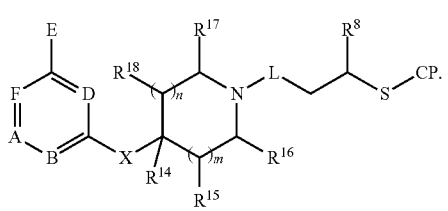

Formula (Ia)

In some embodiments, the compound of Formula (I*) has a structure of Formula (Ib), or a pharmaceutically acceptable salt or solvate thereof:

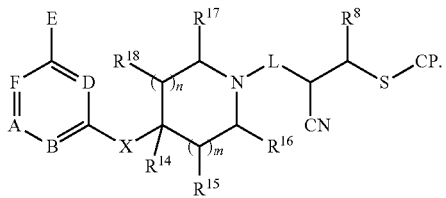

Formula (Ib)

In some embodiments, $R^8$ is H, substituted or unsubstituted $C_1$-$C_6$alkyl, or substituted or unsubstituted $C_1$-$C_6$aminoalkyl.

In some embodiments, $R^8$ is H, unsubstituted $C_1$-$C_6$alkyl; $C_1$-$C_6$alkyl substituted with one or more substituents selected from $C_{6-10}$ aryl, $C_{3-8}$ cycloalkyl, 3-10 membered heterocyclyl, 5-10 membered heteroaryl, halogen, and amine; $C_{1-6}$ alkylene-$C_{6-10}$ aryl substituted with one or more substituents selected from $C_{1-6}$ alkyl, alkoxyl, halogen, and amine; and substituted or unsubstituted $C_1$-$C_6$aminoalkyl.

In some embodiments, A is $C(R^2)$. In some embodiments, $R^2$ is H, halogen, —CN, —N($R^{12}$)$_2$, —OR$^6$, —C(=O)N($R^{12}$)$_2$, —S(=O)$_2$R$^{12}$, or —S(=O)$_2$N($R^{12}$)$_2$.

In some embodiments, B is $C(R^3)$. In some embodiments, $R^3$ is H.

In some embodiments, D is $C(R^4)$. In some embodiments, $R^4$ is H.

In some embodiments, E is H. In some embodiments, E is

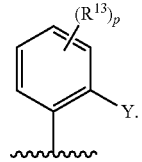

In some embodiments, Y is:
H, —OR$^6$, halogen, substituted or unsubstituted $C_1$-$C_6$alkyl, or substituted or unsubstituted $C_1$-$C_6$haloalkyl; or
H, —OH, —OCH$_3$, —OCH$_2$CH$_3$, —OCF$_3$, F, Cl, Br, —CH$_3$, —CH$_2$CH$_3$, —CH$_2$CH$_2$CH$_3$, —CH(CH$_3$)$_2$, —CF$_3$, —CF$_2$CH$_3$, or —CH$_2$CF$_3$.

In some embodiments, $R^{13}$ is

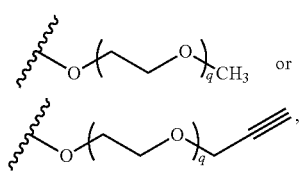

and q is 1, 2, 3, 4, 5, or 6.

In some embodiments, F is $C(R^5)$. In some embodiments, $R^5$ is H.

In some embodiments, X is absent or —O—.

In some embodiments, $R^{14}$ is H.

In some embodiments, one or more of $R^{15}$, $R^{16}$, $R^{17}$, and $R^{18}$ is independently selected from the group consisting of H, F, —OR$^6$, and substituted or unsubstituted $C_1$-$C_4$alkyl.

In some embodiments, m is 0 or 1 and p is 0, 1, or 2.

In some embodiments, the small molecule modulator is selected from:

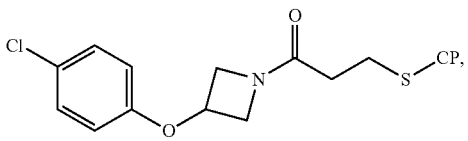

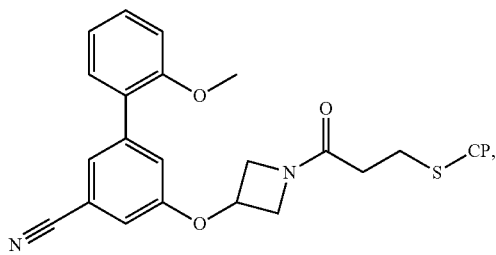

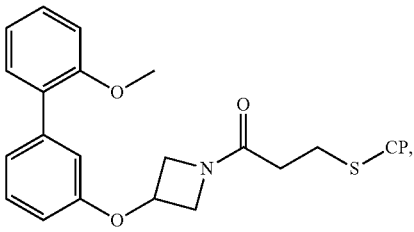

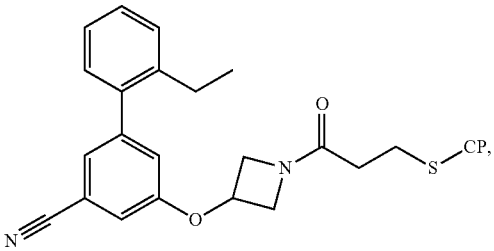

-continued
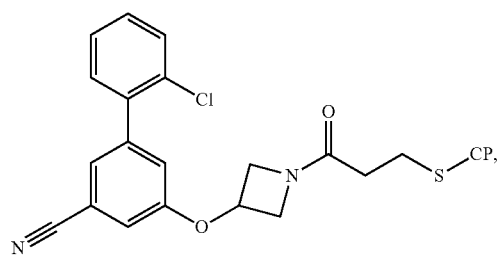
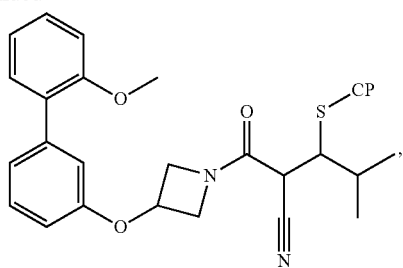
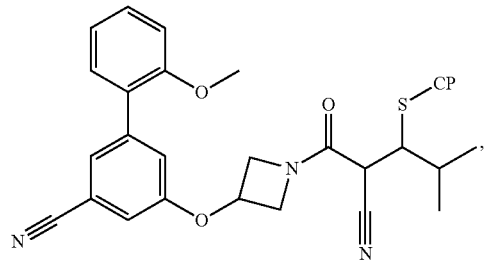
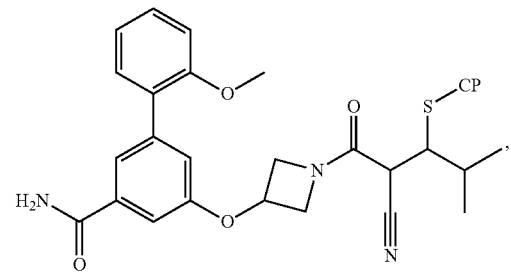
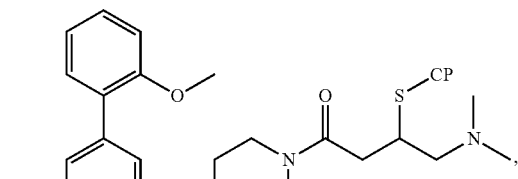
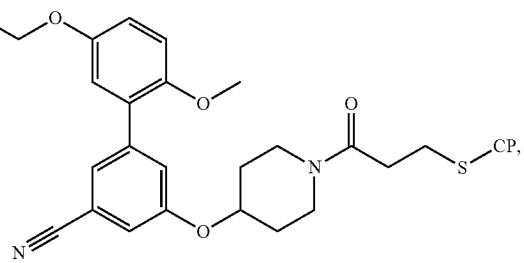
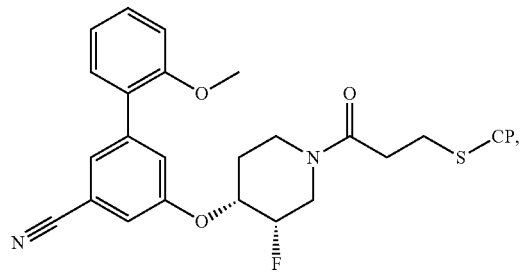
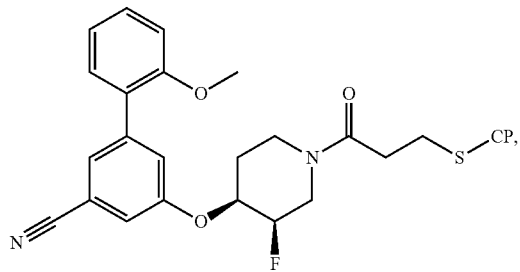
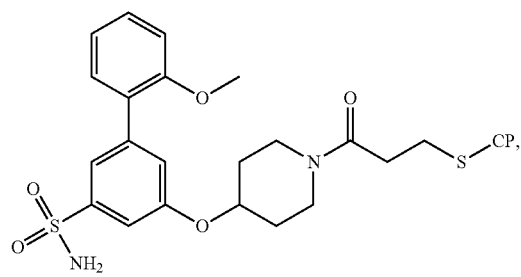
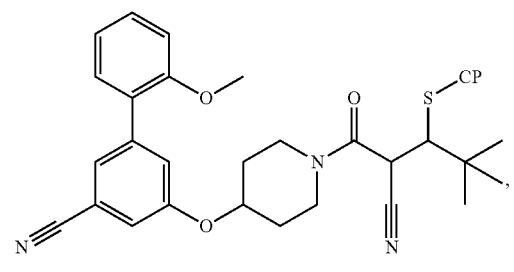

83
84
-continued
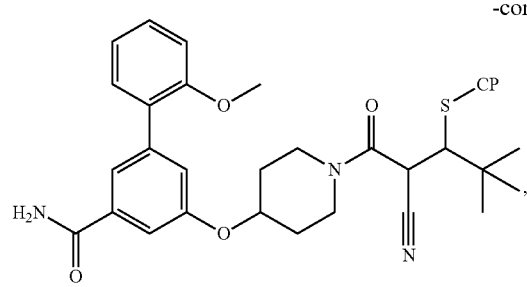
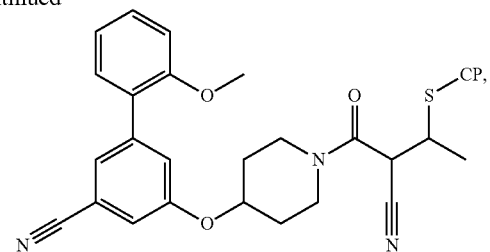
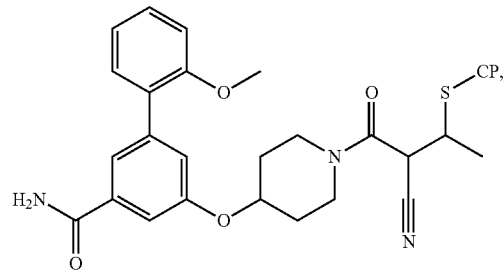
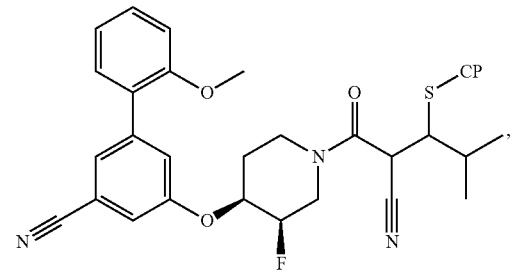
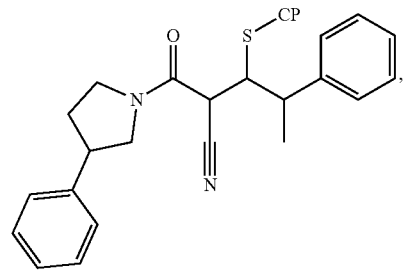
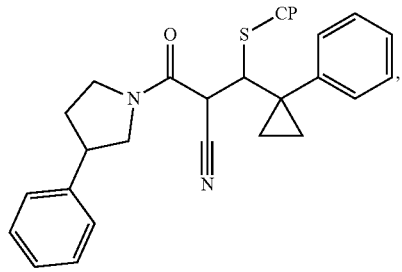
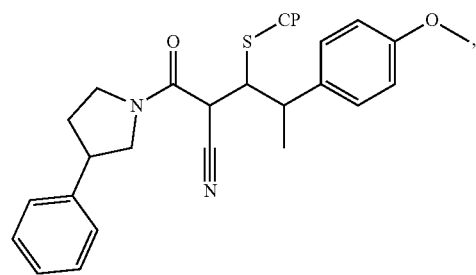
-continued
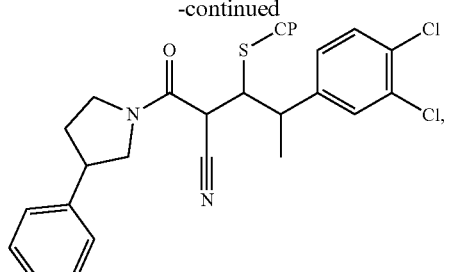
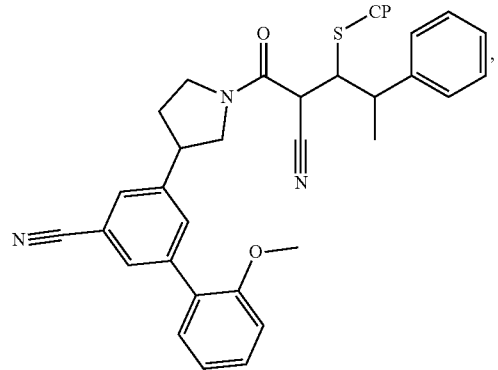
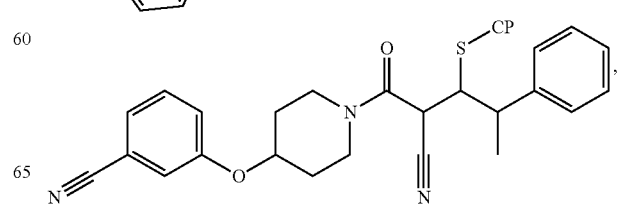

-continued

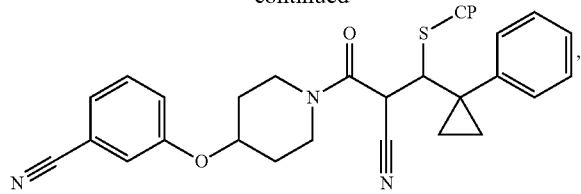

or a pharmaceutically acceptable salt or solvate thereof.

In some embodiments, A is CR$^2$, and B, D, and F are each CH. In some embodiments, R$^2$ is CN.

In some embodiments, E is

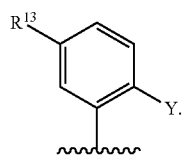

In some embodiments, R$^{13}$ is —(CH$_2$)$_p$—(OCH$_2$CH$_2$)$_q$—O- substituted or unsubstituted C$_{1-4}$ alkyl. In some embodiments, R$^{13}$ is —(OCH$_2$CH$_2$)$_4$.OCH$_2$CN.

In one aspect, the compound of Formula (I), Formula (I*), Formula (Ia), Formula (Ib), Formula (II), Formula (IIA), Formula (III), or Formula (IV) possesses one or more stereocenters and each stereocenter exists independently in either the R or S configuration. The compounds presented herein include all diastereomeric, enantiomeric, and epimeric forms as well as the appropriate mixtures thereof. The compounds and methods provided herein include all cis, trans, syn, anti, entgegen (E), and zusammen (Z) isomers as well as the appropriate mixtures thereof. In certain embodiments, compounds described herein are prepared as their individual stereoisomers by reacting a racemic mixture of the compound with an optically active resolving agent to form a pair of diastereoisomeric compounds/salts, separating the diastereomers and recovering the optically pure enantiomers. In some embodiments, resolution of enantiomers is carried out using covalent diastereomeric derivatives of the compounds described herein. In another embodiment, diastereomers are separated by separation/resolution techniques based upon differences in solubility. In other embodiments, separation of stereoisomers is performed by chromatography or by the forming diastereomeric salts and separation by recrystallization, or chromatography, or any combination thereof. Jean Jacques, Andre Collet, Samuel H. Wilen, "Enantiomers, Racemates and Resolutions", John Wiley And Sons, Inc., 1981. In one aspect, stereoisomers are obtained by stereoselective synthesis.

In some embodiments, the exogenous Michael acceptor does not have a structure of

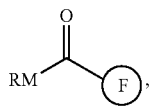
(Formula 1)

wherein: RM is a reactive moiety selected from a Michael acceptor moiety, a leaving group moiety, or a moiety capable of forming a covalent bond with the thiol group of a cysteine residue; and wherein the small molecule fragment can be covalently bond to a cysteine residue of the cysteine-containing polypeptide. In some embodiments, R is selected from:

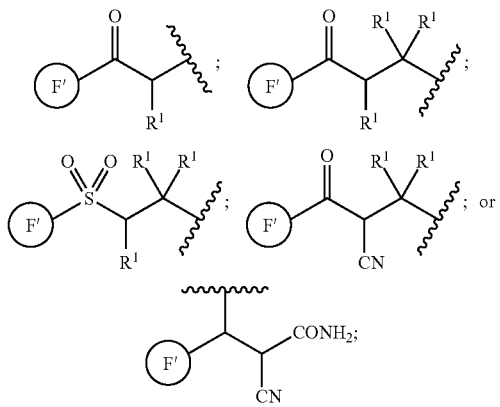

wherein R$^1$ is H, C1-C3 alkyl, or aryl; and F' is a small molecule fragment moiety.

In some embodiments, the exogenous Michael receptor is not a compound selected in Table A.

TABLE A

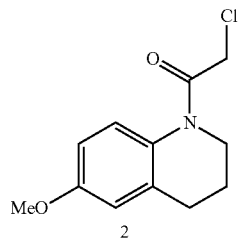

2

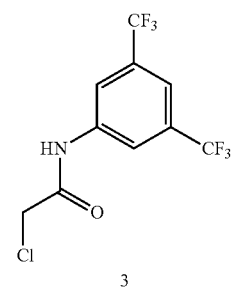

3

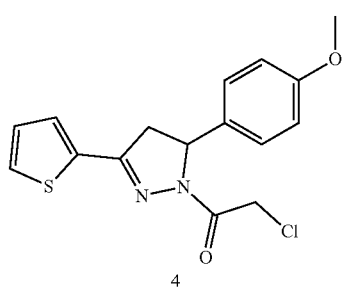

4

TABLE A-continued
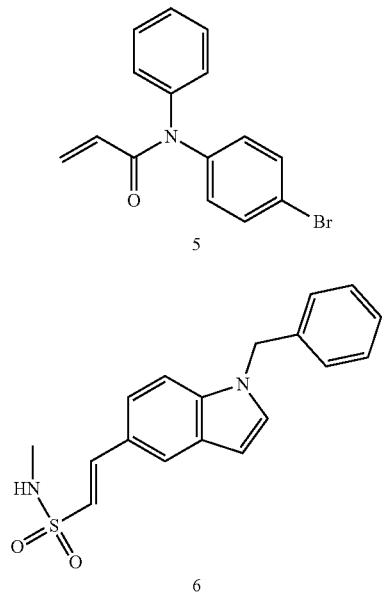
5
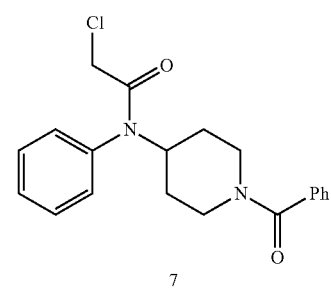
6
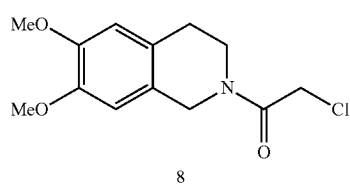
7
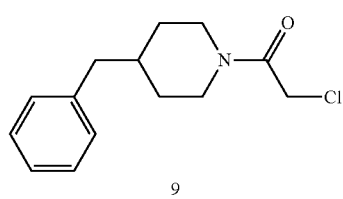
8
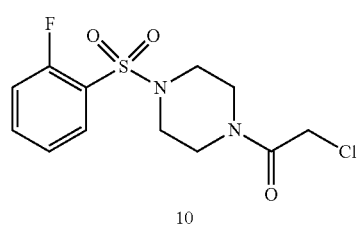
9
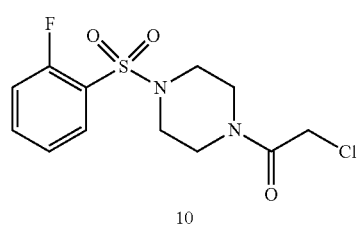
10
TABLE A-continued
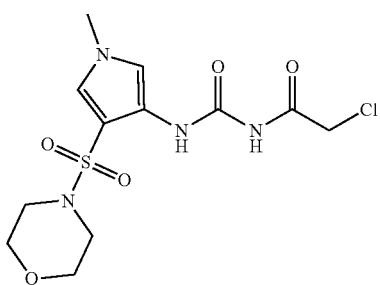 [SMILES: Cn1cc(NC(=O)NC(=O)CCl)c(S(=O)(=O)N2CCOCC2)c1]
11
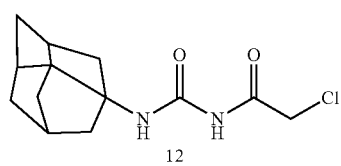
12
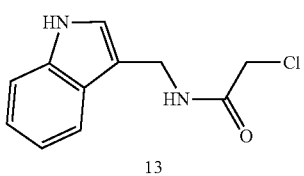
13
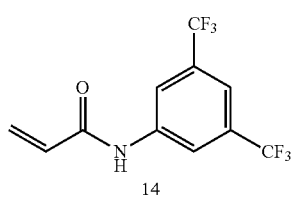
14
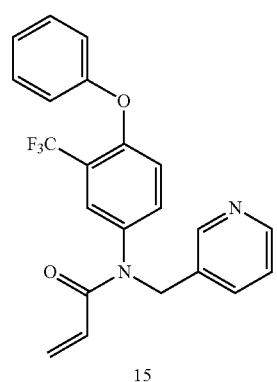
15
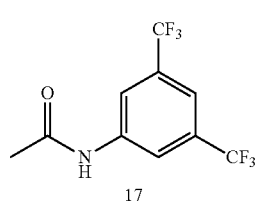
17

TABLE A-continued
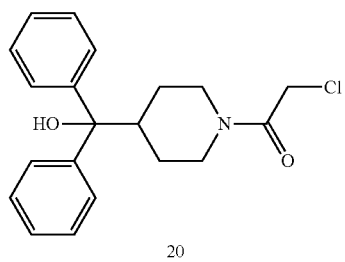
20
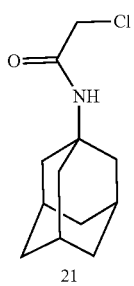
21
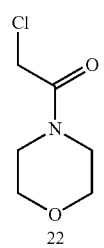
22
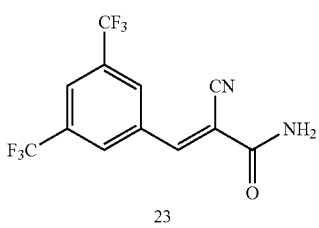
23
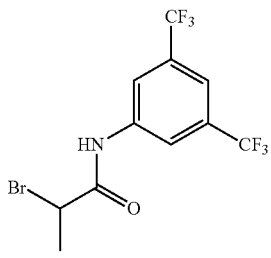
24
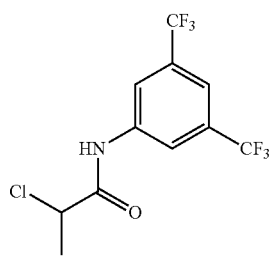 [SMILES: CC(Cl)C(=O)Nc1cc(C(F)(F)F)cc(C(F)(F)F)c1]
25
TABLE A-continued
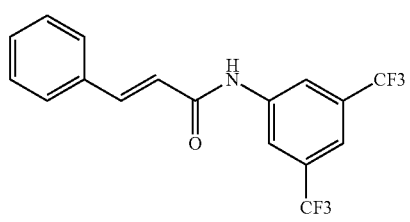 [SMILES: O=C(/C=C/c1ccccc1)Nc1cc(C(F)(F)F)cc(C(F)(F)F)c1]
26
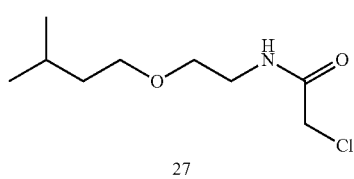
27
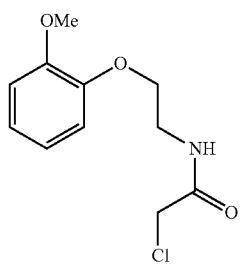 [SMILES: COc1ccccc1OCCNC(=O)CCl]
28
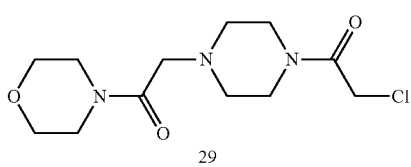
29
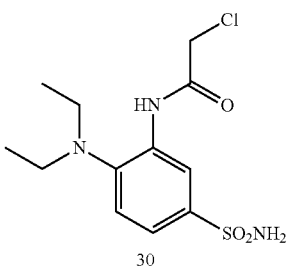
30
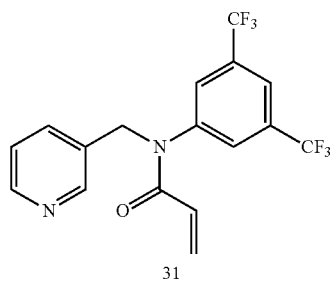
31

TABLE A-continued
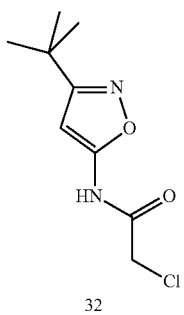
32
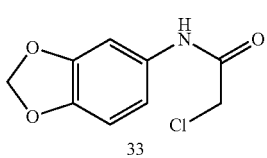
33
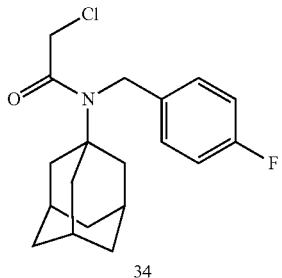
34
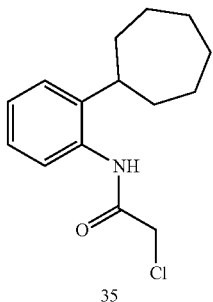
35
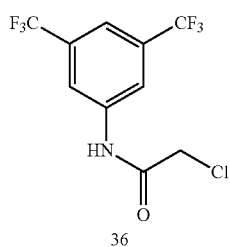
36
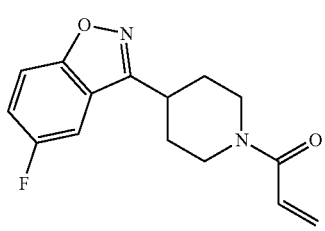 [SMILES: C=CC(=O)N1CCC(c2noc3ccc(F)cc23)CC1]
37
TABLE A-continued
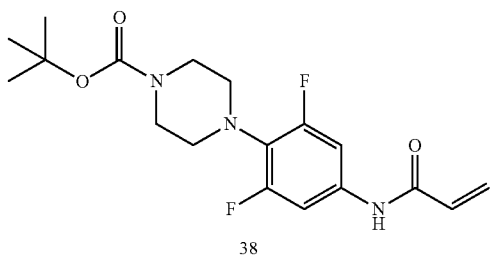
38
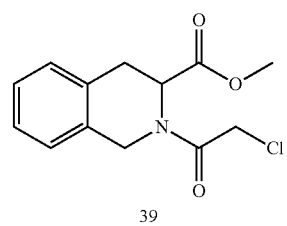
39
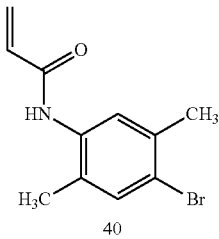
40
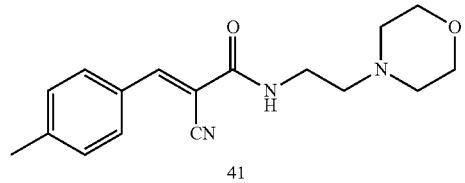
41
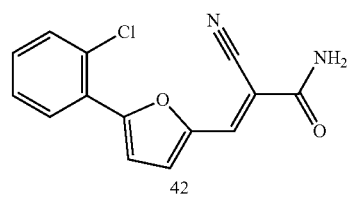
42
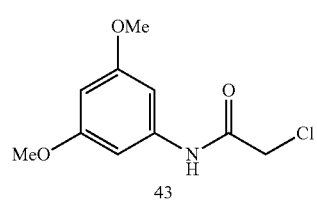
43
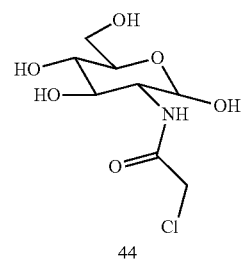
44

TABLE A-continued
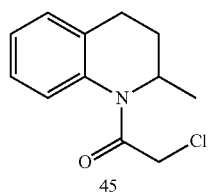
45
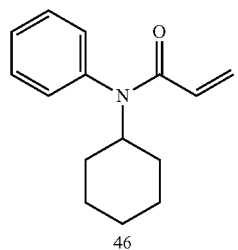
46
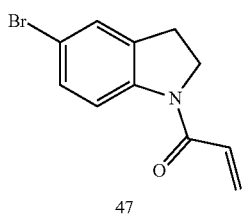
47
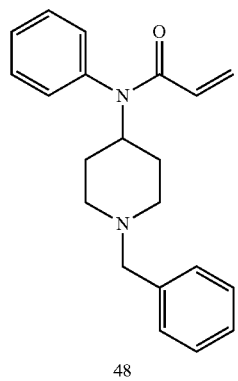
48
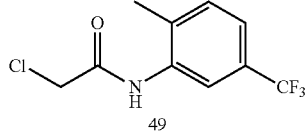
49
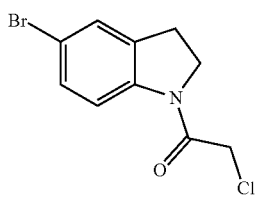 [SMILES: O=C(CCl)N1CCc2cc(Br)ccc21]
50
TABLE A-continued
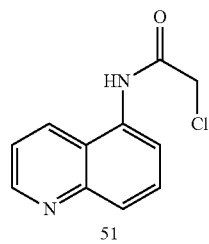
51
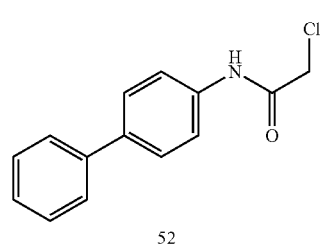
52
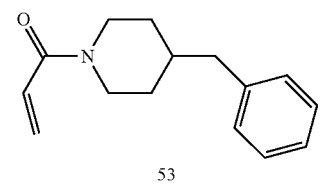
53
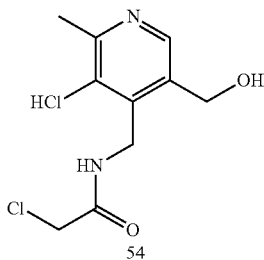
54
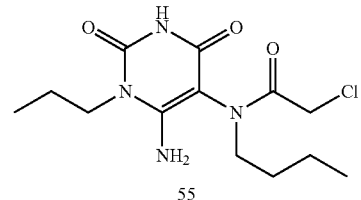
55
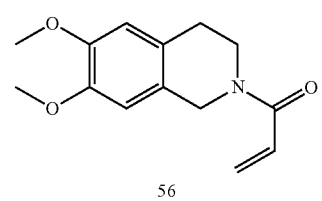
56

TABLE A-continued

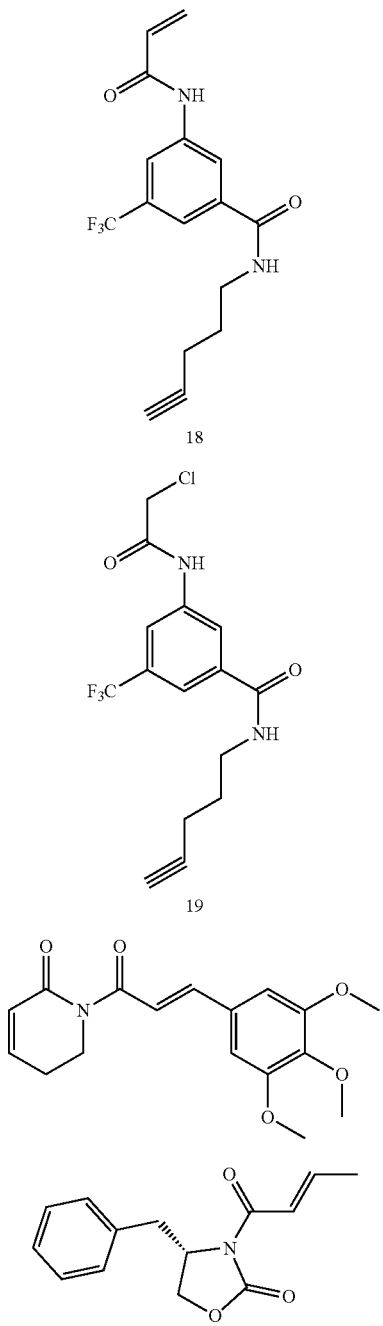

In another embodiment, the compounds described herein are labeled isotopically (e.g. with a radioisotope) or by another other means, including, but not limited to, the use of chromophores or fluorescent moieties, bioluminescent labels, or chemiluminescent labels.

Compounds described herein include isotopically-labeled compounds, which are identical to those recited in the various formulae and structures presented herein, but for the fact that one or more atoms are replaced by an atom having an atomic mass or mass number different from the atomic mass or mass number usually found in nature. Examples of isotopes that can be incorporated into the present compounds include isotopes of hydrogen, carbon, nitrogen, oxygen, sulfur, fluorine and chlorine, such as, for example, $^2H$, $^3H$, $^{13}C$, $^{14}C$, $^{15}N$, $^{18}O$, $^{17}O$, $^{35}S$, $^{18}F$, $^{36}Cl$. In one aspect, isotopically-labeled compounds described herein, for example those into which radioactive isotopes such as $^3H$ and $^{14}C$ are incorporated, are useful in drug and/or substrate tissue distribution assays. In one aspect, substitution with isotopes such as deuterium affords certain therapeutic advantages resulting from greater metabolic stability, such as, for example, increased in vivo half-life or reduced dosage requirements.

Compounds described herein may be formed as, and/or used as, acceptable salts. The type of acceptable salts, include, but are not limited to: (1) acid addition salts, formed by reacting the free base form of the compound with an acceptable: inorganic acid, such as, for example, hydrochloric acid, hydrobromic acid, sulfuric acid, phosphoric acid, metaphosphoric acid, and the like; or with an organic acid, such as, for example, acetic acid, propionic acid, hexanoic acid, cyclopentanepropionic acid, glycolic acid, pyruvic acid, lactic acid, malonic acid, succinic acid, malic acid, maleic acid, fumaric acid, trifluoroacetic acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, toluenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, butyric acid, phenylacetic acid, phenylbutyric acid, valproic acid, and the like; (2) salts formed when an acidic proton present in the parent compound is replaced by a metal ion, e.g., an alkali metal ion (e.g. lithium, sodium, potassium), an alkaline earth ion (e.g. magnesium, or calcium), or an aluminum ion. In some cases, compounds described herein may coordinate with an organic base, such as, but not limited to, ethanolamine, diethanolamine, triethanolamine, tromethamine, N-methylglucamine, dicyclohexylamine, tris (hydroxymethyl)methylamine. In other cases, compounds described herein may form salts with amino acids such as, but not limited to, arginine, lysine, and the like. Acceptable inorganic bases used to form salts with compounds that include an acidic proton, include, but are not limited to, aluminum hydroxide, calcium hydroxide, potassium hydroxide, sodium carbonate, sodium hydroxide, and the like.

It should be understood that a reference to a pharmaceutically acceptable salt includes the solvent addition forms, particularly solvates. Solvates contain either stoichiometric or non-stoichiometric amounts of a solvent, and may be formed during the process of crystallization with pharmaceutically acceptable solvents such as water, ethanol, and the like. Hydrates are formed when the solvent is water, or alcoholates are formed when the solvent is alcohol. Solvates of compounds described herein can be conveniently prepared or formed during the processes described herein. In addition, the compounds provided herein can exist in unsolvated as well as solvated forms. In general, the solvated forms are considered equivalent to the unsolvated forms for the purposes of the compounds and methods provided herein.

Synthesis of Michael Receptor

In some embodiments, the synthesis of compounds described herein are accomplished using means described in the chemical literature, using the methods described herein, or by a combination thereof. In addition, solvents, temperatures and other reaction conditions presented herein may vary.

In other embodiments, the starting materials and reagents used for the synthesis of the compounds described herein are synthesized or are obtained from commercial sources, such as, but not limited to, Sigma-Aldrich, Fisher Scientific (Fisher Chemicals), and Acros Organics.

In further embodiments, the compounds described herein, and other related compounds having different substituents are synthesized using techniques and materials described herein as well as those that are recognized in the field, such as described, for example, in Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), Larock's Comprehensive Organic Transformations (VCH Publishers Inc., 1989), March, Advanced Organic Chemistry $4^{th}$ Ed., (Wiley 1992); Carey and Sundberg, Advanced Organic Chemistry $4^{th}$ Ed., Vols. A and B (Plenum 2000, 2001), and Green and Wuts, Protective Groups in Organic Synthesis $3^{rd}$ Ed., (Wiley 1999) (all of which are incorporated by reference for such disclosure). General methods for the preparation of compounds as disclosed herein may be derived from reactions and the reactions may be modified by the use of appropriate reagents and conditions, for the introduction of the various moieties found in the formulae as provided herein. As a guide the following synthetic methods may be utilized.

In the reactions described, it may be necessary to protect reactive functional groups, for example hydroxy, amino, imino, thio or carboxy groups, where these are desired in the final product, in order to avoid their unwanted participation in reactions. A detailed description of techniques applicable to the creation of protecting groups and their removal are described in Greene and Wuts, Protective Groups in Organic Synthesis, 3rd Ed., John Wiley & Sons, New York, N.Y., 1999, and Kocienski, Protective Groups, Thieme Verlag, New York, N.Y., 1994, which are incorporated herein by reference for such disclosure).

In some embodiments, the compounds of Formula (I), Formula (I*), Formula (Ia), Formula (Ib), Formula (II), Formula (IIA), Formula (III), or Formula (IV) are purchased from a variety of vendors, including Sigma Aldrich, Acros, Fisher, Fluka, Santa Cruz, CombiBlocks, BioBlocks, and Matrix Scientific.

Methods of Modification

Some embodiments relate to method of modifying a cereblon protein, the method comprising contacting a cereblon protein to an exogenous Michael receptor in vivo. In some embodiments, the method further comprises providing an effective amount of the exogenous Michael receptor to allow the cereblon protein to undergo a Michael addition reaction.

In some embodiments, wherein the modification occurs at cysteine 287 as set forth in SEQ ID NO:1, or cysteine 286 as set forth in SEQ ID NO: 2 or 3. In some embodiments, the modification does not occur at cysteine 318 as set forth in SEQ ID NO:1 or cysteine 317 as set forth in SEQ ID NO: 2 or 3.

Cells, Analytical Techniques, and Instrumentation

In certain embodiments, also described herein are methods for profiling cereblon to determine a reactive or ligandable cysteine residue. In some instances, the methods comprising profiling a cereblon cell sample or a cereblon cell lysate sample. In some embodiments, the cell sample or cell lysate sample is obtained from cells of an animal. In some instances, the animal cell includes a cell from a marine invertebrate, fish, insects, amphibian, reptile, or mammal. In some instances, the mammalian cell is a primate, ape, equine, bovine, porcine, canine, feline, or rodent. In some instances, the mammal is a primate, ape, dog, cat, rabbit, ferret, or the like. In some cases, the rodent is a mouse, rat, hamster, gerbil, hamster, chinchilla, or guinea pig. In some embodiments, the bird cell is from a canary, parakeet or parrots. In some embodiments, the reptile cell is from a turtles, lizard or snake. In some cases, the fish cell is from a tropical fish. In some cases, the fish cell is from a zebrafish (e.g. *Danino rerio*). In some cases, the worm cell is from a nematode (e.g. *C. elegans*). In some cases, the amphibian cell is from a frog. In some embodiments, the arthropod cell is from a tarantula or hermit crab.

In some embodiments, the cereblon cell sample or cell lysate sample is obtained from a mammalian cell. In some instances, the mammalian cell is an epithelial cell, connective tissue cell, hormone secreting cell, a nerve cell, a skeletal muscle cell, a blood cell, or an immune system cell.

Exemplary mammalian cells include, but are not limited to, 293A cell line, 293FT cell line, 293F cells, 293 H cells, HEK 293 cells, CHO DG44 cells, CHO—S cells, CHO-K1 cells, Expi293F™ cells, Flp-In™ T-REx™ 293 cell line, Flp-In™-293 cell line, Flp-In™-3T3 cell line, Flp-In™-BHK cell line, Flp-In™-CHO cell line, Flp-In™-CV-1 cell line, Flp-In™-Jurkat cell line, FreeStyle™ 293-F cells, FreeStyle™ CHO—S cells, GripTite™ 293 MSR cell line, GS—CHO cell line, HepaRG™ cells, T-REx™ Jurkat cell line, Per.C6 cells, T-REx™-293 cell line, T-REx™-CHO cell line, T-REx™-HeLa cell line, NC-HIMT cell line, and PC12 cell line.

In some instances, the cereblon cell sample or cell lysate sample is obtained from cells of a tumor cell line. In some instances, the cell sample or cell lysate sample is obtained from cells of a solid tumor cell line. In some instances, the solid tumor cell line is a sarcoma cell line. In some instances, the solid tumor cell line is a carcinoma cell line. In some embodiments, the sarcoma cell line is obtained from a cell line of alveolar rhabdomyosarcoma, alveolar soft part sarcoma, ameloblastoma, angiosarcoma, chondrosarcoma, chordoma, clear cell sarcoma of soft tissue, dedifferentiated liposarcoma, desmoid, desmoplastic small round cell tumor, embryonal rhabdomyosarcoma, epithelioid fibrosarcoma, epithelioid hemangioendothelioma, epithelioid sarcoma, esthesioneuroblastoma, Ewing sarcoma, extrarenal rhabdoid tumor, extraskeletal myxoid chondrosarcoma, extraskeletal osteosarcoma, fibrosarcoma, giant cell tumor, hemangiopericytoma, infantile fibrosarcoma, inflammatory myofibroblastic tumor, Kaposi sarcoma, leiomyosarcoma of bone, liposarcoma, liposarcoma of bone, malignant fibrous histiocytoma (MFH), malignant fibrous histiocytoma (WE) of bone, malignant mesenchymoma, malignant peripheral nerve sheath tumor, mesenchymal chondrosarcoma, myxofibrosarcoma, myxoid liposarcoma, myxoinflammatory fibroblastic sarcoma, neoplasms with perivascular epitheioid cell differentiation, osteosarcoma, parosteal osteosarcoma, neoplasm with perivascular epitheioid cell differentiation, periosteal osteosarcoma, pleomorphic liposarcoma, pleomorphic rhabdomyosarcoma, PNET/extraskeletal Ewing tumor, rhabdomyosarcoma, round cell liposarcoma, small cell osteosarcoma, solitary fibrous tumor, synovial sarcoma, telangiectatic osteosarcoma.

In some embodiments, the carcinoma cell line is obtained from a cell line of adenocarcinoma, squamous cell carcinoma, adenosquamous carcinoma, anaplastic carcinoma, large cell carcinoma, small cell carcinoma, anal cancer, appendix cancer, bile duct cancer (i.e., cholangiocarcinoma), bladder cancer, brain tumor, breast cancer, cervical cancer, colon cancer, cancer of Unknown Primary (CUP), esophageal cancer, eye cancer, fallopian tube cancer, gastroenterological cancer, kidney cancer, liver cancer, lung cancer, medulloblastoma, melanoma, oral cancer, ovarian cancer, pancreatic cancer, parathyroid disease, penile cancer, pituitary tumor, prostate cancer, rectal cancer, skin cancer, stomach cancer, testicular cancer, throat cancer, thyroid cancer, uterine cancer, vaginal cancer, or vulvar cancer.

In some instances, the cereblon cell sample or cell lysate sample is obtained from cells of a hematologic malignant cell line. In some instances, the hematologic malignant cell line is a T-cell cell line. In some instances, B-cell cell line. In some instances, the hematologic malignant cell line is obtained from a T-cell cell line of: peripheral T-cell lymphoma not otherwise specified (PTCL-NOS), anaplastic large cell lymphoma, angioimmunoblastic lymphoma, cutaneous T-cell lymphoma, adult T-cell leukemia/lymphoma (ATLL), blastic NK-cell lymphoma, enteropathy-type T-cell lymphoma, hematosplenic gamma-delta T-cell lymphoma, lymphoblastic lymphoma, nasal NK/T-cell lymphomas, or treatment-related T-cell lymphomas.

In some instances, the hematologic malignant cell line is obtained from a B-cell cell line of: acute lymphoblastic leukemia (ALL), acute myelogenous leukemia (AML), chronic myelogenous leukemia (CML), acute monocytic leukemia (AMoL), chronic lymphocytic leukemia (CLL), high-risk chronic lymphocytic leukemia (CLL), small lymphocytic lymphoma (SLL), high-risk small lymphocytic lymphoma (SLL), follicular lymphoma (FL), mantle cell lymphoma (MCL), Waldenstrom's macroglobulinemia, multiple myeloma, extranodal marginal zone B cell lymphoma, nodal marginal zone B cell lymphoma, Burkitt's lymphoma, non-Burkitt high grade B cell lymphoma, primary mediastinal B-cell lymphoma (PMBL), immunoblastic large cell lymphoma, precursor B-lymphoblastic lymphoma, B cell prolymphocytic leukemia, lymphoplasmacytic lymphoma, splenic marginal zone lymphoma, plasma cell myeloma, plasmacytoma, mediastinal (thymic) large B cell lymphoma, intravascular large B cell lymphoma, primary effusion lymphoma, or lymphomatoid granulomatosis.

In some embodiments, the cereblon cell sample or cell lysate sample is obtained from a tumor cell line. Exemplary tumor cell line includes, but is not limited to, 600MPE, AU565, BT-20, BT-474, BT-483, BT-549, Evsa-T, Hs578T, MCF-7, MDA-MB-231, SkBr3, T-47D, HeLa, DU145, PC3, LNCaP, A549, H1299, NCI-H460, A2780, SKOV-3/Luc, Neuro2a, RKO, RKO-AS45-1, HT-29, SW1417, SW948, DLD-1, SW480, Capan-1, MC/9, B72.3, B25.2, B6.2, B38.1, DMS 153, SU.86.86, SNU-182, SNU-423, SNU-449, SNU-475, SNU-387, Hs 817.T, LMH, LMH/2A, SNU-398, PLHC-1, HepG2/SF, OCI-Ly1, OCI-Ly2, OCI-Ly3, OCI-Ly4, OCI-Ly6, OCI-Ly7, OCI-Ly10, OCI-Ly18, OCI-Ly19, U2932, DB, HBL-1, RIVA, SUDHL2, TMD8, MEC1, MEC2, 8E5, C≡CRF-CEM, MOLT-3, TALL-104, AML-193, THP-1, BDCM, HL-60, Jurkat, RPMI 8226, MOLT-4, RS4, K-562, KASUMI-1, Daudi, GA-10, Raji, JeKo-1, NK-92, and Mino.

In some embodiments, the cereblon cell sample or cell lysate sample is from any tissue or fluid from an individual. Samples include, but are not limited to, tissue (e.g. connective tissue, muscle tissue, nervous tissue, or epithelial tissue), whole blood, dissociated bone marrow, bone marrow aspirate, pleural fluid, peritoneal fluid, central spinal fluid, abdominal fluid, pancreatic fluid, cerebrospinal fluid, brain fluid, ascites, pericardial fluid, urine, saliva, bronchial lavage, sweat, tears, ear flow, sputum, hydrocele fluid, semen, vaginal flow, milk, amniotic fluid, and secretions of respiratory, intestinal or genitourinary tract. In some embodiments, the cell sample or cell lysate sample is a tissue sample, such as a sample obtained from a biopsy or a tumor tissue sample. In some embodiments, the cell sample or cell lysate sample is a blood serum sample. In some embodiments, the cell sample or cell lysate sample is a blood cell sample containing one or more peripheral blood mononuclear cells (PBMCs). In some embodiments, the cell sample or cell lysate sample contains one or more circulating tumor cells (CTCs). In some embodiments, the cell sample or cell lysate sample contains one or more disseminated tumor cells (DTC, e.g., in a bone marrow aspirate sample).

In some embodiments, the cereblon cell sample or cell lysate sample is obtained from the individual by any suitable means of obtaining the sample using well-known and routine clinical methods. Procedures for obtaining tissue samples from an individual are well known. For example, procedures for drawing and processing tissue sample such as from a needle aspiration biopsy is well-known and is employed to obtain a sample for use in the methods provided. Typically, for collection of such a tissue sample, a thin hollow needle is inserted into a mass such as a tumor mass for sampling of cells that, after being stained, will be examined under a microscope.

Sample Preparation and Analysis

In some embodiments, a cereblon sample solution comprises a cell sample, a cell lysate sample, or a sample comprising isolated proteins. In some instances, the sample solution comprises a solution such as a buffer (e.g. phosphate buffered saline) or a media. In some embodiments, the media is an isotopically labeled media. In some instances, the sample solution is a cell solution.

In some embodiments, the cereblon solution sample (e.g., cell sample, cell lysate sample, or comprising isolated proteins) is incubated with a compound of Formula (I), Formula (I*), Formula (Ia), Formula (Ib), Formula (II), Formula (IIA), Formula (III), or Formula (IV) for analysis of protein-probe interactions. In some instances, the solution sample (e.g., cell sample, cell lysate sample, or comprising isolated proteins) is further incubated in the presence of an additional compound probe prior to addition of the compound of Formula (I), Formula (I*), Formula (Ia), Formula (Ib), Formula (II), Formula (IIA), Formula (III), or Formula (IV). In other instances, the solution sample (e.g., cell sample, cell lysate sample, or comprising isolated proteins) is further incubated with a ligand, in which the ligand does not contain a photoreactive moiety and/or an alkyne group. In such instances, the solution sample is incubated with a probe and a ligand for competitive protein profiling analysis.

In some cases, the cereblon cell sample or the cell lysate sample is compared with a control. In some cases, a difference is observed between a set of probe protein interactions between the sample and the control. In some instances, the difference correlates to the interaction between the small molecule fragment and the proteins.

In some embodiments, one or more methods are utilized for labeling a cereblon solution sample (e.g. cell sample, cell lysate sample, or comprising isolated proteins) for analysis of probe protein interactions. In some instances, a method comprises labeling the sample (e.g. cell sample, cell lysate sample, or comprising isolated proteins) with an enriched media. In some cases, the sample (e.g. cell sample, cell lysate sample, or comprising isolated proteins) is labeled with isotope-labeled amino acids, such as $^{13}C$ or $^{15}N$-labeled amino acids. In some cases, the labeled sample is further compared with a non-labeled sample to detect differences in probe protein interactions between the two samples. In some instances, this difference is a difference of a target protein and its interaction with a small molecule ligand in the labeled sample versus the non-labeled sample. In some instances, the difference is an increase, decrease or a lack of protein-probe interaction in the two samples. In some instances, the isotope-labeled method is termed SILAC, stable isotope labeling using amino acids in cell culture.

In some embodiments, a method comprises incubating a solution sample (e.g. cell sample, cell lysate sample, or comprising isolated proteins) with a labeling group (e.g., an isotopically labeled labeling group) to tag one or more proteins of interest for further analysis. In such cases, the labeling group comprises a biotin, a streptavidin, bead, resin, a solid support, or a combination thereof, and further comprises a linker that is optionally isotopically labeled. As described above, the linker can be about 5, 6, 7, 8, 9, 10, 11, 12, 13, 14, 15 or more residues in length and might further comprise a cleavage site, such as a protease cleavage site (e.g., TEV cleavage site). In some cases, the labeling group is a biotin-linker moiety, which is optionally isotopically labeled with $^{13}C$ and $^{15}N$ atoms at one or more amino acid residue positions within the linker. In some cases, the biotin-linker moiety is a isotopically-labeled TEV-tag as described in Weerapana, et al., "Quantitative reactivity profiling predicts functional cysteines in proteomes," *Nature* 468(7325): 790-795.

In some embodiments, an isotopic reductive dimethylation (ReDi) method is utilized for processing a sample. In some cases, the ReDi labeling method involves reacting peptides with formaldehyde to form a Schiff base, which is then reduced by cyanoborohydride. This reaction dimethylates free amino groups on N-termini and lysine side chains and monomethylates N-terminal prolines. In some cases, the ReDi labeling method comprises methylating peptides from a first processed sample with a "light" label using reagents with hydrogen atoms in their natural isotopic distribution and peptides from a second processed sample with a "heavy" label using deuterated formaldehyde and cyanoborohydride. Subsequent proteomic analysis (e.g., mass spectrometry analysis) based on a relative peptide abundance between the heavy and light peptide version might be used for analysis of probe-protein interactions.

In some embodiments, isobaric tags for relative and absolute quantitation (iTRAQ) method is utilized for processing a sample. In some cases, the iTRAQ method is based on the covalent labeling of the N-terminus and side chain amines of peptides from a processed sample. In some cases, reagent such as 4-plex or 8-plex is used for labeling the peptides.

In some embodiments, the probe-protein complex is further conjugated to a chromophore, such as a fluorophore. In some instances, the probe-protein complex is separated and visualized utilizing an electrophoresis system, such as through a gel electrophoresis, or a capillary electrophoresis. Exemplary gel electrophoresis includes agarose based gels, polyacrylamide based gels, or starch based gels. In some instances, the probe-protein is subjected to a native electrophoresis condition. In some instances, the probe-protein is subjected to a denaturing electrophoresis condition.

In some instances, the probe-protein after harvesting is further fragmentized to generate protein fragments. In some instances, fragmentation is generated through mechanical stress, pressure, or chemical means. In some instances, the protein from the probe-protein complexes is fragmented by a chemical means. In some embodiments, the chemical means is a protease. Exemplary proteases include, but are not limited to, serine proteases such as chymotrypsin A, penicillin G acylase precursor, dipeptidase E, DmpA aminopeptidase, subtilisin, prolyl oligopeptidase, D-Ala-D-Ala peptidase C, signal peptidase I, cytomegalovirus assemblin, Lon-A peptidase, peptidase Clp, *Escherichia coli* phage K1F endosialidase CIMCD self-cleaving protein, nucleoporin 145, lactoferrin, murein tetrapeptidase LD-carboxypeptidase, or rhomboid-1; threonine proteases such as ornithine acetyltransferase; cysteine proteases such as TEV protease, amidophosphoribosyltransferase precursor, gamma-glutamyl hydrolase (*Rattus norvegicus*), hedgehog protein, DmpA aminopeptidase, papain, bromelain, cathepsin K, calpain, caspase-1, separase, adenain, pyroglutamyl-peptidase I, sortase A, hepatitis C virus peptidase 2, sindbis virus-type nsP2 peptidase, dipeptidyl-peptidase VI, or DeSI-1 peptidase; aspartate proteases such as beta-secretase 1 (BACE1), beta-secretase 2 (BACE2), cathepsin D, cathepsin E, chymosin, napsin-A, nepenthesin, pepsin, plasmepsin, presenilin, or renin; glutamic acid proteases such as AfuGprA; and metalloproteases such as peptidase_M48.

In some instances, the fragmentation is a random fragmentation. In some instances, the fragmentation generates specific lengths of protein fragments, or the shearing occurs at particular sequence of amino acid regions.

In some instances, the protein fragments are further analyzed by a proteomic method such as by liquid chromatography (LC) (e.g. high performance liquid chromatography), liquid chromatography-mass spectrometry (LC-MS), matrix-assisted laser desorption/ionization (MALDI-TOF), gas chromatography-mass spectrometry (GC-MS), capillary electrophoresis-mass spectrometry (CE-MS), or nuclear magnetic resonance imaging (NMR).

In some embodiments, the LC method is any suitable LC methods well known in the art, for separation of a sample into its individual parts. This separation occurs based on the interaction of the sample with the mobile and stationary phases. Since there are many stationary/mobile phase combinations that are employed when separating a mixture, there are several different types of chromatography that are classified based on the physical states of those phases. In some embodiments, the LC is further classified as normal-phase chromatography, reverse-phase chromatography, size-exclusion chromatography, ion-exchange chromatography, affinity chromatography, displacement chromatography, partition chromatography, flash chromatography, chiral chromatography, and aqueous normal-phase chromatography.

In some embodiments, the LC method is a high performance liquid chromatography (HPLC) method. In some embodiments, the HPLC method is further categorized as normal-phase chromatography, reverse-phase chromatography, size-exclusion chromatography, ion-exchange chromatography, affinity chromatography, displacement chromatography, partition chromatography, chiral chromatography, and aqueous normal-phase chromatography.

In some embodiments, the HPLC method of the present disclosure is performed by any standard techniques well known in the art. Exemplary HPLC methods include hydrophilic interaction liquid chromatography (HILIC), electrostatic repulsion-hydrophilic interaction liquid chromatography (ERLIC) and reverse phase liquid chromatography (RPLC).

In some embodiments, the LC is coupled to a mass spectroscopy as a LC-MS method. In some embodiments, the LC-MS method includes ultra-performance liquid chromatography-electrospray ionization quadrupole time-offlight mass spectrometry (UPLC-ESI-QTOF-MS), ultra-performance liquid chromatography-electrospray ionization tandem mass spectrometry (UPLC-ESI-MS/MS), reverse phase liquid chromatography-mass spectrometry (RPLC-MS), hydrophilic interaction liquid chromatography-mass spectrometry (HILIC-MS), hydrophilic interaction liquid chromatography-triple quadrupole tandem mass spectrometry (HILIC-QQQ), electrostatic repulsion-hydrophilic interaction liquid chromatography-mass spectrometry (ER-LIC-MS), liquid chromatography time-of-flight mass spectrometry (LC-QTOF-MS), liquid chromatography-tandem mass spectrometry (LC-MS/MS), multidimensional liquid chromatography coupled with tandem mass spectrometry (LC/LC-MS/MS). In some instances, the LC-MS method is LC/LC-MS/MS. In some embodiments, the LC-MS methods of the present disclosure are performed by standard techniques well known in the art.

In some embodiments, the GC is coupled to a mass spectroscopy as a GC-MS method. In some embodiments, the GC-MS method includes two-dimensional gas chromatography time-of-flight mass spectrometry (GC*GC-TOFMS), gas chromatography time-of-flight mass spectrometry (GC-QTOF-MS) and gas chromatography-tandem mass spectrometry (GC-MS/MS).

In some embodiments, CE is coupled to a mass spectroscopy as a CE-MS method. In some embodiments, the CE-MS method includes capillary electrophoresis-negative electrospray ionization-mass spectrometry (CE-ESI-MS), capillary electrophoresis-negative electrospray ionization-quadrupole time of flight-mass spectrometry (CE-ESI-QTOF-MS) and capillary electrophoresis-quadrupole time of flight-mass spectrometry (CE-QTOF-MS).

In some embodiments, the nuclear magnetic resonance (NMR) method is any suitable method well known in the art for the detection of one or more cysteine binding proteins or protein fragments disclosed herein. In some embodiments, the NMR method includes one dimensional (1D) NMR methods, two dimensional (2D) NMR methods, solid state NMR methods and NMR chromatography. Exemplary 1D NMR methods include $^1$Hydrogen, $^{13}$Carbon, $^{15}$Nitrogen, $^{17}$Oxygen, $^{19}$Fluorine, $^{31}$Phosphorus, $^{39}$Potassium, $^{23}$Sodium, $^{33}$Sulfur, $^{87}$Strontium, $^{27}$Aluminium, $^{43}$Calcium, $^{35}$Chlorine, $^{37}$Chlorine, $^{63}$Copper, $^{65}$Copper, $^{57}$Iron, $^{25}$Magnesium, $^{199}$Mercury or $^{67}$Zinc NMR method, distortionless enhancement by polarization transfer (DEPT) method, attached proton test (APT) method and 1D-incredible natural abundance double quantum transition experiment (INADEQUATE) method. Exemplary 2D NMR methods include correlation spectroscopy (COSY), total correlation spectroscopy (TOCSY), 2D-INADEQUATE, 2D-adequate double quantum transfer experiment (ADEQUATE), nuclear overhauser effect spectroscopy (NOSEY), rotating-frame NOE spectroscopy (ROESY), heteronuclear multiple-quantum correlation spectroscopy (HMQC), heteronuclear single quantum coherence spectroscopy (HSQC), short range coupling and long range coupling methods. Exemplary solid state NMR method include solid state $^{13}$Carbon NMR, high resolution magic angle spinning (HR-MAS) and cross polarization magic angle spinning (CP-MAS) NMR methods. Exemplary NMR techniques include diffusion ordered spectroscopy (DOSY), DOSY-TOCSY and DOSY-HSQC.

In some embodiments, the protein fragments are analyzed by method as described in Weerapana et al., "Quantitative reactivity profiling predicts functional cysteines in proteomes," *Nature*, 468:790-795 (2010).

In some embodiments, the results from the mass spectroscopy method are analyzed by an algorithm for protein identification. In some embodiments, the algorithm combines the results from the mass spectroscopy method with a protein sequence database for protein identification. In some embodiments, the algorithm comprises ProLuCID algorithm, Probity, Scaffold, SEQUEST, or Mascot.

In some embodiments, a value is assigned to each of the protein from the probe-protein complex. In some embodiments, the value assigned to each of the protein from the probe-protein complex is obtained from the mass spectroscopy analysis. In some instances, the value is the area-under-the curve from a plot of signal intensity as a function of mass-to-charge ratio. In some instances, the value correlates with the reactivity of a Lys residue within a protein.

In some instances, a ratio between a first value obtained from a first protein sample and a second value obtained from a second protein sample is calculated. In some instances, the ratio is greater than 2.5, 3, 3.5, 4, 4.5, 5, 6, 7, 8, 9, 10, 11, 12, 13, 14, 15, 16, 17, 18, 19, or 20. In some cases, the ratio is at most 20.

In some instances, the ratio is calculated based on averaged values. In some instances, the averaged value is an average of at least two, three, or four values of the protein from each cell solution, or that the protein is observed at least two, three, or four times in each cell solution and a value is assigned to each observed time. In some instances, the ratio further has a standard deviation of less than 12, 10, or 8.

In some instances, a value is not an averaged value. In some instances, the ratio is calculated based on value of a protein observed only once in a cell population. In some instances, the ratio is assigned with a value of 20.

Kits/Article of Manufacture

Disclosed herein, in certain embodiments, are kits and articles of manufacture for use to generate a cereblon-probe adduct or with one or more methods described herein. In some embodiments, described herein is a kit for detecting cereblon ligand interaction. In some embodiments, such kit includes small molecule ligands described herein, small molecule fragments or libraries, compound probes described herein, and/or controls, and reagents suitable for carrying out one or more of the methods described herein. In some instances, the kit further comprises samples, such as a cell sample, and suitable solutions such as buffers or media. In some embodiments, the kit further comprises recombinant cereblon protein for use in one or more of the methods described herein. In some embodiments, additional components of the kit comprises a carrier, package, or container that is compartmentalized to receive one or more containers such as vials, tubes, and the like, each of the container(s) comprising one of the separate elements to be used in a method described herein. Suitable containers include, for example, bottles, vials, plates, syringes, and test tubes. In one embodiment, the containers are formed from a variety of materials such as glass or plastic.

The articles of manufacture provided herein contain packaging materials. Examples of pharmaceutical packaging materials include, but are not limited to, bottles, tubes, bags, containers, and any packaging material suitable for a selected formulation and intended mode of use.

For example, the container(s) include probes, test compounds, and one or more reagents for use in a method disclosed herein. Such kits optionally include an identifying description or label or instructions relating to its use in the methods described herein.

A kit typically includes labels listing contents and/or instructions for use, and package inserts with instructions for use. A set of instructions will also typically be included.

In one embodiment, a label is on or associated with the container. In one embodiment, a label is on a container when letters, numbers or other characters forming the label are attached, molded or etched into the container itself; a label is associated with a container when it is present within a receptacle or carrier that also holds the container, e.g., as a package insert. In one embodiment, a label is used to indicate that the contents are to be used for a specific therapeutic application. The label also indicates directions for use of the contents, such as in the methods described herein.

Certain Terminology

Unless defined otherwise, all technical and scientific terms used herein have the same meaning as is commonly understood by one of skill in the art to which the claimed subject matter belongs. It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

The term "promiscuity" as used herein, refers to the percentage of targets that are >40% inhibited by a compound under a given set of conditions. The term "global promiscuity" refer to the number of targets where 500 µM compound inhibits probe labeling by greater than 40% after a 1 hour incubation in a global (TMT) experiment.

The term "$TE_{50}$" refers to the concentration of compound (µM) that must be added for 1 hour in order to inhibit probe labeling by 50%. For example, $TE_{50}$ value can be derived from treating whole cells with a test compound followed by iodoacetamide probe.

As used herein, ranges and amounts can be expressed as "about" a particular value or range. About also includes the exact amount. Hence "about 5 µL" means "about 5 µL" and also "5 µL." Generally, the term "about" includes an amount that would be expected to be within experimental error.

As used herein, $C_1$-$C_x$ (or $C_{1-x}$) includes $C_1$-$C_2$, $C_1$-$C_3$ . . . $C_1$-$C_x$. By way of example only, a group designated as "$C_1$-$C_4$" indicates that there are one to four carbon atoms in the moiety, i.e. groups containing 1 carbon atom, 2 carbon atoms, 3 carbon atoms or 4 carbon atoms. Thus, by way of example only, "$C_1$-$C_4$ alkyl" or "$C_{1-4}$ alkyl" indicates that there are one to four carbon atoms in the alkyl group, i.e., the alkyl group is selected from among methyl, ethyl, propyl, iso-propyl, n-butyl, iso-butyl, sec-butyl, and t-butyl.

"Alkyl" refers to a straight or branched hydrocarbon chain radical, having from one to twenty carbon atoms, and which is attached to the rest of the molecule by a single bond. An alkyl comprising up to 10 carbon atoms is referred to as a $C_1$-$C_{10}$ alkyl, likewise, for example, an alkyl comprising up to 6 carbon atoms is a $C_1$-$C_6$ alkyl. Alkyls (and other moieties defined herein) comprising other numbers of carbon atoms are represented similarly. Alkyl groups include, but are not limited to, $C_1$-$C_{10}$ alkyl, $C_1$-$C_9$ alkyl, $C_1$-$C_8$ alkyl, $C_1$-$C_7$ alkyl, $C_1$-$C_6$ alkyl, $C_1$-$C_5$ alkyl, $C_1$-$C_4$ alkyl, $C_1$-$C_3$ alkyl, $C_1$-$C_2$ alkyl, $C_2$-$C_8$ alkyl, $C_3$-$C_8$ alkyl and $C_4$-$C_8$ alkyl. Representative alkyl groups include, but are not limited to, methyl, ethyl, n-propyl, 1-methylethyl (i-propyl), n-butyl, i-butyl, s-butyl, n-pentyl, 1,1-dimethylethyl (t-butyl), 3-methylhexyl, 2-methylhexyl, 1-ethyl-propyl, and the like. In some embodiments, the alkyl is methyl or ethyl. In some embodiments, the alkyl is —CH(CH$_3$)$_2$ or —C(CH$_3$)$_3$. Unless stated otherwise specifically in the specification, an alkyl group may be optionally substituted as described below. "Alkylene" or "alkylene chain" refers to a straight or branched divalent hydrocarbon chain linking the rest of the molecule to a radical group. In some embodiments, the alkylene is —CH$_2$—, —CH$_2$CH$_2$—, or —CH$_2$CH$_2$CH$_2$—. In some embodiments, the alkylene is —CH$_2$—. In some embodiments, the alkylene is —CH$_2$CH$_2$—. In some embodiments, the alkylene is —CH$_2$CH$_2$CH$_2$—.

"Alkoxy" refers to a radical of the formula —OR where R is an alkyl radical as defined. Unless stated otherwise specifically in the specification, an alkoxy group may be optionally substituted as described below. Representative alkoxy groups include, but are not limited to, methoxy, ethoxy, propoxy, butoxy, pentoxy. In some embodiments, the alkoxy is methoxy. In some embodiments, the alkoxy is ethoxy.

"Alkylamino" refers to a radical of the formula —NHR or —NRR where each R is, independently, an alkyl radical as defined above. Unless stated otherwise specifically in the specification, an alkylamino group may be optionally substituted as described below.

"Aminoalkyl" refers to an alkyl moiety comprising at least one amino substituent. The amino substituent can be on a tertiary, secondary or primary carbon. Unless stated otherwise specifically in the specification, an aminoalkyl group is substituted or unsubstituted.

The term "aromatic" refers to a planar ring having a delocalized π-electron system containing 4n+2 π electrons, where n is an integer. Aromatics can be optionally substituted. The term "aromatic" includes both aryl groups (e.g., phenyl, naphthalenyl) and heteroaryl groups (e.g., pyridinyl, quinolinyl).

"Aryl" refers to an aromatic ring wherein each of the atoms forming the ring is a carbon atom. Aryl groups can be optionally substituted. Examples of aryl groups include, but are not limited to phenyl, and naphthyl. In some embodiments, the aryl is phenyl. Depending on the structure, an aryl group can be a monoradical or a diradical (i.e., an arylene group). Unless stated otherwise specifically in the specification, the term "aryl" or the prefix "ar-" (such as in "aralkyl") is meant to include aryl radicals that are optionally substituted.

"Carboxy" refers to —CO$_2$H. In some embodiments, carboxy moieties may be replaced with a "carboxylic acid bioisostere", which refers to a functional group or moiety that exhibits similar physical and/or chemical properties as a carboxylic acid moiety. A carboxylic acid bioisostere has similar biological properties to that of a carboxylic acid group. A compound with a carboxylic acid moiety can have the carboxylic acid moiety exchanged with a carboxylic acid bioisostere and have similar physical and/or biological properties when compared to the carboxylic acid-containing compound. For example, in one embodiment, a carboxylic acid bioisostere would ionize at physiological pH to roughly the same extent as a carboxylic acid group. Examples of bioisosteres of a carboxylic acid include, but are not limited to:

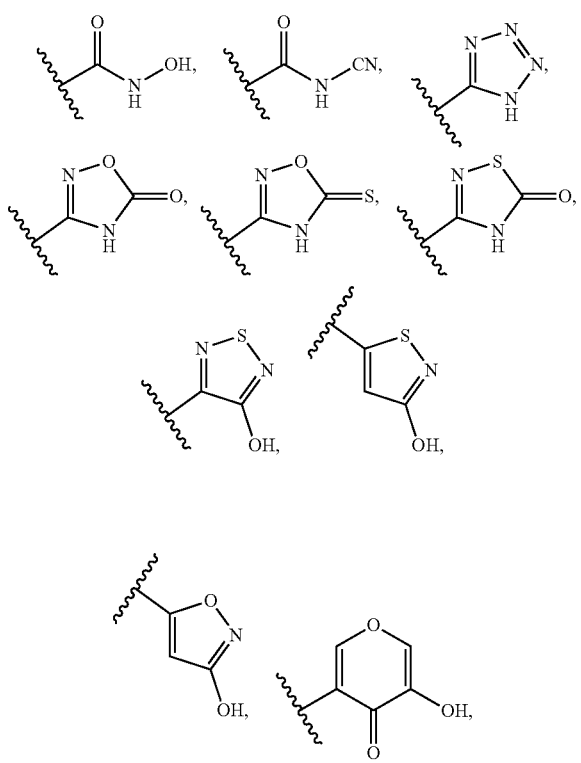

and the like.

"Cycloalkyl" refers to a monocyclic or polycyclic non-aromatic radical, wherein each of the atoms forming the ring (i.e. skeletal atoms) is a carbon atom. Cycloalkyls may be saturated, or partially unsaturated. Cycloalkyls may be fused with an aromatic ring (in which case the cycloalkyl is bonded through a non-aromatic ring carbon atom). Cycloalkyl groups include groups having from 3 to 10 ring atoms. Representative cycloalkyls include, but are not limited to, cycloalkyls having from three to ten carbon atoms, from three to eight carbon atoms, from three to six carbon atoms, or from three to five carbon atoms. Monocyclic cycicoalkyl radicals include, for example, cyclopropyl, cyclobutyl, cyclopentyl, cyclohexyl, cycloheptyl, and cyclooctyl. In some embodiments, the monocyclic cycicoalkyl is cyclopropyl, cyclobutyl, cyclopentyl or cyclohexyl. In some embodiments, the monocyclic cycicoalkyl is cyclopentyl. Polycyclic radicals include, for example, adamantyl, norbornyl, decalinyl, and 3,4-dihydronaphthalen-1 (2H)-one. Unless otherwise stated specifically in the specification, a cycloalkyl group may be optionally substituted.

"Fused" refers to any ring structure described herein which is fused to an existing ring structure. When the fused ring is a heterocyclyl ring or a heteroaryl ring, any carbon atom on the existing ring structure which becomes part of the fused heterocyclyl ring or the fused heteroaryl ring may be replaced with a nitrogen atom.

"Halo" or "halogen" refers to bromo, chloro, fluoro or iodo.

"Haloalkyl" refers to an alkyl radical, as defined above, that is substituted by one or more halo radicals, as defined above, e.g., trifluoromethyl, difluoromethyl, fluoromethyl, trichloromethyl, 2,2,2-trifluoroethyl, 1,2-difluoroethyl, 3-bromo-2-fluoropropyl, 1,2-dibromoethyl, and the like. Unless stated otherwise specifically in the specification, a haloalkyl group may be optionally substituted.

"Haloalkoxy" refers to an alkoxy radical, as defined above, that is substituted by one or more halo radicals, as defined above, e.g., trifluoromethoxy, difluoromethoxy, fluoromethoxy, trichloromethoxy, 2,2,2-trifluoroethoxy, 1,2-difluoroethoxy, 3-bromo-2-fluoropropoxy, 1,2-dibromoethoxy, and the like. Unless stated otherwise specifically in the specification, a haloalkoxy group may be optionally substituted.

"Heteroalkyl" refers to an alkyl radical as described above where one or more carbon atoms of the alkyl is replaced with a O, N or S atom. "Heteroalkylene" or "heteroalkylene chain" refers to a straight or branched divalent heteroalkyl chain linking the rest of the molecule to a radical group. Unless stated otherwise specifically in the specification, the heteroalkyl or heteroalkylene group may be optionally substituted as described below. Representative heteroalkyl groups include, but are not limited to —OCH$_2$OMe, —OCH$_2$CH$_2$OMe, or —OCH$_2$CH$_2$OCH$_2$CH$_2$NH$_2$. Representative heteroalkylene groups include, but are not limited to —OCH$_2$CH$_2$O—, —OCH$_2$CH$_2$OCH$_2$CH$_2$O—, or —OCH$_2$CH$_2$OCH$_2$CH$_2$OCH$_2$CH$_2$O—.

"Heterocycloalkyl" or "heterocyclyl" or "heterocyclic ring" refers to a stable 3- to 14-membered non-aromatic ring radical comprising 2 to 10 carbon atoms and from one to 4 heteroatoms selected from the group consisting of nitrogen, oxygen, and sulfur. Unless stated otherwise specifically in the specification, the heterocycloalkyl radical may be a monocyclic, or bicyclic ring system, which may include fused (when fused with an aryl or a heteroaryl ring, the heterocycloalkyl is bonded through a non-aromatic ring atom) or bridged ring systems. The nitrogen, carbon or sulfur atoms in the heterocyclyl radical may be optionally oxidized. The nitrogen atom may be optionally quaternized. The heterocycloalkyl radical is partially or fully saturated. Examples of such heterocycloalkyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, 1,1-dioxo-thiomorpholinyl. The term heterocycloalkyl also includes all ring forms of carbohydrates, including but not limited to monosaccharides, disaccharides and oligosaccharides. Unless otherwise noted, heterocycloalkyls have from 2 to 10 carbons in the ring. In some embodiments, heterocycloalkyls have from 2 to 8 carbons in the ring. In some embodiments, heterocycloalkyls have from 2 to 8 carbons in the ring and 1 or 2 N atoms. In some embodiments, heterocycloalkyls have from 2 to 10 carbons, 0-2 N atoms, 0-2 O atoms, and 0-1 S atoms in the ring. In some embodiments, heterocycloalkyls have from 2 to 10 carbons, 1-2 N atoms, 0-1 O atoms, and 0-1 S atoms in the ring. It is understood that when referring to the number of carbon atoms in a heterocycloalkyl, the number of carbon atoms in the heterocycloalkyl is not the same as the total number of atoms (including the heteroatoms) that make up the heterocycloalkyl (i.e. skeletal atoms of the heterocycloalkyl ring). Unless stated otherwise specifically in the specification, a heterocycloalkyl group may be optionally substituted.

"Heteroaryl" refers to an aryl group that includes one or more ring heteroatoms selected from nitrogen, oxygen and sulfur. The heteroaryl is monocyclic or bicyclic. Illustrative examples of monocyclic heteroaryls include pyridinyl, imidazolinyl, pyrimidinyl, pyrazolyl, triazolyl, pyrazinyl, tetrazolyl, furyl, thienyl, isoxazolyl, thiazolyl, oxazolyl, isothiazolyl, pyrrolyl, pyridazinyl, triazinyl, oxadiazolyl, thiadiazolyl, furazanyl, indolizine, indole, benzofuran, benzothiophene, indazole, benzimidazole, purine, quinolizine, quinoline, isoquinoline, cinnoline, phthalazine, quinazoline, quinoxaline, 1,8-naphthyridine, and pteridine. Illustrative examples of monocyclic heteroaryls include pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, pyridazinyl, triazinyl, oxadiazolyl, thiadiazolyl, and furazanyl. Illustrative examples of bicyclic heteroaryls include indolizine, indole, benzofuran, benzothiophene, indazole, benzimidazole, purine, quinolizine, quinoline, isoquinoline, cinnoline, phthalazine, quinazoline, quinoxaline, 1,8-naphthyridine, and pteridine. In some embodiments, heteroaryl is pyridinyl, pyrazinyl, pyrimidinyl, thiazolyl, thienyl, thiadiazolyl or furyl. In some embodiments, a heteroaryl contains 0-4 N atoms in the ring. In some embodiments, a heteroaryl contains 1-4 N atoms in the ring. In some embodiments, a heteroaryl contains 0-4 N atoms, 0-1 O atoms, and 0-1 S atoms in the ring. In some embodiments, a heteroaryl contains 1-4 N atoms, 0-1 O atoms, and 0-1 S atoms in the ring. In some embodiments, heteroaryl is a $C_1$-$C_9$heteroaryl. In some embodiments, monocyclic heteroaryl is a $C_1$-$C_5$heteroaryl. In some embodiments, monocyclic heteroaryl is a 5-membered or 6-membered heteroaryl. In some embodiments, a bicyclic heteroaryl is a $C_6$-$C_9$heteroaryl.

The term "optionally substituted" or "substituted" means that the referenced group may be substituted with one or more additional group(s) individually and independently selected from alkyl, haloalkyl, cycloalkyl, aryl, heteroaryl, heterocycloalkyl, —OH, alkoxy, aryloxy, alkylthio, arylthio, alkylsulfoxide, arylsulfoxide, alkylsulfone, arylsulfone, —CN, alkyne, $C_1$-$C_6$alkylalkyne, halogen, acyl, acyloxy, —$CO_2H$, —$CO_2$alkyl, nitro, and amino, including mono- and di-substituted amino groups (e.g. —$NH_2$, —NHR, —$N(R)_2$), and the protected derivatives thereof. In some embodiments, optional substituents are independently selected from alkyl, alkoxy, haloalkyl, cycloalkyl, halogen, —CN, —$NH_2$, —$NH(CH_3)$, —$N(CH_3)_2$, —OH, —$CO_2H$, and —$CO_2$alkyl. In some embodiments, optional substituents are independently selected from fluoro, chloro, bromo, iodo, —$CH_3$, —$CH_2CH_3$, —$CF_3$, —$OCH_3$, and —$OCF_3$. In some embodiments, substituted groups are substituted with one or two of the preceding groups. In some embodiments, an optional substituent on an aliphatic carbon atom (acyclic or cyclic, saturated or unsaturated carbon atoms, excluding aromatic carbon atoms) includes oxo (=O).

The section headings used herein are for organizational purposes only and are not to be construed as limiting the subject matter described.

EXAMPLES

These examples are provided for illustrative purposes only and not to limit the scope of the claims provided herein.
Preparations The preparations set out below are for the synthesis of reagents that were not obtained from commercial sources and were employed for the preparation of compounds disclosed herein. All chiral compounds in the tables and schemes are racemic unless specified otherwise.

Synthesis of 1-[4-(3-bromophenoxy)-1-piperidyl]prop-2-en-1-one

Step 1

To a mixture of 3-bromophenol (12 g, 69.4 mmol) and tert-butyl 4-hydroxypiperidine-1-carboxylate (13.96 g, 69.4 mmol) in THF (350 mL) was added triphenyl phosphine (2.73 g, 104 mmol) in one portion at 0° C. under nitrogen. Diethylazodicarboxylate (DEAD; 18.1 g, 104 mmol) was then added dropwise at 0° C. The mixture was stirred at 20° C. for 12 hours. The mixture was poured into water (100 mL) and extracted with ethyl acetate (100 mL*2). The combined organic phase was washed with brine (100 mL*2), dried with anhydrous sodium sulfate, filtered and concentrated in vacuo. The residue was purified by silica gel chromatography (column height: 250 mm, diameter: 100 mm, 100-200 mesh silica gel, Petroleum ether/Ethyl acetate=80/1, 40/1) to afford tert-butyl 4-(3-bromophenoxy)piperidine-1-carboxylate (6 g, 24% yield) as a yellow oil.

Step 2

A mixture of tert-butyl 4-(3-bromophenoxy)piperidine-1-carboxylate (6 g, 16.8 mmol) in ethyl acetate/HCl (45 mL, 180 mmol) was stirred at 20° C. for 5 hours. The mixture was concentrated in vacuo to afford 4-(3-bromophenoxy)piperidine (5 g, 100% yield) as a yellow solid.

Step 3

To a mixture of the product of 4-(3-bromophenoxy)piperidine (5 g, 19.5 mmol) and triethyl amine (4.08 mL, 29.28 mmol) in dichloromethane (100 mL) under nitrogen was added acryloyl chloride (1.61 mL, 19.5 mmol) dropwise at 0° C. The mixture was stirred at 20° C. for 1 hour. The mixture was poured into water (40 mL) and extracted with dichloromethane (50 mL*2). The combined organic phase was washed with brine (50 mL*2), dried with anhydrous sodium sulfate, filtered and concentrated in vacuo. The residue was purified by silica gel chromatography (column height: 250 mm, diameter: 100 mm, 100-200 mesh silica gel, Petroleum ether/Ethyl acetate=10/1, 2/1) to afford 1-[4-(3-bromophenoxy)-1-piperidyl]prop-2-en-1-one (4 g, 66% yield) as yellow oil.

Example 1: Synthesis of 1-(4-((4'-fluoro-2'-methoxy-[1,1'-biphenyl]-3-yl)oxy)piperidin-1-yl)prop-2-en-1-one

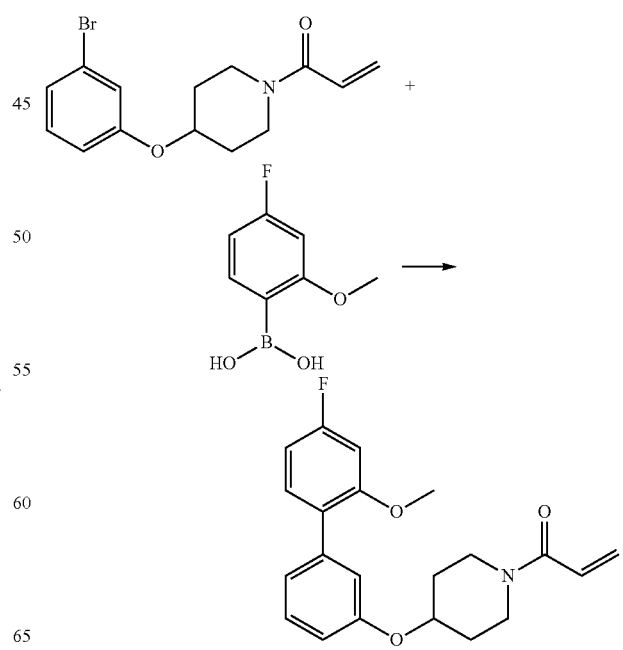

To a mixture of 1-[4-(3-bromophenoxy)-1-piperidyl]prop-2-en-1-one (150 mg, 0.48 mmol) and (4-fluoro-2-methoxyphenyl)boronic acid (106.8 mg, 0.63 mmol) in 1,4-dioxane (4 mL) was added sodium carbonate (102 mg, 0.97 mmol) and tetrakis(triphenylphosphine) palladium (56 mg, 0.048 mmol) in one portion at 20° C. under $N_2$. The mixture was stirred at 100° C. (microwave) for 2 hours. The reaction mixture was quenched by the addition of the saturated aqueous ammonium chloride and extracted with ethyl acetate (15 mL*3). The combined organic layers were washed with brine (10 mL*2), dried over sodium sulfate, filtered and concentrated under reduced pressure to give a residue which was purified by preparative HPLC (neutral conditions; column: Xtimate C18 150*25 mm*5 um; mobile phase: [water (10 mM $NH_4HCO_3$)-ACN]; B %: 40%-60%, 12 min) to give 1-(4-((4'-fluoro-2'-methoxy-[1,1'-biphenyl]-3-yl)oxy)piperidin-1-yl)prop-2-en-1-one (57.4 mg, 33% yield) as a yellow oil. 1H NMR (400 MHz, $CDCl_3$) δ ppm 1.81-2.03 (m, 4H), 3.55 (br s, 1H), 3.80 (s, 6H), 4.52-4.65 (m, 1H), 5.69 (dd, J=10.58, 1.76 Hz, 1H), 6.28 (dd, J=16.76, 1.98 Hz, 1H), 6.60 (dd, J=16.76, 10.58 Hz, 1H), 6.68-6.76 (m, 2H), 6.88 (dd, J=7.83, 2.09 Hz, 1H), 7.02-7.10 (m, 2H), 7.21-7.35, (m, 2H). Mass Spectrometry ("MS") (E+) m/z: 356 ($MH^+$).

The following Examples were prepared in a similar manner to the product of Example 1.

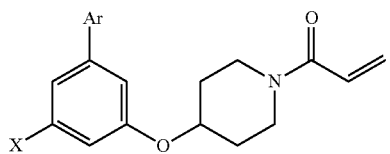

| Example number | Ar | X | m/z [M + H]$^+$ |
|---|---|---|---|
| 2 | 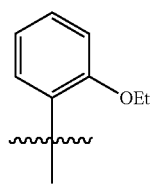 [SMILES: *c1ccccc1OCC] OEt | H | 352 |
| 3 | OH | H | 324 |
| 4 | Cl | H | 342 |
| 5 | OMe | Cl | 372 |
| 6 | Ph | Cl | 342 |
| 7 | OMe | H | 338 |

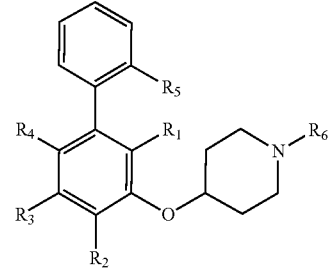

| Example number | R$_1$ | R$_2$ | R$_3$ | R$_4$ | R$_5$ | R$_6$ | m/z [M + H]$^+$ |
|---|---|---|---|---|---|---|---|
| 8 | H | H | H | H | H | 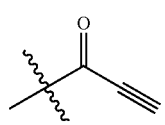 [SMILES: *C(=O)C#C] | 306 |
| 9 | H | H | H | H | OMe | 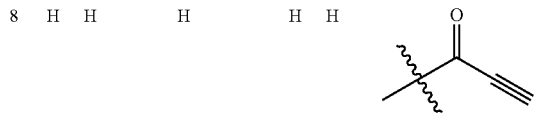 | 336.2 |

-continued
| Example number | R₁ | R₂ | R₃ | R₄ | R₅ | R₆ | m/z [M + H]⁺ |
|---|---|---|---|---|---|---|---|
| 10 | H | H | H | H | H | 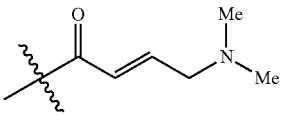 [SMILES: *C(=O)/C=C/CN(C)C] | 365.2 |
| 11 | H | H | H | H | OMe | 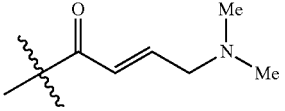 [SMILES: *C(=O)/C=C/CN(C)C] | 395.2 |
| 12 | H | H | CN | H | OMe | 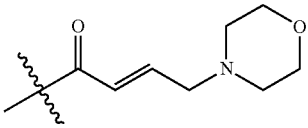 [SMILES: *C(=O)/C=C/CN1CCOCC1] | 462.2 |
| 13 | H | H | CN | H | H | 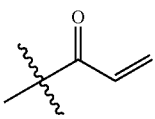 [SMILES: *C(=O)C=C] | 333.2 |
| 14 | H | H | CN | H | OMe | 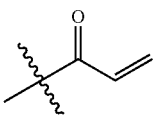 [SMILES: *C(=O)C=C] | 363.2 |
| 15 | H | H | CN | H | Et | 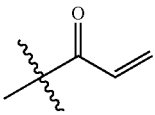 | 361 |
| 16 | H | H | CN | H | OMe | 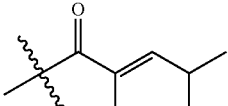 | 430 |
| 17 | H | H | C(O)NH₂ | H | OMe | 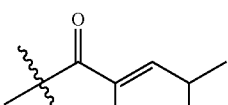 | 4448 |
| 18 | Cl | H | H | H | OMe | 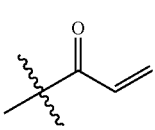 [SMILES: *C(=O)C=C] | 372 |
| 19 | CN | H | H | H | H | 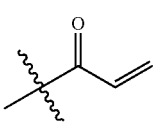 [SMILES: *C(=O)C=C] | 333 |
| 20 | CN | H | H | H | OMe | 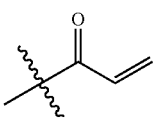 [SMILES: *C(=O)C=C] | 363.2 |

-continued

| Example number | R₁ | R₂ | R₃ | R₄ | R₅ | R₆ | m/z [M + H]⁺ |
|---|---|---|---|---|---|---|---|
| 21 | H | C(O)NH₂ | H | H | OMe | ![acryloyl] | 381.2 |
| 22 | H | H | C(O)NH₂ | H | OMe | ![acryloyl] | 381.2 |
| 23 | H | H | OMe | H | H | ![acryloyl] | 338.2 |
| 24 | H | H | OMe | H | OMe | ![acryloyl] | 368.2 |
| 25 | H | H | C(O)NMe₂ | H | OMe | ![acryloyl] | 409.2 |
| 26 | H | H | C(O)NHMe | H | OMe | ![acryloyl] | 395.2 |

Example 27: Synthesis of 1-(4-((5-(2-methoxyphenyl)pyridazin-3-yl)oxy)piperidin-1-yl)prop-2-en-1-one

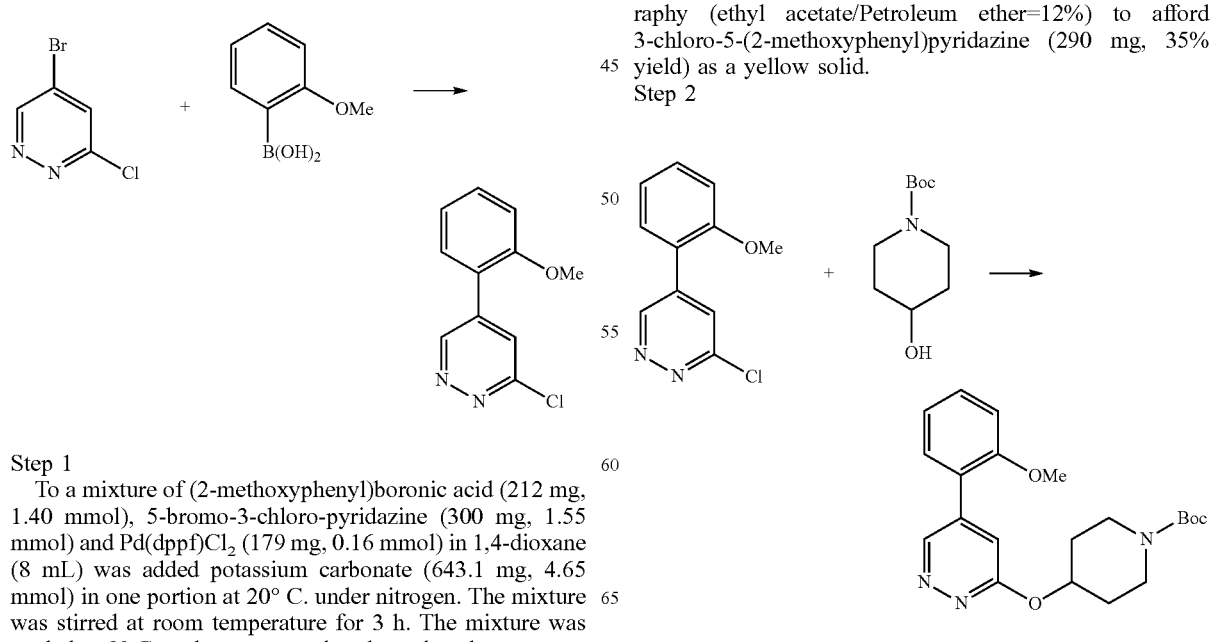

Step 1

To a mixture of (2-methoxyphenyl)boronic acid (212 mg, 1.40 mmol), 5-bromo-3-chloro-pyridazine (300 mg, 1.55 mmol) and Pd(dppf)Cl₂ (179 mg, 0.16 mmol) in 1,4-dioxane (8 mL) was added potassium carbonate (643.1 mg, 4.65 mmol) in one portion at 20° C. under nitrogen. The mixture was stirred at room temperature for 3 h. The mixture was cooled to 0° C. and concentrated under reduced pressure at 40° C. The aqueous phase was extracted with dichloromethane (30 mL*3). The combined organic phase was washed with brine (30 mL), dried with anhydrous sodium sulfate, filtered and concentrated under reduced pressure to give a residue. The residue was purified by silica gel chromatography (ethyl acetate/Petroleum ether=12%) to afford 3-chloro-5-(2-methoxyphenyl)pyridazine (290 mg, 35% yield) as a yellow solid.

Step 2

To a solution of 1-(tert-Butoxycarbonyl)-4-hydroxypiperidine (197 mg, 0.98 mmol) in DMF (3 mL) was added NaH (29.3 mg, 1.22 mmol) and stirred at 0° C. for 30 min. To the mixture was added the product of Step 1 (180 mg, 0.81 mmol) in DMF (2 mL) at 0° C. The reaction was stirred at 100° C. for 3 h. The reaction mixture was concentrated to remove solvent, and then diluted with water (5 mL) and extracted with ethyl acetate (10 mL*3). The combined organic layers were washed with brine (5 mL*3), dried over sodium sulfate, filtered and concentrated under reduced pressure to give a residue. The residue was purified by silica gel chromatography (Ethyl acetate/Petroleum ether=10%) to afford the product (300 mg, 95% yield) which was obtained as a yellow oil.

Step 3

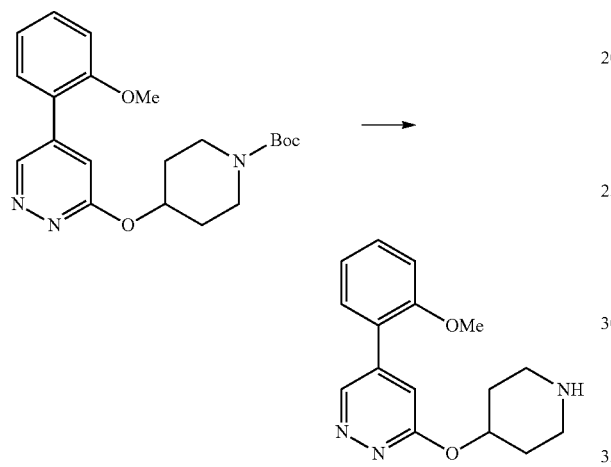

To a solution of the product of Step 2 in dichloromethane (1 mL) was added HCl/EtOAc (10 mL, 4 mol/L). The mixture was stirred at room temperature for 30 min. The reaction was concentrated under reduced pressure to obtain 5-(2-methoxyphenyl)-3-(4-piperidyloxy)pyridazine (45 mg, 86% yield) as a yellow oil.

Step 4

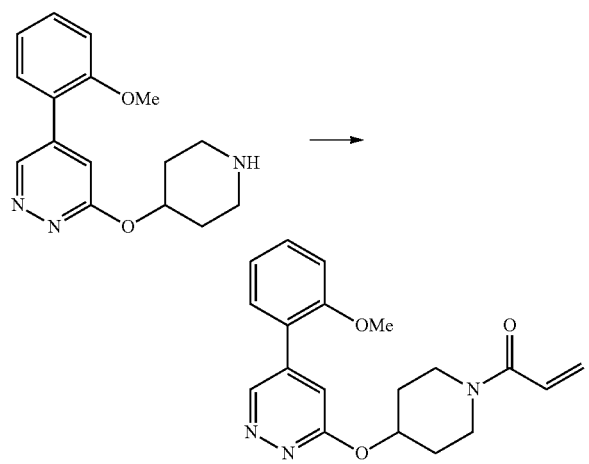

To a solution of the product of Step 3 (63 mg, 0.70 mmol) in dichloromethane (7 mL) was added triethylamine (0.29 mL, 2.10 mmol). To the mixture at 0° C. was added acryloyl chloride (63 mg, 0.70 mmol). The reaction was stirred at room temperature for 3 h. The reaction mixture was concentrated to remove solvent, and then diluted with water (5 mL) and extracted with dichloromethane (10 mL*3), combined organic layers were washed with brine (5 mL), dried over sodium sulfate, filtered and concentrated under reduced pressure to give a residue. The residue was purified by prep-HPLC (neutral condition) to give 1-(4-((5-(2-methoxyphenyl)pyridazin-3-yl)oxy)piperidin-1-yl)prop-2-en-1-one; column: Xbridge C18 150*25 5u; condition: [water (0.04% NH$_3$H$_2$O+10 mM NH$_4$HCO$_3$)-ACN]; B %: 32%-52%, 10.5 min. The title compound was obtained as a white solid (90.9 mg, 38% yield). MS (E+) m/z: 340 (MK).

Example 28: Synthesis of 6-((1-acryloylpiperidin-4-yl)oxy)-4-(2-methoxyphenyl)picolinonitrile Step 1

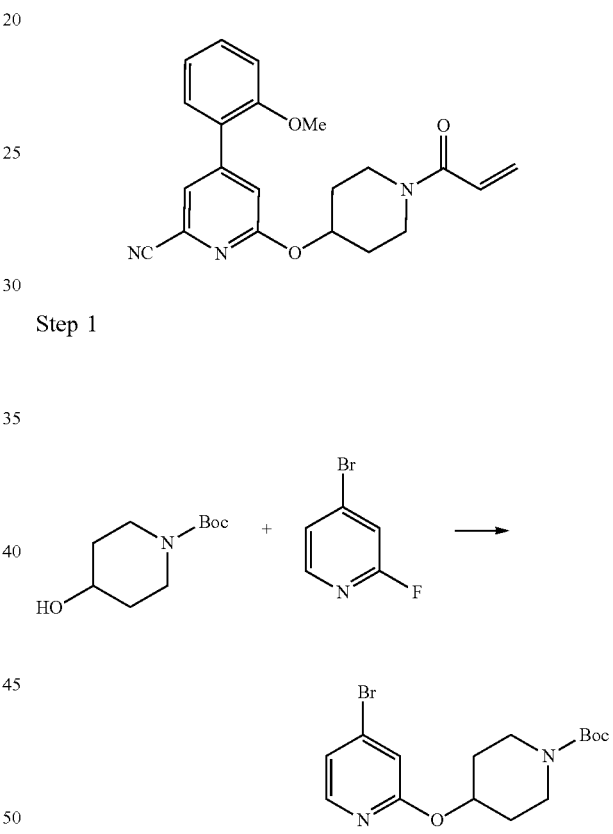

To a solution of 1-(tert-butoxycarbonyl)-4-hydroxypiperidine (2 g, 9.94 mmol) in DMF (20 mL) was added NaH (purity 60 percent, 0.286 g) at 0° C. The mixture was stirred at 0° C. for 10 min. To the reaction at 0° C. was added 4-bromo-2-fluoro-pyridine (1.75 g, 9.94 mmol) in DMF (10 mL) dropwise. The reaction was stirred at room temperature for 12 hours. The reaction was poured into water (30 mL). The aqueous layer was extracted with ethyl acetate (20 mL) twice. The combined organic layers were washed with an aqueous solution of salt and dried over sodium sulfate. The mixture was concentrated under reduced pressure to give a residue which was purified by column chromatography on silica gel (petroleum ether/ethyl acetate=15:1 to 0:1) to give tert-butyl 4-[(4-bromo-2-pyridyl)oxy]piperidine-1-carboxylate (0.90 g, 25% yield) as a white solid.

Step 2

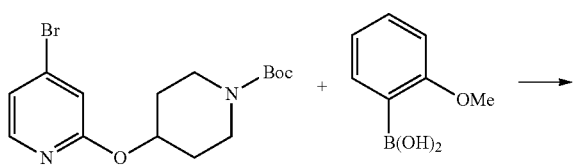

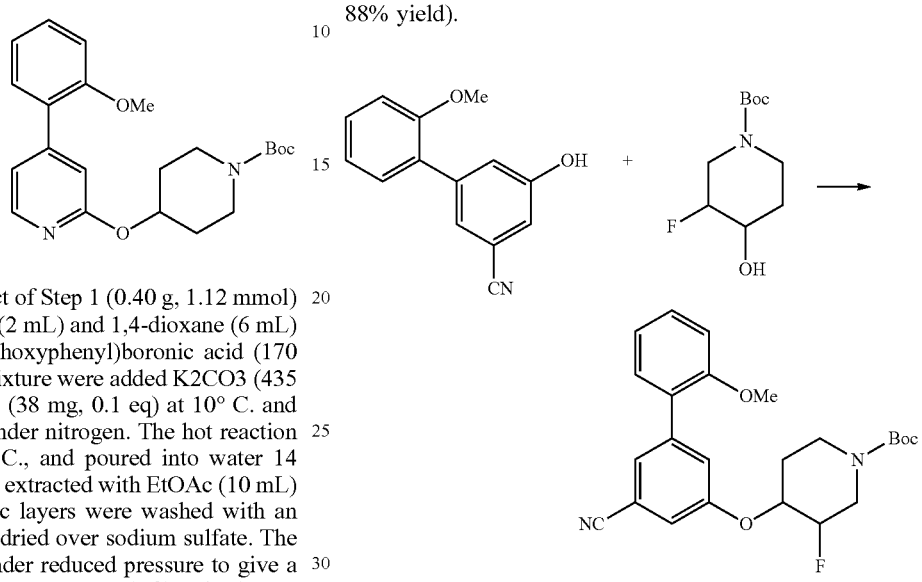

To a solution of the product of Step 1 (0.40 g, 1.12 mmol) in acetonitrile (6 mL), water (2 mL) and 1,4-dioxane (6 mL) at 10° C. was added (2-methoxyphenyl)boronic acid (170 mg, 1.12 mmol). Then the mixture were added K2CO3 (435 mg, 3.0 eq) and Pd(dppf)Cl$_2$ (38 mg, 0.1 eq) at 10° C. and stirred at 80° C. for 3.5 hr under nitrogen. The hot reaction mixture was cooled to 20° C., and poured into water 14 (mL). The aqueous layer was extracted with EtOAc (10 mL) twice. The combined organic layers were washed with an aqueous solution of salt and dried over sodium sulfate. The mixture was concentrated under reduced pressure to give a residue which was purified by prep-TLC (Rf(product)=0.6, petroleum ether:ethyl acetate=3:1) to give product as a colorless oil (400 mg, 93% yield).

Step 3-4

The title compound was prepared from the product of Step 2 in the same manner as described above for the title compound of Example 27.

Examples 29-32

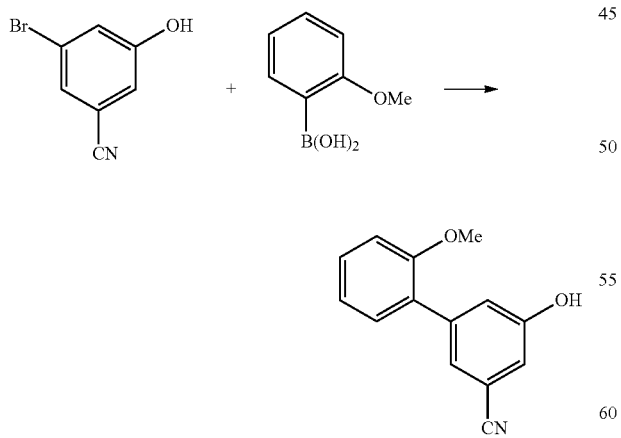

A mixture of 3-bromo-5-hydroxy-benzonitrile (1 g, 5.05 mmol), (2-methoxyphenyl)boronic acid (0.767 g, 5.0 mmol), potassium carbonate (0.698 g, 5.0 mmol), and Pd(dppf)Cl$_2$ (185 mg) in acetonitrile (4 mL), 1,4-dioxane (4 mL) and water (2 mL) was degassed and purged with N$_2$ three times, and then the mixture was stirred at 100° C. for 6 h under N$_2$ atmosphere. The reaction mixture was partitioned between water (15 mL) and EtOAc (10*3 mL). The organic phase was separated, dried over sodium sulfate, filtered and concentrated under reduced pressure to give a residue. The residue was purified by column chromatography (silica, petroleum ether/ethyl acetate=10/1 to 1:1) to give 3-hydroxy-5-(2-methoxyphenyl)benzonitrile (1.0 g, 88% yield).

To a solution of 3-hydroxy-5-(2-methoxyphenyl)benzonitrile (0.62 g, 2.75 mmol), tert-butyl 3-fluoro-4-hydroxy-piperidine-1-carboxylate (0.604 mg, 2.75 mmol) and PPh$_3$ (1 g, 5.51 mmol) in THF (31 mL) at 15° C. under nitrogen was added DIAD (834 mg, 5.51 mmol). The mixture was stirred at 60° C. under nitrogen for 16 hr. The mixture was treated with water (40 mL) and EtOAc (30 mL×2). The organic phase of filtrate was washed with brine (50 mL), dried over sodium sulfate, filtered and concentrated to give the residue. The residue was purified on prep-TLC (petroleum ether:EtOAc=3:1) to give tert-butyl 4-[3-cyano-5-(2-methoxyphenyl)phenoxy]-3-fluoro-piperidine-1-carboxylate (0.50 g, 43% yield) as a yellow oil.

The title compound was prepared from the product of Step 2 in the same manner as described for the preparation of the title compound of Example 27. Separation of the four diastereomers was achieved using supercritical fluid chromatography (SFC).

Example 29: 5-(((3S,4S)-1-acryloyl-3-fluoropiperidin-4-yl)oxy)-2'-methoxy-[1,1'-biphenyl]-3-carbonitrile

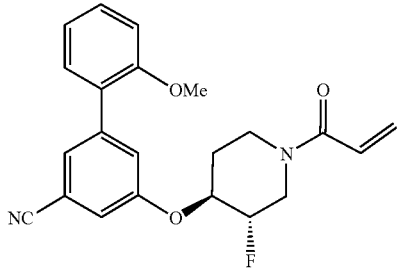 [SMILES: C=CC(=O)N1CC[C@H](Oc2cc(C#N)cc(-c3ccccc3OC)c2)[C@@H](F)C1]

MS (E+) m/z: 381 (MH$^+$).

Example 30: 5-(((3R,4R)-1-acryloyl-3-fluoropiperidin-4-yl)oxy)-2'-methoxy-[1,1'-biphenyl]-3-carbonitrile

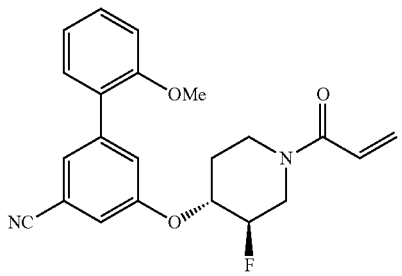 [SMILES: C=CC(=O)N1CC[C@@H](Oc2cc(C#N)cc(-c3ccccc3OC)c2)[C@H](F)C1]

MS (E+) m/z: 381 (MH$^+$)

Example 31: 5-(((3R,4S)-1-acryloyl-3-fluoropiperidin-4-yl)oxy)-2'-methoxy-[1,1'-biphenyl]-3-carbonitrile

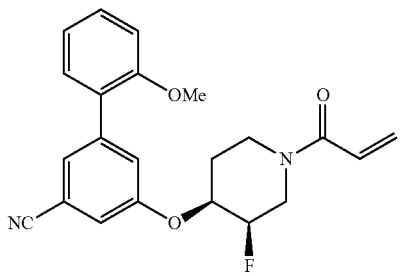 [SMILES: C=CC(=O)N1CC[C@H](Oc2cc(C#N)cc(-c3ccccc3OC)c2)[C@H](F)C1]

MS (E+) m/z: 381 (MH$^+$)

Example 32: 5-(((3S,4R)-1-acryloyl-3-fluoropiperidin-4-yl)oxy)-2'-methoxy-[1,1'-biphenyl]-3-carbonitrile

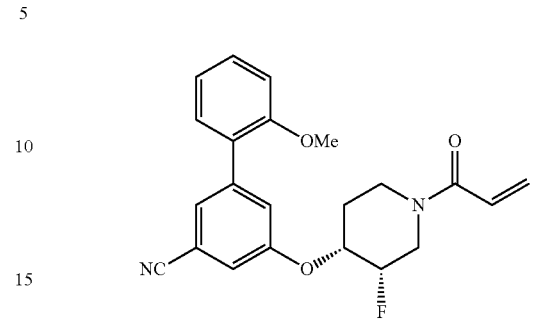

MS (E+) m/z: 381 (MH$^+$).

Examples 33-35: Synthesis of 5-((1-acryloyl-3-methylpiperidin-4-yl)oxy)-2'-methoxy-[1,1'-biphenyl]-3-carbonitrile

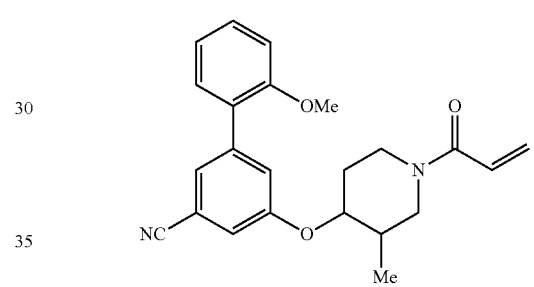

Example 33: trans, single enantiomer of undetermined absolute stereochemistry
Example 34: cis, single enantiomer of undetermined absolute stereochemistry
Example 35: trans, single enantiomer of undetermined absolute stereochemistry (antipode of Example 33)

The title compounds of Examples 33-35 were prepared in the same manner as the title compounds of 29-32, replacing tert-butyl 3-fluoro-4-hydroxy-piperidine-1-carboxylate with tert-butyl 3-methyl-4-hydroxy-piperidine-1-carboxylate.

Example 36: Synthesis of 5-((1-acryloylazetidin-3-yl)oxy)-2'-methoxy-[1,1'-biphenyl]-3-carbonitrile

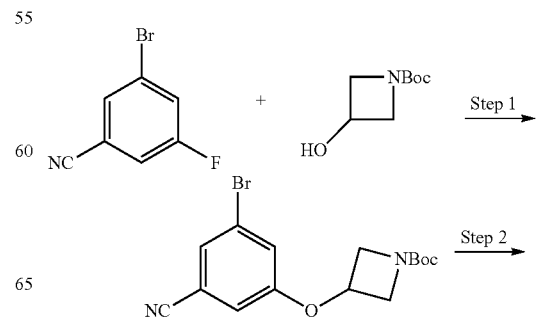

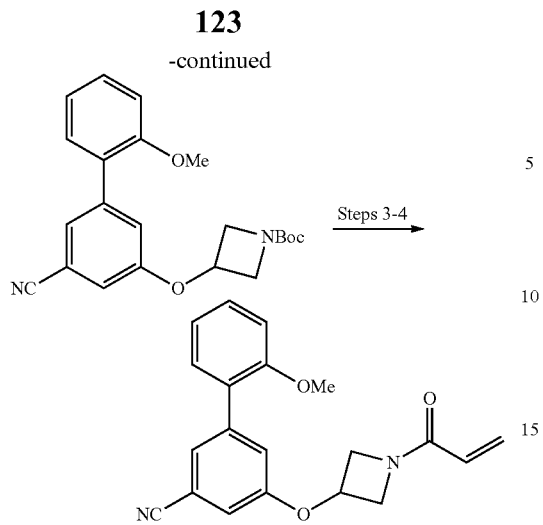

Step 1

To a solution of 1-(tert-Butoxycarbonyl)-3-hydroxyazetidine (2.08 g, 12.0 mmol) in DMF (20 mL) was added NaH (0.6 g, 15.0 mmol) at 0° C. The reaction was stirred at 0° C. for 30 min. Then 3-bromo-5-fluoro-benzonitrile (2.08 g, 12.0 mmol) was dissolved in DMF (5 mL) and added dropwise to the reaction mixture. The reaction was stirred at 20° C. for 12 h. To the mixture was added saturated aqueous ammonium chloride (50 mL), followed by extraction with ethyl acetate (80 mL*3). The combined organic extracts were washed with water (50 mL), brine (50 mL) and dried over anhydrous sodium sulfate. The solution was concentrated under reduced pressure to obtain the crude product (4.8 g). The residue was triturated with MTBE (15 mL) and filtered to afford tert-butyl 3-(3-bromo-5-cyano-phenoxy)azetidine-1-carboxylate (1.8 g, 51% yield) as a white solid.

Step 2

To a solution of tert-butyl 3-(3-bromo-5-cyano-phenoxy)azetidine-1-carboxylate (0.90 g, 2.55 mmol), (2-methoxyphenyl)boronic acid (0.387 g, 2.55 mmol), and potassium acetate (0.75 g) in acetonitrile (6 mL), 1,4-dioxane (6 mL), and water (3 mL) was added Pd(dppf)Cl$_2$—CH$_2$Cl$_2$ (194 mg) under an argon atmosphere. The solution was heated at 80° C. for 12 h. The solvent was removed after cooling. The reaction was poured into water (5 mL) and extracted with ethyl acetate (20 mL*2). The organic layer was dried with sodium sulfate and concentrated under reduced pressure to give a residue. The crude product was purified by chromatography (PE:EtOAc=10:1-2:1; Rf product=0.5) to obtain tert-butyl 3-[3-cyano-5-(2-methoxyphenyl)phenoxy]azetidine-1-carboxylate (0.80 g, 83% yield) as a brown oil.

Steps 3-4

The title compound was prepared from the product of Step 2 in the same manner as the title compound of Example 27.

Example 37: Synthesis of 1-(4-((2'-methoxy-[1,1'-biphenyl]-3-yl)thio)piperidin-1-yl)prop-2-en-1-one

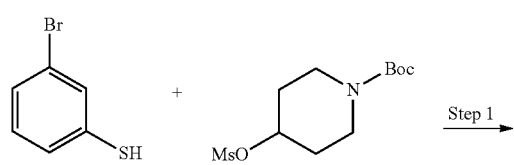

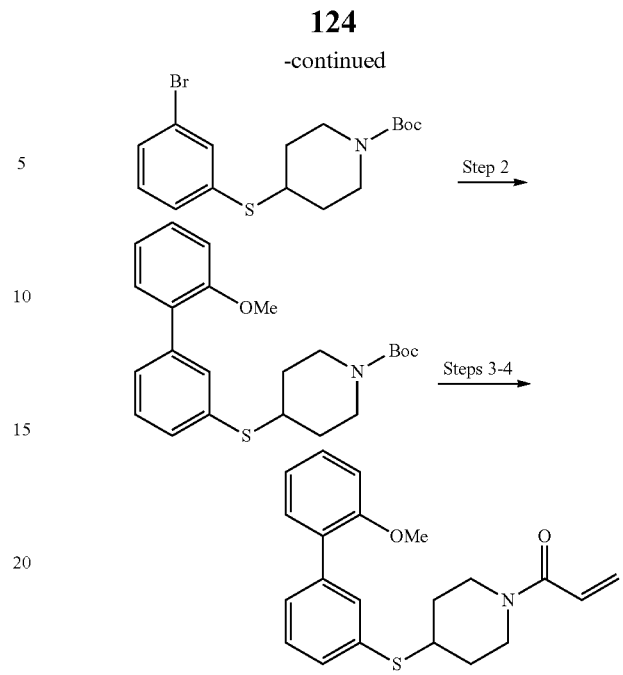

Step 1

To a solution of 3-bromothiophenol (1.0 g, 5.3 mmol) in DMF (5 mL) was added sodium hydride (254 mg, 6.35 mmol) at 0° C. and stirred for 0.5 hr. To the mixture was added tert-butyl 4-methylsulfonyloxypiperidine-1-carboxylate (1.63 g, 5.82 mmol) and the reaction mixture was stirred at 15° C. for 6 hours. The reaction mixture was quenched by addition of water and extracted with ethyl acetate (10 mL*3). The combined organic layers were washed with brine (50 mL), dried over sodium sulfate, filtered and concentrated under reduced pressure to give a residue which was purified by column chromatography (SiO$_2$, petroleum ether/ethyl acetate=100/1 to 50/1) to give tert-butyl 4-(3-bromophenyl)sulfanylpiperidine-1-carboxylate (0.90 g, 46% yield) as a yellow oil.

Step 2

The product of Step 2 was prepared from the product of Step 1 in a similar manner as the product of Step 2 in the preparation of the title compound of Example 36.

Steps 3-4

The title compound was prepared from the product of Step 2 in a similar manner as in the preparation of the title compound of Example 27. MS (E+) m/z: 354 (MH$^+$).

Example 38: Synthesis of 5-(((1R,3S,5S)-8-acryloyl-8-azabicyclo[3.2.1]octan-3-yl)oxy)-2'-methoxy-[1,1'-biphenyl]-3-carbonitrile

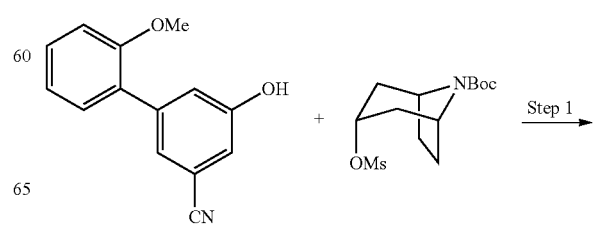

125
-continued

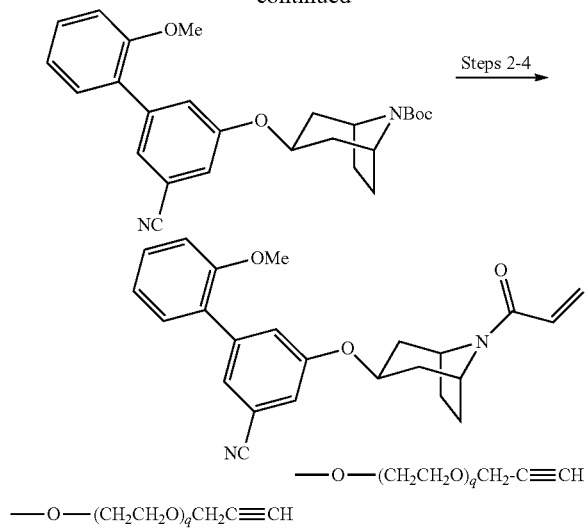

Step 1

To a solution of 3-(2-methoxyphenyl)phenol (0.30 g, 1.50 mmol) in DMF (6.8 mL) was added cesium carbonate (0.98 g, 3.0 mmol) and stirred at 15° C. for 0.5 h. And then added tert-butyl 3-methylsulfonyloxy-8-azabicyclo[3.2.1]octane-8-carboxylate (0.46 g, 1.50 mmol) at 15° C. and stirred at 80° C. for 10 h. To the solution was added water (5 mL) and extracted with MTBE (5 mL*3), washed with brine (5 mL*2), dried over sodium sulfate, concentrated to give the crude product which was purified by silica gel column (petroleum ether:ethyl acetate=1:0 to 1:1) to give tert-butyl 3-[3-(2-methoxyphenyl)phenoxy]-8-azabicyclo[3.2.1]octane-8-carboxylate (0.20 g, 33% yield) as a yellow oil.

Steps 2-3

The title compound 3-(2-methoxyphenyl)-5-[(8-prop-2-enoyl-8-azabicyclo[3.2.1]octan-3-yl)oxy]benzonitrile was prepared from the product of Step 1 in the same manner as in the preparation of the title compound of Example 27.

Example 39: Synthesis of 5-(((1R,3S,5S)-8-acryloyl-8-azabicyclo[3.2.1]octan-3-yl)oxy)-2'-methoxy-[1,1'-biphenyl]-3-carboxamide

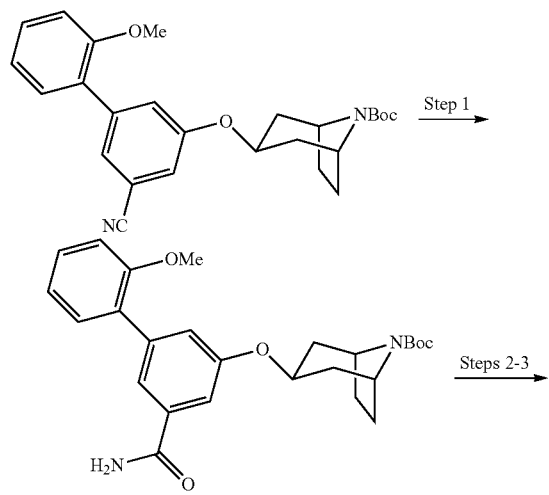

126
-continued

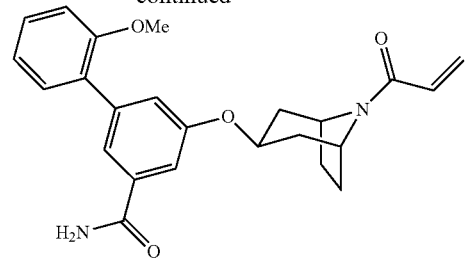

Step 1

To a solution of tert-butyl 3-[3-cyano-5-(2-methoxyphenyl)phenoxy]-8-azabicyclo[3.2.1]octane-8-carboxylate (129 mg, 2.30 mmol) in ethanol (2 mL) and water (1 mL) was added potassium hydroxide (129 mg, 2.30 mmol) at 15° C. under nitrogen. The reaction mixture was stirred at 80° C. for 2 h. The residue was purified by preparative HPLC to give tert-butyl 3-[3-carbamoyl-5-(2-methoxyphenyl)phenoxy]-8-azabicyclo[3.2.1]octane-8-carboxylate (0.080 g, 38% yield) as a white solid.

Steps 2-3

The title compound 3-(2-methoxyphenyl)-5-[(8-prop-2-enoyl-8-azabicyclo[3.2.1]octan-3-yl)oxy]benzamide was prepared from the product of Step 1 in the same manner as in the preparation of the title compound of Example 27.

Example 40: Synthesis of 3-[2-methoxy-5-[2-[2-(2-prop-2-ynoxyethoxy)ethoxy]ethoxy]phenyl]-5-[(1-prop-2-enoyl-4-piperidyl)oxy]benzonitrile

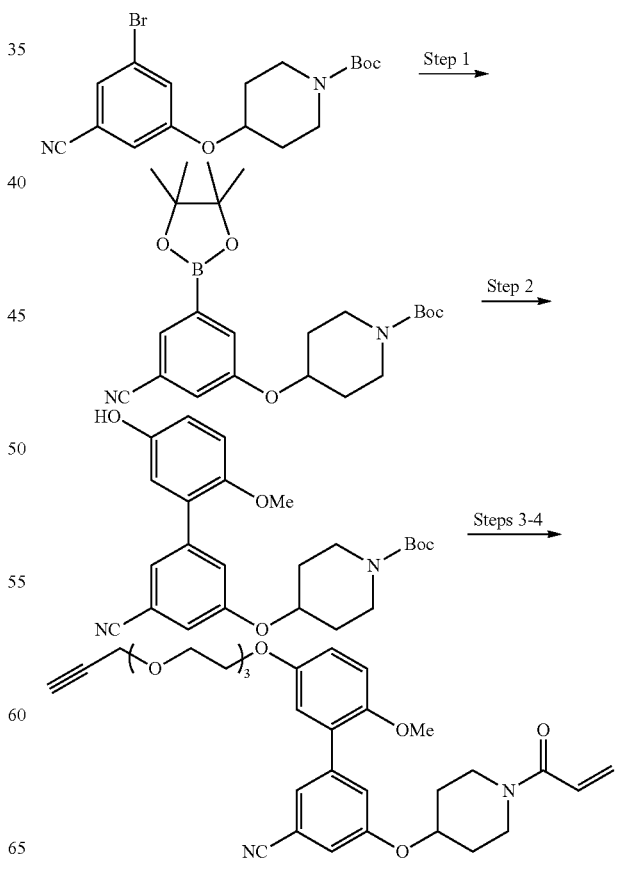

Step 1

To a mixture of tert-butyl 4-(3-bromo-5-cyano-phenoxy)piperidine-1-carboxylate (5.0 g, 13.1 mmol) and 4,4,5,5-tetramethyl-2-(4,4,5,5-tetramethyl-1,3,2-dioxaborolan-2-yl)-1,3,2-dioxaborolane (4.0 g, 15.7 mmol) in 1,4-dioxane (100 mL) was added potassium acetate (2.57 g, 26.19 mmol) and Pd(dppf)Cl$_2$ (479 mg, 0.65 mmol) under nitrogen atmosphere. The mixture was stirred at 100° C. overnight. The reaction mixture was concentrated to remove solvent, and then diluted with water (50 mL) and extracted with EtOAc (30 mL*3). The combined organic layers were washed with brine (20 mL), dried over sodium sulfate, filtered and concentrated under reduced pressure to give a residue. The residue was chromatographed on silica gel (PE/EtOAc 25:1→15:1→0:1) to give the product (tert-butyl 4-[3-cyano-5-(4,4,5,5-tetramethyl-1,3,2-dioxaborolan-2-yl)phenoxy]piperidine-1-carboxylate (6.7 g).

Step 2

To a mixture of the product of Step 1 (2.0 g, 4.7 mmol) and 2-bromo-3-methoxyphenol (0.95 g, 4.67 mmol) in 1,4-dioxane (12 mL) and acetonitrile (12 mL) was added potassium carbonate (1.29 g, 9.3 mmol) and water (6 mL). To the mixture was added Pd(dppf)Cl$_2$ (170.8 mg, 0.23 mmol) under N$_2$ atmosphere. The mixture was stirred at 100° C. overnight. The reaction mixture was concentrated to remove solvent, and then diluted with water (20 mL) and extracted with EtOAc (30 mL*3). The combined organic layers were washed with brine (20 mL), dried over Na$_2$SO$_4$, filtered and concentrated under reduced pressure to give a residue. The crude product was chromatographed on silica gel (PE/EtOAc 25:1→15:1→0:1) to give the product (tert-butyl 4-[3-cyano-5-(2-hydroxy-6-methoxy-phenyl)phenoxy]piperidine-1-carboxylate (0.715 g, 35% yield).

Step 3

A mixture of tert-butyl 4-[3-cyano-5-(5-hydroxy-2-methoxy-phenyl)phenoxy]piperidine-1-carboxylate (0.55 g, 1.30 mmol), 3-[2-[2-(2-iodoethoxy)ethoxy]ethoxy]prop-1-yne (0.386 g, 1.30 mmol) and potassium carbonate (0.358 g, 2.59 mol) in DMF (10 mL) was stirred at 15° C. for 12 hrs. The mixture was quenched with water (100 mL) and extracted with EtOAc (20 mL*3). The combined organic layers were washed with brine (20 mL*2), dried over Na$_2$SO$_4$, filtered and concentrated under reduced pressure to give a residue which was purified by column chromatography (SiO$_2$, Petroleum ether/Ethyl acetate=20/1 to 1/1), solvent removed to give tert-butyl 4-[3-cyano-5-[2-methoxy-5-[2-[2-(2-prop-2-ynoxyethoxy)ethoxy]ethoxy]phenyl]phenoxy]piperidine-1-carboxylate as yellow oil.

Steps 3-4

The title compound 3-[2-methoxy-5-[2-[2-(2-prop-2-ynoxyethoxy)ethoxy]ethoxy]phenyl]-5-[(1-prop-2-enoyl-4-piperidyl)oxy]benzonitrile was prepared from the product of Step 2 in the same manner as in the preparation of the title compound of Example 27.

Example 41: Synthesis of 1-(4-((2'-methoxy-5-(trifluoromethoxy)-[1,1'-biphenyl]-3-yl)oxy)piperidin-1-yl)prop-2-en-1-one

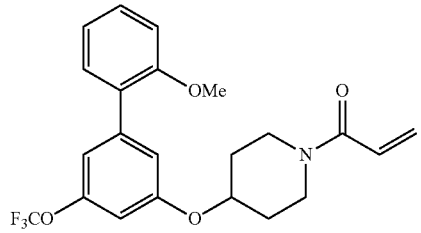 [SMILES: C=CC(=O)N1CCC(Oc2cc(OC(F)(F)F)cc(-c3ccccc3OC)c2)CC1]

The tile compound was prepared in a manner analogous to the preparation of the title compound of Example 1, substituting 1-bromo-3-fluoro-5-(trifluoromethoxy)benzene for 3-bromo-5-fluorobenzonitrile.

| Example | NMR DATA |
|---|---|
| 2 | 1H NMR (400 MHz, CDCl$_3$) δ 1.81-2.03 (m, 4 H), 3.55 (br s, 1 H), 3.80 (s, 6 H), 4.52-4.65 (m, 1 H), 5.69 (dd, J = 10.58, 1.76 Hz, 1 H), 6.28 (dd, J = 16.76, 1.98 Hz, 1 H), 6.60 (dd, J = 16.76, 10.58 Hz, 1 H), 6.68-6.76 (m, 2 H), 6.88 (dd, J = 7.83, 2.09 Hz, 1 H), 7.02-7.10 (m, 2 H), 7.21-7.35 (m, 2 H) |
| 3 | 1H NMR (400 MHz, CDCl$_3$) δ 1.55 (s, 3 H), 1.80-2.09 (m, 4 H), 3.55 (br s, 1 H), 3.80 (br s, 3 H), 4.63 (dt, J = 6.45, 3.06 Hz, 1 H), 5.27 (s, 1 H), 5.71 (dd, J = 10.58, 1.76 Hz, 1 H), 6.30 (dd, J = 16.76, 1.98 Hz, 1 H), 6.59 (d, J = 10.58 Hz, 1 H), 6.93-7.04 (m, 3 H), 7.08 (d, J = 7.72 Hz, 1 H), 7.22-7.27 (m, 3 H), 7.42 (t, J = 7.83 Hz, 1 H) |
| 5 | 1H NMR (400 MHz, CDCl$_3$) δ 7.33-7.39 (m, 1 H) 7.29 (dd, J = 7.53, 1.63 Hz, 1 H) 7.13 (t, J = 1.51 Hz, 1 H) 6.96-7.06 (m, 3 H) 6.89 (t, J = 2.01 Hz, 1 H) 6.61 (dd, J = 16.81, 10.54 Hz, 1 H) 6.30 (dd, J = 16.81, 1.88 Hz, 1 H) 5.71 (dd, J = 10.60, 1.82 Hz, 1 H) 4.54-4.64 (m, 1 H) 3.70-3.89 (m, 6 H) 3.48-3.61 (m, 1 H) 1.82-2.03 (m, 4 H) |
| 6 | 1H NMR (400 MHz, CDCl$_3$) δ 7.52-7.58 (m, 2 H) 7.45 (t, J = 7.40 Hz, 2 H) 7.35-7.41 (m, 1 H) 7.19 (t, J = 1.44 Hz, 1 H) 7.02 (t, J = 1.76 Hz, 1 H) 6.91 (t, J = 1.95 Hz, 1 H) 6.61 (dd, J = 16.81, 10.54 Hz, 1 H) 6.31 (dd, J = 16.81, 1.88 Hz, 1 H) 5.71 (dd, J = 10.54, 1.76 Hz, 1 H) 4.62 (tt, J = 6.31, 3.36 Hz, 1 H) 3.80 (br s, 3 H) 3.58 (br s, 1 H) 1.82-2.06 (m, 4 H) |
| 8 | 1H NMR (400 MHz, CDCl$_3$) δ 1.87-2.04 (m, 4 H), 3.13 (s, 1 H), 3.64-3.77 (m, 1 H), 3.79-4.02 (m, 3 H), 4.68 (quin, J = 4.58 Hz, 1 H), 6.92 (dd, J = 8.16, 2.01 Hz, 1 H), 7.15 (t, J = 1.94 Hz, 1 H), 7.22 (d, J = 7.78 Hz, 1 H), 7.33-7.41 (m, 2 H), 7.45 (t, J = 7.47 Hz, 2 H), 7.55-7.62 (m, 2 H) |
| 9 | 1H NMR (400 MHz, CDCl$_3$) δ ppm 1.92 (q, J = 5.31 Hz, 2 H) 1.98 (q, J = 5.35 Hz, 2 H) 3.13 (s, 1 H) 3.62-3.75 (m, 1 H) 3.83 (s, 3 H) 3.84-3.99 (m, 3 H) 4.63 (quin, J = 4.55 Hz, 1 H) 6.90 (dd, J = 8.03, 2.26 Hz, 1 H) 6.98-7.06 (m, 2 H) 7.10-7.16 (m, 2 H) 7.31-7.37 (m, 3 H) |
| 10 | 1H NMR (400 MHz, CDCl$_3$) δ 1.82-2.00 (m, 4 H) 2.28 (s, 6 H) 3.11 (dd, J = 6.02, 1.25 Hz, 2 H) 3.57 (br s, 1 H) 3.80 (br s, 3 H) 4.64 (dt, |

-continued

| Example | NMR DATA |
|---|---|
| | J = 6.27, 3.01 Hz, 1 H) 6.47 (d, J = 15.18 Hz, 1 H) 6.79-6.94 (m, 2 H) 7.15 (t, J = 1.94 Hz, 1 H) 7.20 (d, J = 7.65 Hz, 1 H) 7.32-7.39 (m, 2 H) 7.44 (t, J = 7.53 Hz, 2 H) 7.55-7.62 (m, 2 H) |
| 11 | 1H NMR (400 MHz, CDCl$_3$) δ 7.37-7.30 (m, 3 H), 7.15-7.09 (m, 2 H), 7.06-6.98 (m, 2 H), 6.92-6.81 (m, 2 H), 6.46 (d, J = 15.2 Hz, 1H), 4.60 (td, J = 2.9, 6.1 Hz, 1 H), 3.87-3.46 (m, 8H), 3.09 (dd, J = 1.1, 6.0 Hz, 2 H), 2.27 (s, 6 H), 2.02-1.82 (m, 5 H) |
| 12 | 1H NMR (400 MHz, CDCl$_3$) δ 1.83-1.90 (m, 2 H) 1.93-2.00 (m, 2 H) 2.41-2.52 (m, 4 H) 3.13 (d, J = 6.06 Hz, 2 H) 3.54 (br s, 1 H) 3.69-3.73 (m, 4 H) 3.82 (s, 5 H) 4.53-4.69 (m, 1 H) 6.45 (d, J = 15.26 Hz, 1 H) 6.84 (dt, J = 15.11, 6.14 Hz, 1 H) 6.96-7.14 (m, 3 H) 7.25-7.30 (m, 2 H) 7.36 (t, J = 7.83 Hz, 1 H) 7.43 (s, 1 H) |
| 13 | 1H NMR (400 MHz, CDCl$_3$) δ 7.52-7.57 (m, 2 H) 7.40-7.51 (m, 4 H) 7.33-7.37 (m, 1 H) 7.14 (dd, J = 2.32, 1.32 Hz, 1 H) 6.62 (dd, J = 16.81, 10.54 Hz, 1 H) 6.32 (dd, J = 16.81, 1.88 Hz, 1 H) 5.73 (dd, J = 10.54, 1.88 Hz, 1 H) 4.66 (tt, J = 6.51, 3.34 Hz, 1 H) 3.81 (br s, 3 H) 3.59 (br s, 1 H) 1.96-2.08 (m, 2 H) 1.84-1.94 (m, 2 H) |
| 14 | 1H NMR (400 MHz, CDCl$_3$) δ 7.44-7.51 (m, 1 H) 7.34-7.42 (m, 1 H) 7.27-7.33 (m, 2 H) 7.11-7.16 (m, 1 H) 6.99-7.09 (m, 2 H) 6.61 (dd, J = 16.81, 10.54 Hz, 1 H) 6.31 (dd, J = 16.81, 1.88 Hz, 1 H) 5.72 (dd, J = 10.54, 1.88 Hz, 1 H) 4.59-4.67 (m, 1 H) 3.74-3.87 (m, 6 H) 3.58 (br s, 1 H) 1.84-2.06 (m, 4 H) |
| 15 | 1H NMR (400 MHz, CDCl$_3$) δ 7.39-7.31 (m, 2 H), 7.24-7.19 (m, 1H), 7.18-7.12 (m, 2 H), 7.09 (s, 1 H), 6.61 (dd, J = 10.7, 16.9 Hz, 1H), 6.31 (br d, J = 15.3 Hz, 1H), 5.72 (br d, J = 10.6 Hz, 1H), 4.61 (br s, 1 H), 3.81 (br s, 3 H), 3.57 (br s, 1 H), 2.57 (q, J = 7.5 Hz, 2 H), 1.99 (br d, J = 3.7 Hz, 2 H), 1.93-1.84 (m, 2 H), 1.12 (t, J = 7.5 Hz, 3 H) |
| 16 | 1H NMR (400 MHz, CDCl$_3$) δ 7.45 (s, 1 H), 7.38 (dt, J = 1.6, 7.8 Hz, 1H), 7.32-7.27 (m, 2 H), 7.12 (s, 1 H), 7.08-6.99 (m, 2 H), 6.94 (d, J = 10.2 Hz, 1H), 4.65 (br t, J = 3.1 Hz, 1H), 3.83 (s, 3 H), 3.73 (br s, 4 H), 3.03-2.91 (m, 1H), 1.97 (br d, J = 4.9 Hz, 4 H), 1.15 (d, J = 6.7 Hz, 6 H) |
| 17 | 1H NMR (400 MHz, CDCl$_3$) δ 7.48 (s, 1 H) 7.28-7.43 (m, 4 H) 7.00-7.09 (m, 2 H) 6.93 (d, J = 10.42 Hz, 1 H) 6.07 (s, 1 H) 5.55 (br s, 1 H) 4.73 (br s, 1 H) 3.84 (s, 7 H) 2.90-3.05 (m, 1 H) 2.00 (br s, 4 H) 1.16 (d, J = 6.65 Hz, 6 H) |
| 18 | 1H NMR (400 MHz, CDCl$_3$) δ 7.36-7.44 (m, 1 H) 7.17-7.26 (m, 2 H) 6.93-7.06 (m, 3 H) 6.93-7.06 (m, 1 H) 6.62 (dd, J = 16.81, 10.54 Hz, 1 H) 6.30 (dd, J = 16.81, 1.88 Hz, 1 H) 5.70 (dd, J = 10.67, 1.88 Hz, 1 H) 4.68 (br s, 1 H) 3.96 (br d, J = 7.40 Hz, 1 H) 3.69-3.87 (m, 5 H) 3.63 (br d, J = 11.04 Hz, 1 H) 1.97 (br s, 4 H) |
| 19 | 1H NMR (400 MHz, CDCl$_3$) δ 7.53-7.60 (m, 3 H) 7.41-7.53 (m, 3 H) 7.09 (d, J = 7.65 Hz, 1 H) 6.98 (d, J = 8.41 Hz, 1 H) 6.62 (dd, J = 16.88, 10.60 Hz, 1 H) 6.30 (dd, J = 16.81, 1.88 Hz, 1 H) 5.71 (dd, J = 10.54, 1.88 Hz, 1 H) 4.78-4.84 (m, 1 H) 4.06 (br d, J = 13.05 Hz, 1 H) 3.77-3.93 (m, 1 H) 3.69 (br d, J = 13.18 Hz, 2 H) 2.00 (br s, 4 H) |
| 20 | 1H NMR (400 MHz, CDCl$_3$) δ 7.54 (t, J = 8.09 Hz, 1 H) 7.39-7.45 (m, 1 H) 7.25 (br d, J = 1.63 Hz, 1 H) 6.94-7.09 (m, 4 H) 6.61 (dd, J = 16.81, 10.54 Hz, 1 H) 6.30 (dd, J = 16.88, 1.94 Hz, 1 H) 5.71 (dd, J = 10.54, 1.88 Hz, 1 H) 4.79 (br s, 1 H) 4.04 (br s, 1 H) 3.86 (s, 4 H) 3.67 (br d, J = 11.04 Hz, 2 H) 2.01 (br s, 4 H) |
| 21 | 1H NMR (400 MHz, CDCl$_3$) δ 8.23 (d, J = 8.16 Hz, 1 H) 7.66 (br s, 1 H) 7.31-7.44 (m, 2 H) 7.20-7.26 (m, 2 H) 7.00-7.10 (m, 2 H) 6.60 (dd, J = 16.69, 10.54 Hz, 1 H) 6.32 (dd, J = 16.81, 1.76 Hz, 1 H) 5.69-5.83 (m, 2 H) 4.71-4.85 (m, 1 H) 4.04 (br s, 1 H) 3.84 (s, 4 H) 3.50 (br s, 2 H) 2.14 (br s, 2 H) 1.92 (br d, J = 7.65 Hz, 2 H) |
| 22 | 1H NMR (400 MHz, CDCl$_3$) δ 7.49 (s, 1 H) 7.32-7.44 (m, 3 H) 7.26-7.28 (m, 1 H) 7.00-7.10 (m, 2 H) 6.63 (dd, J = 16.81, 10.54 Hz, 1 H) 6.31 (dd, J = 16.88, 1.94 Hz, 1 H) 5.72 (dd, J = 10.54, 1.88 Hz, 1 H) 4.64-4.75 (m, 1 H) 3.85 (s, 6 H) 3.57 (br s, 1 H) 1.85-2.08 (m, 4 H) |
| 23 | 1H NMR (400 MHz, CDCl$_3$) δ 7.57 (d, J = 8.16 Hz, 2 H) 7.44 (t, J = 7.61 Hz, 2 H) 7.33-7.40 (m, 1 H) 6.75 (d, J = 1.54 Hz, 2 H) 6.62 (dd, J = 16.98, 10.58 Hz, 1 H) 6.49 (s, 1 H) 6.26-6.33 (m, 1 H) 5.71 (d, J = 10.58 Hz, 1 H) 4.59-4.66 (m, 1 H) 3.86 (s, 3 H) 3.75-3.84 (m, 3 H) 3.50-3.60 (m, 1H) 1.86-2.03 (m, 4 H) |
| 24 | 1H NMR (400 MHz, CDCl$_3$) δ 7.30-7.38 (m, 2 H) 6.96-7.07 (m, 2 H) 6.69-6.72 (m, 2 H) 6.62 (dd, J = 16.81, 10.54 Hz, 1 H) 6.47 (t, J = 2.20 Hz, 1 H) 6.30 (dd, J = 16.81, 1.76 Hz, 1 H) 5.70 (dd, J = 10.54, 1.76 Hz, 1 H) 4.59 (dt, J = 6.15, 2.82 Hz, 1 H) 3.73-3.86 (m, 9 H) 3.55 (br s, 1 H) 1.85-2.01 (m, 4 H) |
| 25 | 1H NMR (400 MHz, CDCl$_3$) δ 7.28-7.38 (m, 2 H) 7.15 (d, J = 12.13 Hz, 2 H) 6.94-7.06 (m, 3 H) 6.61 (dd, J = 16.73, 10.47 Hz, 1 H) 6.29 (dd, J = 16.82, 1.96 Hz, 1 H) 5.70 (dd, J = 10.56, 1.96 Hz, 1 H) 4.56-4.66 (m, 1 H) 3.82 (s, 6 H) 3.55 (br s, 1 H) 3.02-3.16 (m, 6 H) 1.84-2.02 (m, 4 H) |
| 26 | 1H NMR (400 MHz, CDCl$_3$) δ 7.30-7.42 (m, 4 H) 7.22 (s, 1 H) 6.97-7.08 (m, 2 H) 6.61 (dd, J = 16.82, 10.56 Hz, 1 H) 6.30 (dd, J = 16.82, |

| Example | NMR DATA |
|---------|----------|
| | 1.76 Hz, 1 H) 6.13 (br s, 1 H) 5.70 (dd, J = 10.56, 1.76 Hz, 1 H) 4.67 (dt, J = 6.36, 3.08 Hz, 1 H) 3.83 (s, 6 H) 3.55 (br s, 1 H) 3.03 (d, J = 4.89 Hz, 3 H) 1.94-2.02 (m, 2 H) 1.83-1.93 (m, 2 H) |
| 27 | 1H NMR (400 MHz, CDCl$_3$) δ 9.05 (d, J = 1.8 Hz, 1H), 7.48-7.42 (m, 1H), 7.37 (dd, J = 1.8, 7.6 Hz, 1H), 7.32-7.22 (m, 1H), 7.13-7.02 (m, 3 H), 6.63 (dd, J = 10.6, 16.8 Hz, 1H), 6.30 (dd, J = 2.0, 16.8 Hz, 1H), 5.73-5.69 (m, 1H), 5.71 (dd, J = 1.9, 10.7 Hz, 1H), 5.67-5.58 (m, 1H), 5.67-5.51 (m, 1H), 5.77-5.51 (m, 1H), 4.22-4.02 (m, 1H), 3.88 (s, 1 H), 3.93-3.82 (m, 1H), 3.95-3.81 (m, 1H), 3.54 (br d, J = 9.4 Hz, 2 H), 2.29-2.08 (m, 2 H), 2.05-1.97 (m, 1H), 1.95-1.84 (m, 1H), 1.90 (dtd, J = 3.7, 8.4, 12.7 Hz, 1H), 2.01 (s, 1 H) |
| 28 | 1H NMR (400 MHz, CDCl$_3$) δ 1.40-1.50 (m, 2 H) 2.18 (br s, 2 H) 2.98 (br d, J = 12.52 Hz, 1 H) 3.29 (br d, J = 1.17 Hz, 1 H) 3.84 (s, 3 H) 3.95-4.03 (m, 2 H) 4.38 (br d, J = 7.63 Hz, 1 H) 4.55 (br d, J = 12.72 Hz, 1 H) 5.70 (dd, J = 10.66, 1.86 Hz, 1 H) 6.29 (dd, J = 16.82, 1.96 Hz, 1 H) 6.54-6.64 (m, 2 H) 6.77 (dd, J = 5.28, 1.37 Hz, 1 H) 6.97-7.06 (m, 2 H) 7.30-7.40 (m, 2 H) 8.11 (d, J = 5.28 Hz, 1 H) |
| 29 | 1H NMR (400 MHz, CDCl$_3$) δ 7.49(1 H, t, J = 1.37 Hz) 7.36-7.41 (2 H, m) 7.27-7.30 (1 H, m) 7.18 (1 H, dd, J = 2.45, 1.27 Hz) 7.03-7.08 (1 H, m) 7.00-7.03 (1 H, m) 6.60 (1 H, dd, J = 16.73, 10.66 Hz) 6.32 (1 H, br d, J = 16.63 Hz) 5.75 (1 H, dd, J = 10.56, 1.76 Hz) 4.74-4.92 (1 H, m) 4.65 (1 H, br s) 4.12 (1 H, br s) 3.89-4.20 (1 H, m) 3.84(3 H, s) 3.59-3.80 (1 H, m) 3.50(1 H, br s) 1.86-2.23 (2 H, m) |
| 30 | 1H NMR (400 MHz, CDCl$_3$) δ 7.49(1 H, t, J = 1.37 Hz) 7.36-7.41 (2 H, m) 7.27-7.30 (1 H, m) 7.18 (1 H, dd, J = 2.45, 1.27 Hz) 7.03-7.08 (1 H, m) 7.00-7.03 (1 H, m) 6.60 (1 H, dd, J = 16.73, 10.66 Hz) 6.32 (1 H, br d, J = 16.63 Hz) 5.75 (1 H, dd, J = 10.56, 1.76 Hz) 4.74-4.92 (1 H, m) 4.65 (1 H, br s) 4.12 (1 H, br s) 3.89-4.20 (1 H, m) 3.84(3 H, s) 3.59-3.80 (1 H, m) 3.50(1 H, br s) 1.86-2.23 (2 H, m) |
| 31 | 1H NMR (400 MHz, CDCl$_3$) δ 1.91 (br s, 1 H) 2.18 (br s, 1 H) 3.45-3.83 (m, 2 H) 3.84 (s, 3 H) 3.89-4.10 (m, 2 H) 4.57-4.80 (m, 2 H) 5.75 (dd, J = 10.54, 1.76 Hz, 1 H) 6.32 (br d, J = 16.31 Hz, 1 H) 6.59 (dd, J = 16.81, 10.54 Hz, 1 H) 6.99-7.09 (m, 2 H) 7.17 (dd, J = 2.45, 1.32 Hz, 1 H) 7.27-7.30 (m, 1 H) 7.32-7.43 (m, 2 H) 7.49 (t, J = 1.25 Hz, 1 H) |
| 32 | 1H NMR (400 MHz, CDCl$_3$) δ 1.91 (br s, 1 H) 2.18 (br s, 1 H) 3.45-3.83 (m, 2 H) 3.84 (s, 3 H) 3.89-4.10 (m, 2 H) 4.57-4.80 (m, 2 H), 5.75 (dd, J = 10.54, 1.76 Hz, 1 H) 6.32 (br d, J = 16.31 Hz, 1 H) 6.59 (dd, J = 16.81, 10.54 Hz, 1 H) 6.99-7.09 (m, 2 H) 7.17 (dd, J = 2.45, 1.32 Hz, 1 H) 7.27-7.30 (m, 1 H) 7.32-7.43 (m, 2 H) 7.49 (t, J = 1.25 Hz, 1 H) |
| 33 | 1H NMR (400 MHz, CDCl$_3$) δ 7.45 (d, J = 1.37 Hz, 1 H) 7.36-7.42 (m, 1 H) 7.27-7.31 (m, 2 H) 6.98-7.13 (m, 3 H) 6.60 (dd, J = 16.82, 10.56 Hz, 1 H) 6.30 (dd, J = 16.82, 1.96 Hz, 1 H) 5.70 (dd, J = 10.66, 1.86 Hz, 1 H) 4.76 (t, J = 3.03 Hz, 1 H) 3.84 (s, 3 H) 2.18 (s, 1 H) 2.06 (br d, J = 11.93 Hz, 1 H) 1.92-2.00 (m, 1 H) 1.79-1.99 (m, 1 H) 1.57 (d, J = 2.35 Hz, 3 H) 1.41 (d, J = 7.04 Hz, 3 H) |
| 34 | 1H NMR (400 MHz, CDCl$_3$) δ 7.43-7.46 (m, 1 H) 7.36-7.41 (m, 1 H) 7.28-7.32 (m, 2 H) 6.99-7.11 (m, 3 H) 6.60 (dd, J = 16.92, 10.47 Hz, 1 H) 6.29 (dd, J = 16.92, 1.66 Hz, 1 H) 5.71 (dd, J = 10.56, 1.96 Hz, 1 H) 4.60-4.69 (m, 1 H) 3.84 (s, 2 H) 3.83-3.86 (m, 1 H) 2.09-2.25 (m, 2 H) 1.75-1.87 (m, 1 H) 1.59-1.67 (m, 1 H) 1.56 (s, 3 H) 1.33 (br d, J = 7.04 Hz, 3 H) |
| 35 | 1H NMR (400 MHz, CDCl$_3$) δ 7.43-7.46 (m, 1 H) 7.36-7.42 (m, 1 H) 7.27-7.31 (m, 2 H) 6.99-7.12 (m, 3 H) 6.60 (dd, J = 16.92, 10.66 Hz, 1 H) 6.24-6.35 (m, 1 H) 5.70 (dd, J = 10.56, 1.96 Hz, 1 H) 4.76 (t, J = 3.03 Hz, 1 H) 3.84 (s, 3 H) 2.18 (s, 1 H) 2.02-2.13 (m, 2 H) 1.92-1.99(m, 1 H) 1.78- 1.88(m, 1 H) 1.57 (br s, 2 H) 1.41 (d, J = 7.04 Hz, 3 H) |
| 36 | 1H NMR (399 MHz, methanol-d4) δ 7.48 (t, J = 1.6 Hz, 1H), 7.41-7.36(m, 1H), 7.34-7.29 (m, 2 H), 7.15 (dd, J = 1.6, 2.4 Hz, 1H), 7.11 (d, J = 7.6 Hz, 1H), 7.05 (dt, J = 1.2, 7.6 Hz, 1H), 6.41-6.33 (m, 1H), 6.30-6.24 (m, 1H), 5.76 (dd, J = 2.0, 10.0 Hz, 1H), 5.21-5.15 (m, 1H), 4.76 (ddd, J = 1.6, 6.5, 10.0 Hz, 1H), 4.57-4.47 (m, 1H), 4.33 (td, J = 1.6, 10.0 Hz, 1H), 4.07 (dd, J = 2.4, 11.2 Hz, 1H), 3.84 (s, 3 H) |
| 37 | 1H NMR (400 MHz, CDCl$_3$) δ 7.62 (s, 1 H) 7.43-7.47 (m, 1 H) 7.31-7.39 (m, 4 H) 6.97-7.08 (m, 2 H) 6.56 (dd, J = 16.81, 10.54 Hz, 1 H) 6.26 (dd, J = 16.88, 1.82 Hz, 1 H) 5.68 (dd, J = 10.54, 1.88 Hz, 1H) 4.36 (br s, 1 H) 3.96 (br s, 1 H) 3.83 (s, 3 H) 3.17-3.41 (m, 2 H) 3.06 (br s, 1 H) 2.05 (br d, J = 10.42 Hz, 2 H) 1.64 (br s, 2 H) |
| 38 | 1H NMR (400 MHz, CDCl$_3$) δ 7.46-7.36 (m, 2 H), 7.30-7.26 (m, 1H), 7.26 (br s, 1 H), 7.09-6.99 (m, 3 H), 6.57-6.39 (m, 2 H), 5.79 (dd, J = 2.0, 10.0 Hz, 1H), 4.93-4.86 (m, 1H), 4.82-4.71 (m, 1H), 4.50-4.43 (m, 1H), 3.84 (s, 3 H), 2.36-1.69 (m, 8H) |

| Example | NMR DATA |
|---|---|
| 39 | 1H NMR (400 MHz, CDCl$_3$) δ 7.48 (s, 1 H), 7.40-7.29 (m, 3 H), 7.23 (d, J = 1.5 Hz, 1H), 7.07-6.97 (m, 2 H), 6.56-6.46 (m, 1H), 6.44-6.35 (m, 1H), 5.71 (dd, J = 2.2, 10.1 Hz, 1H), 4.89-4.76 (m, 2 H), 4.46-4.38 (m, 1H), 3.82 (s, 3 H), 2.34-2.06 (m, 3 H), 1.99-1.66 (m, 5 H) |
| 40 | 1H NMR (400 MHz, CDCl$_3$) δ 7.44 (t, J = 1.47 Hz, 1 H) 7.30 (dd, J = 2.35, 1.57 Hz, 1 H) 7.12 (dd, J = 2.54, 1.37 Hz, 1 H) 6.91-6.94 (m, 2 H), 6.88-6.91 (m, 1 H) 6.61 (dd, J = 16.82, 10.56 Hz, 1 H) 6.31 (dd, J = 16.82, 1.76 Hz, 1 H) 5.72 (dd, J = 10.66, 1.86 Hz, 1 H) 4.62 (tt, J = 6.43, 3.35 Hz, 1 H) 4.20 (d, J = 2.35 Hz, 2 H) 4.09-4.16 (m, 2 H) 3.85-3.89 (m, 2 H) 3.78 (s, 6 H) 3.73-3.76 (m, 2 H) 3.67-3.73 (m, 6 H) 3.58 (br d, J = 11.93 Hz, 1 H) 2.42 (t, J = 2.35 Hz, 1 H) 1.77-2.10 (m, 4 H) |
| 41 | 1H NMR (400 MHz, CDCl$_3$) δ 7.29-7.41 (m, 2 H) 6.97-7.08 (m, 4 H) 6.74 (s, 1 H) 6.61 (dd, J = 16.81, 10.54 Hz, 1 H), 6.30 (dd, J = 16.88, 1.82 Hz, 1 H) 5.71 (dd, J = 10.54, 1.88 Hz, 1 H) 4.60 (dt, J = 6.40, 2.95 Hz, 1 H) 3.84 (s, 3 H) 3.74-3.82 (m, 3 H) 3.48-3.60 (m, 1 H) 1.84-2.02 (m, 4 H) |

Example 42: CRBN C287 Inhibition

Compounds disclosed herein were tested for CRBN C287 inhibition using a similar assay described in Backus et al. Nature, 2016, 534, 570-574 which is herein incorporated by reference. Assay results are shown in the the table below.

| Example | % inh @ 500 uM (CRBN_C287, lysate 1 h) |
|---|---|
| 1 | 74.8 |
| 2 | 59.8 |
| 3 | 48.9 |
| 4 | 64.8 |
| 5 | 88.5 |
| 6 | 72.2 |
| 7 | 91.2 |
| 8 | 76.8 |
| 9 | 88.8 |
| 10 | 52.4 |
| 11 | 92.9 |
| 12 | 87.2 |
| 13 | 81.3 |
| 14 | 94.5 |
| 15 | TE50: 22.2 uM |
| 16 | TE50: 0.12 uM |
| 17 | TE50: 0.05 uM |
| 18 | 60.4 |
| 19 | 68.2 |
| 20 | 57.6 |
| 21 | 64.6 |
| 22 | 95.2 |
| 23 | 91.1 |
| 24 | 89.3 |
| 25 | 77.6 |
| 26 | 77.4 |
| 27 | TE50: 7.5 uM |
| 28 | TE50: 80 uM |
| 29 | TE50: 1.25 uM |
| 30 | TE50: 0.40 uM |
| 31 | TE50: 0.29 uM |
| 32 | TE50: 1.49 uM |
| 33 | TE50: 4.66 uM |
| 34 | TE50: 8.97 uM |
| 35 | TE50: 9.8 uM |
| 36 | TE50: 0.12 uM |
| 37 | TE50: 31 uM |
| 38 | 78 |
| 39 | TE50: 53 uM |
| 40 | TE50: 2.57 uM |
| 41 | TE50: 31 uM |
| 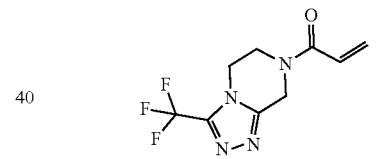 | No activity |
| 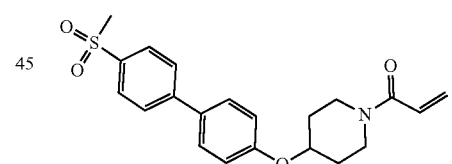 | No activity |

Example 43

Table 1 illustrates exemplary cereblon protein sequences.

| Sequence | | SEQ ID NO: |
|---|---|---|
| Cereblon UniProt - Q96SW2 (homo sapiens) | MAGEGDQQDAAHNMGNHLPLLPAESEEEDEMEVEDQDSK EAKKPNIINFDTSLPTSHTYLGADMEEFHGRTLHDDDSCQVI PVLPQVMMILIPGQTLPLQLFHPQEVSMVRNLIQKDRTFAVL AYSNVQEREAQFGTTAEIYAYREEQDFGIEIVKVKAIGRQRF KVLELRTQSDGIQQAKVQILPECVLPSTMSAVQLESLNKCQI FP SKPV SREDQCSYKWWQKYQKRKFHCANLTSWPRWLYS LYDAETLMDRIKKQLREWDENLKDDSLPSNPIDFSYRVAAC LPIDDVLRIQLLKIGSAIQRLRCELDIMNKCTSLCCKQCQETE | 1 |

-continued

| Sequence | | SEQ ID NO: |
|---|---|---|
| Cereblon<br>NCBI ref. Seq.:<br>NP_001166953.1<br>(human sapiens)<br>(variant 1) | ITTKNEIFSLSLCGPMAAYVNPHGYVHETLTVYKACNLNLIG<br>RPSTEHSWFPGYAWTVAQCKICASHIGWKFTATKKDMSPQ<br>KFWGLTRSALLPTIPDTEDEISPDKVILCL<br>MAGEGDQQDAAHNMGNHLPLLPESEEEDEMEVEDQDSKE<br>AKKPNIINFDTSLPTSHTYLGADMEEFHGRTLHDDDSCQVIP<br>VLPQVMMILIPGQTLPLQLFHPQEVSMVRNLIQKDRTFAVL<br>AYSNVQEREAQFGTTAEIYAYREEQDFGIEIVKVKAIGRQRF<br>KVLELRTQSDGIQQAKVQILPECVLPSTMSAVQLESLNKCQI<br>FP SKPVSREDQCSYKWWQKYQKRKFHCANLTSWPRWLYS<br>LYDAETLMDRIKKQLREWDENLKDDSLPSNPIDFSYRVAAC<br>LPIDDVLRIQLLKIGSAIQRLRCELDIMNKCTSLCCKQCQETE<br>ITTKNEIFSLSLCGPMAAYVNPHGYVHETLTVYKACNLNLIG<br>RPSTEHSWFPGYAWTVAQCKICASHIGWKFTATKKDMSPQ<br>KFWGLTRSALLPTIPDTEDEISPDKVILCL | 2 |
| Cereblon<br>GenBank:<br>AAH67811.1<br>(human sapiens)<br>(variant 2) | MAGEGDQQDAAHNMGNHLPLLPESEEEDEMEVEDQDSKE<br>AKKPNIINFDTSLPTSHTYLGADMEEFHGRTLHDDDSCQVIP<br>VLPQVMMILIPGQTLPLQLFHPQEVSMVRNLIQKDRTFAVL<br>AYSNVQEREAQFGTTAEIYAYREEQDFGIEIVKVKAIGRQRF<br>KVLELRTQSDGIQQAKVQILPECVLPSTMSAVQLESLNKCQI<br>FP SKPVSREDQCSYKWWQKYQRRKFHCANLTSWPRWLYSL<br>YDAETLMDRIKKQLREWDENLKDDSLPSNPIDFSYRVAACL<br>PIDDVLRIQLLKIGSAIQRLRCELDIMNKCTSLCCKQCQETEI<br>TTKNEIFSLSLCGPMAAYVNPHGYVHETLTVYKACNLNLIG<br>RPSTEHSWFPGYAWTVAQCKICASHIGWKFTATKKDMSPQ<br>KFWGLTRSALLPTIPDTEDEISPDKVILCL | 3 |
| Cereblon Lon N-<br>terminal Domain<br>(variant 1) | IPVLPQVMMILIPGQTLPLQLFHPQEVSMVRNLIQKDRTFAV<br>LAYSNVQEREAQFGTTAEIYAYREEQDFGIEIVKVKAIGRQR<br>FKVLELRTQSDGIQQAKVQILPECVLPSTMSAVQLESLNKCQ<br>IFPSKPVSREDQCSYKWWQKYQKRKFHCANLTSWPRWLYS<br>LYDAETLMDRIKKQLREWDENLKDDSLPSNPIDFSYRVAAC<br>LPIDDVLRIQLLKIGSAIQRLRCELDIMNK | 4 |
| Cereblon Lon N-<br>terminal Domain<br>(variant 2) | IPVLPQVMMILIPGQTLPLQLFHPQEVSMVRNLIQKDRTFAV<br>LAYSNVQEREAQFGTTAEIYAYREEQDFGIEIVKVKAIGRQR<br>FKVLELRTQSDGIQQAKVQILPECVLPSTMSAVQLESLNKCQ<br>IFPSKPVSREDQCSYKWWQKYQRRKFHCANLTSWPRWLYS<br>LYDAETLMDRIKKQLREWDENLKDDSLPSNPIDFSYRVAAC<br>LPIDDVLRIQLLKIGSAIQRLRCELDIMNK | 5 |

Example 44

The following 96-well sample prep protocol was used for sample preparation.

Cells were resuspended in cold PBS on ice and sonicated with a probe sonicator to achieve lysis. 200 µL of lysate containing 5 mg/ml proteome was treated with 2 µL of 100× compound stock in a 2-mL deep-well plate. The treated lysate was subsequently incubate at 25° C. for 1 hr with shaking at 600 rpm. The treated lysate was further incubated with 2 µL of 10 mM desthiobiotin iodoacetamide probe at 25° C. for 1 hr with shaking at 600 rpm. Next, the lysate was further treat with 20 µL of solution of PBS containing 11 mM MgSO$_4$ and 2.5% Turbonuclease stock and incubated at 25° C. for 20 minutes with shaking at 600 rpm. 1.7 mL ice-cold acetone was added to each well and incubated at −20° C. for 2 hr, followed by max speed (4200 rpm) spin for 45 min. Acetone was then decanted and the plates were blotted to remove acetone. The plates were then dried in open air for 20 minutes. After drying, the plates were then covered with foil seal and stored at −80° C. overnight.

The next day, samples were re-suspended in 90 µL of solution of 9M urea, 50 mM ammonium bicarbonate and 10 mM DTT by incubating at 65° C. for 20 min with shaking at 1500 rpm. Next, samples were cooled to 37° C. and then 10 µL of 500 mM iodoacetamide solution (92.48 mg/ml) was added. The samples were then incubated at 37° C. for 30 min with shaking at 600 rpm.

ZEBA desalting plates were equilibrated 4 times using 250 µL of 2M urea, 50 mM ammonium bicarbonate solution followed by centrifugation at 1500 rpm for 2 minutes. After equilibration was complete, samples were applied to ZEBA desalting plate and spin at 1500 rpm for 2 min on top of 1 mL 96-well deep-well collection plate to buffer exchange samples. 4 µL of solution containing 25 mM CaCl$_2$ and 0.25 mg/mL trypsin was added to the plate and the plate was then incubated at 37° C. for 2 hrs with shaking at 600 rpm. 300 µL of solution containing 5% high-capacity streptavidin agarose slurry in 25 mM Tris-HCl pH 7.5, 150 mM NaCl, and 0.1% NP-40 then added. The plate was incubated at 25° C. for 2 hrs with shaking at 600 rpm. Samples were transferred to 25 µm filter plate and spin at 1000 rpm for 2 min. Samples were then washed 3 times with 0.75 mL of wash buffer (25 mM Tris-HCl pH 7.5, 150 mM NaCl, and 0.1% NP-40) followed by washing 3 times with 0.75 mL PBS, and then 4 times with 0.75 mL water. After the washing step, samples were eluted into polypropylene 96-well plate by addition of 250 µL of 50% MeCN/water, 0.1% formic acid and allowed to gravity drip for 10 min, followed by centrifugation at 1000 rpm for 2 min. Speedvac was used to dry the plates at about 45° C. for ~5 hrs. Then the plates were covered with foil seal and stored at −20° C.

Samples were resuspended by addition of 20 µl of 12.5% ACN, 0.1% formic acid solution, covered with foil seal, and incubated at 42° C. for 10 minutes with shaking at 600 rpm. Then add 30 µL of 0.1% formic acid solution was added and the plate was covered and incubated at 42° C. for 10 minutes with shaking at 600 rpm. Seal plate was then sealed with a 96-well silicon mat for analysis.

Example 45

The table below shows % inhibition of probe labeling at screening concentration. The proteins were in their native folded context and the results showed that the proteins, after pretreated with the Michael receptor compound, showed inhibited labeling at both C287 & C318. The modification was highly selective relative to more than 120 other target sites, and only C287 was modified.

It was unexpected that after the CRBN was modified with a Michael acceptor, C287 and C318 on CRBN displayed highly correlated structure activity relationship (SAR). After the pretreatment, the protein was tested using a highly reactive labeling probe, and the percentage of inhibition of probe labeling at screening concentration for both C287 and C318 showed significant correlation. The probe labeling inhibition only occurred at C287 and C318 and not at other protein sites, suggesting the inhibition did not occur at a global level.

events to denatured probe labeling events. When the probe was added when the protein was at its native state, the C287 modification prevented further probe labeling at both C287 and C318. In contrast, when the probe was added after the protein was denatured, C318 labeling was no longer inhibited. Therefore, C287 liganding/modification induces conformational changes at C318 and blocks further liganding or binding at C318, and the co-inhibition of C287 and C318 was due to an indirect allosteric mechanism.

Table 2 below shows % inhibition of probe labeling at screening concentration. The two columns for each compound show data for % inhibition of the protein in its native state (Nat.) compared to the denatured state (Den.). The compound in the furthest right column is a highly promiscuous compound which is highly reactive and serves as a

TABLE 1

Percentage inhibition of probe labeling at screening concentration

| Cpd (500 μM) | 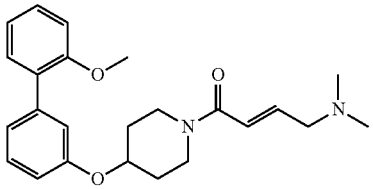 [SMILES: COc1ccccc1-c1cccc(OC2CCN(C(=O)/C=C/CN(C)C)CC2)c1] | 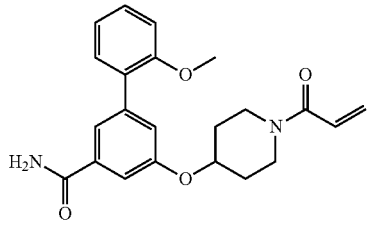 [SMILES: C=CC(=O)N1CCC(Oc2cc(C(N)=O)cc(-c3ccccc3OC)c2)CC1] |
|---|---|---|
| CRBN_287 | 98 | 97 |
| CRBN_318 | 96 | 98 |
| PRTN_A | 10 | −2 |
| PRTN_B | 3 | 0 |
| PRTN_C | 14 | 19 |
| PRTN_D | 17 | 18 |
| PRTN_E | 12 | 8 |
| PRTN_F | 2 | 4 |
| PRTN_G | 13 | 6 |
| PRTN_H | 4 | 6 |
| PRTN_I | 14 | −1 |
| PRTN_J | 11 | 7 |
| PRTN_K | 22 | 12 |

| Cpd (500 μM) | 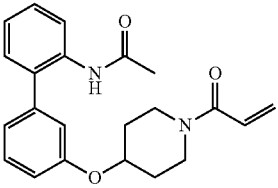 [SMILES: C=CC(=O)N1CCC(Oc2cccc(-c3ccccc3NC(C)=O)c2)CC1] | | 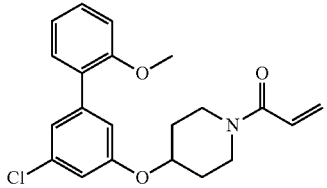 [SMILES: C=CC(=O)N1CCC(Oc2cc(Cl)cc(-c3ccccc3OC)c2)CC1] |
|---|---|---|---|
| CRBN_287 | 69 | 94 | 72 |
| CRBN_318 | 71 | 94 | 76 |
| PRTN_A | 8 | 7 | 5 |
| PRTN_B | 8 | 2 | −1 |
| PRTN_C | 3 | 18 | 15 |
| PRTN_D | 8 | 9 | 2 |
| PRTN_E | 9 | 11 | 2 |
| PRTN_F | 7 | 6 | −12 |
| PRTN_G | 12 | 13 | −8 |
| PRTN_H | 2 | 9 | −5 |
| PRTN_I | −1 | 7 | 0 |
| PRTN_J | 21 | 6 | −2 |
| PRTN_K | 20 | 13 | 17 |

Example 46

Figure 4:
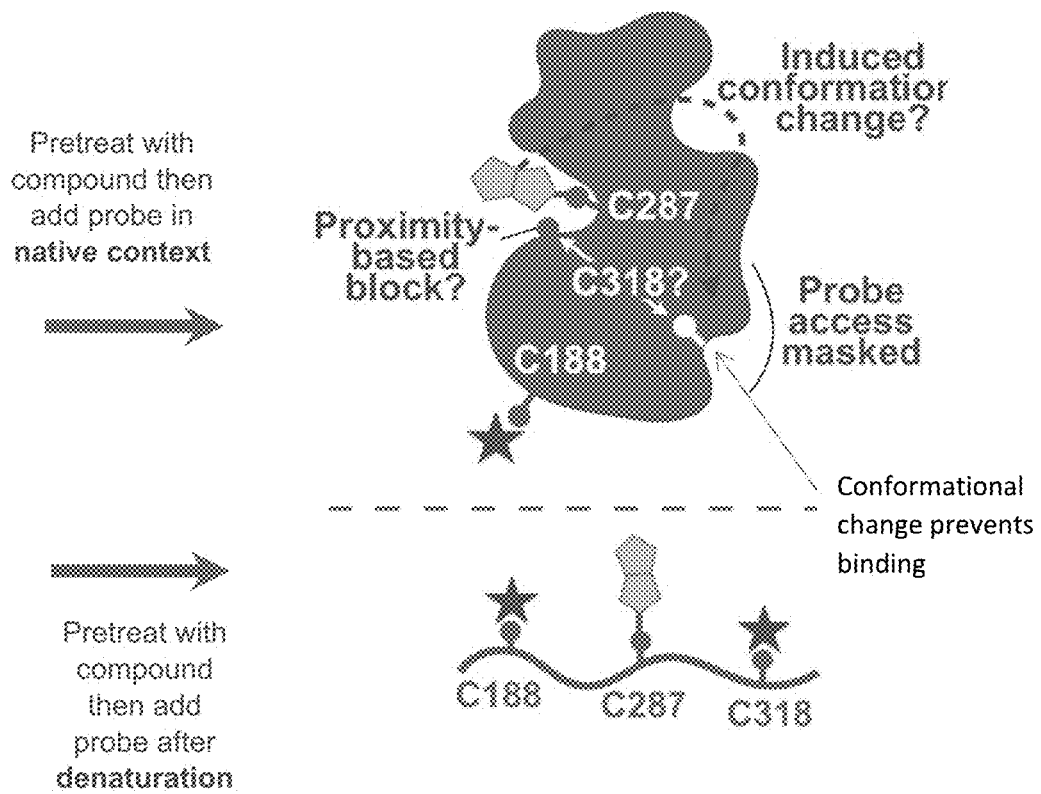
FIG. 4 is a schematic of Example 46 comparing native state probe labeling events to denatured probe labeling events to determine if the co-inhibition of C287 and C318 is due to a direct or indirect mechanism.

To determine whether the co-inhibition of C287 and C318 was due to a direct or indirect mechanism, CRBN was pretreated with various Michael acceptor compounds and then tested for probe labeling in its native and denatured states. FIG. 4 compares the native state probe labeling positive control. The data elucidates whether the change in probe labeling that happens at C318 is due to a direct or indirect effect from exposure to compounds of the present invention. In each the cell lysate was pretreated with compound, for native state the probe was immediately added and for denatured data the probe was added after an additional step of denaturation (schematic shown in FIG. 4).

TABLE 2

Comparison of probe labeling at native and denatured states after pretreatment

| Protein_Site | Nat. | Den. | Nat. | Den. | Nat. | Den. | Nat. | Den. |
|---|---|---|---|---|---|---|---|---|
| CRBN_287 | 98 | 91 | 91 | 76 | 90 | 67 | 61 | 59 |
| CRBN_318 | 92 | 38 | 82 | 28 | 60 | 11 | 59 | 53 |
| CRBN_188 | −18 | −28 | −16 | −44 | −13 | −21 | −36 | −6 |
| CRBN_205 | −4 | 4 | −20 | 0 | −23 | −11 | −23 | 13 |
| CRBN_219 | −36 | −2 | −25 | 12 | −6 | 24 | 40 | 57 |
| CRBN_234 | 11 | 26 | 27 | 21 | −4 | −7 | −4 | 45 |
| CRBN_310 | 54 | 43 | 46 | 35 | 9 | −1 | 2 | 50 |
| CRBN_322 | 25 | 19 | 2 | 27 | 36 | 15 | 29 | 29 |
| CRBN_326 |  | −6 |  | −15 |  | −16 |  | −8 |
| CRBN_343 |  | −5 |  | −12 |  | −28 |  | −10 |
| CRBN_441 |  | −6 |  | −22 |  | −24 |  | −26 |
| BTK_481 | 52 | 21 | 2 | −28 | 99 | 99 | 97 | 98 |
| TEC_449 | 28 | 33 | 4 | −4 | 99 | 98 | 96 | 95 |

Example 47

Table 3A shows the inhibition of probe labeling of various CRBN cysteines at various concentrations. "X@Y" means that x % inhibition of iodoacetamide probe labeling was observed by treatment of cell lysate with the give compound in each row of the table for 1 h at a concentration of y micromolar. There was consistently high inhibition at C318 in addition to C287, which can be attributed to an allosteric inhibition. The compound structures are shown in Table 3B.

TABLE 3A

Inhibition of probe labeling of various CRBN cysteines at various concentrations.

| Comp. | Cys287 | Cys318 | Cys234 | Cys205 | Cys219 | Cys366 | Cys188 | Cys343 |
|---|---|---|---|---|---|---|---|---|
| A1 | 97@500, 90@50, 40@5 | 95@500, 84@500, 86@50, 43@5, 97@500 |  |  |  |  |  |  |
| A2 | 91@500 |  | −20@500 | 18@500 | 31@500 | 2@500 | 9@500 | −6@500 |
| A3 | 96@500, 80@125, 51@31.2, 12@7.8 | 85@500, 64@125, 35@31.2, 21@7.8 | 31@500, 19@125, 6@31.2 | 15@500, 21@125, 7@31.2 | 40@500, 8@125, 19@31.2 | −1@500, −6@125 | 3@500, 5@125 |  |
| A4 | 99@500, 99@125, 97@31.2, 96@7.8 |  |  |  |  |  |  |  |
| A5 | 99@500, 99@125, 98@31.2, 96@7.8, 93@2.0, 83@0.49, 70@0.12 | 96@500, 95@125, 94@31.2, 93@7.8, 85@2.0, 76@0.49, 77@0.12 | 25@500, 60@125, 37@31.2, 35@7.8, 19@2.0 | 31@500, 37@125, 29@31.2, 36@7.8, 19@2.0 | 13@500, 25@125, −3@31.2, 13@7.8, 22@2.0, 17@0.49 | −41@500, −30@125, −39231.2, −22@7.8 | −3@500, 7@125, 13@31.2, 13@7.8, 22@2.0, 17@0.49 |  |
| A6 | 95@500, 94@125, 82@31.2, 772.0, 62@0.49 |  |  |  |  |  |  |  |
| A7 | 92@500, 94@125, 95@31.2, 72@7.8, 71@2.0 | 69@50, 67@5, 39@0.5 | 32@50, 19@5, −12@0.5 | −84@50, −42@5 | 32@50, −3@5 | 26@50, 3@5, 3@0.5 |  | 51@50, 8@5 |
| A8 | 98@500, 96@100, 94@20, 80@0.8 | 96@500, 93@100, 90@20, 76@0.8 | 44@500, 31%100 | 32%500, 19@100 | 4@500, −5@100 |  | −60@500, −18@100 | −2@500, 10@100 |

TABLE 2B

Structures of compounds shown in Table 2A.

| Compound # | Structure |
|---|---|
| A1: (4-phenoxypiperidine acrylamides) | 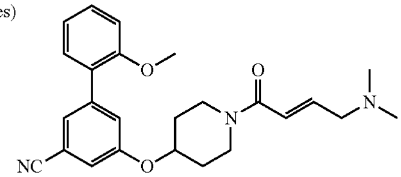 |
| A2 (4-phenoxypiperidine acrylamides) | 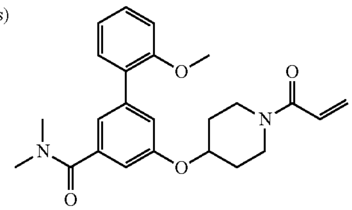 |
| A3: (4-phenoxyazetidine acrylamides) | 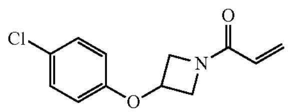 [SMILES: C=CC(=O)N1CC(Oc2ccc(Cl)cc2)C1] |
| A4: (4-phenoxypiperidine cyanoacrylamides) | 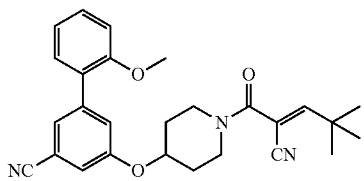 [SMILES: COc1ccccc1-c1cc(C#N)cc(OC2CCN(C(=O)/C(C#N)=C/C(C)(C)C)CC2)c1] |
| A5: (4-phenoxypiperidine cyanoacrylamides) | 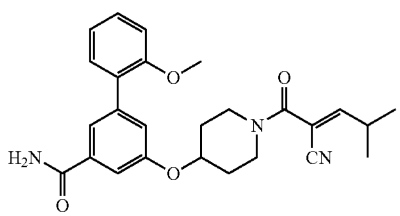 [SMILES: COc1ccccc1-c1cc(OC2CCN(C(=O)/C(C#N)=C/C(C)C)CC2)cc(C(N)=O)c1] |
| A6: (4-phenoxypiperidine cyanoacrylamides) | 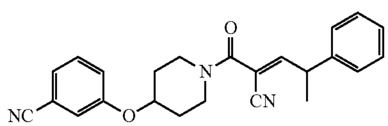 [SMILES: CC(/C=C(\C#N)C(=O)N1CCC(Oc2cccc(C#N)c2)CC1)c1ccccc1] |
| A7: (3-arylpyrrolidine cyanoacrylamides) | 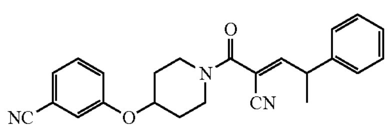 [SMILES: CC(/C=C(\C#N)C(=O)N1CCC(Oc2cccc(C#N)c2)CC1)c1ccccc1] |
| A8: (4-phenoxyazetidine cyanoacrylamides) | 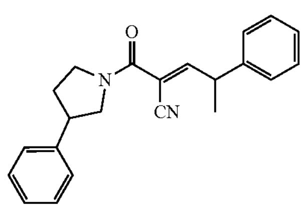 [SMILES: CC(/C=C(\C#N)C(=O)N1CCC(c2ccccc2)C1)c1ccccc1] |

Example 48

Binding of IMiD to cereblon also induced conformational changes that can inhibit binding of C287 and C318. The PBMC lysates were first pretreated with IMiD such as pomalidomide and CC-220 for 1 hour, and then the probes were added for 1 hour in lysates (native context) to track cysteines 287 and 318 labeling. As shown in Table 4, the IMiDs binding inhibits binding at both cysteines 287 and 318.

TABLE 4

| | Pomalidomide | | | CC-220 | | |
|---|---|---|---|---|---|---|
| | 500 µM | 100 µM | 20 µM | 50 µM | 20 µM | 2 µM |
| CRBN-287 | 75 | 70 | 66 | 81 | 77 | 75 |
| CRBN-318 | 71 | 72 | 59 | 72 | 70 | 70 |
| Protein-A | 13 | 10 | 8 | 13 | 19 | 16 |
| Protein-B | 0 | 14 | 0 | 17 | 11 | 23 |
| Protein-C | 10 | 1 | 10 | 0 | 2 | 0 |

Example 49

Figure 5:
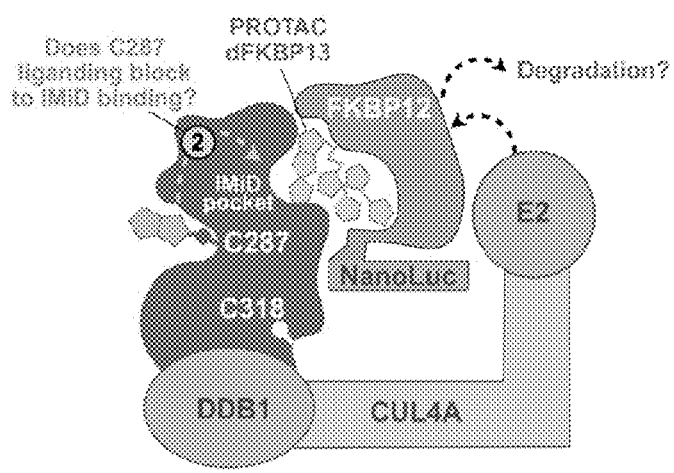
FIG. 5 illustrates that pre-treatment with compounds of the present invention specific for C287 also prevented cereblon-dependent degradation of a dFKBP13 bifunctional degrader.
Figure 5:
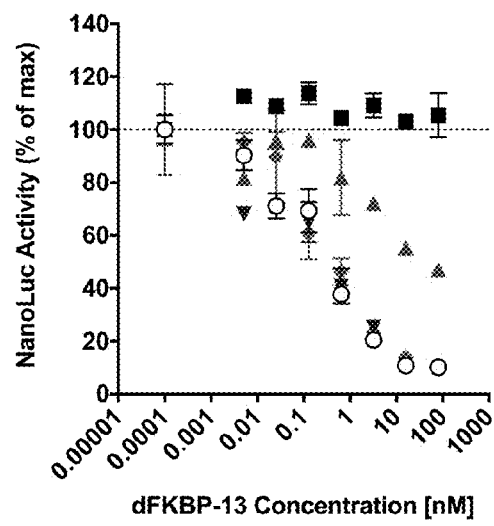
Figure 5:
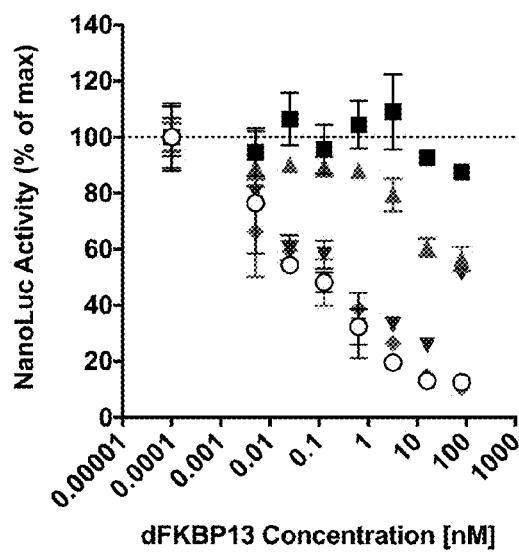

NanoLuc activity assay was used to measure the percent degradation of FKBP12 with known bifunctional degrader dFKBP13 after pretreatment with compounds of the present invention in conditions a) with no compound washout and b) with compound washout. After HEK293 cells were pretreated with Michael acceptor compounds and the cereblon protein was modified by the Michael acceptor compounds, the PROTAC dFKBP13 was added and the activity of a cereblon dependent degradation assay was measured to determine the interaction between C287 and IMiD binding pocket. As shown in FIG. 5, C287 modification inhibited PROTAC dFKBP13 degrader function and induced prevention or inhibition of the IMiD binding pocket. It was unexpected that the modification method described herein can yield in vivo engineered cereblon protein described herein has site specific modification and also has reduced engagement activity at both C318 residue and IMiD binding pocket.

Example 50

The global promiscuity of the compounds were determined based on the number of targets where 500 µM compound inhibits probe labeling by greater than 40% after a 1 hour incubation in a global experiment. Table 3 shows the global promiscuity measured for some Michael receptor compounds.

TABLE 3

Global promiscuity of selective compounds

| Compound | Global Promiscuity |
|---|---|
|  | 0.05484 |
|  | 0.026434 |

TABLE 3-continued

Global promiscuity of selective compounds

| Compound | Global Promiscuity |
|---|---|
|  | 0.277453 |
|  | 0.785066 |
|  | 0.862971 |

TABLE 3-continued

Global promiscuity of selective compounds

| Compound | Global Promiscuity |
|---|---|
| Chiral — (4-phenoxy-3-fluoropiperidine with acryloyl group) | 0.152799 |
| Chiral — (4-phenoxy-3-fluoropiperidine with acryloyl group, different stereochemistry) | 0.094633 |

Example 51 isoTOP-ABPP Sample preparation: Sample preparation and analysis were based on (Backus et al. Nature 534, 570-574, 2016) with modifications noted below.

For analysis of ligandable cysteines in cereblon (H2122, H460 and A549) cells and, lysate was prepared as described in (Backus et al., 2016). Samples were treated with 500 μM of Michael receptor compound or vehicle for 1 h at room temperature.

For analysis of ligands or control compound reactivity, H460 cells or H460 cells expressing luciferase in a 10 cm plate were incubated with indicated compounds in serum/dye-free RPMI for 3 hours at 37° C. Cells were washed once ice-cold PBS and lysed in 1% Triton X-100 dissolved in PBS with protease inhibitors (Sigma) by sonication. Samples were clarified by centrifugation for 10 min at 16,000×g. Lysate was adjusted to 1.5 mg ml$^{-1}$ in 500 μL.

For analysis of cysteines that change following induction of apoptosis, H2122 and H1975 cells were treated with DMSO or staurosporine (1 μM, 4 h) in full RPMI. H1975 cells were treated with DMSO or AZD9291 (1 μM, 24 h) in full RPMI. Cells were lysed as described above.

isoTOP-ABPP IA-alkyne labeling and click chemistry: Samples were labeled for 1 h at ambient temperature with 100 μM iodoacetamide alkyne (alkyne, 5 μL of 10 mM stock in DMSO). Samples were conjugated by copper-catalyzed azide-alkyne cycloaddition (CuAAC) to isotopically labeled, TEV-cleavable tags (TEV-tags). Heavy CuAAC reaction mixtures was added to the DMSO-treated or shGFP control samples and light CuAAC reaction mixture was added to compound-treated samples. The CuAAC reaction mixture consisted of TEV tags (light or heavy, 10 μL of 5 mM stocks in DMSO, final concentration=100 μM), 1 mM tris(2-carboxyethyl)phosphine hydrochloride (TCEP; fresh 50× stock in water, final concentration=1 mM), ligand (17× stock in DMSO:t butanol 1:4, final concentration=100 μM) and 1 mM CuSO$_4$ (50× stock in water, final concentration=1 mM). The samples were allowed to react for 1 h at which point the samples were centrifuged (16,000×g, 5 min, 4° C.). The resulting pellets were sonicated in ice-cold methanol (500 μL) and the resuspended light- and heavy-labeled samples were then combined pairwise and centrifuged (16,000×g, 5 min, 4° C.). The pellets were solubilized in PBS containing 1.2% SDS (1 mL) with sonication and heating (5 min, 95° C.) and any insoluble material was removed by an additional centrifugation step at ambient temperature (14,000×g, 1 min).

isoTOP-ABPP streptavidin enrichment: For each sample, 100 μL of streptavidin-agarose beads slurry (Fisher) was washed in 10 mL PBS and then resuspended in 6 mL PBS (final concentration 0.2% SDS in PBS). The SDS-solubilized proteins were added to the suspension of streptavidin-agarose beads and the bead mixture was rotated for 3 h at ambient temperature. After incubation, the beads were pelleted by centrifugation (1,400×g, 3 min) and were washed (2×10 mL PBS and 2×10 mL water).

isoTOP-ABPP trypsin and TEV digestion: The beads were transferred to eppendorf tubes with 1 mL PBS, centrifuged (1,400×g, 3 min), and resuspended in PBS containing 6 M urea (500 μL). To this was added 10 mM DTT (25 μL of a 200 mM stock in water) and the beads were incubated at 65° C. for 15 mins. 20 mM iodoacetamide (25 μL of a 400 mM stock in water) was then added and allowed to react at 37° C. for 30 mins with shaking. The bead mixture was diluted with 900 μL PBS, pelleted by centrifugation (1,400×g, 3 min), and resuspended in PBS containing 2 M urea (200 μL). To this was added 1 mM CaCl$_2$ (2 μL of a 200 mM stock in water) and trypsin (2 μg, Promega, sequencing grade) and the digestion was allowed to proceed overnight at 37° C. with shaking. The beads were separated from the digest with Micro Bio-Spin columns (Bio-Rad) by centrifugation (1,000×g, 1 min), washed (2×1 mL PBS and 2×1 mL water) and then transferred to fresh eppendorf tubes with 1 mL water. The washed beads were washed once further in 140 μL TEV buffer (50 mM Tris, pH 8, 0.5 mM EDTA, 1 mM DTT) and then resuspended in 140 μL TEV buffer. 5 μL TEV protease (80 μM) was added and the reactions were rotated overnight at 29° C. The TEV digest was separated from the beads with Micro Bio-Spin columns by centrifugation (1,400×g, 3 min) and the beads were washed once with water (100 μL). The samples were then acidified to a final concentration of 5% (v/v) formic acid and stored at −80° C. prior to analysis.

isoTOP-ABPP liquid-chromatography-mass-spectrometry (LC-MS) analysis: Samples processed for multidimensional liquid chromatography tandem mass spectrometry (MudPIT) were pressure loaded onto a 250 μm (inner diameter) fused silica capillary columns packed with C18 resin (Aqua 5 μm, Phenomenex). Samples were analyzed using an LTQVelos Orbitrap mass spectrometer (Thermo Scientific) coupled to an Agilent 1200-series quaternary pump. The peptides were eluted onto a biphasic column with a 5 μm tip (100 μm fused silica, packed with C18 (10 cm) and bulk strong cation exchange resin (3 cm, SCX, Phenomenex)) in a 5-step MudPIT experiment, using 0%, 30%, 60%, 90%, and 100% salt bumps of 500 mM aqueous ammonium acetate and using a gradient of 5-100% buffer B in buffer A (buffer A: 95% water, 5% acetonitrile, 0.1% formic acid; buffer B: 5% water, 95% acetonitrile, 0.1% formic acid) as has been described in (Weerapana et al., 2007). Data were collected in data-dependent acquisition mode with dynamic exclusion enabled (20 s, repeat of 2). One full MS (MS1) scan (400-1800 m/z) was followed by 30 MS2 scans (ITMS) of the nth most abundant ions.

isoTOP-ABPP peptide and protein identification: The MS2 spectra data were extracted from the raw file using RAW Convertor (version 1.000. MS2 spectra data were searched using the ProLuCID algorithm using a reverse concatenated, non-redundant variant of the Human UniProt database (release-20 1 2_1 1). Cysteine residues were searched with a static modification for carboxyamidomethylation (+57.02 1 46) and up to two differential modification for either the light or heavy TEV tags or oxidized methionine (+464.28595, +470.29976, +1 5 0.9949 respectively).

MS2 spectra data were also searched using the ProLuCID algorithm using a custom database containing only selenocysteine proteins, which was generated from a reverse concatenated, nonredundant variant of the Human UniProt database (release-2012_11). In the database, selenocysteine residues (U) were replaced with cysteine (C) and were searched with a static modification for carboxyamidomethylation (+57.02146) and up to two differential modification for either the light or heavy TEV tags or oxidized methionine (+512.2304+ or +518.2442+15.9949). Peptides were required to have at least one tryptic terminus and to contain the TEV modification. ProLuCID data was filtered through DTASelect (version 2.0) to achieve a peptide false-positive rate below 1%.

isoTOP-ABPP R value calculation and processing: The isoTOP-ABPP ratios (R values) of heavy/light for each unique peptide (DMSO/compound treated) were quantified with in-house CIMAGE software (Weerapana et al., Nature 468, 790-795, 2010) using default parameters (3 MS1 acquisitions per peak and signal to noise threshold set to 2.5). Site-specific engagement of cysteine residues was assessed by blockade of IA-alkyne probe labelling. A maximal ratio of 20 was assigned for peptides that showed a >95% reduction in MS1 peak area from the experimental proteome (light TEV tag) when compared to the control proteome (DMSO, shGFP; heavy TEV tag). Ratios for unique peptide sequences entries were calculated for each experiment; overlapping peptides with the same modified cysteine (for example, different charge states, MudPIT chromatographic steps or tryptic termini) were grouped together and the median ratio is reported as the final ratio (R). Additionally, ratios for peptide sequences containing multiple cysteines were grouped together. Biological replicates of the same treatment and cell line were averaged if the standard deviation was below 60% of the mean; otherwise, for cysteines with at least one R value <4 per treatment, the lowest value of the ratio set was taken. For cysteines where all R values were ≥4, the average was reported. The peptide ratios reported by CIMAGE were further filtered to ensure the removal or correction of low-quality ratios in each individual data set. The quality filters applied were the following: removal of half tryptic peptides; removal of peptides which were detected only once across all data sets reported herein; removal of peptides with R=20 and only a single MS2 event triggered during the elution of the parent ion; manual annotation of all the peptides with ratios of 20, removing any peptides with low-quality elution profiles that remained after the previous curation steps.

For selenocysteines, the ratios of heavy/light for each unique peptide (DMSO/compound treated; isoTOP-ABPP ratios, R values) were quantified with in-house CIMAGE software using the default parameters described above, with the modification to allow the definition of selenocysteine (amino acid atom composition and atomic weights). Extracted ion chromatograms were manually inspected to ensure the removal of low quality ratios and false calls.

Cysteine residues were considered liganded in vitro by electrophilic fragments if they had an average R-value ≥5 and were quantified in at least 2 out of 3 replicates. Targets of NR0B1 ligands or control compounds were defined as those cysteine residues that had R-values ≥3 in more than one biological replicate following ligand treatment in cells.

Protein Turnover

For analysis of protein turnover in H460 cells, confluent 10 cm plates were washed twice with warm PBS, then incubated in "heavy" RPMI for 3 h. Cells were washed once ice-cold PBS and lysed in 1% Triton 100-X dissolved in PBS with protease inhibitors (Sigma) by sonication. Lysate was adjusted to 1.5 mg ml$^{-1}$ in 2×500 μL. Samples were processed identically to other samples (lysates were adjusted to 1.5 mg ml$^{-1}$ in 2×500 μL), with the following modification: only isotopically light TEV tag was used. After the "click" reaction, both 2×500 μL were centrifuged (16,000×g, 5 min, 4° C.) and resuspended by sonication in ice-cold methanol (500 μL). Aliquots were then combined and resolubilized in PBS containing 1.2% SDS (1 mL) as detailed in isoTOP-ABPP IA-alkyne labeling and click chemistry. Samples were further processed and analyzed as detailed in: isoTOP-ABPP streptavidin enrichment, isoTOP-ABPP trypsin and TEV digestion, isoTOP-ABPP liquid-chromatography-mass-spectrometry (LC-MS) analysis, isoTOP-ABPP peptide and protein identification and isoTOP-ABPP R value calculation and processing with the following exceptions: Samples processed for protein turnover were searched with ProLuCID with mass shifts of SILAC labeled amino acids (+10.0083 R, +8.0142 K) in addition to carboxyamidomethylation modification (+57.02146) and two differential modification for either the light TEV tag or oxidize methionine (+464.28595, +15.9949 respectively). 1 peptide identification was required for each protein. ProLuCID data was filtered through DTASelect (version 2.0) to achieve a peptide false-positive rate below 1%. Ratios of light/heavy peaks were calculated using in-house CIMAGE software. Median SILAC ratios from one or more unique peptides were combined to generate R values. Proteins were required to be quantified in at least two biological replicates. The mean R values and standard deviation for multiple biological experiments were calculated from the average ratios from each replicate. Proteins were designated as rapid turnover if they had R-values ≤8.

ABPP-SILAC sample preparation and LC-MS analysis: Isotopically labeled H460 cell lines were generated as described above. Light and heavy cells were treated with compounds (20 μM) or DMSO, respectively, for 3 h, followed by labeling with the BPK-29yne (5 μM) for 30 min. Cells were washed once ice-cold PBS and lysed in 1% Triton 100-X dissolved in PBS with protease inhibitors (Sigma) by sonication. Lysate was adjusted to 1.5 mg ml$^{-1}$ in 500 μL. Samples were conjugated by CuAAC to Biotin-PEG4-azide (5 μL of 10 mM stocks in DMSO, final concentration=100 CuAAC "click" mix contained TCEP, TBTA ligand and CuSO4 as detailed for isoTOP-ABPP sample preparation. Samples were further processed as detailed in: isoTOP-ABPP streptavidin enrichment and isoTOP-ABPP trypsin TEV digestion with the following exception: after overnight incubation at 37° C. with trypsin, tryptic digests were separated from the beads with Micro Bio-Spin columns (Bio-Rad) by centrifugation (1,000×g, 1 min). Beads were rinsed once with water (200 μL) and combined with tryptic digests. The samples were then acidified to a final concentration of 5% (v/v) formic acid and stored at −80° C. prior to analysis. Samples were processed for multidimensional liquid chromatography tandem mass spectrometry (MudPIT) as described in isoTOP-ABPP liquid-chromatography-mass-spectrometry (LC-MS) with the exception that peptides were eluted using the 5-step MudPIT protocol with conditions: 0%, 25%, 50%, 80%, and 100% salt bumps of 500 mM aqueous ammonium acetate and using a gradient of 5-100% buffer B in buffer A (buffer A: 95% water, 5% acetonitrile, 0.1% formic acid; buffer B: 5% water, 95% acetonitrile, 0.1% formic acid).

ABPP-SILAC peptide and protein identification and R value calculation and processing: The MS2 spectra data were extracted and searched using RAW Convertor and ProLuCID algorithm as described in isoTOP-ABPP peptide and protein quantification. Briefly, cysteine residues were searched with a static modification for carboxyamidomethylation (+57.02146 C). Searches also included methionine oxidation as a differential modification (+15.9949 M) and mass shifts of SILAC labeled amino acids (+10.0083 R, +8.0142 K) and no enzyme specificity. Peptides were required to have at least one tryptic terminus and unlimited missed cleavage sites. 2 peptide identifications were required for each protein. ProLuCID data was filtered through DTASelect (version 2.0) to achieve a peptide false-positive rate below 1%. Ratios of heavy/light (DMSO/test compound) peaks were calculated using in-house CIMAGE software. Median SILAC ratios from two or more unique peptides were combined to generate R values. The mean R values and standard deviation for multiple biological experiments were calculated from the average ratios from each replicate. Targets of NR0B1 ligands or control compounds were defined as those proteins that had R-values ≥2.5 in two or more biological replicates following ligand treatment in cells.

Site of labeling: For site of labeling with BPK-29, 4×10$^6$ HEK-293T cells were seeded in a 10 cm plate and transfected the next day with 5 μg of FLAG-NR0B1 cDNA in a pRK5-based expression vector. 48 hours after transfection, cells were treated with vehicle, BPK-29 (50 μM) in serum-free RPMI for 3 h at 37° C. FLAG immunoprecipitates were prepared as described above in identification of NR0B1 interacting proteins. FLAG-NR0B1 was eluted from FLAG-M2 beads with 8M urea and subjected to proteolytic digestion, whereupon tryptic peptides harboring C274 were analyzed by LC-MS/MS. The resulting mass spectra were extracted using the ProLuCID algorithm designating a variable peptide modification (+252.986 and +386.1851 for BPK-26 and BPK-29, respectively) for all cysteine residues. For site of labeling with BPK-26, HEK-293T cell lysate transfected with FLAG-NR0B1 as described above was treated with vehicle or BPK-26 (100 μM) for 3 h at 4° C. FLAG immunoprecipitates were processed for proteomic analysis as described above.

Quantification and Statistical Analysis: Statistical analysis was preformed using GraphPad Prism version 6 or 7 for Mac, GraphPad Software, La Jolla Calif. USA, or the R statistical programming language. Statistical values including the exact n and statistical significance are also reported in the Figures. Inhibition curves of the NR0B1-SNW1 interactions by NR0B1-ligand are fit as using log(inhibitor) vs % normalized remaining of NR0B1-SNW1 interaction and data points are plotted as the mean±SD (n=2-5 per group). NR0B1 half-life was calculated from a one-phase exponential decay curve plotted as mean±SD (4-10 per group). Statistical significance was defined as p<0.05 and determined by 2-tailed Student's t-test, two-way Anova with Bonferroni post-test analysis or correlation analysis using Pearson product-moment correlation coefficient.

Example 52

Figure 6:
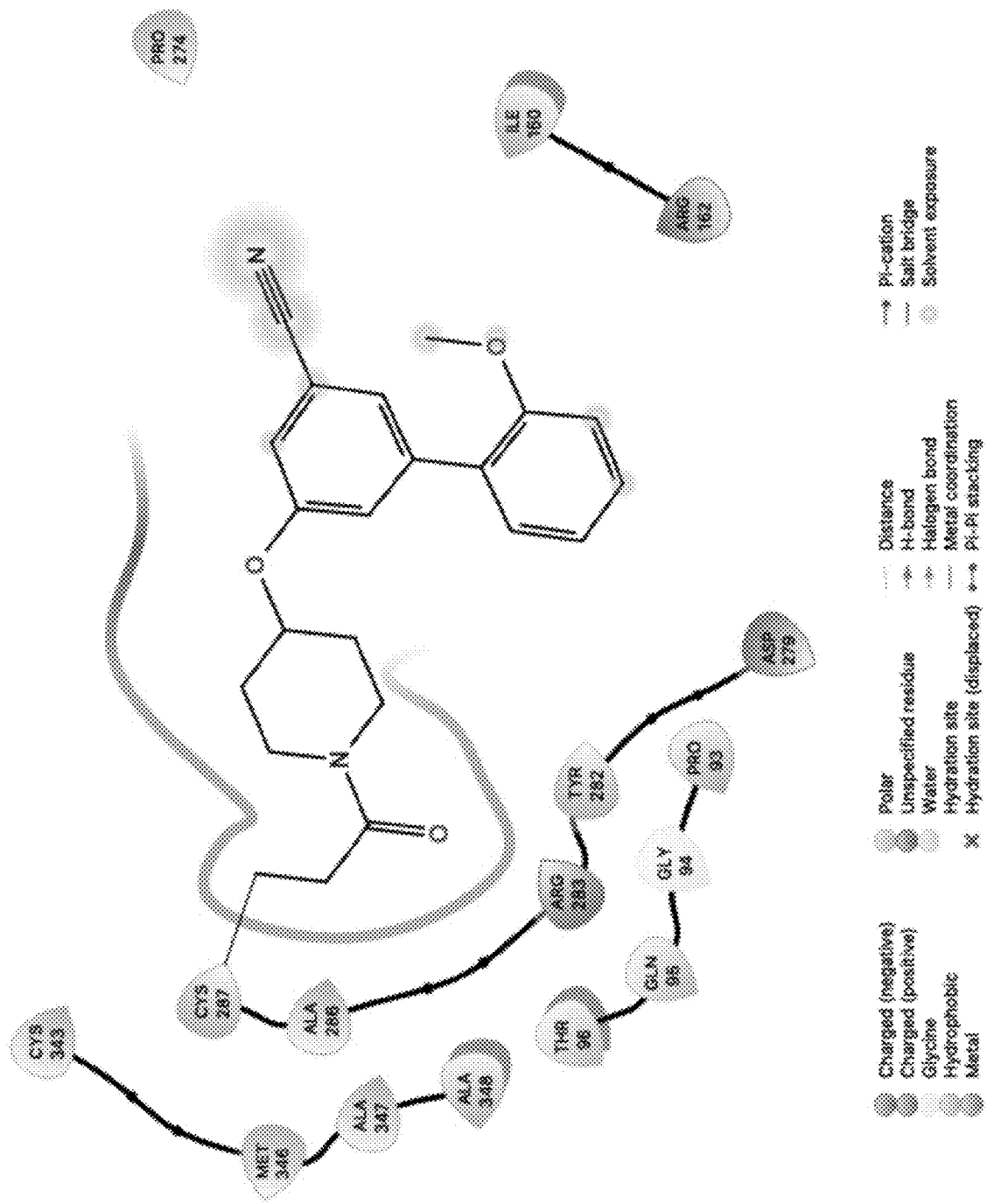
FIG. 6 illustrates a first set of exemplary non-covalent interactions with compound 1.
Figure 7:
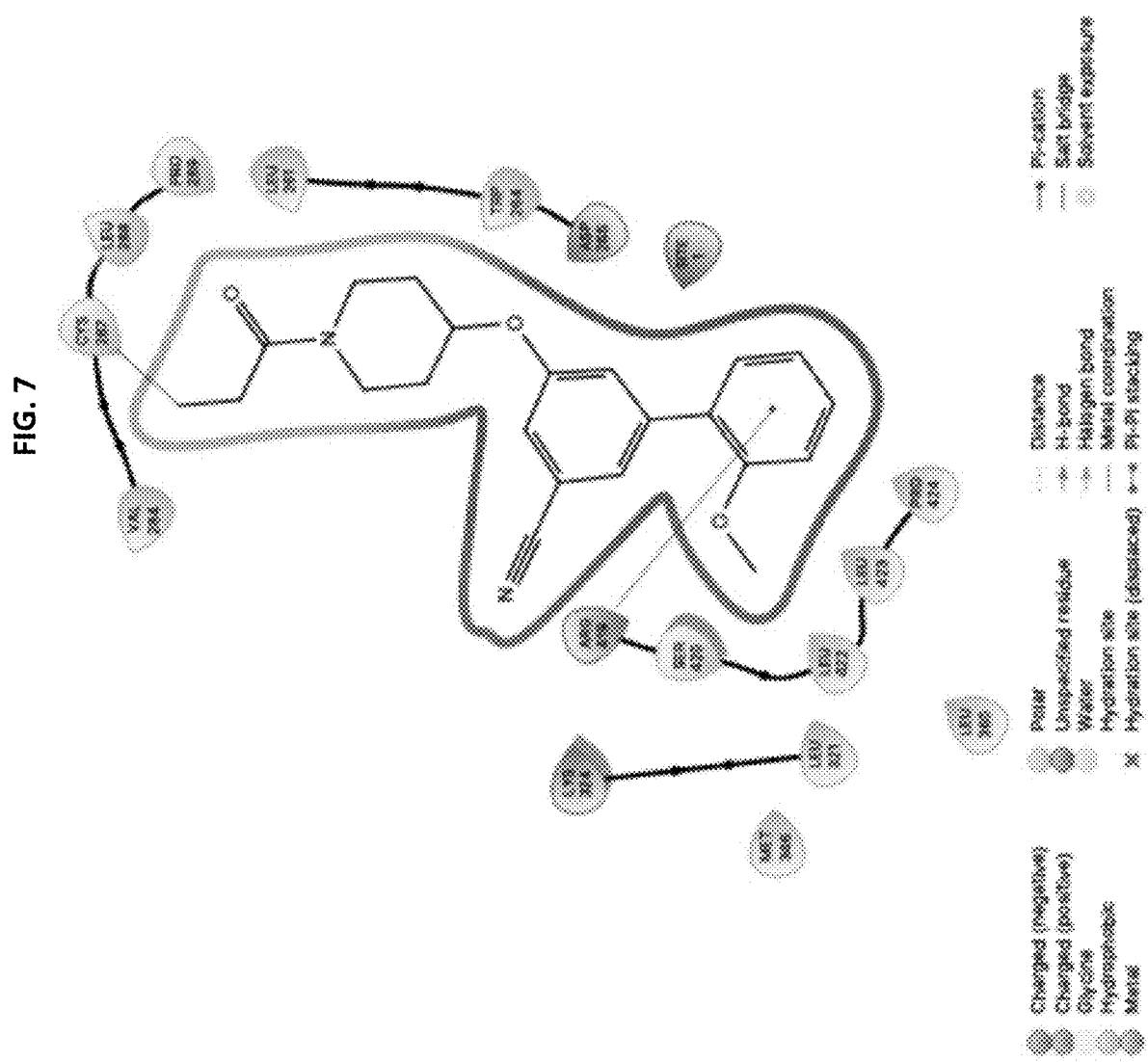
FIG. 7 illustrates a second set of exemplary non-covalent interactions with compound 2.

FIG. 6 and FIG. 7 illustrate in silico studies of two exemplary compounds with Cereblon. FIG. 6 shows a first set of non-covalent interactions with compound A. FIG. 7 illustrates a second set of non-covalent interactions with compound B.

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the disclosure and that methods and structures within the scope of these claims and their equivalents be covered thereby.

What is claimed is:

1. An in vivo engineered cereblon protein consisting of a non-naturally occurring covalent modification at cysteine 287 as set forth in SEQ ID NO:1, or cysteine 286 as set forth in SEQ ID NO: 2 or 3, the modification resulting from an in vivo Michael addition reaction between an exogenous Michael acceptor and the cysteine 287 as set forth in SEQ ID NO:1, or cysteine 286 as set forth in SEQ ID NO: 2 or 3, wherein a sulfur atom at the cysteine residue undergoes the Michael reaction with a double bond of the exogenous Michael acceptor, and wherein the engineered cereblon has reduced engagement potency at cysteine 318 as set forth in SEQ ID NO:1 or at cysteine 317 as set forth in SEQ ID NO: 2 or 3.

2. The in vivo engineered cereblon of claim 1, wherein the IMiD pocket-dependent binding on the engineered cereblon protein is prevented by the modification.

3. The in vivo engineered cereblon of claim 1, wherein the engineered cereblon protein has an inhibited or reduced binding for immunomodulatory drugs as compared to unmodified cereblon.

4. The in vivo engineered cereblon of claim 1, wherein the amino acid residue at cysteine 318 as set forth in SEQ ID NO:1 or cysteine 317 as set forth in SEQ ID NO: 2 or 3 is not modified.

5. The in vivo engineered cereblon of claim 1, wherein the amino acid residues at cysteine 234, cysteine 205, cysteine 219, cysteine 366, cysteine 188, and cysteine 343 as set forth in SEQ ID NO:1 are not modified.

6. The in vivo engineered cereblon of claim 1, wherein the engineered cereblon protein is only modified at cysteine 287 as set forth in SEQ ID NO:1 or cysteine 286 as set forth in SEQ ID NO: 2 or 3.

7. The in vivo engineered cereblon of claim 1, wherein the exogenous Michael acceptor has a global promiscuity that is no greater than the global promiscuity of KB02.

8. The in vivo engineered cereblon of claim 1, wherein the exogenous Michael acceptor has a global promiscuity that is no greater than ⅓ of the global promiscuity of KB02.

9. The in vivo engineered cereblon of claim 1, wherein the exogenous Michael acceptor has a global promiscuity of no greater than 20% at 500 μM.

10. The in vivo engineered cereblon of claim 1, wherein the exogenous Michael acceptor has a global promiscuity of no greater than 10% at 500 μM.

11. The in vivo engineered cereblon protein of claim 1, wherein the exogenous Michael acceptor has a $TE_{50}$ of no greater than 80 μM.

12. The in vivo engineered cereblon protein of claim 1, wherein the exogenous Michael acceptor has a $TE_{50}$ of no greater than 60 μM.

13. The in vivo engineered cereblon of claim 12, wherein the exogenous Michael acceptor has a global promiscuity no greater than 5% at the $TE_{50}$.

14. The in vivo engineered cereblon of claim 12, wherein the exogenous Michael acceptor has a global promiscuity no greater than 2.5% at the $TE_{50}$.

15. The in vivo engineered cereblon of claim 1, wherein the exogenous Michael acceptor has a higher $TE_{50}$ than

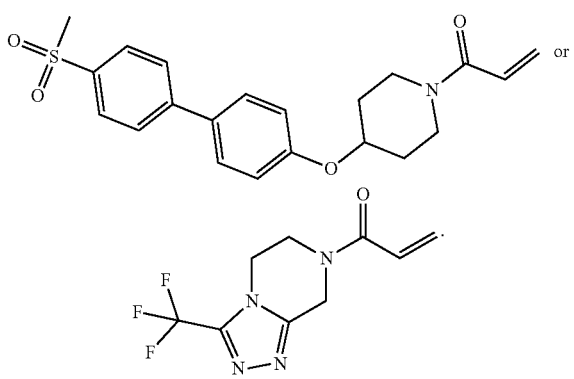

16. The in vivo engineered cereblon of claim 1, wherein the exogenous Michael acceptor is an acrylamide.

17. The in vivo engineered cereblon of claim 1, wherein the cereblon has a sequence as set forth in SEQ ID NO: 1 and the modification is at the cysteine residue C287.

18. The in vivo engineered cereblon of claim 1, wherein the cereblon has a sequence as set forth in SEQ ID NO: 2 or 3 and the modification is at the cysteine residue C286.

19. The in vivo engineered cereblon of claim 1, wherein the exogenous Michael acceptor forms a hydrophobic interaction with the one or more residues selected from Pro 93, Ile 160, Met 246, Pro 274, Tyr 282, Ala 286, Cys 287, Cys 343, Ala 347, Ala 348, or a combination thereof.

20. The in vivo engineered cereblon of claim 1, wherein the exogenous Michael acceptor forms a hydrophobic interaction with the one or more residues selected from Met 345, Leu 321, Leu 422, Leu 423, Pro 424, Leu 360, or a combination thereof.

21. The in vivo engineered cereblon of claim 1, wherein the exogenous Michael acceptor forms a charged interaction with the one or more residues selected from Asp279, Asp 265, Arg 162, Arg 283, Lys 324, Arg 419, or a combination thereof.

22. The in vivo engineered cereblon of claim 1, wherein the exogenous Michael acceptor forms a polar interaction with the one or more residues selected from Gln 95, Thr 96, or Ser 420.

23. The in vivo engineered cereblon of claim 1, wherein the exogenous Michael acceptor comprises at least one double bond.

24. The in vivo engineered cereblon of claim 1, wherein the cereblon is a human cereblon protein.

* * * * *